(12) United States Patent
Yu et al.

(10) Patent No.: US 10,590,056 B2
(45) Date of Patent: Mar. 17, 2020

(54) ERR MODULATORS AND USES THEREOF

(71) Applicant: CITY OF HOPE, Duarte, CA (US)

(72) Inventors: Donna D. Yu, Arcadia, CA (US); Barry M. Forman, Irvine, CA (US)

(73) Assignee: CITY OF HOPE, Duarte, CA (US)

( * ) Notice: Subject to any disclaimer, the term of this patent is extended or adjusted under 35 U.S.C. 154(b) by 0 days.

(21) Appl. No.: 15/950,953

(22) Filed: Apr. 11, 2018

(65) Prior Publication Data
US 2018/0297923 A1    Oct. 18, 2018

Related U.S. Application Data

(60) Provisional application No. 62/484,600, filed on Apr. 12, 2017.

(51) Int. Cl.
| | |
|---|---|
| *C07C 43/166* | (2006.01) |
| *A61P 1/16* | (2006.01) |
| *C07C 59/52* | (2006.01) |
| *C07C 217/00* | (2006.01) |
| *C07C 217/60* | (2006.01) |
| *C07C 69/732* | (2006.01) |

(52) U.S. Cl.
CPC .............. *C07C 43/166* (2013.01); *A61P 1/16* (2018.01); *C07C 59/52* (2013.01); *C07C 69/732* (2013.01); *C07C 217/00* (2013.01); *C07C 217/60* (2013.01)

(58) Field of Classification Search
CPC ......... A61P 1/16; C07C 43/166; C07C 59/52; C07C 69/732; C07C 217/00; C07C 217/60
See application file for complete search history.

(56) References Cited

U.S. PATENT DOCUMENTS

2005/0096384 A1    5/2005   Forman et al.

FOREIGN PATENT DOCUMENTS

KR          1681041       *   12/2016

OTHER PUBLICATIONS

Yu et al., Identification of novel inverse agonist of estrogen-related receptors ERRgamma and ERRbeta. Bioorganic & Medicinal Chemistry, vol. 25(5), pp. 1585-1599 (Year: 2017).*

Wang et al., Organometallic antitumor compounds: Ferrocifens as precursors to quinone methides. Angewandte Chemie, International Edition, vol. 54(35), pp. 10230-10233 (Year: 2015).*

Gust et al., STructure activity relationship studies on C2 side chain substituted 1,1-bis(4-nnethoxyphenyl)-2-phenylalkenes and 1,1,2-tris(4-methoxyphenyl)alkenes. J. Steroid Biochem. Mol. Biol., vol. 87(1), pp. 75-83 (Year: 2003).*

Chao, E.Y. et al. (Feb. 15, 2006, e-published Nov. 22, 2005). "Structure-guided synthesis of tamoxifen analogs with improved selectivity for the orphan ERRgamma," *Bioorg Med Chem Lett* 16(4):821-824.

Eichner, L.J. et al. (Oct. 6, 2010). "miR-378(*) mediates metabolic shift in breast cancer cells via the PGC-1β/ERRγ transcriptional pathway," *Cell Metab* 12(4):352-361.

Forman, B.M. et al. (Jun. 2, 1995). "Identification of a nuclear receptor that is activated by farnesol metabolites," *Cell* 81(5):687-693.

Gauthier, S. et al. (May 31, 1996). "New Highly Stereoselective Synthesis of (Z)-4-Hydroxytamoxifen and (Z)-4-Hydroxytoremifene via McMurry Reaction," *J Org Chem* 61(11):3890-3893.

Giguere, V. (Jul. 2002). "To ERR in the estrogen pathway," *Trends Endocrinol Metab* 13(5):220-225.

Heard, D.J. et al. (Mar. 2000). "Human ERRgamma, a third member of the estrogen receptor-related receptor (ERR) subfamily of orphan nuclear receptors: tissue-specific isoforms are expressed during development and in the adult," *Mol Endocrinol* 14(3):382-392.

Huss, J.M. et al. (Sep. 2015, e-published Jun. 24, 2015). "Constitutive activities of estrogen-related receptors: Transcriptional regulation of metabolism by the ERR pathways in health and disease," *Biochim Biophys Acta* 1852(9):1912-1927.

Ijichi, N. et al. (Jan. 2011, e-published Sep. 29, 2010). "Estrogen-related receptor γ modulates cell proliferation and estrogen signaling in breast cancer," *J Steroid Biochem Mol Biol* 123(1-2):1-7.

Kim, D.K. et al. (Nov. 4, 2011, e-published Sep. 12, 2011). "Estrogen-related receptor γ (ERRγ) is a novel transcriptional regulator of phosphatidic acid phosphatase, LIPIN1, and inhibits hepatic insulin signaling," *J Biol Chem* 286(44):38035-38042.

Lubczyk, V. et al. (Nov. 21, 2002). "Investigations on estrogen receptor binding. The estrogenic, antiestrogenic, and cytotoxic properties of C2-alkyl-substituted 1,1-bis(4-hydroxyphenyl)-2-phenylethenes," *J Med Chem* 45(24):5358-5364.

Lubczyk, V. et al. (Apr. 10, 2003). "Antiestrogenically active 1,1,2-tris(4-hydroxyphenyl)alkenes without basic side chain: synthesis and biological activity," *J Med Chem* 46(8):1484-1491.

McMurry, J.E. et al. (1976). "Improved Procedures for the Reductive Coupling of Carbonyls to Olefins and for the Reduction of Diols to Olefins," *J Org Chem* 41(5):896-897.

Murray, J. et al. (Sep. 2011, e-published May 11, 2011). "Estrogen-related receptor α regulates skeletal myocyte differentiation via modulation of the ERK MAP kinase pathway," *Am J Physiol Cell Physiol* 301(3):C630-C645.

Peng, L. et al. Nov. 10, 2011, e-published Oct. 12, 2011). "Identification of pyrido[1,2-α]pyrimidine-4-ones as new molecules improving the transcriptional functions of estrogen-related receptor α," *J Med Chem* 54(21):7729-7733.

Villena, J.A. et al. (Oct. 2008, e-published Sep. 6, 2008). "ERRalpha: a metabolic function for the oldest orphan," *Trends Endocrinol Metab* 19(8):269-276.

Wang, H. et al. (May 1999). "Endogenous bile acids are ligands for the nuclear receptor FXR/BAR," *Mol Cell* 3(5):543-553.

(Continued)

*Primary Examiner* — Barbara P Badio

(74) *Attorney, Agent, or Firm* — Mintz, Levin, Cohn, Ferris, Glovsky and Popeo, P.C.; Jillian B. Thompson

(57) ABSTRACT

Disclosed herein, inter alia, are compositions and methods useful for treating non-alcoholic fatty liver diseases.

29 Claims, 10 Drawing Sheets

Specification includes a Sequence Listing.

(56) References Cited

OTHER PUBLICATIONS

Yang, X. et al. (Aug. 25, 2006). "Nuclear receptor expression links the circadian clock to metabolism," *Cell* 126(4):801-810.

Yu, D.D. et al. (Nov. 28, 2003). "Simple and efficient production of (Z)-4-hydroxytamoxifen, a potent estrogen receptor modulator," *J Org Chem* 68(24):9489-9491.

Yu, S. et al. (May 22, 2008, e-published Dec. 10, 2007). "Orphan nuclear receptor estrogen-related receptor-beta suppresses in vitro and in vivo growth of prostate cancer cells via p21(WAF1/CIP1) induction and as a potential therapeutic target in prostate cancer," *Oncogene* 27(23):3313-3328.

* cited by examiner

Diethylstilbestrol (DES)

17-estradiol ($E_2$)

4-Hydroxytamoxifen (Z-4-OHT)

GSK5182

Compound 4a (DY40)

$IC_{50} = 10$ nM ERRβ/γ

SEQUENCE LISTING

```
<160> NUMBER OF SEQ ID NOS: 4

<210> SEQ ID NO 1
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 1
ctgcaggtcg tccgactatt c                                                   21

<210> SEQ ID NO 2
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 2
agtgagcctc ctgttgcagg                                                     20
```

```
<210> SEQ ID NO 3
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 3
tcaagtccat tccgaccagc                                              20

<210> SEQ ID NO 4
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 4
aagaaggcca gcgatgtcaa                                              20
```

ERR MODULATORS AND USES THEREOF

CROSS-REFERENCES TO RELATED APPLICATIONS

This application claims the benefit of U.S. Provisional Application No. 62/484,600, filed Apr. 12, 2017, which is incorporated herein by reference in entirety and for all purposes.

BACKGROUND

The Sequence Listing written in file 048440-645001US Sequence Listing_ST25.TXT, created Apr. 11, 2018, 1,051 bytes, machine format IBM-PC, MS-Windows operating system, is hereby incorporated herein by reference in its entirety and for all purposes.

Metabolic diseases, including obesity, diabetes, atherosclerosis and obesity-related cancers, are the leading cause of mortality in industrialized nations. It is estimated that over one-third of the United States population is obese, and these individuals are at greater risk for developing diabetes, cancer and cardiovascular disease. Orphan members of the nuclear receptor superfamily, which have no identified endogenous ligand, are involved in regulation of many aspects of cellular metabolism including mitochondrial energetics as well as cholesterol, bile acid and glucose metabolism. Estrogen-related receptors (ERRs) play an important role in the transcriptional control of metabolic genes involved in the generation and utilization of cellular energy. No endogenous ligand has been identified for any of the ERR isoforms to date. Disclosed herein, inter alia, are solutions to these and other problems in the art.

SUMMARY

In an aspect is provided a method of treating non-alcoholic fatty liver disease or non-alcoholic steatohepatitis, the method including administering to a subject in need thereof an effective amount of a compound having the formula:

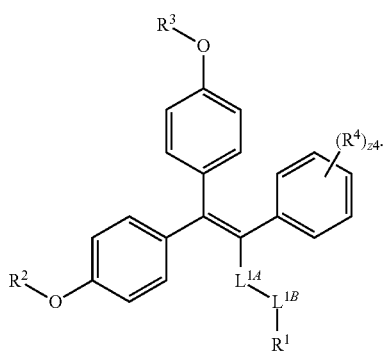

(I)

$L^{1A}$ is a bond, substituted or unsubstituted alkylene, or substituted or unsubstituted heteroalkylene; $L^{1B}$ is a bond, —C(O)O—, —OC(O)—, —O—, —C(O)—, —NH—, —NHC(O)—, or —C(O)NH—; $R^1$ is independently hydrogen, halogen, —$CX^1_3$, —$CHX^1_2$, —$CH_2X^1$, —$OCX^1_3$, —$OCH_2X^1$, —$OCHX^1_2$, —CN, —$SO_{n1}R^{1D}$, —$SO_{v1}NR^{1A}R^{1B}$, —$NHC(O)NR^{1A}R^{1B}$, —$N(O)_{m1}$, —$NR^{1A}R^{1B}$, —$C(O)R^{1C}$, —C(O)—$OR^{1C}$, —C(O)$NR^{1A}R^{1B}$, —$OR^{1D}$, —$NR^{1A}SO_2R^{1D}$, —$NR^{1A}C(O)R^{1C}$, —$NR^{1A}C(O)OR^{1C}$, —$NR^{1A}OR^{1C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^2$ is independently hydrogen, —$CX^2_3$, —$CHX^2_2$, —$CH_2X^2$, —$C(O)R^{2A}$, —$C(O)OR^{2A}$, —$C(O)NR^{2A}R^{2B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^3$ is independently hydrogen, —$CX^3_3$, —$CHX^3_2$, —$CH_2X^3$, —$C(O)R^{3A}$, —$C(O)OR^{3A}$, —$C(O)NR^{3A}R^{3B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^4$ is independently halogen, —$CX^4_3$, —$CHX^4_2$, —$CH_2X^4$, —$OCX^4_3$, —$OCH_2X^4$, —$OCHX^4_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=$(O)NHNH_2$, —NHC=$(O)NH_2$, —$NHSO_2H$, —NHC=$(O)H$, —NHC(O)—OH, —NHOH, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; z4 is an integer from 0 to 5; each $R^{1A}$, $R^{1B}$, $R^{1C}$, $R^{1D}$, $R^{2A}$, $R^{2B}$, $R^{3A}$, and $R^{3B}$ is independently hydrogen, —$CX_3$, —CN, —COOH, —$CONH_2$, —$CHX_2$, —$CH_2X$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{1A}$ and $R^{1B}$ substituents bonded to the same nitrogen atom may optionally be joined to form a substituted or unsubstituted heterocycloalkyl or substituted or unsubstituted heteroaryl; $R^{2A}$ and $R^{2B}$ substituents bonded to the same nitrogen atom may optionally be joined to form a substituted or unsubstituted heterocycloalkyl or substituted or unsubstituted heteroaryl; $R^{3A}$ and $R^{3B}$ substituents bonded to the same nitrogen atom may optionally be joined to form a substituted or unsubstituted heterocycloalkyl or substituted or unsubstituted heteroaryl; each X, $X^1$, $X^2$, $X^3$, and $X^4$ is independently —F, —Cl, —Br, or —I; n1 is an integer from 0 to 4; and m1 and v1 are independently an integer from 1 to 2.

In an aspect is provided a compound having the formula:

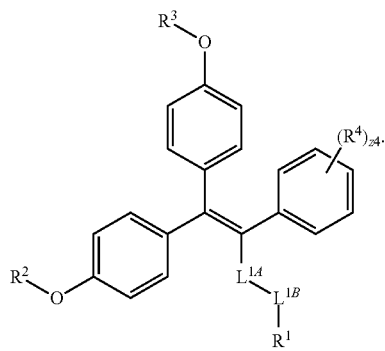

(I)

$L^{1A}$ is substituted or unsubstituted $C_1$-$C_6$ alkylene; $L^{1B}$ is —C(O)O—; $R^1$ is hydrogen or substituted or unsubstituted $C_1$-$C_6$ alkyl; $R^2$ is independently hydrogen, —$CX^2_3$, —$CHX^2_2$, —$CH_2X^2$, —$C(O)R^{2A}$, —$C(O)OR^{2A}$, —$C(O)NR^{2A}R^{2B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^3$ is independently hydrogen, —$CX^3_3$, —$CHX^3_2$, —$CH_2X^3$, —$C(O)R^{3A}$, —$C(O)OR^{3A}$, —$C(O)NR^{3A}R^{3B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^4$ is independently halogen, —$CX^4_3$, —$CHX^4_2$, —$CH_2X^4$, —$OCX^4_3$, —$OCH_2X^4$, —$OCHX^4_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC=(O)H, —NHC(O)—OH, —NHOH, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; z4 is an integer from 0 to 5; Each $R^{2A}$, $R^{2B}$, $R^{3A}$, and $R^{3B}$ is independently hydrogen, —$CX_3$, —CN, —COOH, —$CONH_2$, —$CHX_2$, —$CH_2X$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{2A}$ and $R^{2B}$ substituents bonded to the same nitrogen atom may optionally be joined to form a substituted or unsubstituted heterocycloalkyl or substituted or unsubstituted heteroaryl; $R^{3A}$ and $R^{3B}$ substituents bonded to the same nitrogen atom may optionally be joined to form a substituted or unsubstituted heterocycloalkyl or substituted or unsubstituted heteroaryl; and each X, $X^2$, $X^3$, and $X^4$ is independently —F, —Cl, —Br, or —I.

In an aspect is provided a pharmaceutical composition including a compound described herein and a pharmaceutically acceptable excipient.

In an aspect is provided a method of inhibiting estrogen-related receptor β activity, the method including contacting the estrogen-related receptor β with a compound described herein.

BRIEF DESCRIPTION OF THE DRAWINGS

FIG. 7A. 293 HEK cells expressing either GFP or ERRγ via adenoviral transduction were treated with either vehicle (DMSO) or 100 nM DY40 for 48 hours. Expression of endogenous SHP (NR0B2) was quantitated by real-time PCR. Values are normalized to β-actin transcript and reported relative to GFP untreated levels (=1.0). Data represent mean±S.E.M. for 3 independent trials. FIG. 7B. C2C12 myotubes were treated with either vehicle or 100 nM DY40 for 48 hours. Expression of endogenous SHP was measured by quantitative real-time PCR. Values are normalized to 36b4 (Rp1p0) transcript and reported relative to expression in DMSO treated cells (=1.0). Data represent mean±S.E.M. for 3 independent trials. *, P<0.05 DMSO versus DY40 treated values. FIG. 7C. C2C12 myotubes were treated with either vehicle or 100 nM DY40 for 48 hours. Oxidation of $^3$H-palmitate-BSA was measured as described in Methods. Values are normalized to total cellular protein and reported relative to expression in DMSO treated cells (=1.0). Data represent mean±S.E.M. for 4 independent trials. * P<0.001 DMSO versus DY40 treatment.

FIG. 8A. Docking model of DY181 (3h) (shown as sticks) binding with ERRγ protein. The X-ray crystal structure of compound GSK5182 (PDB code 2EWP) is also overlapped as grey sticks for comparison. It can be seen that DY181 (3h) takes the same binding pocket and similar binding pose as GSK5182. FIG. 8B. Two hydrogen bonds (shown as dots in ligand-protein interaction diagram) are formed between DY181 (3h) and D273/E275 residues in ERRγ. FIG. 8C. Three hydrogen bonds (shown as dots) are formed between DY181 (3h) and D248/E250/Y321 residues in homology model of ERRβ protein

DETAILED DESCRIPTION

I. Definitions

Figure 1:
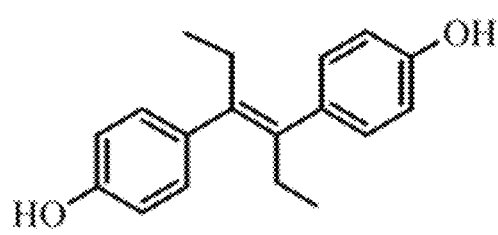
FIG. 1. Chemical structures of $E_2$ (the main physiologically relevant estrogen) and three ERRγ and ERRβ synthetic inverse agonists.
Figure 1:
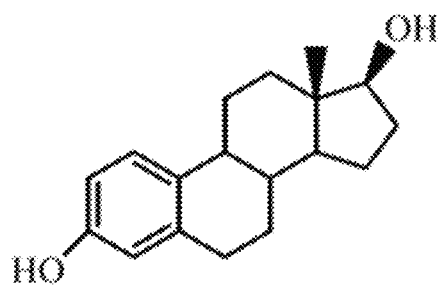
Figure 1:
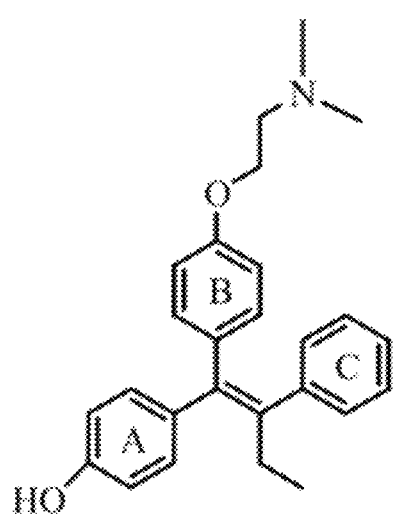
Figure 1:
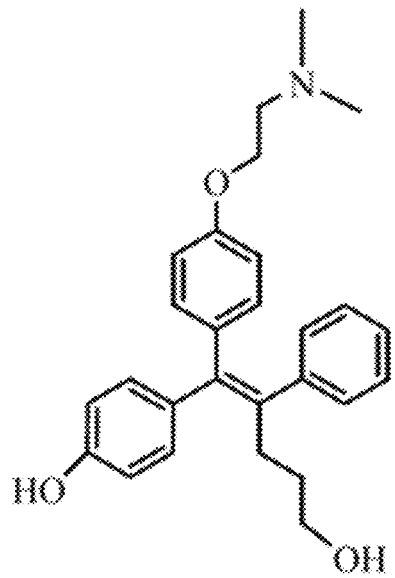

The abbreviations used herein have their conventional meaning within the chemical and biological arts. The chemical structures and formulae set forth herein are constructed according to the standard rules of chemical valency known in the chemical arts.

Where substituent groups are specified by their conventional chemical formulae, written from left to right, they equally encompass the chemically identical substituents that would result from writing the structure from right to left, e.g., —$CH_2O$— is equivalent to —$OCH_2$—.

The term "alkyl," by itself or as part of another substituent, means, unless otherwise stated, a straight (i.e., unbranched) or branched carbon chain (or carbon), or combination thereof, which may be fully saturated, mono- or polyunsaturated and can include mono-, di- and multivalent radicals, having the number of carbon atoms designated (i.e., $C_1$-$C_{10}$ means one to ten carbons). Alkyl is an uncyclized chain. Examples of saturated hydrocarbon radicals include, but are not limited to, groups such as methyl, ethyl, n-propyl, isopropyl, n-butyl, t-butyl, isobutyl, sec-butyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. An alkoxy is an alkyl attached to the remainder of the molecule via an oxygen linker (—O—).

The term "alkylene," by itself or as part of another substituent, means, unless otherwise stated, a divalent radical derived from an alkyl, as exemplified, but not limited by, —CH$_2$CH$_2$CH$_2$CH$_2$—. Typically, an alkyl (or alkylene) group will have from 1 to 24 carbon atoms, with those groups having 10 or fewer carbon atoms being preferred herein. A "lower alkyl" or "lower alkylene" is a shorter chain alkyl or alkylene group, generally having eight or fewer carbon atoms. The term "alkenylene," by itself or as part of another substituent, means, unless otherwise stated, a divalent radical derived from an alkene.

The term "heteroalkyl," by itself or in combination with another term, means, unless otherwise stated, a stable straight or branched chain, or combinations thereof, including at least one carbon atom and at least one heteroatom (e.g., O, N, P, S, B, As, or Si), and wherein the nitrogen and sulfur atoms may optionally be oxidized, and the nitrogen heteroatom may optionally be quaternized. The heteroatom (s) (e.g., O, N, P, S, B, As, or Si) may be placed at any interior position of the heteroalkyl group or at the position at which the alkyl group is attached to the remainder of the molecule. Heteroalkyl is an uncyclized chain. Examples include, but are not limited to: —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$, —S(O)—CH$_3$, —CH$_2$—CH$_2$—S(O)$_2$—CH$_3$, —CH=CH—O—CH$_3$, —Si(CH$_3$)$_3$, —CH$_2$—CH=N—OCH$_3$, —CH=CH—N(CH$_3$)—CH$_3$, —O—CH$_3$, —O—CH$_2$—CH$_3$, and —CN. Up to two or three heteroatoms may be consecutive, such as, for example, —CH$_2$—NH—OCH$_3$ and —CH$_2$—O—Si(CH$_3$)$_3$. A heteroalkyl moiety may include one heteroatom (e.g., O, N, P, S, B, As, or Si). A heteroalkyl moiety may include two optionally different heteroatoms (e.g., O, N, P, S, B, As, or Si). A heteroalkyl moiety may include three optionally different heteroatoms (e.g., O, N, P, S, B, As, or Si). A heteroalkyl moiety may include four optionally different heteroatoms (e.g., O, N, P, S, B, As, or Si). A heteroalkyl moiety may include five optionally different heteroatoms (e.g., O, N, P, S, B, As, or Si). A heteroalkyl moiety may include up to 8 optionally different heteroatoms (e.g., O, N, P, S, B, As, or Si).

Similarly, the term "heteroalkylene," by itself or as part of another substituent, means, unless otherwise stated, a divalent radical derived from heteroalkyl, as exemplified, but not limited by, —CH$_2$—CH$_2$—S—CH$_2$—CH$_2$— and —CH$_2$—S—CH$_2$—CH$_2$—NH—CH$_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—. As described above, heteroalkyl groups, as used herein, include those groups that are attached to the remainder of the molecule through a heteroatom, such as —C(O)R', —C(O)NR', —NR'R", —OR', —SR', and/or —SO$_2$R'. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

The terms "cycloalkyl" and "heterocycloalkyl," by themselves or in combination with other terms, mean, unless otherwise stated, cyclic versions of "alkyl" and "heteroalkyl," respectively. Cycloalkyl and heterocycloalkyl are not aromatic. Additionally, for heterocycloalkyl, a heteroatom can occupy the position at which the heterocycle is attached to the remainder of the molecule. Examples of cycloalkyl include, but are not limited to, cyclopropyl, cyclobutyl, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. A "cycloalkylene" and a "heterocycloalkylene," alone or as part of another substituent, means a divalent radical derived from a cycloalkyl and heterocycloalkyl, respectively.

The terms "halo" or "halogen," by themselves or as part of another substituent, mean, unless otherwise stated, a fluorine, chlorine, bromine, or iodine atom. Additionally, terms such as "haloalkyl" are meant to include monohaloalkyl and polyhaloalkyl. For example, the term "halo(C$_1$-C$_4$)alkyl" includes, but is not limited to, fluoromethyl, difluoromethyl, trifluoromethyl, 2,2,2-trifluoroethyl, 4-chlorobutyl, 3-bromopropyl, and the like.

The term "acyl" means, unless otherwise stated, —C(O)R where R is a substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl.

The term "aryl" means, unless otherwise stated, a polyunsaturated, aromatic, hydrocarbon substituent, which can be a single ring or multiple rings (preferably from 1 to 3 rings) that are fused together (i.e., a fused ring aryl) or linked covalently. A fused ring aryl refers to multiple rings fused together wherein at least one of the fused rings is an aryl ring. The term "heteroaryl" refers to aryl groups (or rings) that contain at least one heteroatom such as N, O, or S, wherein the nitrogen and sulfur atoms are optionally oxidized, and the nitrogen atom(s) are optionally quaternized. Thus, the term "heteroaryl" includes fused ring heteroaryl groups (i.e., multiple rings fused together wherein at least one of the fused rings is a heteroaromatic ring). A 5,6-fused ring heteroarylene refers to two rings fused together, wherein one ring has 5 members and the other ring has 6 members, and wherein at least one ring is a heteroaryl ring. Likewise, a 6,6-fused ring heteroarylene refers to two rings fused together, wherein one ring has 6 members and the other ring has 6 members, and wherein at least one ring is a heteroaryl ring. And a 6,5-fused ring heteroarylene refers to two rings fused together, wherein one ring has 6 members and the other ring has 5 members, and wherein at least one ring is a heteroaryl ring. A heteroaryl group can be attached to the remainder of the molecule through a carbon or heteroatom. Non-limiting examples of aryl and heteroaryl groups include phenyl, naphthyl, pyrrolyl, pyrazolyl, pyridazinyl, triazinyl, pyrimidinyl, imidazolyl, pyrazinyl, purinyl, oxazolyl, isoxazolyl, thiazolyl, furyl, thienyl, pyridyl, pyrimidyl, benzothiazolyl, benzoxazoyl benzimidazolyl, benzofuran, isobenzofuranyl, indolyl, isoindolyl, benzothiophenyl, isoquinolyl, quinoxalinyl, quinolyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. An "arylene" and a "heteroarylene," alone or as part of another substituent, mean a divalent radical derived from an aryl and heteroaryl, respectively. A heteroaryl group substituent may be —O— bonded to a ring heteroatom nitrogen.

Spirocyclic rings are two or more rings wherein adjacent rings are attached through a single atom. The individual rings within spirocyclic rings may be identical or different. Individual rings in spirocyclic rings may be substituted or unsubstituted and may have different substituents from other individual rings within a set of spirocyclic rings. Possible substituents for individual rings within spirocyclic rings are the possible substituents for the same ring when not part of spirocyclic rings (e.g. substituents for cycloalkyl or heterocycloalkyl rings). Spirocylic rings may be substituted or unsubstituted cycloalkyl, substituted or unsubstituted cycloalkylene, substituted or unsubstituted heterocycloalkyl or substituted or unsubstituted heterocycloalkylene and individual rings within a spirocyclic ring group may be any of the immediately previous list, including having all rings of one type (e.g. all rings being substituted heterocycloalkylene wherein each ring may be the same or different substituted heterocycloalkylene). When referring to a spirocyclic ring system, heterocyclic spirocyclic rings means a spirocyclic rings wherein at least one ring is a heterocyclic ring and wherein each ring may be a different ring. When referring to a spirocyclic ring system, substituted spirocyclic rings means that at least one ring is substituted and each substituent may optionally be different.

The symbol "∼∼∼" denotes the point of attachment of a chemical moiety to the remainder of a molecule or chemical formula.

The term "oxo," as used herein, means an oxygen that is double bonded to a carbon atom.

The term "alkylarylene" as an arylene moiety covalently bonded to an alkylene moiety (also referred to herein as an alkylene linker). In embodiments, the alkylarylene group has the formula:

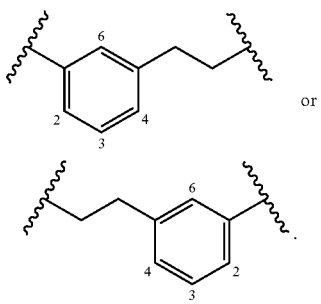

An alkylarylene moiety may be substituted (e.g. with a substituent group) on the alkylene moiety or the arylene linker (e.g. at carbons 2, 3, 4, or 6) with halogen, oxo, —N$_3$, —CF$_3$, —CCl$_3$, —CBr$_3$, —Cl$_3$, —CN, —CHO, —OH, —NH$_2$, —COOH, —CONH$_2$, —NO$_2$, —SH, —SO$_2$CH$_3$—SO$_3$H, —OSO$_3$H, —SO$_2$NH$_2$, —NHNH$_2$, —ONH$_2$, —NHC(O)NHNH$_2$, substituted or unsubstituted C$_1$-C$_5$ alkyl or substituted or unsubstituted 2 to 5 membered heteroalkyl). In embodiments, the alkylarylene is unsubstituted.

Each of the above terms (e.g., "alkyl," "heteroalkyl," "cycloalkyl," "heterocycloalkyl," "aryl," and "heteroaryl") includes both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to, oxo, —OR', =NR', =N—OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —NR'NR"R'", —ONR'R", —NR'C(O)NR"NR'"R"", —CN, —NO$_2$, —NR'SO$_2$R", —NR'C(O)R", —NR'C(O)—OR", —NR'OR", in a number ranging from zero to (2m'+1), where m' is the total number of carbon atoms in such radical. R, R', R", R'", and R"" each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted heteroaryl, substituted or unsubstituted alkyl, alkoxy, or thioalkoxy groups, or arylalkyl groups. When a compound described herein includes more than one R group, for example, each of the R groups is independently selected as are each R', R", R'", and R"" group when more than one of these groups is present. When R' and R" are attached to the same nitrogen atom, they can be combined with the nitrogen atom to form a 4-, 5-, 6-, or 7-membered ring. For example, —NR'R" includes, but is not limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for the alkyl radical, substituents for the aryl and heteroaryl groups are varied and are selected from, for example: —OR', —NR'R", —SR', -halogen, —SiR'R"R'", —OC(O)R', —C(O)R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —NR'NR"R'", —ONR'R", —NR'C(O)NR"NR'"R"", —CN, —NO$_2$, —R', —N$_3$, —CH(Ph)$_2$, fluoro(C$_1$-C$_4$)alkoxy, and fluoro(C$_1$-C$_4$)alkyl, —NR'SO$_2$R", —NR'C(O)R", —NR'C(O)—OR", —NR'OR", in a number ranging from zero to the total number of open valences on the aromatic ring system; and where R', R", R'", and R"" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. When a compound described herein includes more than one R group, for example, each of the R groups is independently selected as are each R', R", R'", and R"" groups when more than one of these groups is present.

Substituents for rings (e.g. cycloalkyl, heterocycloalkyl, aryl, heteroaryl, cycloalkylene, heterocycloalkylene, arylene, or heteroarylene) may be depicted as substituents on the ring rather than on a specific atom of a ring (commonly referred to as a floating substituent). In such a case, the substituent may be attached to any of the ring atoms (obeying the rules of chemical valency) and in the case of fused rings or spirocyclic rings, a substituent depicted as associated with one member of the fused rings or spirocyclic rings (a floating substituent on a single ring), may be a substituent on any of the fused rings or spirocyclic rings (a floating substituent on multiple rings). When a substituent is attached to a ring, but not a specific atom (a floating substituent), and a subscript for the substituent is an integer greater than one, the multiple substituents may be on the same atom, same ring, different atoms, different fused rings, different spirocyclic rings, and each substituent may optionally be different. Where a point of attachment of a ring to the remainder of a molecule is not limited to a single atom (a floating substituent), the attachment point may be any atom of the ring and in the case of a fused ring or spirocyclic ring, any atom of any of the fused rings or spirocyclic rings while obeying the rules of chemical valency. Where a ring, fused rings, or spirocyclic rings contain one or more ring heteroatoms and the ring, fused rings, or spirocyclic rings are shown with one more floating substituents (including, but not limited to, points of attachment to the remainder of the molecule), the floating substituents may be bonded to the heteroatoms. Where the ring heteroatoms are shown bound to one or more hydrogens (e.g. a ring nitrogen with two bonds to ring atoms and a third bond to a hydrogen) in the structure or formula with the floating substituent, when the heteroatom is bonded to the floating substituent, the substituent will be understood to replace the hydrogen, while obeying the rules of chemical valency.

Two or more substituents may optionally be joined to form aryl, heteroaryl, cycloalkyl, or heterocycloalkyl groups. Such so-called ring-forming substituents are typically, though not necessarily, found attached to a cyclic base structure. In one embodiment, the ring-forming substituents are attached to adjacent members of the base structure. For example, two ring-forming substituents attached to adjacent members of a cyclic base structure create a fused ring structure. In another embodiment, the ring-forming substituents are attached to a single member of the base structure. For example, two ring-forming substituents attached to a single member of a cyclic base structure create a spirocyclic structure. In yet another embodiment, the ring-forming substituents are attached to non-adjacent members of the base structure.

Two of the substituents on adjacent atoms of the aryl or heteroaryl ring may optionally form a ring of the formula -T-C(O)—(CRR')$_q$—U—, wherein T and U are independently —NR—, —O—, —CRR'—, or a single bond, and q is an integer of from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'—, or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X'—(C"R"R'")$_d$—, where s and d are independently integers of from 0 to 3, and X' is —O—, —S—, —S(O)—, —S(O)$_2$—, or —S(O)$_2$NR'—. The substituents R, R', R", and R'" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

As used herein, the terms "heteroatom" or "ring heteroatom" are meant to include oxygen (O), nitrogen (N), sulfur (S), phosphorus (P), and silicon (Si).

A "substituent group," as used herein, means a group selected from the following moieties:

(A) oxo,
halogen, —CCl$_3$, —CBr$_3$, —CF$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, unsubstituted alkyl (e.g., C$_1$-C$_8$ alkyl, C$_1$-C$_6$ alkyl, or C$_1$-C$_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., C$_3$-C$_8$ cycloalkyl, C$_3$-C$_6$ cycloalkyl, or C$_5$-C$_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., C$_6$-C$_{10}$ aryl, C$_{10}$ aryl, or phenyl), or unsubstituted heteroaryl (e.g., 5 to 10 membered heteroaryl, 5 to 9 membered heteroaryl, or 5 to 6 membered heteroaryl), and (B) alkyl, heteroalkyl, cycloalkyl, heterocycloalkyl, aryl, heteroaryl, substituted with at least one substituent selected from:

(i) oxo,
halogen, —CCl$_3$, —CBr$_3$, —CF$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, unsubstituted alkyl (e.g., C$_1$-C$_8$ alkyl, C$_1$-C$_6$ alkyl, or C$_1$-C$_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., C$_3$-C$_8$ cycloalkyl, C$_3$-C$_6$ cycloalkyl, or C$_5$-C$_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., C$_6$-C$_{10}$ aryl, C$_{10}$ aryl, or phenyl), or unsubstituted heteroaryl (e.g., 5 to 10 membered heteroaryl, 5 to 9 membered heteroaryl, or 5 to 6 membered heteroaryl), and (ii) alkyl, heteroalkyl, cycloalkyl, heterocycloalkyl, aryl, heteroaryl, substituted with at least one substituent selected from:

(a) oxo,
halogen, —CCl$_3$, —CBr$_3$, —CF$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCH Cl$_2$, —OCHBr$_2$, —OCHI$_2$, —OCHF$_2$, unsubstituted alkyl (e.g., C$_1$-C$_8$ alkyl, C$_1$-C$_6$ alkyl, or C$_1$-C$_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., C$_3$-C$_8$ cycloalkyl, C$_3$-C$_6$ cycloalkyl, or C$_5$-C$_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl), and (b) alkyl, heteroalkyl, cycloalkyl, heterocycloalkyl, aryl, heteroaryl, substituted with at least one substituent selected from: oxo,
halogen, —$CCl_3$, —$CBr_3$, —$CF_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl).

A "size-limited substituent" or "size-limited substituent group," as used herein, means a group selected from all of the substituents described above for a "substituent group," wherein each substituted or unsubstituted alkyl is a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, each substituted or unsubstituted heterocycloalkyl is a substituted or unsubstituted 3 to 8 membered heterocycloalkyl, each substituted or unsubstituted aryl is a substituted or unsubstituted $C_6$-$C_{10}$ aryl, and each substituted or unsubstituted heteroaryl is a substituted or unsubstituted 5 to 10 membered heteroaryl.

A "lower substituent" or "lower substituent group," as used herein, means a group selected from all of the substituents described above for a "substituent group," wherein each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted $C_6$-$C_{10}$ aryl, and each substituted or unsubstituted heteroaryl is a substituted or unsubstituted 5 to 9 membered heteroaryl.

In some embodiments, each substituted group described in the compounds herein is substituted with at least one substituent group. More specifically, in some embodiments, each substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene described in the compounds herein are substituted with at least one substituent group. In other embodiments, at least one or all of these groups are substituted with at least one size-limited substituent group. In other embodiments, at least one or all of these groups are substituted with at least one lower substituent group.

In other embodiments of the compounds herein, each substituted or unsubstituted alkyl may be a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, each substituted or unsubstituted heterocycloalkyl is a substituted or unsubstituted 3 to 8 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 10 membered heteroaryl. In some embodiments of the compounds herein, each substituted or unsubstituted alkylene is a substituted or unsubstituted $C_1$-$C_{20}$ alkylene, each substituted or unsubstituted heteroalkylene is a substituted or unsubstituted 2 to 20 membered heteroalkylene, each substituted or unsubstituted cycloalkylene is a substituted or unsubstituted $C_3$-$C_8$ cycloalkylene, each substituted or unsubstituted heterocycloalkylene is a substituted or unsubstituted 3 to 8 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 10 membered heteroarylene.

In some embodiments, each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 9 membered heteroaryl. In some embodiments, each substituted or unsubstituted alkylene is a substituted or unsubstituted $C_1$-$C_8$ alkylene, each substituted or unsubstituted heteroalkylene is a substituted or unsubstituted 2 to 8 membered heteroalkylene, each substituted or unsubstituted cycloalkylene is a substituted or unsubstituted $C_3$-$C_7$ cycloalkylene, each substituted or unsubstituted heterocycloalkylene is a substituted or unsubstituted 3 to 7 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 9 membered heteroarylene. In some embodiments, the compound is a chemical species set forth in the Examples section, figures, or tables below.

In embodiments, a substituted or unsubstituted moiety (e.g., substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, substituted or unsubstituted alkylene, substituted or unsubstituted heteroalkylene, substituted or unsubstituted cycloalkylene, substituted or unsubstituted heterocycloalkylene, substituted or unsubstituted arylene, and/or substituted or unsubstituted heteroarylene) is unsubstituted (e.g., is an unsubstituted alkyl, unsubstituted heteroalkyl, unsubstituted cycloalkyl, unsubstituted heterocycloalkyl, unsubstituted aryl, unsubstituted heteroaryl, unsubstituted alkylene, unsubstituted heteroalkylene, unsubstituted cycloalkylene, unsubstituted heterocycloalkylene, unsubstituted arylene, and/or unsubstituted heteroarylene, respectively). In embodiments, a substituted or unsubstituted moiety (e.g., substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, substituted or unsubstituted alkylene, substituted or unsubstituted heteroalkylene, substituted or unsubstituted cycloalkylene, substituted or unsubstituted heterocycloalkylene, substituted or unsubstituted arylene, and/or substituted or unsubstituted heteroarylene) is substituted (e.g., is a substituted alkyl, substituted heteroalkyl, substituted cycloalkyl, substituted heterocycloalkyl, substituted aryl, substituted heteroaryl, substituted alkyl ene, substituted heteroalkylene, substituted cycloalkylene, substituted heterocycloalkylene, substituted arylene, and/or substituted heteroarylene, respectively).

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one substituent group, wherein if the substituted moiety is substituted with a plurality of substituent groups, each substituent group may optionally be different. In embodiments, if the substituted moiety is substituted with a plurality of substituent groups, each substituent group is different.

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one size-limited substituent group, wherein if the substituted moiety is substituted with a plurality of size-limited substituent groups, each size-limited substituent group may optionally be different. In embodiments, if the substituted moiety is substituted with a plurality of size-limited substituent groups, each size-limited substituent group is different.

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one lower substituent group, wherein if the substituted moiety is substituted with a plurality of lower substituent groups, each lower substituent group may optionally be different. In embodiments, if the substituted moiety is substituted with a plurality of lower substituent groups, each lower substituent group is different.

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one substituent group, size-limited substituent group, or lower substituent group; wherein if the substituted moiety is substituted with a plurality of groups selected from substituent groups, size-limited substituent groups, and lower substituent groups; each substituent group, size-limited substituent group, and/or lower substituent group may optionally be different. In embodiments, if the substituted moiety is substituted with a plurality of groups selected from substituent groups, size-limited substituent groups, and lower substituent groups; each substituent group, size-limited substituent group, and/or lower substituent group is different.

Certain compounds of the present invention possess asymmetric carbon atoms (optical or chiral centers) or double bonds; the enantiomers, racemates, diastereomers, tautomers, geometric isomers, stereoisometric forms that may be defined, in terms of absolute stereochemistry, as (R)- or (S)- or, as (D)- or (L)- for amino acids, and individual isomers are encompassed within the scope of the present invention. The compounds of the present invention do not include those that are known in art to be too unstable to synthesize and/or isolate. The present invention is meant to include compounds in racemic and optically pure forms. Optically active (R)- and (S)-, or (D)- and (L)-isomers may be prepared using chiral synthons or chiral reagents, or resolved using conventional techniques. When the compounds described herein contain olefinic bonds or other centers of geometric asymmetry, and unless specified otherwise, it is intended that the compounds include both E and Z geometric isomers.

As used herein, the term "isomers" refers to compounds having the same number and kind of atoms, and hence the same molecular weight, but differing in respect to the structural arrangement or configuration of the atoms.

The term "tautomer," as used herein, refers to one of two or more structural isomers which exist in equilibrium and which are readily converted from one isomeric form to another.

It will be apparent to one skilled in the art that certain compounds of this invention may exist in tautomeric forms, all such tautomeric forms of the compounds being within the scope of the invention.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the invention.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}$C- or $^{14}$C-enriched carbon are within the scope of this invention.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}$C- or $^{14}$C-enriched carbon are within the scope of this invention.

The compounds of the present invention may also contain unnatural proportions of atomic isotopes at one or more of the atoms that constitute such compounds. For example, the compounds may be radiolabeled with radioactive isotopes, such as for example tritium ($^{3}$H), iodine-125 ($^{125}$I) or carbon-14 ($^{14}$C). All isotopic variations of the compounds of the present invention, whether radioactive or not, are encompassed within the scope of the present invention.

It should be noted that throughout the application that alternatives are written in Markush groups, for example, each amino acid position that contains more than one possible amino acid. It is specifically contemplated that each member of the Markush group should be considered separately, thereby comprising another embodiment, and the Markush group is not to be read as a single unit.

"Analog," or "analogue" is used in accordance with its plain ordinary meaning within Chemistry and Biology and refers to a chemical compound that is structurally similar to another compound (i.e., a so-called "reference" compound) but differs in composition, e.g., in the replacement of one atom by an atom of a different element, or in the presence of a particular functional group, or the replacement of one functional group by another functional group, or the absolute stereochemistry of one or more chiral centers of the reference compound. Accordingly, an analog is a compound that is similar or comparable in function and appearance but not in structure or origin to a reference compound.

The terms "a" or "an," as used in herein means one or more. In addition, the phrase "substituted with a[n]," as used herein, means the specified group may be substituted with one or more of any or all of the named substituents. For example, where a group, such as an alkyl or heteroaryl group, is "substituted with an unsubstituted $C_1$-$C_{20}$ alkyl, or unsubstituted 2 to 20 membered heteroalkyl," the group may contain one or more unsubstituted $C_1$-$C_{20}$ alkyls, and/or one or more unsubstituted 2 to 20 membered heteroalkyls.

Moreover, where a moiety is substituted with an R substituent, the group may be referred to as "R-substituted." Where a moiety is R-substituted, the moiety is substituted with at least one R substituent and each R substituent is optionally different. Where a particular R group is present in the description of a chemical genus (such as Formula (I)), a Roman alphabetic symbol may be used to distinguish each appearance of that particular R group. For example, where multiple $R^{13}$ substituents are present, each $R^{13}$ substituent may be distinguished as $R^{13A}$, $R^{13B}$, $R^{13C}$, $R^{13D}$, etc., wherein each of $R^{13A}$, $R^{13B}$, $R^{13C}$, $R^{13D}$, etc. is defined within the scope of the definition of $R^3$ and optionally differently.

Description of compounds of the present invention are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

The term "pharmaceutically acceptable salts" is meant to include salts of the active compounds that are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, oxalic, methanesulfonic, and the like. Also included are salts of amino acids such as arginate and the like, and salts of organic acids like glucuronic or galactunoric acids and the like (see, for example, Berge et al., "Pharmaceutical Salts", *Journal of Pharmaceutical Science,* 1977, 66, 1-19). Certain specific compounds of the present invention contain both basic and acidic functionalities that allow the compounds to be converted into either base or acid addition salts.

Thus, the compounds of the present invention may exist as salts, such as with pharmaceutically acceptable acids. The present invention includes such salts. Non-limiting examples of such salts include hydrochlorides, hydrobromides, phosphates, sulfates, methanesulfonates, nitrates, maleates, acetates, citrates, fumarates, propionates, tartrates (e.g., (+)-tartrates, (−)-tartrates, or mixtures thereof including racemic mixtures), succinates, benzoates, and salts with amino acids such as glutamic acid, and quaternary ammonium salts (e.g. methyl iodide, ethyl iodide, and the like). These salts may be prepared by methods known to those skilled in the art.

The neutral forms of the compounds are preferably regenerated by contacting the salt with a base or acid and isolating the parent compound in the conventional manner. The parent form of the compound may differ from the various salt forms in certain physical properties, such as solubility in polar solvents.

In addition to salt forms, the present invention provides compounds, which are in a prodrug form. Prodrugs of the compounds described herein are those compounds that readily undergo chemical changes under physiological conditions to provide the compounds of the present invention. Prodrugs of the compounds described herein may be converted in vivo after administration. Additionally, prodrugs can be converted to the compounds of the present invention by chemical or biochemical methods in an ex vivo environment, such as, for example, when contacted with a suitable enzyme or chemical reagent.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

"Pharmaceutically acceptable excipient" and "pharmaceutically acceptable carrier" refer to a substance that aids the administration of an active agent to and absorption by a subject and can be included in the compositions of the present invention without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethycellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the invention. One of skill in the art will recognize that other pharmaceutical excipients are useful in the present invention.

The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

The terms "polypeptide," "peptide" and "protein" are used interchangeably herein to refer to a polymer of amino acid residues, wherein the polymer may optionally be conjugated to a moiety that does not consist of amino acids. The terms apply to amino acid polymers in which one or more amino acid residue is an artificial chemical mimetic of a corresponding naturally occurring amino acid, as well as to naturally occurring amino acid polymers and non-naturally occurring amino acid polymer.

A polypeptide, or a cell is "recombinant" when it is artificial or engineered, or derived from or contains an artificial or engineered protein or nucleic acid (e.g. non-natural or not wild type). For example, a polynucleotide that is inserted into a vector or any other heterologous location, e.g., in a genome of a recombinant organism, such that it is not associated with nucleotide sequences that normally flank the polynucleotide as it is found in nature is a recombinant polynucleotide. A protein expressed in vitro or in vivo from a recombinant polynucleotide is an example of a recombinant polypeptide. Likewise, a polynucleotide sequence that does not appear in nature, for example a variant of a naturally occurring gene, is recombinant.

An amino acid residue in a protein "corresponds" to a given residue when it occupies the same essential structural position within the protein as the given residue. For example, a selected residue in a selected protein corresponds to Y321 of human estrogen-related receptor when the selected residue occupies the same essential spatial or other structural relationship as Y321 in human estrogen-related receptor β. In some embodiments, where a selected protein is aligned for maximum homology with the human estrogen-related receptor β, the position in the aligned selected protein aligning with Y321 is said to correspond to Y321. Instead of a primary sequence alignment, a three dimensional structural alignment can also be used, e.g., where the structure of the selected protein is aligned for maximum correspondence with the human estrogen-related receptor β protein and the overall structures compared. In this case, an amino acid that occupies the same essential position as Y321 in the structural model is said to correspond to the Y321 residue.

"Contacting" is used in accordance with its plain ordinary meaning and refers to the process of allowing at least two distinct species (e.g. chemical compounds including biomolecules or cells) to become sufficiently proximal to react, interact or physically touch. It should be appreciated; however, the resulting reaction product can be produced directly from a reaction between the added reagents or from an intermediate from one or more of the added reagents that can be produced in the reaction mixture.

The term "contacting" may include allowing two species to react, interact, or physically touch, wherein the two species may be a compound as described herein and a protein or enzyme. In some embodiments contacting includes allowing a compound described herein to interact with a protein or enzyme that is involved in a signaling pathway.

As defined herein, the term "activation", "activate", "activating" and the like in reference to a protein refers to conversion of a protein into a biologically active derivative from an initial inactive or deactivated state. The terms reference activation, or activating, sensitizing, or up-regulating signal transduction or enzymatic activity or the amount of a protein decreased in a disease.

As defined herein, the term "inhibition", "inhibit", "inhibiting" and the like in reference to a protein-inhibitor interaction means negatively affecting (e.g. decreasing) the activity or function of the protein relative to the activity or function of the protein in the absence of the inhibitor. In embodiments inhibition means negatively affecting (e.g. decreasing) the concentration or levels of the protein relative to the concentration or level of the protein in the absence of the inhibitor. In embodiments inhibition refers to reduction of a disease or symptoms of disease. In embodiments, inhibition refers to a reduction in the activity of a particular protein target. Thus, inhibition includes, at least in part, partially or totally blocking stimulation, decreasing, preventing, or delaying activation, or inactivating, desensitizing, or down-regulating signal transduction or enzymatic activity or the amount of a protein. In embodiments, inhibition refers to a reduction of activity of a target protein resulting from a direct interaction (e.g. an inhibitor binds to the target protein). In embodiments, inhibition refers to a reduction of activity of a target protein from an indirect interaction (e.g. an inhibitor binds to a protein that activates the target protein, thereby preventing target protein activation).

The terms "estrogen-related receptor γ" and "estrogen related receptor γ" and "estrogen related receptor gamma" and "estrogen-related receptor gamma" and "ESRRG" refer to a protein (including homologs, isoforms, and functional fragments thereof) with estrogen related receptor gamma activity. The term includes any recombinant or naturally-occurring form of estrogen-related receptor γ or variants thereof that maintain estrogen-related receptor γ activity (e.g. within at least 30%, 40%, 50%, 60%, 70%, 80%, 90%, 95%, or 100% activity compared to wild type estrogen-related receptor γ). In embodiments, the estrogen-related receptor γ protein encoded by the ESRRG gene has the amino acid sequence set forth in or corresponding to Entrez 2104, UniProt P62508, or RefSeq (protein) NP_001429. In embodiments, the estrogen-related receptor γ gene has the nucleic acid sequence set forth in RefSeq (mRNA) NM_001438. In embodiments, the amino acid sequence or nucleic acid sequence is the sequence known at the time of filing of the present application. In embodiments, the sequence corresponds to NP_001429.2. In embodiments, the sequence corresponds to NM_001438.3. In embodiments, the estrogen-related receptor γ is a human estrogen-related receptor γ.

The terms "estrogen-related receptor β" and "estrogen related receptor β" and "estrogen related receptor beta" and "estrogen-related receptor beta" and "ESRRB" refer to a protein (including homologs, isoforms, and functional fragments thereof) with estrogen related receptor beta activity. The term includes any recombinant or naturally-occurring form of estrogen-related receptor β or variants thereof that maintain estrogen-related receptor β activity (e.g. within at least 30%, 40%, 50%, 60%, 70%, 80%, 90%, 95%, or 100% activity compared to wild type estrogen-related receptor β). In embodiments, the estrogen-related receptor β protein encoded by the ESRRB gene has the amino acid sequence set forth in or corresponding to Entrez 2103, UniProt O95718, or RefSeq (protein) NP_004443. In embodiments, the estrogen-related receptor β gene has the nucleic acid sequence set forth in RefSeq (mRNA) NM_004452. In embodiments, the amino acid sequence or nucleic acid sequence is the sequence known at the time of filing of the present application. In embodiments, the sequence corresponds to NP_004443.3. In embodiments, the sequence corresponds to NM_004452.3. In embodiments, the estrogen-related receptor β is a human estrogen-related receptor β.

The terms "estrogen-related receptor α" and "estrogen related receptor α" and "estrogen related receptor alpha" and "estrogen-related receptor alpha" and "ESRRA" refer to a protein (including homologs, isoforms, and functional fragments thereof) with estrogen related receptor alpha activity. The term includes any recombinant or naturally-occurring form of estrogen-related receptor α or variants thereof that maintain estrogen-related receptor α activity (e.g. within at least 30%, 40%, 50%, 60%, 70%, 80%, 90%, 95%, or 100% activity compared to wild type estrogen-related receptor α). In embodiments, the estrogen-related receptor α protein encoded by the ESRRA gene has the amino acid sequence set forth in or corresponding to Entrez 2101, UniProt P11474, or RefSeq (protein) NP_004442. In embodiments, the estrogen-related receptor α gene has the nucleic acid sequence set forth in RefSeq (mRNA) NM_004451. In embodiments, the amino acid sequence or nucleic acid sequence is the sequence known at the time of filing of the present application. In embodiments, the sequence corresponds to NP_004442.3. In embodiments, the sequence corresponds to NM_004451.4. In embodiments, the estrogen-related receptor α is a human estrogen-related receptor α.

The term "expression" includes any step involved in the production of the polypeptide including, but not limited to, transcription, post-transcriptional modification, translation, posttranslational modification, and secretion. Expression can be detected using conventional techniques for detecting protein (e.g., ELISA, Western blotting, flow cytometry, immunofluorescence, immunohistochemistry, etc.).

The terms "disease" or "condition" refer to a state of being or health status of a patient or subject capable of being treated with the compounds or methods provided herein. The disease may be a cancer. The disease may be NAFLD. The disease may be NASH. The disease may be a metabolic disease. The disease may be diabetes. In some further instances, "cancer" refers to human cancers and carcinomas, sarcomas, adenocarcinomas, lymphomas, leukemias, etc., including solid and lymphoid cancers, kidney, breast, lung, bladder, colon, ovarian, prostate, pancreas, stomach, brain, head and neck, skin, uterine, testicular, glioma, esophagus, and liver cancer, including hepatocarcinoma, lymphoma, including B-acute lymphoblastic lymphoma, non-Hodgkin's lymphomas (e.g., Burkitt's, Small Cell, and Large Cell lymphomas), Hodgkin's lymphoma, leukemia (including AML, ALL, and CML), or multiple myeloma.

As used herein, the term "cancer" refers to all types of cancer, neoplasm or malignant tumors found in mammals (e.g. humans), including leukemia, carcinomas and sarcomas. Exemplary cancers that may be treated with a compound or method provided herein include brain cancer, glioma, glioblastoma, neuroblastoma, prostate cancer, colorectal cancer, pancreatic cancer, cervical cancer, gastric cancer, ovarian cancer, lung cancer, and cancer of the head. Exemplary cancers that may be treated with a compound or method provided herein include cancer of the thyroid, endocrine system, brain, breast, cervix, colon, head & neck, liver, kidney, lung, non-small cell lung, melanoma, mesothelioma, ovary, sarcoma, stomach, uterus, Medulloblastoma, colorectal cancer, pancreatic cancer. Additional examples include, Hodgkin's Disease, Non-Hodgkin's Lymphoma, multiple myeloma, neuroblastoma, glioma, glioblastoma multiforme, ovarian cancer, rhabdomyosarcoma, primary thrombocytosis, primary macroglobulinemia, primary brain tumors, cancer, malignant pancreatic insulanoma, malignant carcinoid, urinary bladder cancer, premalignant skin lesions, testicular cancer, lymphomas, thyroid cancer, neuroblastoma, esophageal cancer, genitourinary tract cancer, malignant hypercalcemia, endometrial cancer, adrenal cortical cancer, neoplasms of the endocrine or exocrine pancreas, medullary thyroid cancer, medullary thyroid carcinoma, melanoma, colorectal cancer, papillary thyroid cancer, hepatocellular carcinoma, or prostate cancer.

The term "leukemia" refers broadly to progressive, malignant diseases of the blood-forming organs and is generally characterized by a distorted proliferation and development of leukocytes and their precursors in the blood and bone marrow. Leukemia is generally clinically classified on the basis of (1) the duration and character of the disease-acute or chronic; (2) the type of cell involved; myeloid (myelogenous), lymphoid (lymphogenous), or monocytic; and (3) the increase or non-increase in the number abnormal cells in the blood-leukemic or aleukemic (subleukemic). Exemplary leukemias that may be treated with a compound or method provided herein include, for example, acute nonlymphocytic leukemia, chronic lymphocytic leukemia, acute granulocytic leukemia, chronic granulocytic leukemia, acute promyelocytic leukemia, adult T-cell leukemia, aleukemic leukemia, a leukocythemic leukemia, basophylic leukemia, blast cell leukemia, bovine leukemia, chronic myelocytic leukemia, leukemia cutis, embryonal leukemia, eosinophilic leukemia, Gross' leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia, micromyeloblastic leukemia, monocytic leukemia, myeloblastic leukemia, myelocytic leukemia, myeloid granulocytic leukemia, myelomonocytic leukemia, Naegeli leukemia, plasma cell leukemia, multiple myeloma, plasmacytic leukemia, promyelocytic leukemia, Rieder cell leukemia, Schilling's leukemia, stem cell leukemia, subleukemic leukemia, or undifferentiated cell leukemia.

The term "lymphoma" refers to a group of blood cancers that develop in lymphocytes, the cells of the lymph system. There are two main types of lymphoma: Hodgkin lymphoma and Non-Hodgkin lymphoma. Lymphomas that may be treated with a compound or method provided herein include classic Hodgkin lymphoma, nodular sclerosis Hodgkin lymphoma, mixed cellularity Hodgkin lymphoma, lymphocyte-rich Hodgkin lymphoma, lymphocyte-depleted Hodgkin lymphoma, nodular lymphocyte predominant Hodgkin lymphoma, B-cell lymphomas, diffuse large B-cell lymphoma (DLBCL), primary mediastinal B-cell lymphoma, follicular lymphomas, chronic lymphocytic leukemia (CLL), small lymphocytic lymphoma (SLL), mantle cell lymphoma (MCL), marginal zone lymphomas, extranodal marginal zone B-cell lymphoma (mucosa-associated lymphoid tissue (MALT) lymphoma), nodal marginal zone B-cell lymphoma, splenic marginal zone B-cell lymphoma, Burkitt lymphoma, lymphoplasmacytic lymphoma (Waldenstrom macroglobulinemia), hairy cell leukemia, primary central nervous system (CNS) lymphoma, T-cell lymphomas, precursor T-lymphoblastic lymphoma/leukemia, peripheral T-cell lymphomas, cutaneous T-cell lymphoma, adult T-cell lymphoma, angioimmunoblastic T-cell lymphoma, extranodal natural killer/T-cell lymphoma, nasal type, enteropathy-associated intestinal T-cell lymphoma, anaplastic large cell lymphoma, or peripheral T-cell lymphoma The term "sarcoma" generally refers to a tumor which is made up of a substance like the embryonic connective tissue and is generally composed of closely packed cells embedded in a fibrillar or homogeneous substance. Sarcomas that may be treated with a compound or method provided herein include a chondrosarcoma, fibrosarcoma, lymphosarcoma, melanosarcoma, myxosarcoma, osteosarcoma, Abemethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilms' tumor sarcoma, endometrial sarcoma, stromal sarcoma, Ewing's sarcoma, fascial sarcoma, fibroblastic sarcoma, giant cell sarcoma, granulocytic sarcoma, Hodgkin's sarcoma, idiopathic multiple pigmented hemorrhagic sarcoma, immunoblastic sarcoma of B cells, lymphoma, immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, or telangiectaltic sarcoma.

The term "melanoma" is taken to mean a tumor arising from the melanocytic system of the skin and other organs. Melanomas that may be treated with a compound or method provided herein include, for example, acral-lentiginous melanoma, amelanotic melanoma, benign juvenile melanoma, Cloudman's melanoma, S91 melanoma, Harding-Passey melanoma, juvenile melanoma, lentigo maligna melanoma, malignant melanoma, nodular melanoma, subungal melanoma, or superficial spreading melanoma.

The term "carcinoma" refers to a malignant new growth made up of epithelial cells tending to infiltrate the surrounding tissues and give rise to metastases. Exemplary carcinomas that may be treated with a compound or method provided herein include, for example, medullary thyroid carcinoma, familial medullary thyroid carcinoma, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma *cutaneum*, cylindrical carcinoma, cylindrical cell carcinoma, duct carcinoma, carcinoma durum, embryonal carcinoma, encephaloid carcinoma, epiermoid carcinoma, carcinoma epitheliale adenoides, exophytic carcinoma, carcinoma ex ulcere, carcinoma fibrosum, gelatiniforni carcinoma, gelatinous carcinoma, giant cell carcinoma, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypernephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma mucosum, mucous carcinoma, carcinoma myxomatodes, nasopharyngeal carcinoma, oat cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberosum, tuberous carcinoma, verrucous carcinoma, or carcinoma villosum.

The terms "non-alcoholic fatty liver disease" or "NAFLD" refers to a liver disease characterized by fat deposits in the liver, which are not primarily due to excessive alcohol use. In embodiments, NAFLD may be related to or associated with insulin resistance, metabolic syndrome, diabetes mellitus type 2, obesity, hyperlipidemia, and/or high blood pressure.

The terms "non-alcoholic steatohepatitis" or "NASH" refers to a severe form of NAFLD characterized by fat deposits in the liver, which are not primarily due to excessive alcohol use. In embodiments, NASH may be related to or associated with insulin resistance, metabolic syndrome, diabetes mellitus type 2, obesity, hyperlipidemia, and/or high blood pressure. In embodiments, NASH is characterized by swelling of the liver, liver damage, liver scarring, or liver cirrhosis. In embodiments, NASH is associated with insulin resistance. In embodiments, NASH is characterized by liver inflammation, cell death, and/or fibrosis.

The terms "metabolic disease" refers to a disorder characterized by one or more abnormal metabolic processes in a subject. In embodiments, a metabolic disorder may be associated with, related to, or may be NAFLD, NASH, diabetes, insulin resistance, metabolic syndrome, diabetes mellitus type 2, obesity, hyperlipidemia, hyperglycemia, high serum triglycerides, and/or high blood pressure.

The terms "treating", or "treatment" refers to any indicia of success in the therapy or amelioration of an injury, disease, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being. The treatment or amelioration of symptoms can be based on objective or subjective parameters; including the results of a physical examination, neuropsychiatric exams, and/or a psychiatric evaluation. The term "treating" and conjugations thereof, may include prevention of an injury, pathology, condition, or disease. In embodiments, treating is preventing. In embodiments, treating does not include preventing.

"Patient" or "subject in need thereof" refers to a living organism suffering from or prone to a disease or condition that can be treated by administration of a pharmaceutical composition as provided herein. Non-limiting examples include humans, other mammals, bovines, rats, mice, dogs, monkeys, goat, sheep, cows, deer, and other non-mammalian animals. In some embodiments, a patient is human.

A "effective amount" is an amount sufficient for a compound to accomplish a stated purpose relative to the absence of the compound (e.g. achieve the effect for which it is administered, treat a disease, reduce enzyme activity, increase enzyme activity, reduce a signaling pathway, or reduce one or more symptoms of a disease or condition). An example of an "effective amount" is an amount sufficient to contribute to the treatment, prevention, or reduction of a symptom or symptoms of a disease, which could also be referred to as a "therapeutically effective amount." A "reduction" of a symptom or symptoms (and grammatical equivalents of this phrase) means decreasing of the severity or frequency of the symptom(s), or elimination of the symptom(s). A "prophylactically effective amount" of a drug is an amount of a drug that, when administered to a subject, will have the intended prophylactic effect, e.g., preventing or delaying the onset (or reoccurrence) of an injury, disease, pathology or condition, or reducing the likelihood of the onset (or reoccurrence) of an injury, disease, pathology, or condition, or their symptoms. The full prophylactic effect does not necessarily occur by administration of one dose, and may occur only after administration of a series of doses. Thus, a prophylactically effective amount may be administered in one or more administrations. An "activity decreasing amount," as used herein, refers to an amount of antagonist required to decrease the activity of an enzyme relative to the absence of the antagonist. A "function disrupting amount," as used herein, refers to the amount of antagonist required to disrupt the function of an enzyme or protein relative to the absence of the antagonist. The exact amounts will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy*, 20th Edition, 2003, Gennaro, Ed., Lippincott, Williams & Wilkins).

For any compound described herein, the therapeutically effective amount can be initially determined from cell culture assays. Target concentrations will be those concentrations of active compound(s) that are capable of achieving the methods described herein, as measured using the methods described herein or known in the art.

As is well known in the art, therapeutically effective amounts for use in humans can also be determined from animal models. For example, a dose for humans can be formulated to achieve a concentration that has been found to be effective in animals. The dosage in humans can be adjusted by monitoring compounds effectiveness and adjusting the dosage upwards or downwards, as described above. Adjusting the dose to achieve maximal efficacy in humans based on the methods described above and other methods is well within the capabilities of the ordinarily skilled artisan.

Dosages may be varied depending upon the requirements of the patient and the compound being employed. The dose administered to a patient, in the context of the present invention should be sufficient to effect a beneficial therapeutic response in the patient over time. The size of the dose also will be determined by the existence, nature, and extent of any adverse side-effects. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached. Dosage amounts and intervals can be adjusted individually to provide levels of the administered compound effective for the particular clinical indication being treated. This will provide a therapeutic regimen that is commensurate with the severity of the individual's disease state.

As used herein, the term "administering" means oral administration, administration as a suppository, topical contact, intravenous, intraperitoneal, intramuscular, intralesional, intrathecal, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal) compatible with the preparation. Parenteral administration includes, e.g., intravenous, intramuscular, intraarteriole, intradermal, subcutaneous, intraperitoneal, intraventricular, and intracranial. Other modes of delivery include, but are not limited to, the use of liposomal formulations, intravenous infusion, transdermal patches, etc.

"Co-administer" it is meant that a composition described herein is administered at the same time, just prior to, or just after the administration of one or more additional therapies. The compounds of the invention can be administered alone or can be coadministered to the patient. Coadministration is meant to include simultaneous or sequential administration of the compounds individually or in combination (more than one compound). Thus, the preparations can also be combined, when desired, with other active substances (e.g. to reduce metabolic degradation). The compositions of the present invention can be delivered transdermally, by a topical route, or formulated as applicator sticks, solutions, suspensions, emulsions, gels, creams, ointments, pastes, jellies, paints, powders, and aerosols.

A "cell" as used herein, refers to a cell carrying out metabolic or other function sufficient to preserve or replicate its genomic DNA. A cell can be identified by well-known methods in the art including, for example, presence of an intact membrane, staining by a particular dye, ability to produce progeny or, in the case of a gamete, ability to combine with a second gamete to produce a viable offspring. Cells may include prokaryotic and eukaroytic cells. Prokaryotic cells include but are not limited to bacteria. Eukaryotic cells include but are not limited to yeast cells and cells derived from plants and animals, for example mammalian, insect (e.g., *spodoptera*) and human cells. Cells may be useful when they are naturally nonadherent or have been treated not to adhere to surfaces, for example by trypsinization.

"Control" or "control experiment" is used in accordance with its plain ordinary meaning and refers to an experiment in which the subjects or reagents of the experiment are treated as in a parallel experiment except for omission of a procedure, reagent, or variable of the experiment. In some instances, the control is used as a standard of comparison in evaluating experimental effects. In some embodiments, a control is the measurement of the activity of a protein in the absence of a compound as described herein (including embodiments and examples).

The term "modulator" refers to a composition that increases or decreases the level of a target molecule or the function of a target molecule or the physical state of the target of the molecule. In some embodiments, an estrogen-related receptor (e.g., β or γ) associated disease modulator is a compound that reduces the severity of one or more symptoms of a disease associated with estrogen-related receptor (e.g., β or γ) (e.g. NAFLD, NASH). An estrogen-related receptor (e.g., β or γ) modulator is a compound that increases or decreases the activity or function or level of activity or level of function of estrogen-related receptor (e.g., β or γ).

The term "modulate" is used in accordance with its plain ordinary meaning and refers to the act of changing or varying one or more properties. "Modulation" refers to the process of changing or varying one or more properties. For example, as applied to the effects of a modulator on a target protein, to modulate means to change by increasing or decreasing a property or function of the target molecule or the amount of the target molecule.

The term "associated" or "associated with" in the context of a substance or substance activity or function associated with a disease (e.g. a protein associated disease, a cancer associated with estrogen-related receptor (e.g., β or γ) activity, a metabolic disease (e.g., NAFLD, NASH) associated with estrogen-related receptor (e.g., β or γ) activity, estrogen-related receptor (e.g., β or γ) associated disease) means that the disease (e.g. cancer, NAFLD, NASH) is caused by (in whole or in part), or a symptom of the disease is caused by (in whole or in part) the substance or substance activity or function. For example, a NASH associated with estrogen-related receptor γ activity or function may be a NASH that results (entirely or partially) from aberrant estrogen-related receptor γ function (e.g. enzyme activity, protein-protein interaction, signaling pathway) or a NASH wherein a particular symptom of the disease is caused (entirely or partially) by aberrant estrogen-related receptor γ activity or function. As used herein, what is described as being associated with a disease, if a causative agent, could be a target for treatment of the disease. For example, a NASH associated with estrogen-related receptor γ activity or function or an estrogen-related receptor γ associated NAFLD, may be treated with an estrogen-related receptor γ modulator or estrogen-related receptor γ inhibitor or estrogen-related receptor γ inverse agonist, in the instance where estrogen-related receptor γ activity or function (e.g. signaling pathway activity) causes the NASH or NAFLD.

The term "aberrant" as used herein refers to different from normal. When used to describe enzymatic activity or protein function, aberrant refers to activity or function that is greater or less than a normal control or the average of normal non-diseased control samples. Aberrant activity may refer to an amount of activity that results in a disease, wherein returning the aberrant activity to a normal or non-disease-associated amount (e.g. by administering a compound or using a method as described herein), results in reduction of the disease or one or more disease symptoms.

The term "signaling pathway" as used herein refers to a series of interactions between cellular and optionally extracellular components (e.g. proteins, nucleic acids, small molecules, ions, lipids) that conveys a change in one component to one or more other components, which in turn may convey a change to additional components, which is optionally propagated to other signaling pathway components. For example, binding of an estrogen-related receptor (e.g., β or γ) protein with a compound as described herein may reduce the interactions between the estrogen-related receptor (e.g., β or γ) protein and downstream effectors or signaling pathway components, resulting in changes in cell growth, proliferation, survival, metabolism, secretion, or expression.

II. Compounds

In an aspect is provided a compound having the formula:

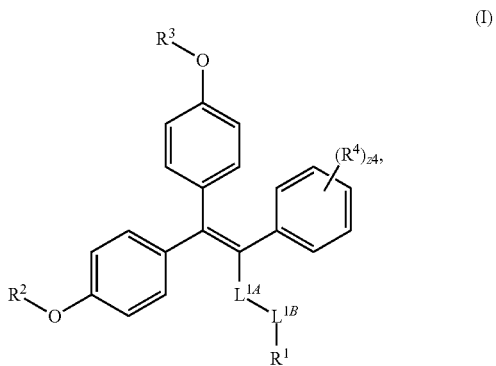

$L^{1A}$ is a bond, substituted or unsubstituted alkylene, or substituted or unsubstituted heteroalkylene.

$L^{1B}$ is a bond, —C(O)O—, —OC(O)—, —O—, —C(O)—, —NH—, —NHC(O)—, or —C(O)NH—.

$R^1$ is independently hydrogen, halogen, —CX$^1_3$, —CHX$^1_2$, —CH$_2$X$^1$, —OCX$^1_3$, —OCH$_2$X$^1$, —OCHX$^1_2$, —CN, —SO$_{n1}$R$^{1D}$, —SO$_{v1}$NR$^{1A}$R$^{1B}$, —NHC(O)NR$^{1A}$R$^{1B}$, —N(O)$_{m1}$, —NR$^{1A}$R$^{1B}$, —C(O)R$^{1C}$, —C(O)—OR$^{1C}$, —C(O)NR$^{1A}$R$^{1B}$, —OR$^{1D}$, —NR$^{1A}$SO$_2$R$^{1D}$, —NR$^{1A}$C(O)R$^{1C}$, —NR$^{1A}$C(O)OR$^{1C}$, —NR$^{1A}$OR$^{1C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^2$ is independently hydrogen, —CX$^2_3$, —CHX$^2_2$, —CH$_2$X$^2$, —C(O)R$^{2A}$, —C(O)OR$^{2A}$, —C(O)NR$^{2A}$R$^{2B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^3$ is independently hydrogen, —CX$^3_3$, —CHX$^3_2$, —CH$_2$X$^3$, —C(O)R$^{3A}$, —C(O)OR$^{3A}$, —C(O)NR$^{3A}$R$^{3B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^4$ is independently halogen, —CX$^4_3$, —CHX$^4_2$, —CH$_2$X$^4$, —OCX$^4_3$, —OCH$_2$X$^4$, —OCHX$^4_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

The symbol z4 is an integer from 0 to 5.

Each $R^{1A}$, $R^{1B}$, $R^{1C}$, $R^{1D}$, $R^{2A}$, $R^{2B}$, $R^{3A}$, and $R^{3B}$ is independently hydrogen, —CX$_3$, —CN, —COOH, —CONH$_2$, —CHX$_2$, —CH$_2$X, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{1A}$ and $R^{1B}$ substituents bonded to the same nitrogen atom may optionally be joined to form a substituted or unsubstituted heterocycloalkyl or substituted or unsubstituted heteroaryl; $R^{2A}$ and $R^{2B}$ substituents bonded to the same nitrogen atom may optionally be joined to form a substituted or unsubstituted heterocycloalkyl or substituted or unsubstituted heteroaryl; $R^{3A}$ and $R^{3B}$ substituents bonded to the same nitrogen atom may optionally be joined to form a substituted or unsubstituted heterocycloalkyl or substituted or unsubstituted heteroaryl.

Each X, $X^1$, $X^2$, $X^3$, and $X^4$ is independently —F, —Cl, —Br, or —I.

The symbol n1 is independently an integer from 0 to 4.

The symbols m1 and v1 are independently an integer from 1 to 2.

In embodiments, the compound has the formula:

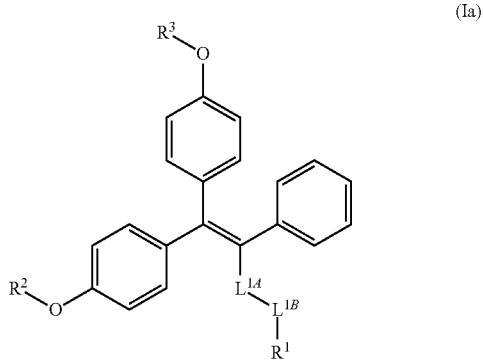

(Ia)

and $L^{1A}$, $L^{1B}$, $R^1$, $R^2$, and $R^3$ are as described herein. In embodiments, the compound has the formula:

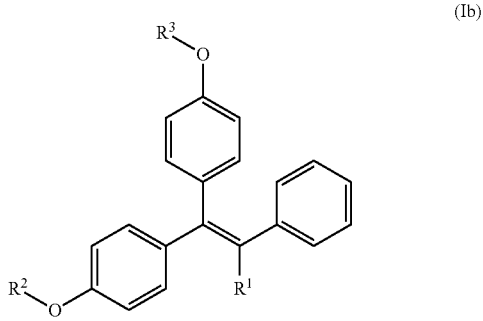

(Ib)

and $R^1$, $R^2$, and $R^3$ are as described herein.

In embodiments, $R^1$ is independently hydrogen. In embodiments, $R^1$ is independently halogen. In embodiments, $R^1$ is independently unsubstituted methyl. In embodiments, $R^1$ is independently unsubstituted ethyl. In embodiments, $R^1$ is independently unsubstituted propyl. In embodiments, $R^1$ is independently unsubstituted isopropyl. In embodiments, $R^1$ is independently unsubstituted n-propyl. In embodiments, $R^1$ is independently unsubstituted butyl. In embodiments, $R^1$ is independently unsubstituted n-butyl. In embodiments, $R^1$ is independently unsubstituted t-butyl. In embodiments, $R^1$ is independently unsubstituted iso-butyl. In embodiments, $R^1$ is independently unsubstituted pentyl. In embodiments, $R^1$ is independently unsubstituted n-pentyl. In embodiments, $R^1$ is independently unsubstituted hexyl. In embodiments, $R^1$ is independently unsubstituted n-hexyl. In embodiments, $R^1$ is independently unsubstituted heptyl. In embodiments, $R^1$ is independently unsubstituted n-heptyl. In embodiments, $R^1$ is independently unsubstituted octyl. In embodiments, $R^1$ is independently unsubstituted n-octyl. In embodiments, $R^1$ is independently unsubstituted $C_1$-$C_8$ alkyl. In embodiments, $R^1$ is independently halo-substituted methyl. In embodiments, $R^1$ is independently halo-substituted ethyl. In embodiments, $R^1$ is independently halo-substituted isopropyl. In embodiments, $R^1$ is independently halo-substituted n-propyl. In embodiments, $R^1$ is independently halo-substituted n-butyl. In embodiments, $R^1$ is independently halo-substituted t-butyl. In embodiments, $R^1$ is independently halo-substituted n-pentyl. In embodiments, $R^1$ is independently halo-substituted $C_1$-$C_8$ alkyl. In embodiments, $R^1$ is independently chloro-substituted methyl. In embodiments, $R^1$ is independently chloro-substituted ethyl. In embodiments, $R^1$ is independently chloro-substituted isopropyl. In embodiments, $R^1$ is independently chloro-substituted n-propyl. In embodiments, $R^1$ is independently chloro-substituted n-butyl. In embodiments, $R^1$ is independently chloro-substituted t-butyl. In embodiments, $R^1$ is independently chloro-substituted n-pentyl. In embodiments, $R^1$ is independently chloro-substituted $C_1$-$C_8$ alkyl. In embodiments, $R^1$ is independently hydroxy-substituted methyl. In embodiments, $R^1$ is independently hydroxy-substituted ethyl. In embodiments, $R^1$ is independently hydroxy-substituted isopropyl. In embodiments, $R^1$ is independently hydroxy-substituted n-propyl. In embodiments, $R^1$ is independently hydroxy-substituted n-butyl. In embodiments, $R^1$ is independently hydroxy-substituted t-butyl. In embodiments, $R^1$ is independently hydroxy-substituted n-pentyl. In embodiments, $R^1$ is independently hydroxy-substituted $C_1$-$C_8$ alkyl. In embodiments, $R^1$ is independently $CH_3C(O)O$-substituted methyl. In embodiments, $R^1$ is independently $CH_3C(O)O$-substituted ethyl. In embodiments, $R^1$ is independently $CH_3C(O)O$-substituted isopropyl. In embodiments, $R^1$ is independently $CH_3C(O)O$-substituted n-propyl. In embodiments, $R^1$ is independently $CH_3C(O)O$-substituted n-butyl. In embodiments, $R^1$ is independently $CH_3C(O)O$-substituted t-butyl. In embodiments, $R^1$ is independently $CH_3C(O)O$-substituted n-pentyl. In embodiments, $R^1$ is independently $CH_3C(O)O$-substituted $C_1$-$C_8$ alkyl. In embodiments, $R^1$ is independently unsubstituted 2 to 6 membered heteroalkyl. In embodiments, $R^1$ is independently unsubstituted 2 to 7 membered heteroalkyl. In embodiments, $R^1$ is independently unsubstituted 2 to 8 membered heteroalkyl. In embodiments, $R^1$ is independently unsubstituted 2 to 9 membered heteroalkyl. In embodiments, $R^1$ is independently unsubstituted 2 to 10 membered heteroalkyl. In embodiments, $R^1$ is independently unsubstituted 3 to 10 membered heteroalkyl. In embodiments, $R^1$ is independently unsubstituted 4 to 10 membered heteroalkyl. In embodiments, $R^1$ is independently unsubstituted 5 to 10 membered heteroalkyl. In embodiments, $R^1$ is independently unsubstituted 6 to 10 membered heteroalkyl. In embodiments, $R^1$ is independently unsubstituted 7 to 10 membered heteroalkyl. In embodiments, $R^1$ is independently unsubstituted 8 to 10 membered heteroalkyl. In embodiments, $R^1$ is independently unsubstituted 6 to 10 membered heteroalkyl. In embodiments, $R^1$ is independently unsubstituted 7 to 9 membered heteroalkyl.

In embodiments, $R^1$ is independently —$CX^1_3$. In embodiments, $R^1$ is independently —$CHX^1_2$. In embodiments, $R^1$ is independently —$CH_2X^1$. In embodiments, $R^1$ is independently —$OCX^1_3$. In embodiments, $R^1$ is independently —$OCH_2X^1$. In embodiments, $R^1$ is independently —$OCHX^1_2$. In embodiments, $R^1$ is independently —CN. In embodiments, $R^1$ is independently —$SO_{n1}R^{1D}$. In embodiments, $R^1$ is independently —$SO_{v1}NR^{1A}R^{1B}$. In embodiments, $R^1$ is independently —NHC(O)N$R^{1A}R^{1B}$. In embodiments, $R^1$ is independently —N(O)$_{m1}$. In embodiments, $R^1$ is independently —N$R^{1A}R^{1B}$. In embodiments, $R^1$ is independently —C(O)$R^{1C}$. In embodiments, $R^1$ is independently —C(O)—O$R^{1C}$. In embodiments, $R^1$ is independently —C(O)N$R^{1A}R^{1B}$. In embodiments, $R^1$ is independently —O$R^{1D}$. In embodiments, $R^1$ is independently —N$R^{1A}$SO$_2R^{1D}$. In embodiments, $R^1$ is independently —N$R^{1A}$C(O)$R^{1C}$. In embodiments, $R^1$ is independently —N$R^{1A}$C(O)O$R^{1C}$. In embodiments, $R^1$ is independently —N$R^{1A}$O$R^{1C}$. In embodiments, $R^1$ is independently —OH. In embodiments, $R^1$ is independently —NH$_2$. In embodiments, $R^1$ is independently —COOH. In embodiments, $R^1$ is independently —CONH$_2$. In embodiments, $R^1$ is independently —NO$_2$. In embodiments, $R^1$ is independently —SH. In embodiments, $R^1$ is independently halogen. In embodiments, $R^1$ is independently —F. In embodiments, $R^1$ is independently —Cl. In embodiments, $R^1$ is independently —Br. In embodiments, $R^1$ is independently —I. In embodiments, $R^1$ is independently —CF$_3$. In embodiments, $R^1$ is independently —CHF$_2$. In embodiments, $R^1$ is independently —CH$_2$F. In embodiments, $R^1$ is independently —OCF$_3$. In embodiments, $R^1$ is independently —OCH$_2$F. In embodiments, $R^1$ is independently —OCHF$_2$. In embodiments, $R^1$ is independently —OCH$_3$. In embodiments, $R^1$ is independently —OCH$_2$CH$_3$. In embodiments, $R^1$ is independently —OCH$_2$CH$_2$CH$_3$. In embodiments, $R^1$ is independently —OCH(CH$_3$)$_2$. In embodiments, $R^1$ is independently —OC(CH$_3$)$_3$. In embodiments, $R^1$ is independently —SCH$_3$. In embodiments, $R^1$ is independently —SCH$_2$CH$_3$. In embodiments, $R^1$ is independently —SCH$_2$CH$_2$CH$_3$. In embodiments, $R^1$ is independently —SCH(CH$_3$)$_2$. In embodiments, $R^1$ is independently —SC(CH$_3$)$_3$. In embodiments, $R^1$ is independently —CH$_3$. In embodiments, $R^1$ is independently —CH$_2$CH$_3$. In embodiments, $R^1$ is independently —CH$_2$CH$_2$CH$_3$. In embodiments, $R^1$ is independently —CH(CH$_3$)$_2$. In embodiments, $R^1$ is independently —C(CH$_3$)$_3$. In embodiments, $R^1$ is independently —CH$_2$CH$_2$C(O)OCH$_3$. In embodiments, $R^1$ is independently —CH$_2$CH(CH$_3$)C(O)OCH$_3$.

In embodiments, $R^1$ is independently hydrogen, halogen, —CX$^1_3$, —CHX$^1_2$, —CH$_2$X$^1$, —OCX$^1_3$, —OCH$_2$X$^1$, —OCHX$^1_2$, —CN, —SO$_{n1}R^{1D}$, —SO$_{v1}$N$R^{1A}R^{1B}$, —NHC(O)N$R^{1A}R^{1B}$, —N(O)$_{m1}$, —N$R^{1A}R^{1B}$, —C(O)—O$R^{1C}$, —C(O)—O$R^{1C}$, —C(O)N$R^{1A}R^{1B}$, —O$R^{1D}$, —N$R^{1A}$SO$_2R^{1D}$, —N$R^{1A}$C(O)$R^{1C}$, —N$R^{1A}$C(O)O$R^{1C}$, —N$R^{1A}$O$R^{1C}$, substituted or unsubstituted alkyl (e.g., C$_1$-C$_8$, C$_1$-C$_6$, C$_1$-C$_4$, or C$_1$-C$_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., C$_3$-C$_8$, C$_3$-C$_6$, C$_4$-C$_6$, or C$_5$-C$_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., C$_6$-C$_{12}$, C$_6$-C$_{10}$, or phenyl), or substituted or unsubstituted heteroaryl (e.g., 5 to 12, 5 to 10 membered, 5 to 9 membered, or 5 to 6 membered).

In embodiments, $R^1$ is independently substituted or unsubstituted alkyl (e.g., C$_1$-C$_8$, C$_1$-C$_6$, C$_1$-C$_4$, or C$_1$-C$_2$). In embodiments, $R^1$ is independently substituted alkyl (e.g., C$_1$-C$_8$, C$_1$-C$_6$, C$_1$-C$_4$, or C$_1$-C$_2$). In embodiments, $R^1$ is independently unsubstituted alkyl (e.g., C$_1$-C$_8$, C$_1$-C$_6$, C$_1$-C$_4$, or C$_1$-C$_2$). In embodiments, $R^1$ is independently unsubstituted methyl. In embodiments, $R^1$ is independently unsubstituted ethyl. In embodiments, $R^1$ is independently unsubstituted propyl. In embodiments, $R^1$ is independently unsubstituted isopropyl. In embodiments, $R^1$ is independently unsubstituted tert-butyl. In embodiments, $R^1$ is independently substituted or unsubstituted heteroalkyl (e.g., 2 to 8 membered, 2 to 6 membered, 4 to 6 membered, 2 to 3 membered, or 4 to 5 membered). In embodiments, $R^1$ is independently substituted heteroalkyl (e.g., 2 to 8 membered, 2 to 6 membered, 4 to 6 membered, 2 to 3 membered, or 4 to 5 membered). In embodiments, $R^1$ is independently unsubstituted heteroalkyl (e.g., 2 to 8 membered, 2 to 6 membered, 4 to 6 membered, 2 to 3 membered, or 4 to 5 membered). In embodiments, $R^1$ is independently substituted or unsubstituted cycloalkyl (e.g., C$_3$-C$_8$, C$_3$-C$_6$, C$_4$-C$_6$, or C$_5$-C$_6$). In embodiments, $R^1$ is independently substituted cycloalkyl (e.g., C$_3$-C$_8$, C$_3$-C$_6$, C$_4$-C$_6$, or C$_5$-C$_6$). In embodiments, $R^1$ is independently unsubstituted cycloalkyl (e.g., C$_3$-C$_8$, C$_3$-C$_6$, C$_4$-C$_6$, or C$_5$-C$_6$). In embodiments, $R^1$ is independently substituted or unsubstituted heterocycloalkyl (e.g., 3 to 8 membered, 3 to 6 membered, 4 to 6 membered, 4 to 5 membered, or 5 to 6 membered). In embodiments, $R^1$ is independently substituted heterocycloalkyl (e.g., 3 to 8 membered, 3 to 6 membered, 4 to 6 membered, 4 to 5 membered, or 5 to 6 membered). In embodiments, $R^1$ is independently unsubstituted heterocycloalkyl (e.g., 3 to 8 membered, 3 to 6 membered, 4 to 6 membered, 4 to 5 membered, or 5 to 6 membered). In embodiments, $R^1$ is independently substituted or unsubstituted aryl (e.g., C$_6$-C$_{12}$, C$_6$-C$_{10}$, or phenyl). In embodiments, $R^1$ is independently substituted aryl (e.g., C$_6$-C$_{12}$, C$_6$-C$_{10}$, or phenyl). In embodiments, $R^1$ is independently unsubstituted aryl (e.g., C$_6$-C$_{12}$, C$_6$-C$_{10}$, or phenyl). In embodiments, $R^1$ is independently substituted or unsubstituted heteroaryl (e.g., 5 to 12 membered, 5 to 10 membered, 5 to 9 membered, or 5 to 6 membered). In embodiments, $R^1$ is independently substituted heteroaryl (e.g., 5 to 12 membered, 5 to 10 membered, 5 to 9 membered, or 5 to 6 membered). In embodiments, $R^1$ is independently unsubstituted heteroaryl (e.g., 5 to 12 membered, 5 to 10 membered, 5 to 9 membered, or 5 to 6 membered).

In embodiments, $R^1$ is independently hydrogen, halogen, —CX$^1_3$, —CHX$^1_2$, —CH$_2$X$^1$, —OCX$^1_3$, —OCH$_2$X$^1$, —OCHX$^1_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, $R^{20}$-substituted or unsubstituted alkyl (e.g., C$_1$-C$_8$, C$_1$-C$_6$, C$_1$-C$_4$, or C$_1$-C$_2$), $R^{20}$-substituted or unsubstituted heteroalkyl (e.g., 2 to 8 membered, 2 to 6 membered, 4 to 6 membered, 2 to 3 membered, or 4 to 5 membered), $R^{20}$-substituted or unsubstituted cycloalkyl (e.g., C$_3$-C$_8$, C$_3$-C$_6$, C$_4$-C$_6$, or C$_5$-C$_6$), $R^{20}$-substituted or unsubstituted heterocycloalkyl (e.g., 3 to 8 membered, 3 to 6 membered, 4 to 6 membered, 4 to 5 membered, or 5 to 6 membered), $R^{20}$-substituted or unsubstituted aryl (e.g., C$_6$-C$_{12}$, C$_6$-C$_{10}$, or phenyl), or $R^{20}$-substituted or unsubstituted heteroaryl (e.g., 5 to 12 membered, 5 to 10 membered, 5 to 9 membered, or 5 to 6 membered). In embodiments, $R^1$ is independently hydrogen, halogen, —CX$^1_3$, —CHX$^1_2$, —CH$_2$X$^1$, —OCX$^1_3$, —OCH$_2$X$^1$, —OCHX$^1_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, unsubstituted alkyl (e.g., C$_1$-C$_8$, C$_1$-C$_6$, C$_1$-C$_4$, or C$_1$-C$_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., C$_3$-C$_8$, C$_3$-C$_6$, C$_4$-C$_6$, or C$_5$-C$_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered). $X^1$ is independently —F, —Cl, —Br, or —I. In embodiments, $R^1$ is independently hydrogen. In embodiments, $R^1$ is independently unsubstituted methyl. In embodiments, $R^1$ is independently unsubstituted ethyl.

$R^{20}$ is independently oxo, halogen, —$CX^{20}_3$, —$CHX^{20}_2$, —$CH_2X^{20}$, —$OCX^{20}_3$, —$OCH_2X^{20}$, —$OCHX^{20}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, $R^{21}$-substituted or unsubstituted alkyl (e.g., $C_1$-$C_8$, $C_1$-$C_6$, $C_1$-$C_4$, or $C_1$-$C_2$), $R^{21}$-substituted or unsubstituted heteroalkyl (e.g., 2 to 8 membered, 2 to 6 membered, 4 to 6 membered, 2 to 3 membered, or 4 to 5 membered), $R^{21}$-substituted or unsubstituted cycloalkyl (e.g., $C_3$-$C_8$, $C_3$-$C_6$, $C_4$-$C_6$, or $C_5$-$C_6$), $R^{21}$-substituted or unsubstituted heterocycloalkyl (e.g., 3 to 8 membered, 3 to 6 membered, 4 to 6 membered, 4 to 5 membered, or 5 to 6 membered), $R^{21}$-substituted or unsubstituted aryl (e.g., $C_6$-$C_{12}$, $C_6$-$C_{10}$, or phenyl), or $R^{21}$-substituted or unsubstituted heteroaryl (e.g., 5 to 12 membered, 5 to 10 membered, 5 to 9 membered, or 5 to 6 membered). In embodiments, $R^{20}$ is independently oxo, halogen, —$CX^{20}_3$, —$CHX^{20}_2$, —$CH_2X^{20}$, —$OCX^{20}_3$, —$OCH_2X^{20}$, —$OCHX^{20}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered). $X^{20}$ is independently —F, —Cl, —Br, or —I. In embodiments, $R^{20}$ is independently unsubstituted methyl. In embodiments, $R^{20}$ is independently unsubstituted ethyl.

$R^{21}$ is independently oxo, halogen, —$CX^{21}_3$, —$CHX^{21}_2$, —$CH_2X^{21}$, —$OCX^{21}_3$, —$OCH_2X^{21}$, —$OCHX^{21}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, $R^{22}$-substituted or unsubstituted alkyl (e.g., $C_1$-$C_8$, $C_1$-$C_6$, $C_1$-$C_4$, or $C_1$-$C_2$), $R^{22}$-substituted or unsubstituted heteroalkyl (e.g., 2 to 8 membered, 2 to 6 membered, 4 to 6 membered, 2 to 3 membered, or 4 to 5 membered), $R^{22}$-substituted or unsubstituted cycloalkyl (e.g., $C_3$-$C_8$, $C_3$-$C_6$, $C_4$-$C_6$, or $C_5$-$C_6$), $R^{22}$-substituted or unsubstituted heterocycloalkyl (e.g., 3 to 8 membered, 3 to 6 membered, 4 to 6 membered, 4 to 5 membered, or 5 to 6 membered), $R^{22}$-substituted or unsubstituted aryl (e.g., $C_6$-$C_{12}$, $C_6$-$C_{10}$, or phenyl), or $R^{22}$-substituted or unsubstituted heteroaryl (e.g., 5 to 12 membered, 5 to 10 membered, 5 to 9 membered, or 5 to 6 membered). In embodiments, $R^{21}$ is independently oxo, halogen, —$CX^{21}_3$, —$CHX^{21}_2$, —$CH_2X^{21}$, —$OCX^{21}_3$, —$OCH_2X^{21}$, —$OCHX^{21}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered). $X^{21}$ is independently —F, —Cl, —Br, or —I. In embodiments, $R^{21}$ is independently unsubstituted methyl. In embodiments, $R^{21}$ is independently unsubstituted ethyl.

$R^{22}$ is independently oxo, halogen, —$CX^{22}_3$, —$CHX^{22}_2$, —$CH_2X^{22}$, —$OCX^{22}_3$, —$OCH_2X^{22}$, —$OCHX^{22}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered). $X^{22}$ is independently —F, —Cl, —Br, or —I. In embodiments, $R^{22}$ is independently unsubstituted methyl. In embodiments, $R^{22}$ is independently unsubstituted ethyl.

In embodiments, $R^{1A}$ is independently hydrogen. In embodiments, $R^{1A}$ is independently —$CX^{1A}_3$. In embodiments, $R^{1A}$ is independently —$CHX^{1A}_2$. In embodiments, $R^{1A}$ is independently —$CH_2X^{1A}$. In embodiments, $R^{1A}$ is independently —CN. In embodiments, $R^{1A}$ is independently —COOH. In embodiments, $R^{1A}$ is independently —$CONH_2$. In embodiments, $X^{1A}$ is independently —F, —Cl, —Br, or —I.

In embodiments, $R^{1A}$ is independently substituted or unsubstituted alkyl (e.g., $C_1$-$C_8$, $C_1$-$C_6$, $C_1$-$C_4$, or $C_1$-$C_2$). In embodiments, $R^{1A}$ is independently substituted alkyl (e.g., $C_1$-$C_8$, $C_1$-$C_6$, $C_1$-$C_4$, or $C_1$-$C_2$). In embodiments, $R^{1A}$ is independently unsubstituted alkyl (e.g., $C_1$-$C_8$, $C_1$-$C_6$, $C_1$-$C_4$, or $C_1$-$C_2$). In embodiments, $R^{1A}$ is independently unsubstituted methyl. In embodiments, $R^{1A}$ is independently unsubstituted ethyl. In embodiments, $R^{1A}$ is independently unsubstituted propyl. In embodiments, $R^{1A}$ is independently unsubstituted isopropyl. In embodiments, $R^{1A}$ is independently unsubstituted tert-butyl. In embodiments, $R^{1A}$ is independently substituted or unsubstituted heteroalkyl (e.g., 2 to 8 membered, 2 to 6 membered, 4 to 6 membered, 2 to 3 membered, or 4 to 5 membered). In embodiments, $R^{1A}$ is independently substituted heteroalkyl (e.g., 2 to 8 membered, 2 to 6 membered, 4 to 6 membered, 2 to 3 membered, or 4 to 5 membered). In embodiments, $R^{1A}$ is independently unsubstituted heteroalkyl (e.g., 2 to 8 membered, 2 to 6 membered, 4 to 6 membered, 2 to 3 membered, or 4 to 5 membered). In embodiments, $R^{1A}$ is independently substituted or unsubstituted cycloalkyl (e.g., $C_3$-$C_8$, $C_3$-$C_6$, $C_4$-$C_6$, or $C_5$-$C_6$). In embodiments, $R^{1A}$ is independently substituted cycloalkyl (e.g., $C_3$-$C_8$, $C_3$-$C_6$, $C_4$-$C_6$, or $C_5$-$C_6$). In embodiments, $R^{1A}$ is independently unsubstituted cycloalkyl (e.g., $C_3$-$C_8$, $C_3$-$C_6$, $C_4$-$C_6$, or $C_5$-$C_6$). In embodiments, $R^{1A}$ is independently substituted or unsubstituted heterocycloalkyl (e.g., 3 to 8 membered, 3 to 6 membered, 4 to 6 membered, 4 to 5 membered, or 5 to 6 membered). In embodiments, $R^{1A}$ is independently substituted heterocycloalkyl (e.g., 3 to 8 membered, 3 to 6 membered, 4 to 6 membered, 4 to 5 membered, or 5 to 6 membered). In embodiments, $R^{1A}$ is independently unsubstituted heterocycloalkyl (e.g., 3 to 8 membered, 3 to 6 membered, 4 to 6 membered, 4 to 5 membered, or 5 to 6 membered). In embodiments, $R^{1A}$ is independently substituted or unsubstituted aryl (e.g., $C_6$-$C_{12}$, $C_6$-$C_{10}$, or phenyl). In embodiments, $R^{1A}$ is independently substituted aryl (e.g., $C_6$-$C_{12}$, $C_6$-$C_{10}$, or phenyl). In embodiments, $R^{1A}$ is independently unsubstituted aryl (e.g., $C_6$-$C_{12}$, $C_6$-$C_{10}$, or phenyl). In embodiments, $R^{1A}$ is independently substituted or unsubstituted heteroaryl (e.g., 5 to 12 membered, 5 to 10 membered, 5 to 9 membered, or 5 to 6 membered). In embodiments, $R^{1A}$ is independently substituted heteroaryl (e.g., 5 to 12 membered, 5 to 10 membered, 5 to 9 membered, or 5 to 6 membered). In embodiments, $R^{1A}$ is independently unsubstituted heteroaryl (e.g., 5 to 12 membered, 5 to 10 membered, 5 to 9 membered, or 5 to 6 membered).

In embodiments, $R^{1A}$ is independently hydrogen, —$CX^{1A}{}_3$, —$CHX^{1A}{}_2$, —$CH_2X^{1A}$, —CN, —COOH, —$CONH_2$, $R^{20A}$-substituted or unsubstituted alkyl (e.g., $C_1$-$C_8$, $C_1$-$C_6$, $C_1$-$C_4$, or $C_1$-$C_2$), $R^{20A}$-substituted or unsubstituted heteroalkyl (e.g., 2 to 8 membered, 2 to 6 membered, 4 to 6 membered, 2 to 3 membered, or 4 to 5 membered), $R^{20A}$-substituted or unsubstituted cycloalkyl (e.g., $C_3$-$C_8$, $C_3$-$C_6$, $C_4$-$C_6$, or $C_5$-$C_6$), $R^{20A}$-substituted or unsubstituted heterocycloalkyl (e.g., 3 to 8 membered, 3 to 6 membered, 4 to 6 membered, 4 to 5 membered, or 5 to 6 membered), $R^{20A}$-substituted or unsubstituted aryl (e.g., $C_6$-$C_{12}$, $C_6$-$C_{10}$, or phenyl), or $R^{20A}$-substituted or unsubstituted heteroaryl (e.g., 5 to 12 membered, 5 to 10 membered, 5 to 9 membered, or 5 to 6 membered). In embodiments, $R^{1A}$ is independently hydrogen, —$CX^{1A}{}_3$, —$CHX^{1A}{}_2$, —$CH_2X^{1A}$, —CN, —COOH, —$CONH_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered). $X^{1A}$ is independently —F, —Cl, —Br, or —I. In embodiments, $R^{1A}$ is independently hydrogen. In embodiments, $R^{1A}$ is independently unsubstituted methyl. In embodiments, $R^{1A}$ is independently unsubstituted ethyl.

In embodiments, $R^{1A}$ and $R^{1B}$ substituents bonded to the same nitrogen atom may optionally be joined to form a $R^{20A}$-substituted or unsubstituted heterocycloalkyl (e.g., 3 to 8 membered, 3 to 6 membered, 4 to 6 membered, 4 to 5 membered, or 5 to 6 membered) or $R^{20A}$-substituted or unsubstituted heteroaryl (e.g., 5 to 12 membered, 5 to 10 membered, 5 to 9 membered, or 5 to 6 membered). In embodiments, $R^{1A}$ and $R^{1B}$ substituents bonded to the same nitrogen atom may optionally be joined to form an unsubstituted heterocycloalkyl (e.g., 3 to 8 membered, 3 to 6 membered, 4 to 6 membered, 4 to 5 membered, or 5 to 6 membered) or unsubstituted heteroaryl (e.g., 5 to 12 membered, 5 to 10 membered, 5 to 9 membered, or 5 to 6 membered). In embodiments, $R^{1A}$ and $R^{1B}$ substituents bonded to the same nitrogen atom may optionally be joined to form a $R^{20A}$-substituted or unsubstituted heterocycloalkyl (e.g., 3 to 8 membered, 3 to 6 membered, 4 to 6 membered, 4 to 5 membered, or 5 to 6 membered). In embodiments, $R^{1A}$ and $R^{1B}$ substituents bonded to the same nitrogen atom may optionally be joined to form an unsubstituted heterocycloalkyl (e.g., 3 to 8 membered, 3 to 6 membered, 4 to 6 membered, 4 to 5 membered, or 5 to 6 membered).

$R^{20A}$ is independently oxo, halogen, —$CX^{20A}{}_3$, —$CHX^{20A}{}_2$, —$CH_2X^{20A}$, —$OCX^{20A}{}_3$, —$OCH_2X^{20A}$, —$OCHX^{20A}{}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, $R^{21A}$-substituted or unsubstituted alkyl (e.g., $C_1$-$C_8$, $C_1$-$C_6$, $C_1$-$C_4$, or $C_1$-$C_2$), $R^{21A}$-substituted or unsubstituted heteroalkyl (e.g., 2 to 8 membered, 2 to 6 membered, 4 to 6 membered, 2 to 3 membered, or 4 to 5 membered), $R^{21A}$-substituted or unsubstituted cycloalkyl (e.g., $C_3$-$C_8$, $C_3$-$C_6$, $C_4$-$C_6$, or $C_5$-$C_6$), $R^{21A}$-substituted or unsubstituted heterocycloalkyl (e.g., 3 to 8 membered, 3 to 6 membered, 4 to 6 membered, 4 to 5 membered, or 5 to 6 membered), $R^{21A}$-substituted or unsubstituted aryl (e.g., $C_6$-$C_{12}$, $C_6$-$C_{10}$, or phenyl), or $R^{21A}$-substituted or unsubstituted heteroaryl (e.g., 5 to 12 membered, 5 to 10 membered, 5 to 9 membered, or 5 to 6 membered). In embodiments, $R^{20A}$ is independently oxo, halogen, —$CX^{20A}{}_3$, —$CHX^{20A}{}_2$, —$CH_2X^{20A}$, —$OCX^{20A}{}_3$, —$OCH_2X^{20A}$, —$OCHX^{20A}{}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered). $X^{20A}$ is independently —F, —Cl, —Br, or —I. In embodiments, $R^{20A}$ is independently unsubstituted methyl. In embodiments, $R^{20A}$ is independently unsubstituted ethyl.

$R^{21A}$ is independently oxo, halogen, —$CX^{21A}{}_3$, —$CHX^{21A}{}_2$, —$CH_2X^{21A}$, —$OCX^{21A}{}_3$, —$OCH_2X^{21A}$, —$OCHX^{21A}{}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, $R^{22A}$-substituted or unsubstituted alkyl (e.g., $C_1$-$C_8$, $C_1$-$C_6$, $C_1$-$C_4$, or $C_1$-$C_2$), $R^{22A}$-substituted or unsubstituted heteroalkyl (e.g., 2 to 8 membered, 2 to 6 membered, 4 to 6 membered, 2 to 3 membered, or 4 to 5 membered), $R^{22A}$-substituted or unsubstituted cycloalkyl (e.g., $C_3$-$C_8$, $C_3$-$C_6$, $C_4$-$C_6$, or $C_5$-$C_6$), $R^{22A}$-substituted or unsubstituted heterocycloalkyl (e.g., 3 to 8 membered, 3 to 6 membered, 4 to 6 membered, 4 to 5 membered, or 5 to 6 membered), $R^{22A}$-substituted or unsubstituted aryl (e.g., $C_6$-$C_{12}$, $C_6$-$C_{10}$, or phenyl), or $R^{22A}$-substituted or unsubstituted heteroaryl (e.g., 5 to 12 membered, 5 to 10 membered, 5 to 9 membered, or 5 to 6 membered). In embodiments, $R^{21A}$ is independently oxo, halogen, —$CX^{21A}{}_3$, —$CHX^{21A}{}_2$, —$CH_2X^{21A}$, —$OCX^{21A}{}_3$, —$OCH_2X^{21A}$, —$OCHX^{21A}{}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered). $X^{21A}$ is independently —F, —Cl, —Br, or —I. In embodiments, $R^{21A}$ is independently unsubstituted methyl. In embodiments, $R^{21A}$ is independently unsubstituted ethyl.

$R^{22A}$ is independently oxo, halogen, —$CX^{22A}{}_3$, —$CHX^{22A}{}_2$, —$CH_2X^{22A}$, —$OCX^{22A}{}_3$, —$OCH_2X^{22A}$, —$OCHX^{22A}{}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)NHNH$_2$, —NHC=(O)NH$_2$, —$NHSO_2H$, —NHC=(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered). $X^{22A}$ is independently —F, —Cl, —Br, or —I. In embodiments, $R^{22A}$ is independently unsubstituted methyl. In embodiments, $R^{22A}$ is independently unsubstituted ethyl.

In embodiments, $R^{1B}$ is independently hydrogen. In embodiments, $R^{1B}$ is independently —$CX^{1B}{}_3$. In embodiments, $R^{1B}$ is independently —$CHX^{1B}{}_2$. In embodiments, $R^{1B}$ is independently —$CH_2X^{1B}$. In embodiments, $R^{1B}$ is independently —CN. In embodiments, $R^{1B}$ is independently —COOH. In embodiments, $R^{1B}$ is independently —$CONH_2$. In embodiments, $X^{1B}$ is independently —F, —Cl, —Br, or —I.

In embodiments, $R^{1B}$ is independently substituted or unsubstituted alkyl (e.g., $C_1$-$C_8$, $C_1$-$C_6$, $C_1$-$C_4$, or $C_1$-$C_2$). In embodiments, $R^{1B}$ is independently substituted alkyl (e.g., $C_1$-$C_8$, $C_1$-$C_6$, $C_1$-$C_4$, or $C_1$-$C_2$). In embodiments, $R^{1B}$ is independently unsubstituted alkyl (e.g., $C_1$-$C_8$, $C_1$-$C_6$, $C_1$-$C_4$, or $C_1$-$C_2$). In embodiments, $R^{1B}$ is independently unsubstituted methyl. In embodiments, $R^{1B}$ is independently unsubstituted ethyl. In embodiments, $R^{1B}$ is independently unsubstituted propyl. In embodiments, $R^{1B}$ is independently unsubstituted isopropyl. In embodiments, $R^{1B}$ is independently unsubstituted tert-butyl. In embodiments, $R^{1B}$ is independently substituted or unsubstituted heteroalkyl (e.g., 2 to 8 membered, 2 to 6 membered, 4 to 6 membered, 2 to 3 membered, or 4 to 5 membered). In embodiments, $R^{1B}$ is independently substituted heteroalkyl (e.g., 2 to 8 membered, 2 to 6 membered, 4 to 6 membered, 2 to 3 membered, or 4 to 5 membered). In embodiments, $R^{1B}$ is independently unsubstituted heteroalkyl (e.g., 2 to 8 membered, 2 to 6 membered, 4 to 6 membered, 2 to 3 membered, or 4 to 5 membered). In embodiments, $R^{1B}$ is independently substituted or unsubstituted cycloalkyl (e.g., $C_3$-$C_8$, $C_3$-$C_6$, $C_4$-$C_6$, or $C_5$-$C_6$). In embodiments, $R^{1B}$ is independently substituted cycloalkyl (e.g., $C_3$-$C_8$, $C_3$-$C_6$, $C_4$-$C_6$, or $C_5$-$C_6$). In embodiments, $R^{1B}$ is independently unsubstituted cycloalkyl (e.g., $C_3$-$C_8$, $C_3$-$C_6$, $C_4$-$C_6$, or $C_5$-$C_6$). In embodiments, $R^{1B}$ is independently substituted or unsubstituted heterocycloalkyl (e.g., 3 to 8 membered, 3 to 6 membered, 4 to 6 membered, 4 to 5 membered, or 5 to 6 membered). In embodiments, $R^{1B}$ is independently substituted heterocycloalkyl (e.g., 3 to 8 membered, 3 to 6 membered, 4 to 6 membered, 4 to 5 membered, or 5 to 6 membered). In embodiments, $R^{1B}$ is independently unsubstituted heterocycloalkyl (e.g., 3 to 8 membered, 3 to 6 membered, 4 to 6 membered, 4 to 5 membered, or 5 to 6 membered). In embodiments, $R^{1B}$ is independently substituted or unsubstituted aryl (e.g., $C_6$-$C_{12}$, $C_6$-$C_{10}$, or phenyl). In embodiments, $R^{1B}$ is independently substituted aryl (e.g., $C_6$-$C_{12}$, $C_6$-$C_{10}$, or phenyl). In embodiments, $R^{1B}$ is independently unsubstituted aryl (e.g., $C_6$-$C_{12}$, $C_6$-$C_{10}$, or phenyl). In embodiments, $R^{1B}$ is independently substituted or unsubstituted heteroaryl (e.g., 5 to 12 membered, 5 to 10 membered, 5 to 9 membered, or 5 to 6 membered). In embodiments, $R^{1B}$ is independently substituted heteroaryl (e.g., 5 to 12 membered, 5 to 10 membered, 5 to 9 membered, or 5 to 6 membered). In embodiments, $R^{1B}$ is independently unsubstituted heteroaryl (e.g., 5 to 12 membered, 5 to 10 membered, 5 to 9 membered, or 5 to 6 membered).

In embodiments, $R^{1A}$ and $R^{1B}$ substituents bonded to the same nitrogen atom may be joined to form a substituted or unsubstituted heterocycloalkyl (e.g., 3 to 8 membered, 3 to 6 membered, 4 to 6 membered, 4 to 5 membered, or 5 to 6 membered). In embodiments, $R^{1A}$ and $R^{1B}$ substituents bonded to the same nitrogen atom may be joined to form a substituted heterocycloalkyl (e.g., 3 to 8 membered, 3 to 6 membered, 4 to 6 membered, 4 to 5 membered, or 5 to 6 membered). In embodiments, $R^{1A}$ and $R^{1B}$ substituents bonded to the same nitrogen atom may be joined to form an unsubstituted heterocycloalkyl (e.g., 3 to 8 membered, 3 to 6 membered, 4 to 6 membered, 4 to 5 membered, or 5 to 6 membered).

In embodiments, $R^{1A}$ and $R^{1B}$ substituents bonded to the same nitrogen atom may be joined to form a substituted or unsubstituted heteroaryl (e.g., 5 to 12 membered, 5 to 10 membered, 5 to 9 membered, or 5 to 6 membered). In embodiments, $R^{1A}$ and $R^{1B}$ substituents bonded to the same nitrogen atom may be joined to form a substituted heteroaryl (e.g., 5 to 12 membered, 5 to 10 membered, 5 to 9 membered, or 5 to 6 membered). In embodiments, $R^{1A}$ and $R^{1B}$ substituents bonded to the same nitrogen atom may be joined to form an unsubstituted heteroaryl (e.g., 5 to 12 membered, 5 to 10 membered, 5 to 9 membered, or 5 to 6 membered).

In embodiments, $R^{1B}$ is independently hydrogen, —$CX^{1B}{}_3$, —$CHX^{1B}{}_2$, —$CH_2X^{1B}$, —CN, —COOH, —$CONH_2$, $R^{20B}$-substituted or unsubstituted alkyl (e.g., $C_1$-$C_8$, $C_1$-$C_6$, $C_1$-$C_4$, or $C_1$-$C_2$), $R^{20B}$-substituted or unsubstituted heteroalkyl (e.g., 2 to 8 membered, 2 to 6 membered, 4 to 6 membered, 2 to 3 membered, or 4 to 5 membered), $R^{20B}$-substituted or unsubstituted cycloalkyl (e.g., $C_3$-$C_8$, $C_3$-$C_6$, $C_4$-$C_6$, or $C_5$-$C_6$), $R^{20B}$-substituted or unsubstituted heterocycloalkyl (e.g., 3 to 8 membered, 3 to 6 membered, 4 to 6 membered, 4 to 5 membered, or 5 to 6 membered), $R^{20B}$-substituted or unsubstituted aryl (e.g., $C_6$-$C_{12}$, $C_6$-$C_{10}$, or phenyl), or $R^{20B}$-substituted or unsubstituted heteroaryl (e.g., 5 to 12 membered, 5 to 10 membered, 5 to 9 membered, or 5 to 6 membered). In embodiments, $R^{1B}$ is independently hydrogen, —$CX^{1B}{}_3$, —$CHX^{1B}{}_2$, —$CH_2X^{1B}$, —CN, —COOH, —$CONH_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered). $X^{1B}$ is independently —F, —Cl, —Br, or —I. In embodiments, $R^{1B}$ is independently hydrogen. In embodiments, $R^{1B}$ is independently unsubstituted methyl. In embodiments, $R^{1B}$ is independently unsubstituted ethyl.

In embodiments, $R^{1A}$ and $R^{1B}$ substituents bonded to the same nitrogen atom may optionally be joined to form a $R^{20B}$-substituted or unsubstituted heterocycloalkyl (e.g., 3 to 8 membered, 3 to 6 membered, 4 to 6 membered, 4 to 5 membered, or 5 to 6 membered) or $R^{20B}$-substituted or unsubstituted heteroaryl (e.g., 5 to 12 membered, 5 to 10 membered, 5 to 9 membered, or 5 to 6 membered). In embodiments, $R^{1A}$ and $R^{1B}$ substituents bonded to the same nitrogen atom may optionally be joined to form an unsubstituted heterocycloalkyl (e.g., 3 to 8 membered, 3 to 6 membered, 4 to 6 membered, 4 to 5 membered, or 5 to 6 membered) or unsubstituted heteroaryl (e.g., 5 to 12 membered, 5 to 10 membered, 5 to 9 membered, or 5 to 6 membered). In embodiments, $R^{1A}$ and $R^{1B}$ substituents bonded to the same nitrogen atom may optionally be joined to form a $R^{20B}$-substituted or unsubstituted heterocycloalkyl (e.g., 3 to 8 membered, 3 to 6 membered, 4 to 6 membered, 4 to 5 membered, or 5 to 6 membered). In embodiments, $R^{1A}$ and $R^{1B}$ substituents bonded to the same nitrogen atom may optionally be joined to form an unsubstituted heterocycloalkyl (e.g., 3 to 8 membered, 3 to 6 membered, 4 to 6 membered, 4 to 5 membered, or 5 to 6 membered).

$R^{20B}$ is independently oxo, halogen, —$CX^{20B}_3$, —$CHX^{20B}_2$, —$CH_2X^{20B}$, —$OCX^{20B}_3$, —$OCH_2X^{20B}$, —$OCHX^{20B}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, $R^{21B}$-substituted or unsubstituted alkyl (e.g., $C_1$-$C_8$, $C_1$-$C_6$, $C_1$-$C_4$, or $C_1$-$C_2$), $R^{21B}$-substituted or unsubstituted heteroalkyl (e.g., 2 to 8 membered, 2 to 6 membered, 4 to 6 membered, 2 to 3 membered, or 4 to 5 membered), $R^{21B}$-substituted or unsubstituted cycloalkyl (e.g., $C_3$-$C_8$, $C_3$-$C_6$, $C_4$-$C_6$, or $C_5$-$C_6$), $R^{21B}$-substituted or unsubstituted heterocycloalkyl (e.g., 3 to 8 membered, 3 to 6 membered, 4 to 6 membered, 4 to 5 membered, or 5 to 6 membered), $R^{21B}$-substituted or unsubstituted aryl (e.g., $C_6$-$C_{12}$, $C_6$-$C_{10}$, or phenyl), or $R^{21B}$-substituted or unsubstituted heteroaryl (e.g., 5 to 12 membered, 5 to 10 membered, 5 to 9 membered, or 5 to 6 membered). In embodiments, $R^{20B}$ is independently oxo, halogen, —$CX^{20B}_3$, —$CHX^{20B}_2$, —$CH_2X^{20B}$, —$OCX^{20B}_3$, —$OCH_2X^{20B}$, —$OCHX^{20B}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered). $X^{20B}$ is independently —F, —Cl, —Br, or —I. In embodiments, $R^{20B}$ is independently unsubstituted methyl. In embodiments, $R^{20B}$ is independently unsubstituted ethyl.

$R^{21B}$ is independently oxo, halogen, —$CX^{21B}_3$, —$CHX^{21B}_2$, —$CH_2X^{21B}$, —$OCX^{21B}_3$, —$OCH_2X^{21B}$, —$OCHX^{21B}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, $R^{22B}$-substituted or unsubstituted alkyl (e.g., $C_1$-$C_8$, $C_1$-$C_6$, $C_1$-$C_4$, or $C_1$-$C_2$), $R^{22B}$-substituted or unsubstituted heteroalkyl (e.g., 2 to 8 membered, 2 to 6 membered, 4 to 6 membered, 2 to 3 membered, or 4 to 5 membered), $R^{22B}$-substituted or unsubstituted cycloalkyl (e.g., $C_3$-$C_8$, $C_3$-$C_6$, $C_4$-$C_6$, or $C_5$-$C_6$), $R^{22B}$-substituted or unsubstituted heterocycloalkyl (e.g., 3 to 8 membered, 3 to 6 membered, 4 to 6 membered, 4 to 5 membered, or 5 to 6 membered), $R^{22B}$-substituted or unsubstituted aryl (e.g., $C_6$-$C_{12}$, $C_6$-$C_{10}$, or phenyl), or $R^{22B}$-substituted or unsubstituted heteroaryl (e.g., 5 to 12 membered, 5 to 10 membered, 5 to 9 membered, or 5 to 6 membered). In embodiments, $R^{21B}$ is independently oxo, halogen, —$CX^{21B}_3$, —$CHX^{21B}_2$, —$CH_2X^{21B}$, —$OCX^{21B}_3$, —$OCH_2X^{21B}$, —$OCHX^{21B}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered). $X^{21B}$ is independently —F, —Cl, —Br, or —I. In embodiments, $R^{21B}$ is independently unsubstituted methyl. In embodiments, $R^{21B}$ is independently unsubstituted ethyl.

$R^{22B}$ is independently oxo, halogen, —$CX^{22B}_3$, —$CHX^{22B}_2$, —$CH_2X^{22B}$, —$OCX^{22B}_3$, —$OCH_2X^{22B}$, —$OCHX^{22B}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered). $X^{22B}$ is independently —F, —Cl, —Br, or —I. In embodiments, $R^{22B}$ is independently unsubstituted methyl. In embodiments, $R^{22B}$ is independently unsubstituted ethyl.

In embodiments, $R^{1C}$ is independently hydrogen. In embodiments, $R^{1C}$ is independently —$CX^{1C}_3$. In embodiments, $R^{1C}$ is independently —$CHX^{1C}_2$. In embodiments, $R^{1C}$ is independently —$CH_2X^{1C}$. In embodiments, $R^{1C}$ is independently —CN. In embodiments, $R^{1C}$ is independently —COOH. In embodiments, $R^{1C}$ is independently —$CONH_2$. In embodiments, $X^{1C}$ is independently —F, —Cl, —Br, or —I.

In embodiments, $R^{1C}$ is independently substituted or unsubstituted alkyl (e.g., $C_1$-$C_8$, $C_1$-$C_6$, $C_1$-$C_4$, or $C_1$-$C_2$). In embodiments, $R^{1C}$ is independently substituted alkyl (e.g., $C_1$-$C_8$, $C_1$-$C_6$, $C_1$-$C_4$, or $C_1$-$C_2$). In embodiments, $R^{1C}$ is independently unsubstituted alkyl (e.g., $C_1$-$C_8$, $C_1$-$C_6$, $C_1$-$C_4$, or $C_1$-$C_2$). In embodiments, $R^{1C}$ is independently unsubstituted methyl. In embodiments, $R^{1C}$ is independently unsubstituted ethyl. In embodiments, $R^{1C}$ is independently unsubstituted propyl. In embodiments, $R^{1C}$ is independently unsubstituted isopropyl. In embodiments, $R^{1C}$ is independently unsubstituted tert-butyl. In embodiments, $R^{1C}$ is independently substituted or unsubstituted heteroalkyl (e.g., 2 to 8 membered, 2 to 6 membered, 4 to 6 membered, 2 to 3 membered, or 4 to 5 membered). In embodiments, $R^{1C}$ is independently substituted heteroalkyl (e.g., 2 to 8 membered, 2 to 6 membered, 4 to 6 membered, 2 to 3 membered, or 4 to 5 membered). In embodiments, $R^{1C}$ is independently unsubstituted heteroalkyl (e.g., 2 to 8 membered, 2 to 6 membered, 4 to 6 membered, 2 to 3 membered, or 4 to 5 membered). In embodiments, $R^{1C}$ is independently substituted or unsubstituted cycloalkyl (e.g., $C_3$-$C_8$, $C_3$-$C_6$, $C_4$-$C_6$, or $C_5$-$C_6$). In embodiments, $R^{1C}$ is independently substituted cycloalkyl (e.g., $C_3$-$C_8$, $C_3$-$C_6$, $C_4$-$C_6$, or $C_5$-$C_6$). In embodiments, $R^{1C}$ is independently unsubstituted cycloalkyl (e.g., $C_3$-$C_8$, $C_3$-$C_6$, $C_4$-$C_6$, or $C_5$-$C_6$). In embodiments, $R^{1C}$ is independently substituted or unsubstituted heterocycloalkyl (e.g., 3 to 8 membered, 3 to 6 membered, 4 to 6 membered, 4 to 5 membered, or 5 to 6 membered). In embodiments, $R^{1C}$ is independently substituted heterocycloalkyl (e.g., 3 to 8 membered, 3 to 6 membered, 4 to 6 membered, 4 to 5 membered, or 5 to 6 membered). In embodiments, $R^{1C}$ is independently unsubstituted heterocycloalkyl (e.g., 3 to 8 membered, 3 to 6 membered, 4 to 6 membered, 4 to 5 membered, or 5 to 6 membered). In embodiments, $R^{1C}$ is independently substituted or unsubstituted aryl (e.g., $C_6$-$C_{12}$, $C_6$-$C_{10}$, or phenyl). In embodiments, $R^{1C}$ is independently substituted aryl (e.g., $C_6$-$C_{12}$, $C_6$-$C_{10}$, or phenyl). In embodiments, $R^{1C}$ is independently unsubstituted aryl (e.g., $C_6$-$C_{12}$, $C_6$-$C_{10}$, or phenyl). In embodiments, $R^{1C}$ is independently substituted or unsubstituted heteroaryl (e.g., 5 to 12 membered, 5 to 10 membered, 5 to 9 membered, or 5 to 6 membered). In embodiments, $R^{1C}$ is independently substituted heteroaryl (e.g., 5 to 12 membered, 5 to 10 membered, 5 to 9 membered, or 5 to 6 membered). In embodiments, $R^{1C}$ is independently unsubstituted heteroaryl (e.g., 5 to 12 membered, 5 to 10 membered, 5 to 9 membered, or 5 to 6 membered).

In embodiments, $R^{1C}$ is independently hydrogen, —$CX^{1C}_3$, —$CHX^{1C}_2$, —$CH_2X^{1C}$, —CN, —COOH, —$CONH_2$, $R^{20C}$-substituted or unsubstituted alkyl (e.g., $C_1$-$C_8$, $C_1$-$C_6$, $C_1$-$C_4$, or $C_1$-$C_2$), $R^{20C}$-substituted or unsubstituted heteroalkyl (e.g., 2 to 8 membered, 2 to 6 membered, 4 to 6 membered, 2 to 3 membered, or 4 to 5 membered), $R^{20C}$-substituted or unsubstituted cycloalkyl (e.g., $C_3$-$C_8$, $C_3$-$C_6$, $C_4$-$C_6$, or $C_5$-$C_6$), $R^{20C}$-substituted or unsubstituted heterocycloalkyl (e.g., 3 to 8 membered, 3 to 6 membered, 4 to 6 membered, 4 to 5 membered, or 5 to 6 membered), $R^{20C}$-substituted or unsubstituted aryl (e.g., $C_6$-$C_{12}$, $C_6$-$C_{10}$, or phenyl), or $R^{20C}$-substituted or unsubstituted heteroaryl (e.g., 5 to 12 membered, 5 to 10 membered, 5 to 9 membered, or 5 to 6 membered). In embodiments, $R^{1C}$ is independently hydrogen, —$CX^{1C}_3$, —$CHX^{1C}_2$, —$CH_2X^{1C}$, —CN, —COOH, —$CONH_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered). $X^{1C}$ is independently —F, —Cl, —Br, or —I. In embodiments, $R^{1C}$ is independently hydrogen. In embodiments, $R^{1C}$ is independently unsubstituted methyl. In embodiments, $R^{1C}$ is independently unsubstituted ethyl.

$R^{20C}$ is independently oxo, halogen, —$CX^{20C}_3$, —$CHX^{20C}_2$, —$CH_2X^{20C}$, —$OCX^{20C}_3$, —$OCH_2X^{20C}$, —$OCHX^{20C}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, $R^{21C}$-substituted or unsubstituted alkyl (e.g., $C_1$-$C_8$, $C_1$-$C_6$, $C_1$-$C_4$, or $C_1$-$C_2$), $R^{21C}$-substituted or unsubstituted heteroalkyl (e.g., 2 to 8 membered, 2 to 6 membered, 4 to 6 membered, 2 to 3 membered, or 4 to 5 membered), $R^{21C}$-substituted or unsubstituted cycloalkyl (e.g., $C_3$-$C_8$, $C_3$-$C_6$, $C_4$-$C_6$, or $C_5$-$C_6$), $R^{21C}$-substituted or unsubstituted heterocycloalkyl (e.g., 3 to 8 membered, 3 to 6 membered, 4 to 6 membered, 4 to 5 membered, or 5 to 6 membered), $R^{21C}$-substituted or unsubstituted aryl (e.g., $C_6$-$C_{12}$, $C_6$-$C_{10}$, or phenyl), or $R^{21C}$-substituted or unsubstituted heteroaryl (e.g., 5 to 12 membered, 5 to 10 membered, 5 to 9 membered, or 5 to 6 membered). In embodiments, $R^{20C}$ is independently oxo, halogen, —$CX^{20C}_3$, —$CHX^{20C}_2$, —$CH_2X^{20C}$, —$OCX^{20C}_3$, —$OCH_2X^{20C}$, —$OCHX^{20C}_2$, —CN, —OH, —$NH_2$, —COOH, —$CONH_2$, —$NO_2$, —SH, —$SO_3H$, —$SO_4H$, —$SO_2NH_2$, —$NHNH_2$, —NHC=(O)$NHNH_2$, —NHC=(O)$NH_2$, —$NHSO_2H$, —NHC=(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered). $X^{20C}$ is independently —F, —Cl, —Br, or —I. In embodiments, $R^{20C}$ is independently unsubstituted methyl. In embodiments, $R^{20C}$ is independently unsubstituted ethyl.

$R^{21C}$ is independently oxo, halogen, —$CX^{21C}_3$, —$CHX^{21C}_2$, —$CH_2X^{21C}$, —$OCX^{21C}_3$, —$OCH_2X^{21C}$, —$OCHX^{21C}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, $R^{22C}$-substituted or unsubstituted alkyl (e.g., $C_1$-$C_8$, $C_1$-$C_6$, $C_1$-$C_4$, or $C_1$-$C_2$), $R^{22C}$-substituted or unsubstituted heteroalkyl (e.g., 2 to 8 membered, 2 to 6 membered, 4 to 6 membered, 2 to 3 membered, or 4 to 5 membered), $R^{22C}$-substituted or unsubstituted cycloalkyl (e.g., $C_3$-$C_8$, $C_3$-$C_6$, $C_4$-$C_6$, or $C_5$-$C_6$), $R^{22C}$-substituted or unsubstituted heterocycloalkyl (e.g., 3 to 8 membered, 3 to 6 membered, 4 to 6 membered, 4 to 5 membered, or 5 to 6 membered), $R^{22C}$-substituted or unsubstituted aryl (e.g., $C_6$-$C_{12}$, $C_6$-$C_{10}$, or phenyl), or $R^{22C}$-substituted or unsubstituted heteroaryl (e.g., 5 to 12 membered, 5 to 10 membered, 5 to 9 membered, or 5 to 6 membered). In embodiments, $R^{21C}$ is independently oxo, halogen, —$CX^{21C}_3$, —$CHX^{21C}_2$, —$CH_2X^{21C}$, —$OCX^{21C}_3$, —$OCH_2X^{21C}$, —$OCHX^{21C}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered). $X^{21C}$ is independently —F, —Cl, —Br, or —I. In embodiments, $R^{21C}$ is independently unsubstituted methyl. In embodiments, $R^{21C}$ is independently unsubstituted ethyl.

$R^{22C}$ is independently oxo, halogen, —$CX^{22C}_3$, —$CHX^{22C}_2$, —$CH_2X^{22C}$, —$OCX^{22C}_3$, —$OCH_2X^{22C}$, —$OCHX^{22C}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered). $X^{22C}$ is independently —F, —Cl, —Br, or —I. In embodiments, $R^{22C}$ is independently unsubstituted methyl. In embodiments, $R^{22C}$ is independently unsubstituted ethyl.

In embodiments, $R^{1D}$ is independently hydrogen. In embodiments, $R^{1D}$ is independently —$CX^{1D}_3$. In embodiments, $R^{1D}$ is independently —$CHX^{1D}2$. In embodiments, $R^{1D}$ is independently —$CH_2X^{1D}$. In embodiments, $R^{1D}$ is independently —CN. In embodiments, $R^{1D}$ is independently —COOH. In embodiments, $R^{1D}$ is independently —$CONH_2$. In embodiments, $X^{1D}$ is independently —F, —Cl, —Br, or —I.

In embodiments, $R^{1D}$ is independently substituted or unsubstituted alkyl (e.g., $C_1$-$C_8$, $C_1$-$C_6$, $C_1$-$C_4$, or $C_1$-$C_2$). In embodiments, $R^{1D}$ is independently substituted alkyl (e.g., $C_1$-$C_8$, $C_1$-$C_6$, $C_1$-$C_4$, or $C_1$-$C_2$). In embodiments, $R^{1D}$ is independently unsubstituted alkyl (e.g., $C_1$-$C_8$, $C_1$-$C_6$, $C_1$-$C_4$, or $C_1$-$C_2$). In embodiments, $R^{1D}$ is independently unsubstituted methyl. In embodiments, $R^{1D}$ is independently unsubstituted ethyl. In embodiments, $R^{1D}$ is independently unsubstituted propyl. In embodiments, $R^{1D}$ is independently unsubstituted isopropyl. In embodiments, $R^{1D}$ is independently unsubstituted tert-butyl. In embodiments, $R^{1D}$ is independently substituted or unsubstituted heteroalkyl (e.g., 2 to 8 membered, 2 to 6 membered, 4 to 6 membered, 2 to 3 membered, or 4 to 5 membered). In embodiments, $R^{1D}$ is independently substituted heteroalkyl (e.g., 2 to 8 membered, 2 to 6 membered, 4 to 6 membered, 2 to 3 membered, or 4 to 5 membered). In embodiments, $R^{1D}$ is independently unsubstituted heteroalkyl (e.g., 2 to 8 membered, 2 to 6 membered, 4 to 6 membered, 2 to 3 membered, or 4 to 5 membered). In embodiments, $R^{1D}$ is independently substituted or unsubstituted cycloalkyl (e.g., $C_3$-$C_8$, $C_3$-$C_6$, $C_4$-$C_6$, or $C_5$-$C_6$). In embodiments, $R^{1D}$ is independently substituted cycloalkyl (e.g., $C_3$-$C_8$, $C_3$-$C_6$, $C_4$-$C_6$, or $C_5$-$C_6$). In embodiments, $R^{1D}$ is independently unsubstituted cycloalkyl (e.g., $C_3$-$C_8$, $C_3$-$C_6$, $C_4$-$C_6$, or $C_5$-$C_6$). In embodiments, $R^{1D}$ is independently substituted or unsubstituted heterocycloalkyl (e.g., 3 to 8 membered, 3 to 6 membered, 4 to 6 membered, 4 to 5 membered, or 5 to 6 membered). In embodiments, $R^{1D}$ is independently substituted heterocycloalkyl (e.g., 3 to 8 membered, 3 to 6 membered, 4 to 6 membered, 4 to 5 membered, or 5 to 6 membered). In embodiments, $R^{1D}$ is independently unsubstituted heterocycloalkyl (e.g., 3 to 8 membered, 4 to 6 membered, 4 to 5 membered, or 5 to 6 membered). In embodiments, $R^{1D}$ is independently substituted or unsubstituted aryl (e.g., $C_6$-$C_{12}$, $C_6$-$C_{10}$, or phenyl). In embodiments, $R^{1D}$ is independently substituted aryl (e.g., $C_6$-$C_{12}$, $C_6$-$C_{10}$, or phenyl). In embodiments, $R^{1D}$ is independently unsubstituted aryl (e.g., $C_6$-$C_{12}$, $C_6$-$C_{10}$, or phenyl). In embodiments, $R^{1D}$ is independently substituted or unsubstituted heteroaryl (e.g., 5 to 12 membered, 5 to 10 membered, 5 to 9 membered, or 5 to 6 membered). In embodiments, $R^{1D}$ is independently substituted heteroaryl (e.g., 5 to 12 membered, 5 to 10 membered, 5 to 9 membered, or 5 to 6 membered). In embodiments, $R^{1D}$ is independently unsubstituted heteroaryl (e.g., 5 to 12 membered, 5 to 10 membered, 5 to 9 membered, or 5 to 6 membered).

In embodiments, $R^{1D}$ is independently hydrogen, —$CX^{1D}_3$, —$CHX^{1D}_2$, —$CH_2X^{1D}$, —CN, —COOH, —$CONH_2$, $R^{20D}$-substituted or unsubstituted alkyl (e.g., $C_1$-$C_8$, $C_1$-$C_6$, $C_1$-$C_4$, or $C_1$-$C_2$), $R^{20D}$-substituted or unsubstituted heteroalkyl (e.g., 2 to 8 membered, 2 to 6 membered, 4 to 6 membered, 2 to 3 membered, or 4 to 5 membered), $R^{20D}$-substituted or unsubstituted cycloalkyl (e.g., $C_3$-$C_8$, $C_3$-$C_6$, $C_4$-$C_6$, or $C_5$-$C_6$), $R^{20D}$-substituted or unsubstituted heterocycloalkyl (e.g., 3 to 8 membered, 3 to 6 membered, 4 to 6 membered, 4 to 5 membered, or 5 to 6 membered), $R^{20D}$-substituted or unsubstituted aryl (e.g., $C_6$-$C_{12}$, $C_6$-$C_{10}$, or phenyl), or $R^{20D}$-substituted or unsubstituted heteroaryl (e.g., 5 to 12 membered, 5 to 10 membered, 5 to 9 membered, or 5 to 6 membered). In embodiments, $R^{1D}$ is independently hydrogen, —$CX^{1D}_3$, —$CHX^{1D}_2$, —$CH_2X^{1D}$, —CN, —COOH, —$CONH_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered). $X^{1D}$ is independently —F, —Cl, —Br, or —I. In embodiments, $R^{1D}$ is independently hydrogen. In embodiments, $R^{1D}$ is independently unsubstituted methyl. In embodiments, $R^{1D}$ is independently unsubstituted ethyl.

$R^{20D}$ is independently oxo, halogen, —$CX^{20D}_3$, —$CHX^{20D}_2$, —$CH_2X^{20D}$, —$OCX^{20D}_3$, —$OCH_2X^{20D}$, —$OCHX^{20D}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, $R^{21D}$-substituted or unsubstituted alkyl (e.g., $C_1$-$C_8$, $C_1$-$C_6$, $C_1$-$C_4$, or $C_1$-$C_2$), $R^{21D}$-substituted or unsubstituted heteroalkyl (e.g., 2 to 8 membered, 2 to 6 membered, 4 to 6 membered, 2 to 3 membered, or 4 to 5 membered), $R^{21D}$-substituted or unsubstituted cycloalkyl (e.g., $C_3$-$C_8$, $C_3$-$C_6$, $C_4$-$C_6$, or $C_5$-$C_6$), $R^{21D}$-substituted or unsubstituted heterocycloalkyl (e.g., 3 to 8 membered, 3 to 6 membered, 4 to 6 membered, 4 to 5 membered, or 5 to 6 membered), $R^{21D}$-substituted or unsubstituted aryl (e.g., $C_6$-$C_{12}$, $C_6$-$C_{10}$, or phenyl), or $R^{21D}$-substituted or unsubstituted heteroaryl (e.g., 5 to 12 membered, 5 to 10 membered, 5 to 9 membered, or 5 to 6 membered). In embodiments, $R^{20D}$ is independently oxo, halogen, —$CX^{20D}_3$, —$CHX^{20D}_2$, —$CH_2X^{20D}$, —$OCX^{20D}_3$, —$OCH_2X^{20D}$, —$OCHX^{20D}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered). $X^{20D}$ is independently —F, —Cl, —Br, or —I. In embodiments, $R^{20D}$ is independently unsubstituted methyl. In embodiments, $R^{20D}$ is independently unsubstituted ethyl.

$R^{21D}$ is independently oxo, halogen, —$CX^{21D}_3$, —$CHX^{21D}_2$, —$CH_2X^{21D}$, —$OCX^{21D}_3$, —$OCH_2X^{21D}$, —$OCHX^{21D}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, $R^{22D}$-substituted or unsubstituted alkyl (e.g., $C_1$-$C_8$, $C_1$-$C_6$, $C_1$-$C_4$, or $C_1$-$C_2$), $R^{22D}$-substituted or unsubstituted heteroalkyl (e.g., 2 to 8 membered, 2 to 6 membered, 4 to 6 membered, 2 to 3 membered, or 4 to 5 membered), $R^{22D}$-substituted or unsubstituted cycloalkyl (e.g., $C_3$-$C_8$, $C_3$-$C_6$, $C_4$-$C_6$, or $C_5$-$C_6$), $R^{22D}$-substituted or unsubstituted heterocycloalkyl (e.g., 3 to 8 membered, 3 to 6 membered, 4 to 6 membered, 4 to 5 membered, or 5 to 6 membered), $R^{22D}$-substituted or unsubstituted aryl (e.g., $C_6$-$C_{12}$, $C_6$-$C_{10}$, or phenyl), or $R^{22D}$-substituted or unsubstituted heteroaryl (e.g., 5 to 12 membered, 5 to 10 membered, 5 to 9 membered, or 5 to 6 membered). In embodiments, $R^{21D}$ is independently oxo, halogen, —$CX^{21D}_3$, —$CHX^{21D}_2$, —$CH_2X^{21D}$, —$OCX^{21D}_3$, —$OCH_2X^{21D}$, —$OCHX^{21D}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered). $X^{21D}$ is independently —F, —Cl, —Br, or —I. In embodiments, $R^{21D}$ is independently unsubstituted methyl. In embodiments, $R^{21D}$ is independently unsubstituted ethyl.

$R^{22D}$ is independently oxo, halogen, —$CX^{22D}_3$, —$CHX^{22D}_2$, —$CH_2X^{22D}$, —$OCX^{22D}_3$, —$OCH_2X^{22D}$, —$OCHX^{22D}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC=(O)$NH_2$, —$NHSO_2H$, —NHC=(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered). $X^{22D}$ is independently —F, —Cl, —Br, or —I. In embodiments, $R^{22D}$ is independently unsubstituted methyl. In embodiments, $R^{22D}$ is independently unsubstituted ethyl.

In embodiments, $R^1$ is substituted or unsubstituted alkyl or substituted or unsubstituted heteroalkyl. In embodiments, $R^1$ is substituted or unsubstituted $C_1$-$C_6$ alkyl or substituted or unsubstituted 2 to 6 heteroalkyl. In embodiments, $R^1$ is $R^{20}$-substituted or unsubstituted $C_1$-$C_6$ alkyl or $R^{20}$-substituted or unsubstituted 2 to 6 heteroalkyl; In embodiments, $R^1$ is -(unsubstituted $C_2$-$C_4$ alkylene)-C(O)O-(unsubstituted $C_1$-$C_3$ alkyl). In embodiments, $R^1$ is -(unsubstituted $C_2$-$C_4$ alkylene)-C(O)$OCH_3$. In embodiments, $R^1$ is —$CH_2CH(CH_3)C(O)OCH_3$. In embodiments, $R^1$ is unsubstituted $C_1$-$C_6$ alkyl. In embodiments, $R^1$ is unsubstituted $C_2$-$C_4$ alkyl. In embodiments, $R^1$ is unsubstituted isopropyl.

In embodiments, $R^1$ is substituted or unsubstituted $C_1$-$C_6$ alkyl. In embodiments, $R^1$ is unsubstituted $C_1$-$C_3$ alkyl. In embodiments, $R^1$ is —$CH_3$. In embodiments, $L^{1A}$ is a bond. In embodiments, $L^{1B}$ is a bond. In embodiments, $R^1$ is independently substituted or unsubstituted heteroalkyl (e.g., 2 to 8 membered, 2 to 6 membered, 4 to 6 membered, 2 to 3 membered, or 4 to 5 membered). In embodiments, $R^1$ is independently $R^{20}$-substituted heteroalkyl (e.g., 2 to 8 membered, 2 to 6 membered, 4 to 6 membered, 2 to 3 membered, or 4 to 5 membered). In embodiments, $R^1$ is independently $R^{20}$-substituted 2 to 8 membered heteroalkyl. In embodiments, $R^1$ is independently $R^{20}$-substituted 2 to 6 membered heteroalkyl. In embodiments, $R^1$ is independently $R^{20}$-substituted 4 to 8 membered heteroalkyl. In embodiments, $R^1$ is independently $R^{20}$-substituted 4 to 6 membered heteroalkyl. In embodiments, $R^1$ is independently $R^{20}$-substituted 5 to 8 membered heteroalkyl. In embodiments, $R^{20}$ is oxo.

In embodiments, $R^2$ is independently hydrogen, —$CX^2_3$, —$CHX^2_2$, —$CH_2X^2$, —$C(O)R^{2A}$, —$C(O)OR^{2A}$, —$C(O)NR^{2A}R^{2B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In embodiments, $R^2$ is independently hydrogen, —$CX^2_3$, —$CHX^2_2$, —$CH_2X^2$, —$C(O)CH_3$, —$C(O)OH$, —$C(O)NH_2$, substituted or unsubstituted $C_1$-$C_8$ alkyl, substituted or unsubstituted 2 to 8 membered heteroalkyl; substituted or unsubstituted $C_3$-$C_8$ cycloalkyl, substituted or unsubstituted 3 to 8 membered heterocycloalkyl, substituted or unsubstituted $C_6$-$C_{12}$ aryl, or substituted or unsubstituted 5 to 12 membered heteroaryl.

In embodiments, $R^2$ is independently hydrogen, —$CX^2_3$, —$CHX^2_2$, —$CH_2X^2$, —$C(O)CH_3$, —$C(O)OH$, —$C(O)NH_2$, substituted or unsubstituted $C_1$-$C_8$ alkyl, substituted or unsubstituted 2 to 8 membered heteroalkyl; substituted or unsubstituted $C_3$-$C_8$ cycloalkyl, substituted or unsubstituted 3 to 8 membered heterocycloalkyl, substituted or unsubstituted phenyl, or substituted or unsubstituted 5 to 6 membered heteroaryl.

In embodiments, $R^2$ is independently hydrogen. In embodiments, $R^2$ is independently —$CX^2_3$. In embodiments, $R^2$ is independently —$CHX^2_2$. In embodiments, $R^2$ is independently —$CH_2X^2$. In embodiments, $R^2$ is independently —$C(O)R^{2A}$. In embodiments, $R^2$ is independently —C(O)—$OR^{2A}$. In embodiments, $R^2$ is independently —$C(O)NR^{2A}R^{2B}$. In embodiments, $R^2$ is independently —COOH. In embodiments, $R^2$ is independently —$CONH_2$.

In embodiments, R² is independently —CF₃. In embodiments, R² is independently —CHF₂. In embodiments, R² is independently —CH₂F. In embodiments, R² is independently —CH₃. In embodiments, R² is independently —CH₂CH₃. In embodiments, R² is independently —CH₂CH₂CH₃. In embodiments, R² is independently —CH(CH₃)₂. In embodiments, R² is independently —C(CH₃)₃. In embodiments, R² is independently —C(O)CF₃. In embodiments, R² is independently —C(O)CHF₂. In embodiments, R² is independently —C(O)CH₂F. In embodiments, R² is independently —C(O)CH₃. In embodiments, R² is independently —C(O)CH₂CH₃. In embodiments, R² is independently —C(O)CH₂CH₂CH₃. In embodiments, R² is independently —C(O)CH(CH₃)₂. In embodiments, R² is independently —C(O)C(CH₃)₃.

In embodiments, R² is

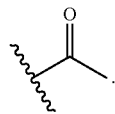 [SMILES: *C(C)=O]

In embodiments, R² is

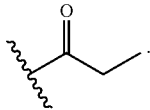 [SMILES: *C(=O)CC]

In embodiments, R² is

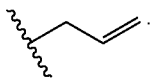 [SMILES: *CC=C]

In embodiments, R² is

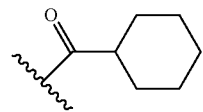

In embodiments, R² is

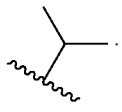 [SMILES: *C(C)C]

In embodiments, R² is

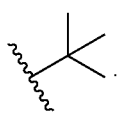

In embodiments, R² is

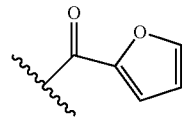 [SMILES: *C(=O)c1ccco1]

In embodiments, R² is

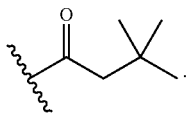 [SMILES: *C(=O)CC(C)(C)C]

In embodiments, R² is

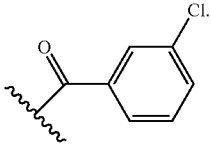

In embodiments, R² is

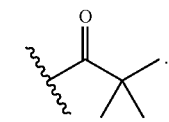 [SMILES: *C(=O)C(C)(C)C]

In embodiments, R² is

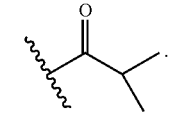 [SMILES: *C(=O)C(C)C]

In embodiments, R² is

In embodiments, R² is

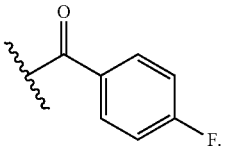 [SMILES: *C(=O)c1ccc(F)cc1]

In embodiments, R² is
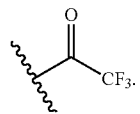 [SMILES: *C(=O)C(F)(F)F]
In embodiments, R² is
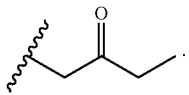 [SMILES: *CC(=O)CC]
In embodiments, R² is
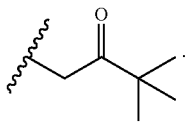 [SMILES: *CC(=O)C(C)(C)C]
In embodiments, R² is
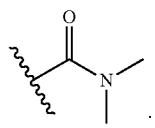 [SMILES: *C(=O)N(C)C]
In embodiments, R² is
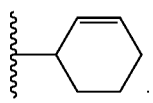 [SMILES: *C1C=CCCC1]
In embodiments, R² is
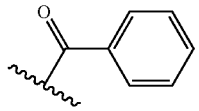
In embodiments, R² is
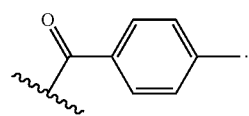 [SMILES: *C(=O)c1ccc(C)cc1]
In embodiments, R² is
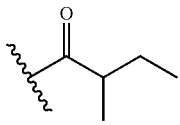 [SMILES: *C(=O)C(C)CC]
In embodiments, R² is
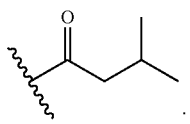 [SMILES: *C(=O)CC(C)C]
In embodiments, R² is
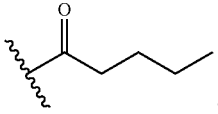
In embodiments, R² is
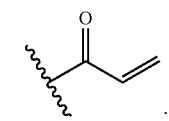
In embodiments, R² is
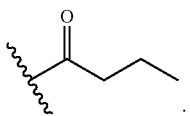 [SMILES: *C(=O)CCC]
In embodiments, R² is
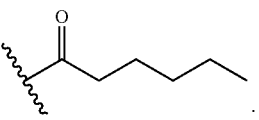 [SMILES: *C(=O)CCCCC]

In embodiments, R² is
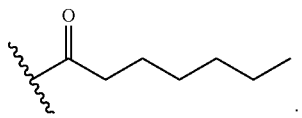 [SMILES: *C(=O)CCCCCC]
In embodiments, R² is
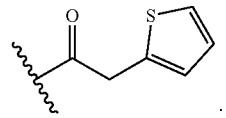
In embodiments, R² is
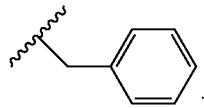
In embodiments, R² is
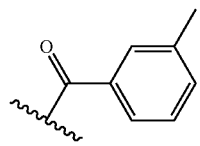 [SMILES: *C(=O)c1cccc(C)c1]
In embodiments, R² is
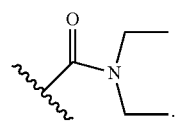
In embodiments, R² is
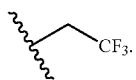
In embodiments, R² is
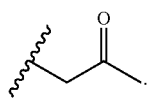 [SMILES: *CC(C)=O]
In embodiments, R² is
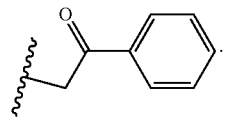 [SMILES: *CC(=O)c1ccccc1]
In embodiments, R² is
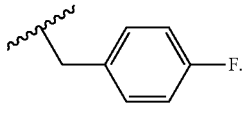 [SMILES: *Cc1ccc(F)cc1]
In embodiments, R² is
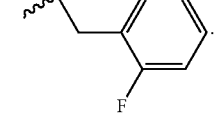
In embodiments, R² is
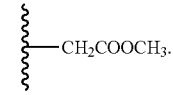
In embodiments, R² is
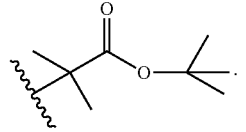 [SMILES: *C(C)(C)C(=O)OC(C)(C)C]
In embodiments, R² is
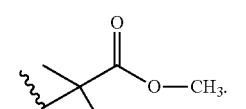
In embodiments, R² is
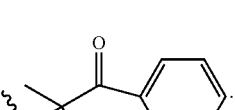
In embodiments, R² is

In embodiments, $R^2$ is

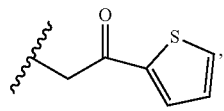 [SMILES: *CC(=O)c1cccs1]

In embodiments, $R^2$ is

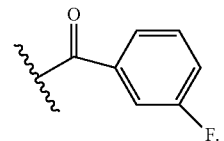 [SMILES: *C(=O)c1cccc(F)c1]

In embodiments, $R^2$ is

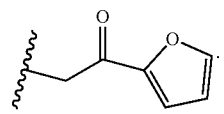 [SMILES: *CC(=O)c1ccco1]

In embodiments, $R^2$ is

In embodiments, $R^2$ is

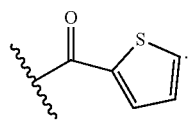 [SMILES: *C(=O)c1cccs1]

In embodiments, $R^2$ is

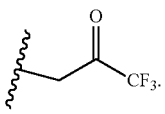 [SMILES: *CC(=O)C(F)(F)F]

In embodiments, $R^2$ is

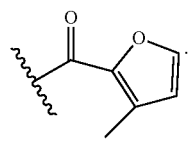 [SMILES: *C(=O)c1occc1C]

In embodiments, $R^2$ is independently —C(O)$R^{2A}$. In embodiments, $R^{2A}$ is independently methyl. In embodiments, $R^{2A}$ is independently ethyl. In embodiments, $R^{2A}$ is independently unsubstituted $C_1$-$C_8$ alkyl. In embodiments, $R^{2A}$ is independently unsubstituted $C_1$-$C_4$ haloalkyl. In embodiments, $R^{2A}$ is independently —C$X^{2A}_3$. In embodiments, $R^{2A}$ is independently —CH$X^{2A}_2$. In embodiments, $R^{2A}$ is independently —CH$_2$$X^{2A}$. In embodiments, $X^{2A}$ is independently —F, —Cl, —Br, or —I. In embodiments, $R^{2A}$ is independently cyclohexyl. In embodiments, $R^{2A}$ is independently cyclohexenyl. In embodiments, $R^{2A}$ is independently unsubstituted $C_4$-$C_7$ cycloalkyl. In embodiments, $R^{2A}$ is independently unsubstituted 4 to 7 membered heterocycloalkyl. In embodiments, $R^{2A}$ is independently substituted or unsubstituted $C_6$-$C_{12}$ aryl. In embodiments, $R^{2A}$ is independently substituted or unsubstituted phenyl. In embodiments, $R^{2A}$ is independently unsubstituted phenyl. In embodiments, $R^{2A}$ is independently $R^{23A}$-substituted phenyl. In embodiments, $R^{2A}$ is independently substituted or unsubstituted 5 to 12 membered heteroaryl. In embodiments, $R^{2A}$ is independently substituted or unsubstituted 5 to 6 membered heteroaryl. In embodiments, $R^{2A}$ is independently unsubstituted 5 to 6 membered heteroaryl. In embodiments, $R^{2A}$ is independently $R^{23A}$-substituted 5 to 6 membered heteroaryl. In embodiments, $R^{23A}$ is independently halogen, —C$X^{23A}_3$, —CH$X^{23A}_2$, —CH$_2$$X^{23A}$, —OC$X^{23A}_3$, —OCH$_2$$X^{23A}$, —OCH$X^{23A}_2$, unsubstituted alkyl (e.g., $C_1$-$C_4$, or $C_1$-$C_2$), or unsubstituted haloalkyl (e.g., $C_1$-$C_4$, or $C_1$-$C_2$). In embodiments, $X^{23A}$ is independently —F, —Cl, —Br, or —I.

In embodiments, $R^2$ is independently —C(O)N$R^{2A}R^{2B}$. In embodiments, $R^{2A}$ is independently hydrogen. In embodiments, $R^{2A}$ is independently methyl. In embodiments, $R^{2A}$ is independently ethyl. In embodiments, $R^{2A}$ is independently unsubstituted $C_1$-$C_4$ alkyl. In embodiments, $R^{2A}$ is independently unsubstituted $C_1$-$C_4$ haloalkyl. In embodiments, $R^{2A}$ is independently unsubstituted $C_1$-$C_4$ haloalkyl. In embodiments, $R^{2B}$ is independently hydrogen. In embodiments, $R^{2B}$ is independently methyl. In embodiments, $R^{2B}$ is independently ethyl. In embodiments, $R^{2B}$ is independently unsubstituted $C_1$-$C_4$ alkyl. In embodiments, $R^{2B}$ is independently unsubstituted $C_1$-$C_4$ haloalkyl. In embodiments, $R^{2B}$ is independently unsubstituted $C_1$-$C_4$ haloalkyl.

In embodiments, $R^2$ is independently substituted or unsubstituted $C_1$-$C_8$ alkyl (e.g., $C_1$-$C_8$, $C_1$-$C_6$, $C_1$-$C_4$, or $C_1$-$C_2$). In embodiments, $R^2$ is independently unsubstituted $C_1$-$C_8$ alkyl. In embodiments, $R^2$ is independently $R^{23}$-substituted $C_1$-$C_8$ alkyl. In embodiments, $R^2$ is independently $R^{23}$-substituted $C_1$-$C_4$ alkyl. In embodiments, $R^2$ is independently $R^{23}$-substituted $C_2$-$C_4$ alkenyl. In embodiments, $R^2$ is independently unsubstituted $C_2$-$C_4$ alkenyl. In embodiments, $R^2$ is independently substituted or unsubstituted $C_1$-$C_4$ haloalkyl (e.g., $C_1$-$C_4$, or $C_1$-$C_2$). In embodiments, $R^2$ is independently unsubstituted $C_1$-$C_4$ haloalkyl. In embodiments, $R^2$ is independently $R^{23}$-substituted $C_1$-$C_4$ haloalkyl. In embodiments, $R^2$ is independently $R^{23}$-substituted $C_1$-$C_2$ haloalkyl. In embodiments, $R^{23}$ is independently halogen, —C$X^{23}_3$, —CH$X^{23}_2$, —CH$_2$$X^{23}$, —OC$X^{23}_3$, —OCH$_2$$X^{23}$, —OCH$X^{23}_2$, —CN, —OH, —NH$_2$, —C(O)$R^{24}$, —COOH, —CONH$_2$, $R^{24}$-substituted or unsubstituted alkyl (e.g., $C_1$-$C_8$, $C_1$-$C_6$, $C_1$-$C_4$, or $C_1$-$C_2$), $R^{24}$-substituted or unsubstituted heteroalkyl (e.g., 2 to 6 membered, 4 to 6 membered, 2 to 3 membered, or 4 to 5 membered), $R^{24}$-substituted or unsubstituted phenyl, or $R^{24}$-substituted or unsubstituted 5 to 6 membered heteroaryl. In embodiments, $R^{24}$ is independently halogen, —C$X^{23A}_3$, —CH$X^{23A}_2$, —CH$_2$$X^{23A}$, —OC$X^{23A}_3$, —OCH$_2$$X^{23A}$, —OCH$X^{23A}_2$, unsubstituted alkyl (e.g., $C_1$-$C_4$, or $C_1$-$C_2$), or unsubstituted haloalkyl (e.g., $C_1$-$C_4$, or $C_1$-$C_2$). In embodiments, $X^{23A}$ is independently —F, —Cl, —Br, or —I. In embodiments, $R^{23}$ is independently oxo.

In embodiments, $R^2$ is independently unsubstituted cyclohexyl. In embodiments, $R^2$ is independently unsubstituted cyclohexenyl. In embodiments, $R^2$ is independently unsubstituted $C_4$-$C_7$ cycloalkyl. In embodiments, $R^2$ is independently unsubstituted $C_4$-$C_7$ cycloalkenyl. In embodiments, $R^2$ is independently unsubstituted 4 to 7 membered heterocycloalkyl.

In embodiments, $R^{24}$ is independently $R^{23A}$-substituted $C_1$-$C_4$ alkyl. In embodiments, $R^{23A}$ is independently unsubstituted 5 to 6 membered heteroaryl.

In embodiments, $R^{24}$ is independently unsubstituted $C_1$-$C_4$ alkoxy. In embodiments, $R^{24}$ is independently unsubstituted $C_1$-$C_6$ alkoxy. In embodiments, $R^{24}$ is independently unsubstituted $C_1$-$C_4$ alkyl. In embodiments, $R^{24}$ is independently unsubstituted $C_1$-$C_6$ alkyl. In embodiments, $R^{24}$ is independently unsubstituted phenyl. In embodiments, $R^{24}$ is independently unsubstituted 5 to 6 membered heteroaryl.

In embodiments, $R^2$ is independently hydrogen, $-CX^2_3$, $-CHX^2_2$, $-CH_2X^2$, $-C(O)R^{24}$, $-C(O)OR^{24}$, $-C(O)NR^{24}R^{2B}$, substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{12}$, $C_6$-$C_{10}$, or phenyl), or substituted or unsubstituted heteroaryl (e.g., 5 to 12, 5 to 10 membered, 5 to 9 membered, or 5 to 6 membered).

In embodiments, $R^2$ is independently substituted or unsubstituted alkyl (e.g., $C_1$-$C_8$, $C_1$-$C_6$, $C_1$-$C_4$, or $C_1$-$C_2$). In embodiments, $R^2$ is independently substituted alkyl (e.g., $C_1$-$C_8$, $C_1$-$C_6$, $C_1$-$C_4$, or $C_1$-$C_2$). In embodiments, $R^2$ is independently unsubstituted alkyl (e.g., $C_1$-$C_8$, $C_1$-$C_6$, $C_1$-$C_4$, or $C_1$-$C_2$). In embodiments, $R^2$ is independently unsubstituted methyl. In embodiments, $R^2$ is independently unsubstituted ethyl. In embodiments, $R^2$ is independently unsubstituted propyl. In embodiments, $R^2$ is independently unsubstituted isopropyl. In embodiments, $R^2$ is independently unsubstituted tert-butyl. In embodiments, $R^2$ is independently substituted or unsubstituted heteroalkyl (e.g., 2 to 8 membered, 2 to 6 membered, 4 to 6 membered, 2 to 3 membered, or 4 to 5 membered). In embodiments, $R^2$ is independently substituted heteroalkyl (e.g., 2 to 8 membered, 2 to 6 membered, 4 to 6 membered, 2 to 3 membered, or 4 to 5 membered). In embodiments, $R^2$ is independently unsubstituted heteroalkyl (e.g., 2 to 8 membered, 2 to 6 membered, 4 to 6 membered, 2 to 3 membered, or 4 to 5 membered). In embodiments, $R^2$ is independently substituted or unsubstituted cycloalkyl (e.g., $C_3$-$C_8$, $C_3$-$C_6$, $C_4$-$C_6$, or $C_5$-$C_6$). In embodiments, $R^2$ is independently substituted cycloalkyl (e.g., $C_3$-$C_8$, $C_3$-$C_6$, $C_4$-$C_6$, or $C_5$-$C_6$). In embodiments, $R^2$ is independently unsubstituted cycloalkyl (e.g., $C_3$-$C_8$, $C_3$-$C_6$, $C_4$-$C_6$, or $C_5$-$C_6$). In embodiments, $R^2$ is independently substituted or unsubstituted heterocycloalkyl (e.g., 3 to 8 membered, 3 to 6 membered, 4 to 6 membered, 4 to 5 membered, or 5 to 6 membered). In embodiments, $R^2$ is independently substituted heterocycloalkyl (e.g., 3 to 8 membered, 3 to 6 membered, 4 to 6 membered, 4 to 5 membered, or 5 to 6 membered). In embodiments, $R^2$ is independently unsubstituted heterocycloalkyl (e.g., 3 to 8 membered, 3 to 6 membered, 4 to 6 membered, 4 to 5 membered, or 5 to 6 membered). In embodiments, $R^2$ is independently substituted or unsubstituted aryl (e.g., $C_6$-$C_{12}$, $C_6$-$C_{10}$, or phenyl). In embodiments, $R^2$ is independently substituted aryl (e.g., $C_6$-$C_{12}$, $C_6$-$C_{10}$, or phenyl). In embodiments, $R^2$ is independently unsubstituted aryl (e.g., $C_6$-$C_{12}$, $C_6$-$C_{10}$, or phenyl). In embodiments, $R^2$ is independently substituted or unsubstituted heteroaryl (e.g., 5 to 12 membered, 5 to 10 membered, 5 to 9 membered, or 5 to 6 membered). In embodiments, $R^2$ is independently substituted heteroaryl (e.g., 5 to 12 membered, 5 to 10 membered, 5 to 9 membered, or 5 to 6 membered). In embodiments, $R^2$ is independently unsubstituted heteroaryl (e.g., 5 to 12 membered, 5 to 10 membered, 5 to 9 membered, or 5 to 6 membered).

In embodiments, $R^2$ is independently hydrogen, $-CX^2_3$, $-CHX^2_2$, $-CH_2X^2$, $-C(O)OH$, $-C(O)NH_2$, $R^{23}$-substituted or unsubstituted alkyl (e.g., $C_1$-$C_8$, $C_1$-$C_6$, $C_1$-$C_4$, or $C_1$-$C_2$), $R^{23}$-substituted or unsubstituted heteroalkyl (e.g., 2 to 8 membered, 2 to 6 membered, 4 to 6 membered, 2 to 3 membered, or 4 to 5 membered), $R^{23}$-substituted or unsubstituted cycloalkyl (e.g., $C_3$-$C_8$, $C_3$-$C_6$, $C_4$-$C_6$, or $C_5$-$C_6$), $R^{23}$-substituted or unsubstituted heterocycloalkyl (e.g., 3 to 8 membered, 3 to 6 membered, 4 to 6 membered, 4 to 5 membered, or 5 to 6 membered), $R^{23}$-substituted or unsubstituted aryl (e.g., $C_6$-$C_{12}$, $C_6$-$C_{10}$, or phenyl), or $R^{23}$-substituted or unsubstituted heteroaryl (e.g., 5 to 12 membered, 5 to 10 membered, 5 to 9 membered, or 5 to 6 membered). In embodiments, $R^2$ is independently hydrogen, $-CX^2_3$, $-CHX^2_2$, $-CH_2X^2$, $-C(O)OH$, $-C(O)NH_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered). $X^2$ is independently $-F$, $-Cl$, $-Br$, or $-I$. In embodiments, $R^2$ is independently hydrogen. In embodiments, $R^2$ is independently unsubstituted methyl. In embodiments, $R^2$ is independently unsubstituted ethyl.

$R^{23}$ is independently oxo, halogen, $-CX^{23}_3$, $-CHX^{23}_2$, $-CH_2X^{23}$, $-OCX^{23}_3$, $-OCH_2X^{23}$, $-OCHX^{23}_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $R^{24}$-substituted or unsubstituted alkyl (e.g., $C_1$-$C_8$, $C_1$-$C_6$, $C_1$-$C_4$, or $C_1$-$C_2$), $R^{24}$-substituted or unsubstituted heteroalkyl (e.g., 2 to 8 membered, 2 to 6 membered, 4 to 6 membered, 2 to 3 membered, or 4 to 5 membered), $R^{24}$-substituted or unsubstituted cycloalkyl (e.g., $C_3$-$C_8$, $C_3$-$C_6$, $C_4$-$C_6$, or $C_5$-$C_6$), $R^{24}$-substituted or unsubstituted heterocycloalkyl (e.g., 3 to 8 membered, 3 to 6 membered, 4 to 6 membered, 4 to 5 membered, or 5 to 6 membered), $R^{24}$-substituted or unsubstituted aryl (e.g., $C_6$-$C_{12}$, $C_6$-$C_{10}$, or phenyl), or $R^{24}$-substituted or unsubstituted heteroaryl (e.g., 5 to 12 membered, 5 to 10 membered, 5 to 9 membered, or 5 to 6 membered). In embodiments, $R^{23}$ is independently oxo, halogen, $-CX^{23}_3$, $-CHX^{23}_2$, $-CH_2X^{23}$, $-OCX^{23}_3$, $-OCH_2X^{23}$, $-OCHX^{23}_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered). $X^{23}$ is independently —F, —Cl, —Br, or —I. In embodiments, $R^{23}$ is independently unsubstituted methyl. In embodiments, $R^{23}$ is independently unsubstituted ethyl.

$R^{24}$ is independently oxo, halogen, —$CX^{24}_3$, —$CHX^{24}_2$, —$CH_2X^{24}$, —$OCX^{24}_3$, —$OCH_2X^{24}$, —$OCHX^{24}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, $R^{25}$-substituted or unsubstituted alkyl (e.g., $C_1$-$C_8$, $C_1$-$C_6$, $C_1$-$C_4$, or $C_1$-$C_2$), $R^{25}$-substituted or unsubstituted heteroalkyl (e.g., 2 to 8 membered, 2 to 6 membered, 4 to 6 membered, 2 to 3 membered, or 4 to 5 membered), $R^{25}$-substituted or unsubstituted cycloalkyl (e.g., $C_3$-$C_8$, $C_3$-$C_6$, $C_4$-$C_6$, or $C_5$-$C_6$), $R^{25}$-substituted or unsubstituted heterocycloalkyl (e.g., 3 to 8 membered, 3 to 6 membered, 4 to 6 membered, 4 to 5 membered, or 5 to 6 membered), $R^{25}$-substituted or unsubstituted aryl (e.g., $C_6$-$C_{12}$, $C_6$-$C_{10}$, or phenyl), or $R^{25}$-substituted or unsubstituted heteroaryl (e.g., 5 to 12 membered, 5 to 10 membered, 5 to 9 membered, or 5 to 6 membered). In embodiments, $R^{24}$ is independently oxo, halogen, —$CX^{24}_3$, —$CHX^{24}_2$, —$CH_2X^{24}$, —$OCX^{24}_3$, —$OCH_2X^{24}$, —$OCHX^{24}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered). $X^{24}$ is independently —F, —Cl, —Br, or —I. In embodiments, $R^{24}$ is independently unsubstituted methyl. In embodiments, $R^{24}$ is independently unsubstituted ethyl.

$R^{25}$ is independently oxo, halogen, —$CX^{25}_3$, —$CHX^{25}_2$, —$CH_2X^{25}$, —$OCX^{25}_3$, —$OCH_2X^{25}$, —$OCHX^{25}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered). $X^{25}$ is independently —F, —Cl, —Br, or —I. In embodiments, $R^{25}$ is independently unsubstituted methyl. In embodiments, $R^{25}$ is independently unsubstituted ethyl.

In embodiments, $R^{2A}$ is independently hydrogen. In embodiments, $R^{2A}$ is independently —$CX^{2A}_3$. In embodiments, $R^{2A}$ is independently —$CHX^{2A}_2$. In embodiments, $R^{2A}$ is independently —$CH_2X^{2A}$. In embodiments, $R^{2A}$ is independently —CN. In embodiments, $R^{2A}$ is independently —COOH. In embodiments, $R^{2A}$ is independently —$CONH_2$. In embodiments, $X^{2A}$ is independently —F, —Cl, —Br, or —I.

In embodiments, $R^{2A}$ is independently substituted or unsubstituted alkyl (e.g., $C_1$-$C_8$, $C_1$-$C_6$, $C_1$-$C_4$, or $C_1$-$C_2$). In embodiments, $R^{2A}$ is independently substituted alkyl (e.g., $C_1$-$C_8$, $C_1$-$C_6$, $C_1$-$C_4$, or $C_1$-$C_2$). In embodiments, $R^{2A}$ is independently unsubstituted alkyl (e.g., $C_1$-$C_8$, $C_1$-$C_6$, $C_1$-$C_4$, or $C_1$-$C_2$). In embodiments, $R^{2A}$ is independently unsubstituted methyl. In embodiments, $R^{2A}$ is independently unsubstituted ethyl. In embodiments, $R^{2A}$ is independently unsubstituted propyl. In embodiments, $R^{2A}$ is independently unsubstituted isopropyl. In embodiments, $R^{2A}$ is independently unsubstituted tert-butyl. In embodiments, $R^{2A}$ is independently substituted or unsubstituted heteroalkyl (e.g., 2 to 8 membered, 2 to 6 membered, 4 to 6 membered, 2 to 3 membered, or 4 to 5 membered). In embodiments, $R^{2A}$ is independently substituted heteroalkyl (e.g., 2 to 8 membered, 2 to 6 membered, 4 to 6 membered, 2 to 3 membered, or 4 to 5 membered). In embodiments, $R^{2A}$ is independently unsubstituted heteroalkyl (e.g., 2 to 8 membered, 2 to 6 membered, 4 to 6 membered, 2 to 3 membered, or 4 to 5 membered). In embodiments, $R^{2A}$ is independently substituted or unsubstituted cycloalkyl (e.g., $C_3$-$C_8$, $C_3$-$C_6$, $C_4$-$C_6$, or $C_5$-$C_6$). In embodiments, $R^{2A}$ is independently substituted cycloalkyl (e.g., $C_3$-$C_8$, $C_3$-$C_6$, $C_4$-$C_6$, or $C_5$-$C_6$). In embodiments, $R^{2A}$ is independently unsubstituted cycloalkyl (e.g., $C_3$-$C_8$, $C_3$-$C_6$, $C_4$-$C_6$, or $C_5$-$C_6$). In embodiments, $R^{2A}$ is independently substituted or unsubstituted heterocycloalkyl (e.g., 3 to 8 membered, 3 to 6 membered, 4 to 6 membered, 4 to 5 membered, or 5 to 6 membered). In embodiments, $R^{2A}$ is independently substituted heterocycloalkyl (e.g., 3 to 8 membered, 3 to 6 membered, 4 to 6 membered, 4 to 5 membered, or 5 to 6 membered). In embodiments, $R^{2A}$ is independently unsubstituted heterocycloalkyl (e.g., 3 to 8 membered, 3 to 6 membered, 4 to 6 membered, 4 to 5 membered, or 5 to 6 membered). In embodiments, $R^{2A}$ is independently substituted or unsubstituted aryl (e.g., $C_6$-$C_{12}$, $C_6$-$C_{10}$, or phenyl). In embodiments, $R^{2A}$ is independently substituted aryl (e.g., $C_6$-$C_{12}$, $C_6$-$C_{10}$, or phenyl). In embodiments, $R^{2A}$ is independently unsubstituted aryl (e.g., $C_6$-$C_{12}$, $C_6$-$C_{10}$, or phenyl). In embodiments, $R^{2A}$ is independently substituted or unsubstituted heteroaryl (e.g., 5 to 12 membered, 5 to 10 membered, 5 to 9 membered, or 5 to 6 membered). In embodiments, $R^{2A}$ is independently substituted heteroaryl (e.g., 5 to 12 membered, 5 to 10 membered, 5 to 9 membered, or 5 to 6 membered). In embodiments, $R^{2A}$ is independently unsubstituted heteroaryl (e.g., 5 to 12 membered, 5 to 10 membered, 5 to 9 membered, or 5 to 6 membered).

In embodiments, $R^{2A}$ is independently hydrogen, —$CX^{2A}_3$, —$CHX^{2A}_2$, —$CH_2X^{2A}$, —CN, —COOH, —$CONH_2$, $R^{23A}$-substituted or unsubstituted alkyl (e.g., $C_1$-$C_8$, $C_1$-$C_6$, $C_1$-$C_4$, or $C_1$-$C_2$), $R^{23A}$-substituted or unsubstituted heteroalkyl (e.g., 2 to 8 membered, 2 to 6 membered, 4 to 6 membered, 2 to 3 membered, or 4 to 5 membered), $R^{23A}$-substituted or unsubstituted cycloalkyl (e.g., $C_3$-$C_8$, $C_3$-$C_6$, $C_4$-$C_6$, or $C_5$-$C_6$), $R^{23A}$-substituted or unsubstituted heterocycloalkyl (e.g., 3 to 8 membered, 3 to 6 membered, 4 to 6 membered, 4 to 5 membered, or 5 to 6 membered), $R^{23A}$-substituted or unsubstituted aryl (e.g., $C_6$-$C_{12}$, $C_6$-$C_{10}$, or phenyl), or $R^{23A}$-substituted or unsubstituted heteroaryl (e.g., 5 to 12 membered, 5 to 10 membered, 5 to 9 membered, or 5 to 6 membered). In embodiments, $R^{2A}$ is independently hydrogen, —$CX^{2A}_3$, —$CHX^{2A}_2$, —$CH_2X^{2A}$, —CN, —COOH, —$CONH_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered). $X^{2A}$ is independently —F, —Cl, —Br, or —I. In embodiments, $R^{2A}$ is independently hydrogen. In embodiments, $R^{2A}$ is independently unsubstituted methyl. In embodiments, $R^{2A}$ is independently unsubstituted ethyl.

In embodiments, $R^{2A}$ and $R^{2B}$ substituents bonded to the same nitrogen atom may optionally be joined to form a $R^{23A}$-substituted or unsubstituted heterocycloalkyl (e.g., 3 to 8 membered, 3 to 6 membered, 4 to 6 membered, 4 to 5 membered, or 5 to 6 membered) or $R^{23A}$-substituted or unsubstituted heteroaryl (e.g., 5 to 12 membered, 5 to 10 membered, 5 to 9 membered, or 5 to 6 membered). In embodiments, $R^{2A}$ and $R^{2B}$ substituents bonded to the same nitrogen atom may optionally be joined to form an unsubstituted heterocycloalkyl (e.g., 3 to 8 membered, 3 to 6 membered, 4 to 6 membered, 4 to 5 membered, or 5 to 6 membered) or unsubstituted heteroaryl (e.g., 5 to 12 membered, 5 to 10 membered, 5 to 9 membered, or 5 to 6 membered). In embodiments, $R^{2A}$ and $R^{2B}$ substituents bonded to the same nitrogen atom may optionally be joined to form a $R^{23A}$-substituted or unsubstituted heterocycloalkyl (e.g., 3 to 8 membered, 3 to 6 membered, 4 to 6 membered, 4 to 5 membered, or 5 to 6 membered). In embodiments, $R^{2A}$ and $R^{2B}$ substituents bonded to the same nitrogen atom may optionally be joined to form an unsubstituted heterocycloalkyl (e.g., 3 to 8 membered, 3 to 6 membered, 4 to 6 membered, 4 to 5 membered, or 5 to 6 membered).

$R^{23A}$ is independently oxo, halogen, —$CX^{23A}_3$, —$CHX^{23A}_2$, —$CH_2X^{23A}$, —$OCX^{23A}_3$, —$OCH_2X^{23A}$, —$OCHX^{23A}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, $R^{24A}$-substituted or unsubstituted alkyl (e.g., $C_1$-$C_8$, $C_1$-$C_6$, $C_1$-$C_4$, or $C_1$-$C_2$), $R^{24A}$-substituted or unsubstituted heteroalkyl (e.g., 2 to 8 membered, 2 to 6 membered, 4 to 6 membered, 2 to 3 membered, or 4 to 5 membered), $R^{24A}$-substituted or unsubstituted cycloalkyl (e.g., $C_3$-$C_8$, $C_3$-$C_6$, $C_4$-$C_6$, or $C_5$-$C_6$), $R^{24A}$-substituted or unsubstituted heterocycloalkyl (e.g., 3 to 8 membered, 3 to 6 membered, 4 to 6 membered, 4 to 5 membered, or 5 to 6 membered), $R^{24A}$-substituted or unsubstituted aryl (e.g., $C_6$-$C_{12}$, $C_6$-$C_{10}$, or phenyl), or $R^{24A}$-substituted or unsubstituted heteroaryl (e.g., 5 to 12 membered, 5 to 10 membered, 5 to 9 membered, or 5 to 6 membered).

In embodiments, $R^{23A}$ is independently oxo, halogen, —$CX^{23A}_3$, —$CHX^{23A}_2$, —$CH_2X^{23A}$, —$OCX^{23A}_3$, —$OCH_2X^{23A}$, —$OCHX^{23A}_2$, —CN, —OH, —$NH_2$, —COOH, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered). $X^{23A}$ is independently —F, —Cl, —Br, or —I. In embodiments, $R^{23A}$ is independently unsubstituted methyl. In embodiments, $R^{23A}$ is independently unsubstituted ethyl.

$R^{24A}$ is independently oxo, halogen, —$CX^{24A}_3$, —$CHX^{24A}_2$, —$CH_2X^{24A}$, —$OCX^{24A}_3$, —$OCH_2X^{24A}$, —$OCHX^{24A}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, $R^{25A}$-substituted or unsubstituted alkyl (e.g., $C_1$-$C_8$, $C_1$-$C_6$, $C_1$-$C_4$, or $C_1$-$C_2$), $R^{25A}$-substituted or unsubstituted heteroalkyl (e.g., 2 to 8 membered, 2 to 6 membered, 4 to 6 membered, 2 to 3 membered, or 4 to 5 membered), $R^{25A}$-substituted or unsubstituted cycloalkyl (e.g., $C_3$-$C_8$, $C_3$-$C_6$, $C_4$-$C_6$, or $C_5$-$C_6$), $R^{25A}$-substituted or unsubstituted heterocycloalkyl (e.g., 3 to 8 membered, 3 to 6 membered, 4 to 6 membered, 4 to 5 membered, or 5 to 6 membered), $R^{25A}$-substituted or unsubstituted aryl (e.g., $C_6$-$C_{12}$, $C_6$-$C_{10}$, or phenyl), or $R^{25A}$-substituted or unsubstituted heteroaryl (e.g., 5 to 12 membered, 5 to 10 membered, 5 to 9 membered, or 5 to 6 membered). In embodiments, $R^{24A}$ is independently oxo, halogen, —$CX^{24A}_3$, —$CHX^{24A}_2$, —$CH_2X^{24A}$, —$OCX^{24A}_3$, —$OCH_2X^{24A}$, —$OCHX^{24A}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered). $X^{24A}$ is independently —F, —Cl, —Br, or —I. In embodiments, $R^{24A}$ is independently unsubstituted methyl. In embodiments, $R^{24A}$ is independently unsubstituted ethyl.

$R^{25A}$ is independently oxo, halogen, —$CX^{25A}_3$, —$CHX^{25A}_2$, —$CH_2X^{25A}$, —$OCX^{25A}_3$, —$OCH_2X^{25A}$, —$OCHX^{25A}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered). $X^{25A}$ is independently —F, —Cl, —Br, or —I. In embodiments, $R^{25A}$ is independently unsubstituted methyl. In embodiments, $R^{25A}$ is independently unsubstituted ethyl.

In embodiments, $R^{2B}$ is independently hydrogen. In embodiments, $R^{2B}$ is independently —$CX^{2B}_3$. In embodiments, $R^{2B}$ is independently —$CHX^{2B}_2$. In embodiments, $R^{2B}$ is independently —$CH_2X^{2B}$. In embodiments, $R^{2B}$ is independently —CN. In embodiments, $R^{2B}$ is independently —COOH. In embodiments, $R^{2B}$ is independently —CONH$_2$. In embodiments, $X^{2B}$ is independently —F, —Cl, —Br, or —I.

In embodiments, $R^{2B}$ is independently substituted or unsubstituted alkyl (e.g., $C_1$-$C_8$, $C_1$-$C_6$, $C_1$-$C_4$, or $C_1$-$C_2$). In embodiments, $R^{2B}$ is independently substituted alkyl (e.g., $C_1$-$C_8$, $C_1$-$C_6$, $C_1$-$C_4$, or $C_1$-$C_2$). In embodiments, $R^{2B}$ is independently unsubstituted alkyl (e.g., $C_1$-$C_8$, $C_1$-$C_6$, $C_1$-$C_4$, or $C_1$-$C_2$). In embodiments, $R^{2B}$ is independently unsubstituted methyl. In embodiments, $R^{2B}$ is independently unsubstituted ethyl. In embodiments, $R^{2B}$ is independently unsubstituted propyl. In embodiments, $R^{2B}$ is independently unsubstituted isopropyl. In embodiments, $R^{2B}$ is independently unsubstituted tert-butyl. In embodiments, $R^{2B}$ is independently substituted or unsubstituted heteroalkyl (e.g., 2 to 8 membered, 2 to 6 membered, 4 to 6 membered, 2 to 3 membered, or 4 to 5 membered). In embodiments, $R^{2B}$ is independently substituted heteroalkyl (e.g., 2 to 8 membered, 2 to 6 membered, 4 to 6 membered, 2 to 3 membered, or 4 to 5 membered). In embodiments, $R^{2B}$ is independently unsubstituted heteroalkyl (e.g., 2 to 8 membered, 2 to 6 membered, 4 to 6 membered, 2 to 3 membered, or 4 to 5 membered). In embodiments, $R^{2B}$ is independently substituted or unsubstituted cycloalkyl (e.g., $C_3$-$C_8$, $C_3$-$C_6$, $C_4$-$C_6$, or $C_5$-$C_6$). In embodiments, $R^{2B}$ is independently substituted cycloalkyl (e.g., $C_3$-$C_8$, $C_3$-$C_6$, $C_4$-$C_6$, or $C_5$-$C_6$). In embodiments, $R^{2B}$ is independently unsubstituted cycloalkyl (e.g., $C_3$-$C_8$, $C_3$-$C_6$, $C_4$-$C_6$, or $C_5$-$C_6$). In embodiments, $R^{2B}$ is independently substituted or unsubstituted heterocycloalkyl (e.g., 3 to 8 membered, 3 to 6 membered, 4 to 6 membered, 4 to 5 membered, or 5 to 6 membered). In embodiments, $R^{2B}$ is independently substituted heterocycloalkyl (e.g., 3 to 8 membered, 3 to 6 membered, 4 to 6 membered, 4 to 5 membered, or 5 to 6 membered). In embodiments, $R^{2B}$ is independently unsubstituted heterocycloalkyl (e.g., 3 to 8 membered, 3 to 6 membered, 4 to 6 membered, 4 to 5 membered, or 5 to 6 membered). In embodiments, $R^{2B}$ is independently substituted or unsubstituted aryl (e.g., $C_6$-$C_{12}$, $C_6$-$C_{10}$, or phenyl). In embodiments, $R^{2B}$ is independently substituted aryl (e.g., $C_6$-$C_{12}$, $C_6$-$C_{10}$, or phenyl). In embodiments, $R^{2B}$ is independently unsubstituted aryl (e.g., $C_6$-$C_{12}$, $C_6$-$C_{10}$, or phenyl). In embodiments, $R^{2B}$ is independently substituted or unsubstituted heteroaryl (e.g., 5 to 12 membered, 5 to 10 membered, 5 to 9 membered, or 5 to 6 membered). In embodiments, $R^{2B}$ is independently substituted heteroaryl (e.g., 5 to 12 membered, 5 to 10 membered, 5 to 9 membered, or 5 to 6 membered). In embodiments, $R^{2B}$ is independently unsubstituted heteroaryl (e.g., 5 to 12 membered, 5 to 10 membered, 5 to 9 membered, or 5 to 6 membered).

In embodiments, $R^{2A}$ and $R^{2B}$ substituents bonded to the same nitrogen atom may be joined to form a substituted or unsubstituted heterocycloalkyl (e.g., 3 to 8 membered, 3 to 6 membered, 4 to 6 membered, 4 to 5 membered, or 5 to 6 membered). In embodiments, $R^{2A}$ and $R^{2B}$ substituents bonded to the same nitrogen atom may be joined to form a substituted heterocycloalkyl (e.g., 3 to 8 membered, 3 to 6 membered, 4 to 6 membered, 4 to 5 membered, or 5 to 6 membered). In embodiments, $R^{2A}$ and $R^{2B}$ substituents bonded to the same nitrogen atom may be joined to form an unsubstituted heterocycloalkyl (e.g., 3 to 8 membered, 3 to 6 membered, 4 to 6 membered, 4 to 5 membered, or 5 to 6 membered). In embodiments, $R^{2A}$ and $R^{2B}$ substituents bonded to the same nitrogen atom may be joined to form a substituted or unsubstituted heteroaryl (e.g., 5 to 12 membered, 5 to 10 membered, 5 to 9 membered, or 5 to 6 membered). In embodiments, $R^{2A}$ and $R^{2B}$ substituents bonded to the same nitrogen atom may be joined to form a substituted heteroaryl (e.g., 5 to 12 membered, 5 to 10 membered, 5 to 9 membered, or 5 to 6 membered). In embodiments, $R^{2A}$ and $R^{2B}$ substituents bonded to the same nitrogen atom may be joined to form an unsubstituted heteroaryl (e.g., 5 to 12 membered, 5 to 10 membered, 5 to 9 membered, or 5 to 6 membered).

In embodiments, $R^{2B}$ is independently hydrogen, —CX$^{2B}_3$, —CHX$^{2B}_2$, —CH$_2$X$^{2B}$, —CN, —COOH, —CONH$_2$, $R^{23B}$-substituted or unsubstituted alkyl (e.g., $C_1$-$C_8$, $C_1$-$C_6$, $C_1$-$C_4$, or $C_1$-$C_2$), $R^{23B}$-substituted or unsubstituted heteroalkyl (e.g., 2 to 8 membered, 2 to 6 membered, 4 to 6 membered, 2 to 3 membered, or 4 to 5 membered), $R^{23B}$-substituted or unsubstituted cycloalkyl (e.g., $C_3$-$C_8$, $C_3$-$C_6$, $C_4$-$C_6$, or $C_5$-$C_6$), $R^{23B}$-substituted or unsubstituted heterocycloalkyl (e.g., 3 to 8 membered, 3 to 6 membered, 4 to 6 membered, 4 to 5 membered, or 5 to 6 membered), $R^{23B}$-substituted or unsubstituted aryl (e.g., $C_6$-$C_{12}$, $C_6$-$C_{10}$, or phenyl), or $R^{23B}$-substituted or unsubstituted heteroaryl (e.g., 5 to 12 membered, 5 to 10 membered, 5 to 9 membered, or 5 to 6 membered). In embodiments, $R^{2B}$ is independently hydrogen, —CX$^{2B}_3$, —CHX$^{2B}_2$, —CH$_2$X$^{2B}$, —CN, —COOH, —CONH$_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered). $X^{2B}$ is independently —F, —Cl, —Br, or —I. In embodiments, $R^{2B}$ is independently hydrogen. In embodiments, $R^{2B}$ is independently unsubstituted methyl. In embodiments, $R^{2B}$ is independently unsubstituted ethyl.

In embodiments, $R^{2A}$ and $R^{2B}$ substituents bonded to the same nitrogen atom may optionally be joined to form a $R^{23B}$-substituted or unsubstituted heterocycloalkyl (e.g., 3 to 8 membered, 3 to 6 membered, 4 to 6 membered, 4 to 5 membered, or 5 to 6 membered) or $R^{23B}$-substituted or unsubstituted heteroaryl (e.g., 5 to 12 membered, 5 to 10 membered, 5 to 9 membered, or 5 to 6 membered). In embodiments, $R^{2A}$ and $R^{2B}$ substituents bonded to the same nitrogen atom may optionally be joined to form an unsubstituted heterocycloalkyl (e.g., 3 to 8 membered, 3 to 6 membered, 4 to 6 membered, 4 to 5 membered, or 5 to 6 membered) or unsubstituted heteroaryl (e.g., 5 to 12 membered, 5 to 10 membered, 5 to 9 membered, or 5 to 6 membered). In embodiments, $R^{2A}$ and $R^{2B}$ substituents bonded to the same nitrogen atom may optionally be joined to form a $R^{23B}$-substituted or unsubstituted heterocycloalkyl (e.g., 3 to 8 membered, 3 to 6 membered, 4 to 6 membered, 4 to 5 membered, or 5 to 6 membered). In embodiments, $R^{2A}$ and $R^{2B}$ substituents bonded to the same nitrogen atom may optionally be joined to form an unsubstituted heterocycloalkyl (e.g., 3 to 8 membered, 3 to 6 membered, 4 to 6 membered, 4 to 5 membered, or 5 to 6 membered).

$R^{23B}$ is independently oxo, halogen, —CX$^{23B}_3$, —CHX$^{23B}_2$, —CH$_2$X$^{23B}$, —OCX$^{23B}_3$, —OCH$_2$X$^{23B}$, —OCHX$^{23B}_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, $R^{24B}$-substituted or unsubstituted alkyl (e.g., $C_1$-$C_8$, $C_1$-$C_6$, $C_1$-$C_4$, or $C_1$-$C_2$), $R^{24B}$-substituted or unsubstituted heteroalkyl (e.g., 2 to 8 membered, 2 to 6 membered, 4 to 6 membered, 2 to 3 membered, or 4 to 5 membered), $R^{24B}$-substituted or unsubstituted cycloalkyl (e.g., $C_3$-$C_8$, $C_3$-$C_6$, $C_4$-$C_6$, or $C_5$-$C_6$), $R^{24B}$-substituted or unsubstituted heterocycloalkyl (e.g., 3 to 8 membered, 3 to 6 membered, 4 to 6 membered, 4 to 5 membered, or 5 to 6 membered), $R^{24B}$-substituted or unsubstituted aryl (e.g., $C_6$-$C_{12}$, $C_6$-$C_{10}$, or phenyl), or $R^{24B}$-substituted or unsubstituted heteroaryl (e.g., 5 to 12 membered, 5 to 10 membered, 5 to 9 membered, or 5 to 6 membered). In embodiments, $R^{23B}$ is independently oxo, halogen, —$CX^{23B}_3$, —$CHX^{23B}_2$, —$CH_2X^{23B}$, —$OCX^{23B}_3$, —$OCH_2X^{23B}$, —$OCHX^{23B}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered). $X^{23B}$ is independently —F, —Cl, —Br, or —I. In embodiments, $R^{23B}$ is independently unsubstituted methyl. In embodiments, $R^{23B}$ is independently unsubstituted ethyl.

$R^{24B}$ is independently oxo, halogen, —$CX^{24B}_3$, —$CHX^{24B}_2$, —$CH_2X^{24B}$, —$OCX^{24B}_3$, —$OCH_2X^{24B}$, —$OCHX^{24B}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, $R^{25B}$-substituted or unsubstituted alkyl (e.g., $C_1$-$C_8$, $C_1$-$C_6$, $C_1$-$C_4$, or $C_1$-$C_2$), $R^{25B}$-substituted or unsubstituted heteroalkyl (e.g., 2 to 8 membered, 2 to 6 membered, 4 to 6 membered, 2 to 3 membered, or 4 to 5 membered), $R^{25B}$-substituted or unsubstituted cycloalkyl (e.g., $C_3$-$C_8$, $C_3$-$C_6$, $C_4$-$C_6$, or $C_5$-$C_6$), $R^{25B}$-substituted or unsubstituted heterocycloalkyl (e.g., 3 to 8 membered, 3 to 6 membered, 4 to 6 membered, 4 to 5 membered, or 5 to 6 membered), $R^{25B}$-substituted or unsubstituted aryl (e.g., $C_6$-$C_{12}$, $C_6$-$C_{10}$, or phenyl), or $R^{25B}$-substituted or unsubstituted heteroaryl (e.g., 5 to 12 membered, 5 to 10 membered, 5 to 9 membered, or 5 to 6 membered). In embodiments, $R^{24B}$ is independently oxo, halogen, —$CX^{24B}_3$, —$CHX^{24B}_2$, —$CH_2X^{24B}$, —$OCX^{24B}_3$, —$OCH_2X^{24B}$, —$OCHX^{24B}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered). $X^{24B}$ is independently —F, —Cl, —Br, or —I. In embodiments, $R^{24B}$ is independently unsubstituted methyl. In embodiments, $R^{24B}$ is independently unsubstituted ethyl.

$R^{25B}$ is independently oxo, halogen, —$CX^{25B}_3$, —$CHX^{25B}_2$, —$CH_2X^{25B}$, —$OCX^{25B}_3$, —$OCH_2X^{25B}$, —$OCHX^{25B}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered). $X^{25B}$ is independently —F, —Cl, —Br, or —I. In embodiments, $R^{25B}$ is independently unsubstituted methyl. In embodiments, $R^{25B}$ is independently unsubstituted ethyl.

In embodiments, $R^2$ is independently hydrogen, —C(O)$R^{2A}$, —C(O)—O$R^{2A}$, —C(O)N$R^{2A}R^{2B}$, $R^{23}$-substituted or unsubstituted alkyl, $R^{23}$-substituted or unsubstituted heteroalkyl, $R^{23}$-substituted or unsubstituted cycloalkyl, $R^{23}$-substituted or unsubstituted heterocycloalkyl, $R^{23}$-substituted or unsubstituted aryl, or $R^{23}$-substituted or unsubstituted heteroaryl. In embodiments, $R^{2B}$ is independently hydrogen, —$CX^{2B}_3$, —$CHX^{2B}_2$, —$CH_2X^{2B}$, —CN, —COOH, —$CONH_2$, unsubstituted alkyl, unsubstituted heteroalkyl, unsubstituted cycloalkyl, unsubstituted heterocycloalkyl, unsubstituted aryl, or unsubstituted heteroaryl. In embodiments, $R^2$ is independently hydrogen, —C(O)-(unsubstituted $C_1$-$C_3$ alkyl), or unsubstituted $C_1$-$C_3$ alkyl. In embodiments, $R^2$ is independently hydrogen. In embodiments, $R^2$ is independently —C(O)$CH_3$. In embodiments, $R^2$ is independently hydrogen, —C(O)-(unsubstituted $C_1$-$C_3$ alkyl), or $R^{23}$-substituted or unsubstituted $C_1$-$C_6$ alkyl. In embodiments, $R^2$ is independently hydrogen, —C(O)-(unsubstituted $C_1$-$C_3$ alkyl), or unsubstituted $C_1$-$C_3$ alkyl. In embodiments, $R^2$ is independently hydrogen. In embodiments, $R^2$ is independently —C(O)$CH_3$.

In embodiments, $R^2$ is independently —C(O)$R^{2A}$. In embodiments, $R^{2A}$ is independently unsubstituted methyl. In embodiments, $R^{2A}$ is independently unsubstituted ethyl. In embodiments, $R^{2A}$ is independently unsubstituted propyl. In embodiments, $R^{2A}$ is independently unsubstituted isopropyl. In embodiments, $R^{2A}$ is independently unsubstituted n-propyl. In embodiments, $R^{2A}$ is independently unsubstituted butyl. In embodiments, $R^{2A}$ is independently unsubstituted n-butyl. In embodiments, $R^{2A}$ is independently unsubstituted t-butyl. In embodiments, $R^{2A}$ is independently unsubstituted iso-butyl. In embodiments, $R^{2A}$ is independently unsubstituted pentyl. In embodiments, $R^{2A}$ is independently unsubstituted n-pentyl. In embodiments, $R^{2A}$ is independently unsubstituted hexyl. In embodiments, $R^{2A}$ is independently unsubstituted n-hexyl. In embodiments, $R^{2A}$ is independently unsubstituted heptyl. In embodiments, $R^{2A}$ is independently unsubstituted n-heptyl. In embodiments, $R^{2A}$ is independently unsubstituted octyl. In embodiments, $R^{2A}$ is independently unsubstituted n-octyl. In embodiments, $R^{2A}$ is independently unsubstituted $C_1$-$C_8$ alkyl. In embodiments, $R^{2A}$ is independently $R^{23A}$-substituted methyl. In embodiments, $R^{2A}$ is independently $R^{23A}$-substituted ethyl. In embodiments, $R^{2A}$ is independently $R^{23A}$-substituted propyl.

In embodiments, $R^{2A}$ is independently $R^{23A}$-substituted isopropyl. In embodiments, $R^{2A}$ is independently $R^{23A}$-substituted n-propyl. In embodiments, $R^{2A}$ is independently $R^{23A}$-substituted butyl. In embodiments, $R^{2A}$ is independently $R^{23A}$-substituted n-butyl. In embodiments, $R^{2A}$ is independently $R^{23A}$-substituted t-butyl. In embodiments, $R^{2A}$ is independently $R^{23A}$-substituted iso-butyl. In embodiments, $R^{2A}$ is independently $R^{23A}$-substituted pentyl. In embodiments, $R^{2A}$ is independently $R^{23A}$-substituted n-pentyl. In embodiments, $R^{2A}$ is independently $R^{23A}$-substituted hexyl. In embodiments, $R^{2A}$ is independently $R^{23A}$-substituted n-hexyl. In embodiments, $R^{2A}$ is independently $R^{23A}$-substituted heptyl. In embodiments, $R^{2A}$ is independently $R^{23A}$-substituted n-heptyl. In embodiments, $R^{2A}$ is independently $R^{23A}$-substituted octyl. In embodiments, $R^{2A}$ is independently $R^{23A}$-substituted n-octyl. In embodiments, $R^{2A}$ is independently $R^{23A}$-substituted $C_1$-$C_8$ alkyl. In embodiments, $R^{23A}$ is halogen.

In embodiments, $R^2$ is independently hydrogen, $-CX^2_3$, $-CHX^2_2$, $-CH_2X^2$, $-C(O)R^{2A}$, $-C(O)OR^{2A}$, $-C(O)NR^{2A}R^{2B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In embodiments, $R^2$ is independently hydrogen, $-C(O)$-(unsubstituted $C_1$-$C_3$ alkyl), or $R^{23}$-substituted or unsubstituted $C_1$-$C_6$ alkyl and $R^{23}$ is independently oxo, halogen, $-CX^{23}_3$, $-CHX^{23}_2$, $-CH_2X^{23}$, $-OCX^{23}_3$, $-OCH_2X^{23}$, $-OCHX^{23}_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, unsubstituted $C_1$-$C_6$ alkyl, unsubstituted 2 to 6 membered heteroalkyl, unsubstituted $C_3$-$C_6$ cycloalkyl, unsubstituted 3 to 6 membered heterocycloalkyl, unsubstituted phenyl, or unsubstituted 5 to 6 membered heteroaryl.

In embodiments, $R^2$ is independently hydrogen, $-C(O)R^{2A}$, $-C(O)OR^{2A}$, $-C(O)NR^{2A}R^{2B}$, -(unsubstituted $C_1$-$C_4$ alkylene)-COOR$^{24}$, -(unsubstituted $C_1$-$C_4$ alkylene)-C(O)R$^{24}$, -(unsubstituted $C_1$-$C_4$ alkylene)-CONHR$^{24}$, $R^{23}$-substituted or unsubstituted $C_1$-$C_6$ alkyl, $R^{23}$-substituted or unsubstituted 2 to 6 membered heteroalkyl, $R^{23}$-substituted or unsubstituted $C_3$-$C_6$ cycloalkyl, $R^{23}$-substituted or unsubstituted 3 to 6 membered heterocycloalkyl, $R^{23}$-substituted or unsubstituted phenyl, or $R^{23}$-substituted or unsubstituted 5 to 6 membered heteroaryl. In embodiments, $R^{23}$ is independently oxo, halogen, $-CX^{23}_3$, $-CHX^{23}_2$, $-CH_2X^{23}$, $-OCX^{23}_3$, $-OCH_2X^{23}$, $-OCHX^{23}_2$, $-CN$, $-OH$, $-NH_2$, $-COOH$, $-CONH_2$, $-NO_2$, $-SH$, $R^{24}$-substituted or unsubstituted $C_1$-$C_6$ alkyl, $R^{24}$-substituted or unsubstituted 2 to 6 membered heteroalkyl, $R^{24}$-substituted or unsubstituted $C_3$-$C_6$ cycloalkyl, $R^{24}$-substituted or unsubstituted 3 to 6 membered heterocycloalkyl, $R^{24}$-substituted or unsubstituted phenyl, or $R^{24}$-substituted or unsubstituted 5 to 6 membered heteroaryl. In embodiments, $R^{24}$ is independently oxo, halogen, $-CX^{24}_3$, $-CHX^{24}_2$, $-CH_2X^{24}$, $-OCX^{24}_3$, $-OCH_2X^{24}$, $-OCHX^{24}_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $R^{25}$-substituted or unsubstituted $C_1$-$C_6$ alkyl, $R^{25}$-substituted or unsubstituted 2 to 6 membered heteroalkyl, $R^{25}$-substituted or unsubstituted $C_3$-$C_6$ cycloalkyl, $R^{25}$-substituted or unsubstituted 3 to 6 membered heterocycloalkyl, $R^{25}$-substituted or unsubstituted phenyl, or $R^{25}$-substituted or unsubstituted 5 to 6 membered heteroaryl. In embodiments, $R^{25}$ is independently oxo, halogen, $-CX^{25}_3$, $-CHX^{25}_2$, $-CH_2X^{25}$, $-OCX^{25}_3$, $-OCH_2X^{25}$, $-OCHX^{25}_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, unsubstituted $C_1$-$C_6$ alkyl, unsubstituted 2 to 6 membered heteroalkyl, unsubstituted $C_3$-$C_6$ cycloalkyl, unsubstituted 3 to 6 membered heterocycloalkyl, unsubstituted phenyl, or unsubstituted 5 to 6 membered heteroaryl.

In embodiments, $R^{2A}$ is independently hydrogen, $-CX^{2A}_3$, $-CHX^{2A}_2$, $-CH_2X^{2A}$, $-CN$, $-COOH$, $-CONH_2$, $R^{23A}$-substituted or unsubstituted $C_1$-$C_6$ alkyl, $R^{23A}$-substituted or unsubstituted 2 to 6 membered heteroalkyl, $R^{23A}$-substituted or unsubstituted $C_3$-$C_6$ cycloalkyl, $R^{23A}$-substituted or unsubstituted 3 to 6 membered heterocycloalkyl, $R^{23A}$-substituted or unsubstituted phenyl, or $R^{23A}$-substituted or unsubstituted 5 to 6 membered heteroaryl. In embodiments, $R^{23A}$ is independently oxo, halogen, $-CX^{23A}_3$, $-CHX^{23A}_2$, $-CH_2X^{23A}$, $-OCX^{23A}_3$, $-OCH_2X^{23A}$, $-OCHX^{23A}_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $R^{24A}$-substituted or unsubstituted $C_1$-$C_6$ alkyl, $R^{24A}$-substituted or unsubstituted 2 to 6 membered heteroalkyl, $R^{24A}$-substituted or unsubstituted $C_3$-$C_6$ cycloalkyl, $R^{24A}$-substituted or unsubstituted 3 to 6 membered heterocycloalkyl, $R^{24A}$-substituted or unsubstituted phenyl, or $R^{24A}$-substituted or unsubstituted 5 to 6 membered heteroaryl. In embodiments, $R^{24A}$ is independently oxo, halogen, $-CX^{24A}_3$, $-CHX^{24A}_2$, $-CH_2X^{24A}$, $-OCX^{24A}_3$, $-OCH_2X^{24A}$, $-OCHX^{24A}_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $R^{25A}$-substituted or unsubstituted $C_1$-$C_6$ alkyl, $R^{25A}$-substituted or unsubstituted 2 to 6 membered heteroalkyl, $R^{25A}$-substituted or unsubstituted $C_3$-$C_6$ cycloalkyl, $R^{25A}$-substituted or unsubstituted 3 to 6 membered heterocycloalkyl, $R^{25A}$-substituted or unsubstituted phenyl, or $R^{25A}$-substituted or unsubstituted 5 to 6 membered heteroaryl. In embodiments, $R^{25A}$ is independently oxo, halogen, $-CX^{25A}_3$, $-CHX^{25A}_2$, $-CH_2X^{25A}$, $-OCX^{25A}_3$, $-OCH_2X^{25A}$, $-OCHX^{25A}_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, unsubstituted $C_1$-$C_6$ alkyl, unsubstituted 2 to 6 membered heteroalkyl, unsubstituted $C_3$-$C_6$ cycloalkyl, unsubstituted 3 to 6 membered heterocycloalkyl, unsubstituted phenyl, or unsubstituted 5 to 6 membered heteroaryl. In embodiments, $R^{2B}$ is independently hydrogen, $-CX^{2B}_3$, $-CHX^{2B}_2$, $-CH_2X^{2B}$, $-CN$, $-COOH$, $-CONH_2$, unsubstituted $C_1$-$C_6$ alkyl, unsubstituted 2 to 6 membered heteroalkyl, unsubstituted $C_3$-$C_6$ cycloalkyl, unsubstituted 3 to 6 membered heterocycloalkyl, unsubstituted phenyl, or unsubstituted 5 to 6 membered heteroaryl.

In embodiments, each $R^{2A}$, $R^{2B}$, $R^{3A}$, and $R^{3B}$ is independently hydrogen, $-CX_3$, $-CN$, $-COOH$, $-CONH_2$, $-CHX_2$, $-CH_2X$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{2A}$ and $R^{2B}$ substituents bonded to the same nitrogen atom may optionally be joined to form a substituted or unsubstituted heterocycloalkyl or substituted or unsubstituted heteroaryl; $R^{3A}$ and $R^{3B}$ substituents bonded to the same nitrogen atom may optionally be joined to form a substituted or unsubstituted heterocycloalkyl or substituted or unsubstituted heteroaryl.

In embodiments, $R^2$ is independently $R^{23}$-substituted $C_1$-$C_4$ alkyl. In embodiments, $R^{23}$ is independently —C(O)$R^{24}$. In embodiments, $R^{23}$ is independently unsubstituted phenyl. In embodiments, $R^{23}$ is independently $R^{24}$-substituted phenyl. In embodiments, $R^{24}$ is independently halogen. In embodiments, $R^{24}$ is independently unsubstituted phenyl. In embodiments, $R^{24}$ is independently unsubstituted $C_1$-$C_4$ alkyl. In embodiments, $R^{24}$ is independently unsubstituted $C_1$-$C_4$ haloalkyl. In embodiments, $R^{24}$ is independently unsubstituted $C_1$-$C_4$ alkoxy. In embodiments, $R^{24}$ is independently $R^{25}$-substituted phenyl. In embodiments, $R^{25}$ is independently halogen. In embodiments, $R^{24}$ is independently unsubstituted 5 to 6 membered heteroaryl.

In embodiments, $R^2$ is independently —C(O)$R^{2A}$. In embodiments, $R^{2A}$ is independently unsubstituted cyclohexyl. In embodiments, $R^{2A}$ is independently unsubstituted cyclohexenyl. In embodiments, $R^{2A}$ is independently $R^{23A}$-substituted phenyl. In embodiments, $R^{23A}$ is independently unsubstituted $C_1$-$C_4$ alkyl. In embodiments, $R^{2A}$ is independently unsubstituted $C_2$-$C_4$ alkenyl. In embodiments, $R^{2A}$ is independently $R^{23A}$-substituted $C_1$-$C_4$ alkyl. In embodiments, $R^{23A}$ is independently unsubstituted 5 to 6 membered heteroaryl.

In embodiments, $R^{2A}$ is independently $R^{23A}$-substituted 5 to 6 membered heteroaryl. In embodiments, $R^{23A}$ is independently unsubstituted $C_1$-$C_4$ alkyl.

In embodiments, $R^3$ is independently hydrogen, —CX$^3_3$, —CHX$^3_2$, —CH$_2$X$^3$, —C(O)$R^{3A}$, —C(O)OR$^{3A}$, —C(O)NR$^{3A}$R$^{3B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In embodiments, $R^3$ is independently hydrogen, —CX$^3_3$, —CHX$^3_2$, —CH$_2$X$^3$, —C(O)OH, —C(O)NH$_2$, substituted or unsubstituted $C_1$-$C_8$ alkyl, or substituted or unsubstituted 2 to 8 membered heteroalkyl; substituted or unsubstituted $C_3$-$C_8$ cycloalkyl, substituted or unsubstituted 3 to 8 membered heterocycloalkyl, substituted or unsubstituted $C_6$-$C_{12}$ aryl, or substituted or unsubstituted 5 to 12 membered heteroaryl.

In embodiments, $R^3$ is independently hydrogen, —CX$^3_3$, —CHX$^3_2$, —CH$_2$X$^3$, —C(O)OH, —C(O)NH$_2$, substituted or unsubstituted $C_1$-$C_8$ alkyl, or substituted or unsubstituted 2 to 8 membered heteroalkyl; substituted or unsubstituted $C_3$-$C_8$ cycloalkyl, substituted or unsubstituted 3 to 8 membered heterocycloalkyl, substituted or unsubstituted phenyl, or substituted or unsubstituted 5 to 6 membered heteroaryl.

In embodiments, $R^3$ is independently hydrogen. In embodiments, $R^3$ is independently —CX$^3_3$. In embodiments, $R^3$ is independently —CHX$^3_2$. In embodiments, $R^3$ is independently —CH$_2$X$^3$. In embodiments, $R^3$ is independently —C(O)$R^{3A}$. In embodiments, $R^3$ is independently —C(O)—OR$^{3A}$. In embodiments, $R^3$ is independently —C(O)NR$^{3A}$R$^{3B}$. In embodiments, $R^3$ is independently —COOH. In embodiments, $R^3$ is independently —CONH$_2$. In embodiments, $R^3$ is independently —CF$_3$. In embodiments, $R^3$ is independently —CHF$_2$. In embodiments, $R^3$ is independently —CH$_2$F. In embodiments, $R^3$ is independently —CH$_3$. In embodiments, $R^3$ is independently —CH$_2$CH$_3$. In embodiments, $R^3$ is independently —CH$_2$CH$_2$CH$_3$. In embodiments, $R^3$ is independently —CH(CH$_3$)$_2$. In embodiments, $R^3$ is independently —C(CH$_3$)$_3$. In embodiments, $R^3$ is independently —CH$_2$CH$_2$NR$^{3A}$R$^{3B}$. In embodiments, $R^3$ is independently —CH$_2$NR$^{3A}$R$^{3B}$. In embodiments, $R^3$ is independently —CH$_2$CH$_2$CH$_2$NR$^{3A}$R$^{3B}$. In embodiments, $R^3$ is independently —CH$_2$CH(CH$_3$)NR$^{3A}$R$^{3B}$. In embodiments, $R^3$ is independently —CH(CH$_3$)CH$_2$NR$^{3A}$R$^{3B}$. In embodiments, $R^3$ is independently —CH$_2$CH$_2$NHR$^{3B}$. In embodiments, $R^3$ is independently —CH$_2$NHR$^{3B}$. In embodiments, $R^3$ is independently —CH$_2$CH$_2$CH$_2$NHR$^{3B}$. In embodiments, $R^3$ is independently —CH$_2$CH(CH$_3$)NHR$^{3B}$. In embodiments, $R^3$ is independently —CH(CH$_3$)CH$_2$NHR$^{3B}$. In embodiments, $R^3$ is independently —CH$_2$CH$_2$N(CH$_3$)R$^{3B}$. In embodiments, $R^3$ is independently —CH$_2$N(CH$_3$)R$^{3B}$. In embodiments, $R^3$ is independently —CH$_2$CH$_2$CH$_2$N(CH$_3$)R$^{3B}$. In embodiments, $R^3$ is independently —CH$_2$CH(CH$_3$)N(CH$_3$)R$^{3B}$. In embodiments, $R^3$ is independently —CH(CH$_3$)CH$_2$N(CH$_3$)R$^{3B}$. In embodiments, $R^3$ is independently —CH$_2$CH$_2$N(CH$_2$CH$_3$)R$^{3B}$. In embodiments, $R^3$ is independently —CH$_2$N(CH$_2$CH$_3$)R$^{3B}$. In embodiments, $R^3$ is independently —CH$_2$CH$_2$CH$_2$N(CH$_2$CH$_3$)R$^{3B}$. In embodiments, $R^3$ is independently —CH$_2$CH(CH$_3$)N(CH$_2$CH$_3$)R$^{3B}$. In embodiments, $R^3$ is independently —CH(CH$_3$)CH$_2$N(CH$_2$CH$_3$)R$^{3B}$. In embodiments, $R^3$ is independently —CH$_2$CH$_2$N(CH$_3$)$_2$. In embodiments, $R^3$ is independently —CH$_2$N(CH$_3$)$_2$. In embodiments, $R^3$ is independently —CH$_2$CH$_2$CH$_2$N(CH$_3$)$_2$. In embodiments, $R^3$ is independently —CH$_2$CH(CH$_3$)N(CH$_3$)$_2$. In embodiments, $R^3$ is independently —CH(CH$_3$)CH$_2$N(CH$_3$)$_2$. In embodiments, $R^3$ is independently —CH$_2$CH$_2$NH$_2$. In embodiments, $R^3$ is independently —CH$_2$NH$_2$. In embodiments, $R^3$ is independently —CH$_2$CH$_2$CH$_2$NH$_2$. In embodiments, $R^3$ is independently —CH$_2$CH(CH$_3$)NH$_2$. In embodiments, $R^3$ is independently —CH(CH$_3$)CH$_2$NH$_2$. In embodiments, $R^3$ is independently —CH$_2$CH$_2$N(R$^{26}$)$_2$. In embodiments, $R^3$ is independently —CH$_2$N(R$^{26}$)$_2$. In embodiments, $R^3$ is independently —CH$_2$CH$_2$CH$_2$N(R$^{26}$)$_2$. In embodiments, $R^3$ is independently —CH$_2$CH(CH$_3$)N(R$^{26}$)$_2$. In embodiments, $R^3$ is independently —CH(CH$_3$)CH$_2$N(R$^{26}$)$_2$. In embodiments, $R^3$ is independently —CH$_2$CH$_2$NHR$^{26}$. In embodiments, $R^3$ is independently —CH$_2$NHR$^{26}$. In embodiments, $R^3$ is independently —CH$_2$CH$_2$CH$_2$NHR$^{26}$. In embodiments, $R^3$ is independently —CH$_2$CH(CH$_3$)NHR$^{26}$. In embodiments, $R^3$ is independently —CH(CH$_3$)CH$_2$NHR$^{26}$. In embodiments, $R^3$ is independently —CH$_2$CH$_2$N(CH$_3$)R$^{26}$. In embodiments, $R^3$ is independently —CH$_2$N(CH$_3$)R$^{26}$. In embodiments, $R^3$ is independently —CH$_2$CH$_2$CH$_2$N(CH$_3$)R$^{26}$. In embodiments, $R^3$ is independently —CH$_2$CH(CH$_3$)N(CH$_3$)R$^{26}$. In embodiments, $R^3$ is independently —CH(CH$_3$)CH$_2$N(CH$_3$)R$^{26}$. In embodiments, $R^3$ is independently —CH$_2$CH$_2$N(CH$_2$CH$_3$)R$^{26}$. In embodiments, $R^3$ is independently —CH$_2$N(CH$_2$CH$_3$)R$^{26}$. In embodiments, $R^3$ is independently —CH$_2$CH$_2$CH$_2$N(CH$_2$CH$_3$)R$^{26}$. In embodiments, $R^3$ is independently —CH$_2$CH(CH$_3$)N(CH$_2$CH$_3$)R$^{26}$. In embodiments, $R^3$ is independently —CH(CH$_3$)CH$_2$N(CH$_2$CH$_3$)R$^{26}$.

In embodiments, $R^3$ is independently hydrogen, —CX$^3_3$, —CHX$^3_2$, —CH$_2$X$^3$, —C(O)$R^{3A}$, —C(O)OR$^{3A}$, —C(O)NR$^{3A}$R$^{3B}$, substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{12}$, $C_6$-$C_{10}$, or phenyl), or substituted or unsubstituted heteroaryl (e.g., 5 to 12, 5 to 10 membered, 5 to 9 membered, or 5 to 6 membered).

In embodiments, $R^3$ is independently substituted or unsubstituted alkyl (e.g., $C_1$-$C_8$, $C_1$-$C_6$, $C_1$-$C_4$, or $C_1$-$C_2$). In embodiments, $R^3$ is independently substituted alkyl (e.g., $C_1$-$C_8$, $C_1$-$C_6$, $C_1$-$C_4$, or $C_1$-$C_2$). In embodiments, $R^3$ is independently unsubstituted alkyl (e.g., $C_1$-$C_8$, $C_1$-$C_6$, $C_1$-$C_4$, or $C_1$-$C_2$). In embodiments, $R^3$ is independently unsubstituted methyl. In embodiments, $R^3$ is independently unsubstituted ethyl. In embodiments, $R^3$ is independently unsubstituted propyl. In embodiments, $R^3$ is independently unsubstituted isopropyl. In embodiments, $R^3$ is independently unsubstituted tert-butyl. In embodiments, $R^3$ is independently substituted or unsubstituted heteroalkyl (e.g., 2 to 8 membered, 2 to 6 membered, 4 to 6 membered, 2 to 3 membered, or 4 to 5 membered). In embodiments, $R^3$ is independently substituted heteroalkyl (e.g., 2 to 8 membered, 2 to 6 membered, 4 to 6 membered, 2 to 3 membered, or 4 to 5 membered). In embodiments, $R^3$ is independently unsubstituted heteroalkyl (e.g., 2 to 8 membered, 2 to 6 membered, 4 to 6 membered, 2 to 3 membered, or 4 to 5 membered). In embodiments, $R^3$ is independently substituted or unsubstituted cycloalkyl (e.g., $C_3$-$C_8$, $C_3$-$C_6$, $C_4$-$C_6$, or $C_5$-$C_6$). In embodiments, $R^3$ is independently substituted cycloalkyl (e.g., $C_3$-$C_8$, $C_3$-$C_6$, $C_4$-$C_6$, or $C_5$-$C_6$). In embodiments, $R^3$ is independently unsubstituted cycloalkyl (e.g., $C_3$-$C_8$, $C_3$-$C_6$, $C_4$-$C_6$, or $C_5$-$C_6$). In embodiments, $R^3$ is independently substituted or unsubstituted heterocycloalkyl (e.g., 3 to 8 membered, 3 to 6 membered, 4 to 6 membered, 4 to 5 membered, or 5 to 6 membered). In embodiments, $R^3$ is independently substituted heterocycloalkyl (e.g., 3 to 8 membered, 3 to 6 membered, 4 to 6 membered, 4 to 5 membered, or 5 to 6 membered). In embodiments, $R^3$ is independently unsubstituted heterocycloalkyl (e.g., 3 to 8 membered, 3 to 6 membered, 4 to 6 membered, 4 to 5 membered, or 5 to 6 membered). In embodiments, $R^3$ is independently substituted or unsubstituted aryl (e.g., $C_6$-$C_{12}$, $C_6$-$C_{10}$, or phenyl). In embodiments, $R^3$ is independently substituted aryl (e.g., $C_6$-$C_{12}$, $C_6$-$C_{10}$, or phenyl). In embodiments, $R^3$ is independently unsubstituted aryl (e.g., $C_6$-$C_{12}$, $C_6$-$C_{10}$, or phenyl). In embodiments, $R^3$ is independently substituted or unsubstituted heteroaryl (e.g., 5 to 12 membered, 5 to 10 membered, 5 to 9 membered, or 5 to 6 membered). In embodiments, $R^3$ is independently substituted heteroaryl (e.g., 5 to 12 membered, 5 to 10 membered, 5 to 9 membered, or 5 to 6 membered). In embodiments, $R^3$ is independently unsubstituted heteroaryl (e.g., 5 to 12 membered, 5 to 10 membered, 5 to 9 membered, or 5 to 6 membered).

In embodiments, $R^3$ is independently hydrogen, —$CX^3_3$, —$CHX^3_2$, —$CH_2X^3$, —C(O)OH, —C(O)NH$_2$, $R^{26}$-substituted or unsubstituted alkyl (e.g., $C_1$-$C_8$, $C_1$-$C_6$, $C_1$-$C_4$, or $C_1$-$C_2$), $R^{26}$-substituted or unsubstituted heteroalkyl (e.g., 2 to 8 membered, 2 to 6 membered, 4 to 6 membered, 2 to 3 membered, or 4 to 5 membered), $R^{26}$-substituted or unsubstituted cycloalkyl (e.g., $C_3$-$C_8$, $C_3$-$C_6$, $C_4$-$C_6$, or $C_5$-$C_6$), $R^{26}$-substituted or unsubstituted heterocycloalkyl (e.g., 3 to 8 membered, 3 to 6 membered, 4 to 6 membered, 4 to 5 membered, or 5 to 6 membered), $R^{26}$-substituted or unsubstituted aryl (e.g., $C_6$-$C_{12}$, $C_6$-$C_{10}$, or phenyl), or $R^{26}$-substituted or unsubstituted heteroaryl (e.g., 5 to 12 membered, 5 to 10 membered, 5 to 9 membered, or 5 to 6 membered). In embodiments, $R^3$ is independently hydrogen, —$CX^3_3$, —$CHX^3_2$, —$CH_2X^3$, —C(O)OH, —C(O)NH$_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered). $X^3$ is independently —F, —Cl, —Br, or —I. In embodiments, $R^3$ is independently hydrogen. In embodiments, $R^3$ is independently unsubstituted methyl. In embodiments, $R^3$ is independently unsubstituted ethyl.

$R^{26}$ is independently oxo, halogen, —$CX^{26}_3$, —$CHX^{26}_2$, —$CH_2X^{26}$, —$OCX^{26}_3$, —$OCH_2X^{26}$, —$OCHX^{26}_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, $R^{27}$-substituted or unsubstituted alkyl (e.g., $C_1$-$C_8$, $C_1$-$C_6$, $C_1$-$C_4$, or $C_1$-$C_2$), $R^{27}$-substituted or unsubstituted heteroalkyl (e.g., 2 to 8 membered, 2 to 6 membered, 4 to 6 membered, 2 to 3 membered, or 4 to 5 membered), $R^{27}$-substituted or unsubstituted cycloalkyl (e.g., $C_3$-$C_8$, $C_3$-$C_6$, $C_4$-$C_6$, or $C_5$-$C_6$), $R^{27}$-substituted or unsubstituted heterocycloalkyl (e.g., 3 to 8 membered, 3 to 6 membered, 4 to 6 membered, 4 to 5 membered, or 5 to 6 membered), $R^{27}$-substituted or unsubstituted aryl (e.g., $C_6$-$C_{12}$, $C_6$-$C_{10}$, or phenyl), or $R^{27}$-substituted or unsubstituted heteroaryl (e.g., 5 to 12 membered, 5 to 10 membered, 5 to 9 membered, or 5 to 6 membered). In embodiments, $R^{26}$ is independently oxo, halogen, —$CX^{26}_3$, —$CHX^{26}_2$, —$CH_2X^{26}$, —$OCX^{26}_3$, —$OCH_2X^{26}$, —$OCHX^{26}_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered). $X^{26}$ is independently —F, —Cl, —Br, or —I. In embodiments, $R^{26}$ is independently unsubstituted methyl. In embodiments, $R^{26}$ is independently unsubstituted ethyl. In embodiments, $R^{26}$ is independently unsubstituted propyl. In embodiments, $R^{26}$ is independently unsubstituted isopropyl. In embodiments, $R^{26}$ is independently unsubstituted n-propyl. In embodiments, $R^{26}$ is independently unsubstituted butyl. In embodiments, $R^{26}$ is independently unsubstituted n-butyl. In embodiments, $R^{26}$ is independently unsubstituted t-butyl. In embodiments, $R^{26}$ is independently unsubstituted iso-butyl. In embodiments, $R^{26}$ is independently unsubstituted pentyl. In embodiments, $R^{26}$ is independently unsubstituted n-pentyl. In embodiments, $R^{26}$ is independently unsubstituted hexyl. In embodiments, $R^{26}$ is independently unsubstituted n-hexyl. In embodiments, $R^{26}$ is independently unsubstituted heptyl. In embodiments, $R^{26}$ is independently unsubstituted n-heptyl. In embodiments, $R^{26}$ is independently unsubstituted octyl. In embodiments, $R^{26}$ is independently unsubstituted n-octyl. In embodiments, $R^{26}$ is independently unsubstituted $C_1$-$C_8$ alkyl.

$R^{27}$ is independently oxo, halogen, $-CX^{27}_3$, $-CHX^{27}_2$, $-CH_2X^{27}$, $-OCX^{27}_3$, $-OCH_2X^{27}$, $-OCHX^{27}_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $R^{28}$-substituted or unsubstituted alkyl (e.g., $C_1$-$C_8$, $C_1$-$C_6$, $C_1$-$C_4$, or $C_1$-$C_2$), $R^{28}$-substituted or unsubstituted heteroalkyl (e.g., 2 to 8 membered, 2 to 6 membered, 4 to 6 membered, 2 to 3 membered, or 4 to 5 membered), $R^{28}$-substituted or unsubstituted cycloalkyl (e.g., $C_3$-$C_8$, $C_3$-$C_6$, $C_4$-$C_6$, or $C_5$-$C_6$), $R^{28}$-substituted or unsubstituted heterocycloalkyl (e.g., 3 to 8 membered, 3 to 6 membered, 4 to 6 membered, 4 to 5 membered, or 5 to 6 membered), $R^{28}$-substituted or unsubstituted aryl (e.g., $C_6$-$C_{12}$, $C_6$-$C_{10}$, or phenyl), or $R^{28}$-substituted or unsubstituted heteroaryl (e.g., 5 to 12 membered, 5 to 10 membered, 5 to 9 membered, or 5 to 6 membered). In embodiments, $R^{27}$ is independently oxo, halogen, $-CX^{27}_3$, $-CHX^{27}_2$, $-CH_2X^{27}$, $-OCX^{27}_3$, $-OCH_2X^{27}$, $-OCHX^{27}_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered). $X^{27}$ is independently $-F$, $-Cl$, $-Br$, or $-I$. In embodiments, $R^{27}$ is independently unsubstituted methyl. In embodiments, $R^{27}$ is independently unsubstituted ethyl.

$R^{28}$ is independently oxo, halogen, $-CX^{28}_3$, $-CHX^{28}_2$, $-CH_2X^{28}$, $-OCX^{28}_3$, $-OCH_2X^{28}$, $-OCHX^{28}_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC=(O)NH_2$, $-NHSO_2H$, $-NHC=(O)H$, $-NHC(O)-OH$, $-NHOH$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{12}$, or phenyl), or unsubstituted heteroaryl (e.g., 5 to 12 membered, 5 to 10 membered, 5 to 9 membered, or 5 to 6 membered). $X^{28}$ is independently $-F$, $-Cl$, $-Br$, or $-I$. In embodiments, $R^{28}$ is independently unsubstituted methyl. In embodiments, $R^{28}$ is independently unsubstituted ethyl.

In embodiments, $R^{3A}$ is independently hydrogen. In embodiments, $R^{3A}$ is independently $-CX^{3A}_3$. In embodiments, $R^{3A}$ is independently $-CHX^{3A}_2$. In embodiments, $R^{3A}$ is independently $-CH_2X^{3A}$. In embodiments, $R^{3A}$ is independently $-CN$. In embodiments, $R^{3A}$ is independently $-COOH$. In embodiments, $R^{3A}$ is independently $-CONH_2$. In embodiments, $X^{3A}$ is independently $-F$, $-Cl$, $-Br$, or $-I$.

In embodiments, $R^{3A}$ is independently substituted or unsubstituted alkyl (e.g., $C_1$-$C_8$, $C_1$-$C_6$, $C_1$-$C_4$, or $C_1$-$C_2$). In embodiments, $R^{3A}$ is independently substituted alkyl (e.g., $C_1$-$C_8$, $C_1$-$C_6$, $C_1$-$C_4$, or $C_1$-$C_2$). In embodiments, $R^{3A}$ is independently unsubstituted alkyl (e.g., $C_1$-$C_8$, $C_1$-$C_6$, $C_1$-$C_4$, or $C_1$-$C_2$). In embodiments, $R^{3A}$ is independently unsubstituted methyl. In embodiments, $R^{3A}$ is independently unsubstituted ethyl. In embodiments, $R^{3A}$ is independently unsubstituted propyl. In embodiments, $R^{3A}$ is independently unsubstituted isopropyl. In embodiments, $R^{3A}$ is independently unsubstituted tert-butyl. In embodiments, $R^{3A}$ is independently substituted or unsubstituted heteroalkyl (e.g., 2 to 8 membered, 2 to 6 membered, 4 to 6 membered, 2 to 3 membered, or 4 to 5 membered). In embodiments, $R^{3A}$ is independently substituted heteroalkyl (e.g., 2 to 8 membered, 2 to 6 membered, 4 to 6 membered, 2 to 3 membered, or 4 to 5 membered). In embodiments, $R^{3A}$ is independently unsubstituted heteroalkyl (e.g., 2 to 8 membered, 2 to 6 membered, 4 to 6 membered, 2 to 3 membered, or 4 to 5 membered). In embodiments, $R^{3A}$ is independently substituted or unsubstituted cycloalkyl (e.g., $C_3$-$C_8$, $C_3$-$C_6$, $C_4$-$C_6$, or $C_5$-$C_6$). In embodiments, $R^{3A}$ is independently substituted cycloalkyl (e.g., $C_3$-$C_8$, $C_4$-$C_6$, or $C_5$-$C_6$). In embodiments, $R^{3A}$ is independently unsubstituted cycloalkyl (e.g., $C_3$-$C_8$, $C_3$-$C_6$, $C_4$-$C_6$, or $C_5$-$C_6$). In embodiments, $R^{3A}$ is independently substituted or unsubstituted heterocycloalkyl (e.g., 3 to 8 membered, 3 to 6 membered, 4 to 6 membered, 4 to 5 membered, or 5 to 6 membered). In embodiments, $R^{3A}$ is independently substituted heterocycloalkyl (e.g., 3 to 8 membered, 3 to 6 membered, 4 to 6 membered, 4 to 5 membered, or 5 to 6 membered). In embodiments, $R^{3A}$ is independently unsubstituted heterocycloalkyl (e.g., 3 to 8 membered, 3 to 6 membered, 4 to 6 membered, 4 to 5 membered, or 5 to 6 membered). In embodiments, $R^{3A}$ is independently substituted or unsubstituted aryl (e.g., $C_6$-$C_{12}$, $C_6$-$C_{10}$, or phenyl). In embodiments, $R^{3A}$ is independently substituted aryl (e.g., $C_6$-$C_{12}$, $C_6$-$C_{10}$, or phenyl). In embodiments, $R^{3A}$ is independently unsubstituted aryl (e.g., $C_6$-$C_{12}$, $C_6$-$C_{10}$, or phenyl). In embodiments, $R^{3A}$ is independently substituted or unsubstituted heteroaryl (e.g., 5 to 12 membered, 5 to 10 membered, 5 to 9 membered, or 5 to 6 membered). In embodiments, $R^{3A}$ is independently substituted heteroaryl (e.g., 5 to 12 membered, 5 to 10 membered, 5 to 9 membered, or 5 to 6 membered). In embodiments, $R^{3A}$ is independently unsubstituted heteroaryl (e.g., 5 to 12 membered, 5 to 10 membered, 5 to 9 membered, or 5 to 6 membered).

In embodiments, $R^{3A}$ is independently hydrogen, $-CX^{3A}_3$, $-CHX^{3A}_2$, $-CH_2X^{3A}$, $-CN$, $-COOH$, $-CONH_2$, $R^{26A}$-substituted or unsubstituted alkyl (e.g., $C_1$-$C_8$, $C_1$-$C_6$, $C_1$-$C_4$, or $C_1$-$C_2$), $R^{26A}$-substituted or unsubstituted heteroalkyl (e.g., 2 to 8 membered, 2 to 6 membered, 4 to 6 membered, 2 to 3 membered, or 4 to 5 membered), $R^{26A}$-substituted or unsubstituted cycloalkyl (e.g., $C_3$-$C_8$, $C_3$-$C_6$, $C_4$-$C_6$, or $C_5$-$C_6$), $R^{26A}$-substituted or unsubstituted heterocycloalkyl (e.g., 3 to 8 membered, 3 to 6 membered, 4 to 6 membered, 4 to 5 membered, or 5 to 6 membered), $R^{26A}$-substituted or unsubstituted aryl (e.g., $C_6$-$C_{12}$, $C_6$-$C_{10}$, or phenyl), or $R^{26A}$-substituted or unsubstituted heteroaryl (e.g., 5 to 12 membered, 5 to 10 membered, 5 to 9 membered, or 5 to 6 membered). In embodiments, $R^{3A}$ is independently hydrogen, $-CX^{3A}_3$, $-CHX^{3A}_2$, $-CH_2X^{3A}$, $-CN$, $-COOH$, $-CONH_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered). $X^{3A}$ is independently —F, —Cl, —Br, or —I. In embodiments, $R^{3A}$ is independently hydrogen. In embodiments, $R^{3A}$ is independently unsubstituted methyl. In embodiments, $R^{3A}$ is independently unsubstituted ethyl.

In embodiments, $R^{3A}$ and $R^{3B}$ substituents bonded to the same nitrogen atom may optionally be joined to form a $R^{26A}$-substituted or unsubstituted heterocycloalkyl (e.g., 3 to 8 membered, 3 to 6 membered, 4 to 6 membered, 4 to 5 membered, or 5 to 6 membered) or $R^{26A}$-substituted or unsubstituted heteroaryl (e.g., 5 to 12 membered, 5 to 10 membered, 5 to 9 membered, or 5 to 6 membered). In embodiments, $R^{3A}$ and $R^{3B}$ substituents bonded to the same nitrogen atom may optionally be joined to form an unsubstituted heterocycloalkyl (e.g., 3 to 8 membered, 3 to 6 membered, 4 to 6 membered, 4 to 5 membered, or 5 to 6 membered) or unsubstituted heteroaryl (e.g., 5 to 12 membered, 5 to 10 membered, 5 to 9 membered, or 5 to 6 membered). In embodiments, $R^{3A}$ and $R^{3B}$ substituents bonded to the same nitrogen atom may optionally be joined to form a $R^{26A}$-substituted or unsubstituted heterocycloalkyl (e.g., 3 to 8 membered, 3 to 6 membered, 4 to 6 membered, 4 to 5 membered, or 5 to 6 membered). In embodiments, $R^{3A}$ and $R^{3B}$ substituents bonded to the same nitrogen atom may optionally be joined to form an unsubstituted heterocycloalkyl (e.g., 3 to 8 membered, 3 to 6 membered, 4 to 6 membered, 4 to 5 membered, or 5 to 6 membered).

$R^{26A}$ is independently oxo, halogen, —$CX^{26A}_3$, —$CHX^{26A}_2$, —$CH_2X^{26A}$, —$OCX^{26A}_3$, —$OCH_2X^{26A}$, —$OCHX^{26A}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, $R^{27A}$-substituted or unsubstituted alkyl (e.g., $C_1$-$C_8$, $C_1$-$C_6$, $C_1$-$C_4$, or $C_1$-$C_2$), $R^{27A}$-substituted or unsubstituted heteroalkyl (e.g., 2 to 8 membered, 2 to 6 membered, 4 to 6 membered, 2 to 3 membered, or 4 to 5 membered), $R^{27A}$-substituted or unsubstituted cycloalkyl (e.g., $C_3$-$C_8$, $C_3$-$C_6$, $C_4$-$C_6$, or $C_5$-$C_6$), $R^{27A}$-substituted or unsubstituted heterocycloalkyl (e.g., 3 to 8 membered, 3 to 6 membered, 4 to 6 membered, 4 to 5 membered, or 5 to 6 membered), $R^{27A}$-substituted or unsubstituted aryl (e.g., $C_6$-$C_{12}$, $C_6$-$C_{10}$, or phenyl), or $R^{27A}$-substituted or unsubstituted heteroaryl (e.g., 5 to 12 membered, 5 to 10 membered, 5 to 9 membered, or 5 to 6 membered). In embodiments, $R^{26A}$ is independently oxo, halogen, —$CX^{26A}_3$, —$CHX^{26A}_2$, —$CH_2X^{26A}$, —$OCX^{26A}_3$, —$OCH_2X^{26A}$, —$OCHX^{26A}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered). $X^{26A}$ is independently —F, —Cl, —Br, or —I. In embodiments, $R^{26A}$ is independently unsubstituted methyl. In embodiments, $R^{26A}$ is independently unsubstituted ethyl.

$R^{27A}$ is independently oxo, halogen, —$CX^{27A}_3$, —$CHX^{27A}_2$, —$CH_2X^{27A}$, —$OCX^{27A}_3$, —$OCH_2X^{27A}$, —$OCHX^{27A}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, $R^{28A}$-substituted or unsubstituted alkyl (e.g., $C_1$-$C_8$, $C_1$-$C_6$, $C_1$-$C_4$, or $C_1$-$C_2$), $R^{28A}$-substituted or unsubstituted heteroalkyl (e.g., 2 to 8 membered, 2 to 6 membered, 4 to 6 membered, 2 to 3 membered, or 4 to 5 membered), $R^{28A}$-substituted or unsubstituted cycloalkyl (e.g., $C_3$-$C_8$, $C_3$-$C_6$, $C_4$-$C_6$, or $C_5$-$C_6$), $R^{28A}$-substituted or unsubstituted heterocycloalkyl (e.g., 3 to 8 membered, 3 to 6 membered, 4 to 6 membered, 4 to 5 membered, or 5 to 6 membered), $R^{28A}$-substituted or unsubstituted aryl (e.g., $C_6$-$C_{12}$, $C_6$-$C_{10}$, or phenyl), or $R^{28A}$-substituted or unsubstituted heteroaryl (e.g., 5 to 12 membered, 5 to 10 membered, 5 to 9 membered, or 5 to 6 membered). In embodiments, $R^{27A}$ is independently oxo, halogen, —$CX^{27A}_3$, —$CHX^{27A}_2$, —$CH_2X^{27A}$, —$OCX^{27A}_3$, —$OCH_2X^{27A}$, —$OCHX^{27A}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered). $X^{27A}$ is independently —F, —Cl, —Br, or —I. In embodiments, $R^{27A}$ is independently unsubstituted methyl. In embodiments, $R^{27A}$ is independently unsubstituted ethyl.

$R^{28A}$ is independently oxo, halogen, —$CX^{28A}_3$, —$CHX^{28A}_2$, —$CH_2X^{28A}$, —$OCX^{28A}_3$, —$OCH_2X^{28A}$, —$OCHX^{28A}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered). $X^{28A}$ is independently —F, —Cl, —Br, or —I. In embodiments, $R^{28A}$ is independently unsubstituted methyl. In embodiments, $R^{28A}$ is independently unsubstituted ethyl.

In embodiments, $R^{3B}$ is independently hydrogen. In embodiments, $R^{3B}$ is independently —$CX^{3B}_3$. In embodiments, $R^{3B}$ is independently —$CHX^{3B}_2$. In embodiments, $R^{3B}$ is independently —$CH_2X^{3B}$. In embodiments, $R^{3B}$ is independently —CN. In embodiments, $R^{3B}$ is independently —COOH. In embodiments, $R^{3B}$ is independently —$CONH_2$. In embodiments, $X^{3B}$ is independently —F, —Cl, —Br, or —I.

In embodiments, $R^{3B}$ is independently substituted or unsubstituted alkyl (e.g., $C_1$-$C_8$, $C_1$-$C_6$, $C_1$-$C_4$, or $C_1$-$C_2$). In embodiments, $R^{3B}$ is independently substituted alkyl (e.g., $C_1$-$C_8$, $C_1$-$C_6$, $C_1$-$C_4$, or $C_1$-$C_2$). In embodiments, $R^{3B}$ is independently unsubstituted alkyl (e.g., $C_1$-$C_8$, $C_1$-$C_6$, $C_1$-$C_4$, or $C_1$-$C_2$). In embodiments, $R^{3B}$ is independently unsubstituted methyl. In embodiments, $R^{3B}$ is independently unsubstituted ethyl. In embodiments, $R^{3B}$ is independently unsubstituted propyl. In embodiments, $R^{3B}$ is independently unsubstituted isopropyl. In embodiments, $R^{3B}$ is independently unsubstituted tert-butyl. In embodiments, $R^{3B}$ is independently substituted or unsubstituted heteroalkyl (e.g., 2 to 8 membered, 2 to 6 membered, 4 to 6 membered, 2 to 3 membered, or 4 to 5 membered). In embodiments, $R^{3B}$ is independently substituted heteroalkyl (e.g., 2 to 8 membered, 2 to 6 membered, 4 to 6 membered, 2 to 3 membered, or 4 to 5 membered). In embodiments, $R^{3B}$ is independently unsubstituted heteroalkyl (e.g., 2 to 8 membered, 2 to 6 membered, 4 to 6 membered, 2 to 3 membered, or 4 to 5 membered). In embodiments, $R^{3B}$ is independently substituted or unsubstituted cycloalkyl (e.g., $C_3$-$C_8$, $C_3$-$C_6$, $C_4$-$C_6$, or $C_5$-$C_6$). In embodiments, $R^{3B}$ is independently substituted cycloalkyl (e.g., $C_3$-$C_8$, $C_3$-$C_6$, $C_4$-$C_6$, or $C_5$-$C_6$). In embodiments, $R^{3B}$ is independently unsubstituted cycloalkyl (e.g., $C_3$-$C_8$, $C_3$-$C_6$, $C_4$-$C_6$, or $C_5$-$C_6$). In embodiments, $R^{3B}$ is independently substituted or unsubstituted heterocycloalkyl (e.g., 3 to 8 membered, 3 to 6 membered, 4 to 6 membered, 4 to 5 membered, or 5 to 6 membered). In embodiments, $R^{3B}$ is independently substituted heterocycloalkyl (e.g., 3 to 8 membered, 3 to 6 membered, 4 to 6 membered, 4 to 5 membered, or 5 to 6 membered). In embodiments, $R^{3B}$ is independently unsubstituted heterocycloalkyl (e.g., 3 to 8 membered, 3 to 6 membered, 4 to 6 membered, 4 to 5 membered, or 5 to 6 membered). In embodiments, $R^{3B}$ is independently substituted or unsubstituted aryl (e.g., $C_6$-$C_{12}$, $C_6$-$C_{10}$, or phenyl). In embodiments, $R^{3B}$ is independently substituted aryl (e.g., $C_6$-$C_{12}$, $C_6$-$C_{10}$, or phenyl). In embodiments, $R^{3B}$ is independently unsubstituted aryl (e.g., $C_6$-$C_{12}$, $C_6$-$C_{10}$, or phenyl). In embodiments, $R^{3B}$ is independently substituted or unsubstituted heteroaryl (e.g., 5 to 12 membered, 5 to 10 membered, 5 to 9 membered, or 5 to 6 membered). In embodiments, $R^{3B}$ is independently substituted heteroaryl (e.g., 5 to 12 membered, 5 to 10 membered, 5 to 9 membered, or 5 to 6 membered). In embodiments, $R^{3B}$ is independently unsubstituted heteroaryl (e.g., 5 to 12 membered, 5 to 10 membered, 5 to 9 membered, or 5 to 6 membered).

In embodiments, $R^{3A}$ and $R^{3B}$ substituents bonded to the same nitrogen atom may be joined to form a substituted or unsubstituted heterocycloalkyl (e.g., 3 to 8 membered, 3 to 6 membered, 4 to 6 membered, 4 to 5 membered, or 5 to 6 membered). In embodiments, $R^{3A}$ and $R^{3B}$ substituents bonded to the same nitrogen atom may be joined to form a substituted heterocycloalkyl (e.g., 3 to 8 membered, 3 to 6 membered, 4 to 6 membered, 4 to 5 membered, or 5 to 6 membered). In embodiments, $R^{3A}$ and $R^{3B}$ substituents bonded to the same nitrogen atom may be joined to form an unsubstituted heterocycloalkyl (e.g., 3 to 8 membered, 3 to 6 membered, 4 to 6 membered, 4 to 5 membered, or 5 to 6 membered). In embodiments, $R^{3A}$ and $R^{3B}$ substituents bonded to the same nitrogen atom may be joined to form a substituted or unsubstituted heteroaryl (e.g., 5 to 12 membered, 5 to 10 membered, 5 to 9 membered, or 5 to 6 membered). In embodiments, $R^{3A}$ and $R^{3B}$ substituents bonded to the same nitrogen atom may be joined to form a substituted heteroaryl (e.g., 5 to 12 membered, 5 to 10 membered, 5 to 9 membered, or 5 to 6 membered). In embodiments, $R^{3A}$ and $R^{3B}$ substituents bonded to the same nitrogen atom may be joined to form an unsubstituted heteroaryl (e.g., 5 to 12 membered, 5 to 10 membered, 5 to 9 membered, or 5 to 6 membered).

In embodiments, $R^{3B}$ is independently hydrogen, —$CX^{3B}_3$, —$CHX^{3B}_2$, —$CH_2X^{3B}$, —CN, —COOH, —$CONH_2$, $R^{26B}$-substituted or unsubstituted alkyl (e.g., $C_1$-$C_8$, $C_1$-$C_6$, $C_1$-$C_4$, or $C_1$-$C_2$), $R^{26B}$-substituted or unsubstituted heteroalkyl (e.g., 2 to 8 membered, 2 to 6 membered, 4 to 6 membered, 2 to 3 membered, or 4 to 5 membered), $R^{26B}$-substituted or unsubstituted cycloalkyl (e.g., $C_3$-$C_8$, $C_3$-$C_6$, $C_4$-$C_6$, or $C_5$-$C_6$), $R^{26B}$-substituted or unsubstituted heterocycloalkyl (e.g., 3 to 8 membered, 3 to 6 membered, 4 to 6 membered, 4 to 5 membered, or 5 to 6 membered), $R^{26B}$-substituted or unsubstituted aryl (e.g., $C_6$-$C_{12}$, $C_6$-$C_{10}$, or phenyl), or $R^{26B}$-substituted or unsubstituted heteroaryl (e.g., 5 to 12 membered, 5 to 10 membered, 5 to 9 membered, or 5 to 6 membered). In embodiments, $R^{3B}$ is independently hydrogen, —$CX^{3B}_3$, —$CHX^{3B}_2$, —$CH_2X^{3B}$, —CN, —COOH, —$CONH_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered). $X^{3B}$ is independently —F, —Cl, —Br, or —I. In embodiments, $R^{3B}$ is independently hydrogen. In embodiments, $R^{3B}$ is independently unsubstituted methyl. In embodiments, $R^{3B}$ is independently unsubstituted ethyl.

In embodiments, $R^{3A}$ and $R^{3B}$ substituents bonded to the same nitrogen atom may optionally be joined to form a $R^{26B}$-substituted or unsubstituted heterocycloalkyl (e.g., 3 to 8 membered, 3 to 6 membered, 4 to 6 membered, 4 to 5 membered, or 5 to 6 membered) or $R^{26B}$-substituted or unsubstituted heteroaryl (e.g., 5 to 12 membered, 5 to 10 membered, 5 to 9 membered, or 5 to 6 membered). In embodiments, $R^{3A}$ and $R^{3B}$ substituents bonded to the same nitrogen atom may optionally be joined to form an unsubstituted heterocycloalkyl (e.g., 3 to 8 membered, 3 to 6 membered, 4 to 6 membered, 4 to 5 membered, or 5 to 6 membered) or unsubstituted heteroaryl (e.g., 5 to 12 membered, 5 to 10 membered, 5 to 9 membered, or 5 to 6 membered). In embodiments, $R^{3A}$ and $R^{3B}$ substituents bonded to the same nitrogen atom may optionally be joined to form a $R^{26B}$-substituted or unsubstituted heterocycloalkyl (e.g., 3 to 8 membered, 3 to 6 membered, 4 to 6 membered, 4 to 5 membered, or 5 to 6 membered). In embodiments, $R^{3A}$ and $R^{3B}$ substituents bonded to the same nitrogen atom may optionally be joined to form an unsubstituted heterocycloalkyl (e.g., 3 to 8 membered, 3 to 6 membered, 4 to 6 membered, 4 to 5 membered, or 5 to 6 membered).

$R^{26B}$ is independently oxo, halogen, —$CX^{26B}_3$, —$CHX^{26B}_2$, —$CH_2X^{26B}$, —$OCX^{26B}_3$, —$OCH_2X^{26B}$, —$OCHX^{26B}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, $R^{27B}$-substituted or unsubstituted alkyl (e.g., $C_1$-$C_8$, $C_1$-$C_6$, $C_1$-$C_4$, or $C_1$-$C_2$), $R^{27B}$-substituted or unsubstituted heteroalkyl (e.g., 2 to 8 membered, 2 to 6 membered, 4 to 6 membered, 2 to 3 membered, or 4 to 5 membered), $R^{27B}$-substituted or unsubstituted cycloalkyl (e.g., $C_3$-$C_8$, $C_3$-$C_6$, $C_4$-$C_6$, or $C_5$-$C_6$), $R^{27B}$-substituted or unsubstituted heterocycloalkyl (e.g., 3 to 8 membered, 3 to 6 membered, 4 to 6 membered, 4 to 5 membered, or 5 to 6 membered), $R^{27B}$-substituted or unsubstituted aryl (e.g., $C_6$-$C_{12}$, $C_6$-$C_{10}$, or phenyl), or $R^{27B}$-substituted or unsubstituted heteroaryl (e.g., 5 to 12 membered, 5 to 10 membered, 5 to 9 membered, or 5 to 6 membered). In embodiments, $R^{26B}$ is independently oxo, halogen, —$CX^{26B}_3$, —$CHX^{26B}_2$, —$CH_2X^{26B}$, —$OCX^{26B}_3$, —$OCH_2X^{26B}$, —$OCHX^{26B}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered). $X^{26B}$ is independently —F, —Cl, —Br, or —I. In embodiments, $R^{26B}$ is independently unsubstituted methyl. In embodiments, $R^{26B}$ is independently unsubstituted ethyl.

$R^{27B}$ is independently oxo, halogen, —$CX^{27B}_3$, —$CHX^{27B}_2$, —$CH_2X^{27B}$, —$OCX^{27B}_3$, —$OCH_2X^{27B}$, —$OCHX^{27B}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, $R^{28B}$-substituted or unsubstituted alkyl (e.g., $C_1$-$C_8$, $C_1$-$C_6$, $C_1$-$C_4$, or $C_1$-$C_2$), $R^{28B}$-substituted or unsubstituted heteroalkyl (e.g., 2 to 8 membered, 2 to 6 membered, 4 to 6 membered, 2 to 3 membered, or 4 to 5 membered), $R^{28B}$-substituted or unsubstituted cycloalkyl (e.g., $C_3$-$C_8$, $C_3$-$C_6$, $C_4$-$C_6$, or $C_5$-$C_6$), $R^{28B}$-substituted or unsubstituted heterocycloalkyl (e.g., 3 to 8 membered, 3 to 6 membered, 4 to 6 membered, 4 to 5 membered, or 5 to 6 membered), $R^{28B}$-substituted or unsubstituted aryl (e.g., $C_6$-$C_{12}$, $C_6$-$C_{10}$, or phenyl), or $R^{28B}$-substituted or unsubstituted heteroaryl (e.g., 5 to 12 membered, 5 to 10 membered, 5 to 9 membered, or 5 to 6 membered). In embodiments, $R^{27B}$ is independently oxo, halogen, —$CX^{27B}_3$, —$CHX^{27B}_2$, —$CH_2X^{27B}$, —$OCX^{27B}_3$, —$OCH_2X^{27B}$, —$OCHX^{27B}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered). $X^{27B}$ is independently —F, —Cl, —Br, or —I. In embodiments, $R^{27B}$ is independently unsubstituted methyl. In embodiments, $R^{27B}$ is independently unsubstituted ethyl.

$R^{28B}$ is independently oxo, halogen, —$CX^{28B}_3$, —$CHX^{28B}_2$, —$CH_2X^{28B}$, —$OCX^{28B}_3$, —$OCH_2X^{28B}$, —$OCHX^{28B}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{12}$, or phenyl), or unsubstituted heteroaryl (e.g., 5 to 12 membered, 5 to 10 membered, 5 to 9 membered, or 5 to 6 membered). $X^{28B}$ is independently —F, —Cl, —Br, or —I. In embodiments, $R^{28B}$ is independently unsubstituted methyl. In embodiments, $R^{28B}$ is independently unsubstituted ethyl.

In embodiments, $R^3$ is independently hydrogen, —$CX^3_3$, —$CHX^3_2$, —$CH_2X^3$, substituted or unsubstituted $C_1$-$C_6$ alkyl, or substituted or unsubstituted 2 to 8 membered heteroalkyl. In embodiments, $R^3$ is independently hydrogen, $R^{26}$-substituted or unsubstituted alkyl, or $R^{26}$-substituted or unsubstituted heteroalkyl. In embodiments, $R^{26}$ is independently oxo, halogen, —$CX^{26}_3$, —$CHX^{26}_2$, —$CH_2X^{26}$, —$OCX^{26}_3$, —$OCH_2X^{26}$, —$OCHX^{26}_2$, —CN, —OH, —$NH_2$, —COOH, —$CONH_2$, —$NO_2$, —SH, $R^{27}$-substituted or unsubstituted $C_1$-$C_6$ alkyl, $R^{27}$-substituted or unsubstituted 2 to 6 membered heteroalkyl, $R^{27}$-substituted or unsubstituted $C_3$-$C_6$ cycloalkyl, $R^{27}$-substituted or unsubstituted 3 to 6 membered heterocycloalkyl, $R^{27}$-substituted or unsubstituted phenyl, or $R^{27}$-substituted or unsubstituted 5 to 6 membered heteroaryl. In embodiments, $R^{27}$ is independently oxo, halogen, —$CX^{27}_3$, —$CHX^{27}_2$, —$CH_2X^{27}$, —$OCX^{27}_3$, —$OCH_2X^{27}$, —$OCHX^{27}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, $R^{28}$-substituted or unsubstituted $C_1$-$C_6$ alkyl, $R^{28}$-substituted or unsubstituted 2 to 6 membered heteroalkyl, $R^{28}$-substituted or unsubstituted $C_3$-$C_6$ cycloalkyl, $R^{28}$-substituted or unsubstituted 3 to 6 membered heterocycloalkyl, $R^{28}$-substituted or unsubstituted phenyl, or $R^{28}$-substituted or unsubstituted 5 to 6 membered heteroaryl. In embodiments, $R^{28}$ is independently oxo, halogen, —$CX^{28}_3$, —$CHX^{28}_2$, —$CH_2X^{28}$, —$OCX^{28}_3$, —$OCH_2X^{28}$, —$OCHX^{28}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, unsubstituted $C_1$-$C_6$ alkyl, unsubstituted 2 to 6 membered heteroalkyl, unsubstituted $C_3$-$C_6$ cycloalkyl, unsubstituted 3 to 6 membered heterocycloalkyl, unsubstituted phenyl, or unsubstituted 5 to 6 membered heteroaryl.

In embodiments, $R^3$ is independently $R^{26}$-substituted alkyl (e.g., $C_1$-$C_8$, $C_1$-$C_6$, $C_1$-$C_4$, or $C_1$-$C_2$). In embodiments, $R^{26}$ is independently —$NH_2$ or unsubstituted heteroalkyl (e.g., 2 to 8 membered, 2 to 6 membered, 4 to 6 membered, 2 to 3 membered, or 4 to 5 membered). In embodiments, $R^{26}$ is independently —$NH_2$. In embodiments, $R^{26}$ is independently unsubstituted heteroalkyl (e.g., 2 to 8 membered, 2 to 6 membered, 4 to 6 membered, 2 to 3 membered, or 4 to 5 membered). In embodiments, $R^{26}$ is independently —N(unsubstituted $C_1$-$C_3$ alkyl)$_2$. In embodiments, $R^{26}$ is independently —N($CH_3$)$_2$. In embodiments, $R^{26}$ is independently —N(unsubstituted $C_3$ alkyl)$_2$. In embodiments, $R^{26}$ is independently —N(unsubstituted $C_2$ alkyl)$_2$. In embodiments, $R^{26}$ is independently —NH(unsubstituted $C_1$-$C_3$ alkyl). In embodiments, $R^{26}$ is independently —NH(unsubstituted $C_1$-$C_2$ alkyl). In embodiments, $R^{26}$ is independently —N(unsubstituted $C_1$-$C_3$ alkyl)(unsubstituted $C_1$-$C_3$ alkyl).

In embodiments, $R^3$ is independently $R^{26}$-substituted alkyl (e.g., $C_1$-$C_8$, $C_1$-$C_6$, $C_1$-$C_4$, or $C_1$-$C_2$). In embodiments, $R^{26}$ is independently —$NH_2$ or $R^{27}$-substituted heteroalkyl (e.g., 2 to 8 membered, 2 to 6 membered, 4 to 6 membered, 2 to 3 membered, or 4 to 5 membered). In embodiments, $R^{26}$ is independently —$NH_2$. In embodiments, $R^{26}$ is independently $R^{27}$-substituted heteroalkyl (e.g., 2 to 8 membered, 2 to 6 membered, 4 to 6 membered, 2 to 3 membered, or 4 to 5 membered). In embodiments, $R^{26}$ is independently —N($R^{27}$-substituted $C_1$-$C_3$ alkyl)$_2$. In embodiments, $R^{26}$ is independently —N($CH_3$)$_2$. In embodiments, $R^{26}$ is independently —N($R^{27}$-substituted $C_3$ alkyl)$_2$. In embodiments, $R^{26}$ is independently —N($R^{27}$-substituted $C_2$ alkyl)$_2$. In embodiments, $R^{26}$ is independently —NH ($R^{27}$-substituted $C_1$-$C_3$ alkyl). In embodiments, $R^{26}$ is independently —NH($R^{27}$-substituted $C_1$-$C_2$ alkyl). In embodiments, $R^{26}$ is independently —N($R^{27}$-substituted $C_1$-$C_3$ alkyl)($R^{27}$-substituted $C_1$-$C_3$ alkyl).

In embodiments, $R^3$ is independently hydrogen or —$CH_2CH_2$N(unsubstituted $C_1$-$C_3$ alkyl)$_2$. In embodiments, $R^3$ is hydrogen. In embodiments, $R^3$ is —$CH_2CH_2$N($CH_3$)$_2$. In embodiments, $R^3$ is independently hydrogen, —$CX^3{}_3$, —$CHX^3{}_2$, —$CH_2X^3$, —C(O)$R^{3A}$, —C(O)O$R^{3A}$, —C(O)N$R^{3A}R^{3B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiments, $R^3$ is independently hydrogen or —$CH_2CH_2$N(unsubstituted $C_1$-$C_3$ alkyl)$_2$. In embodiments, $R^3$ is hydrogen. In embodiments, $R^3$ is —$CH_2CH_2$N($CH_3$)$_2$. In embodiments, $R^3$ is —$CH_2CH_2$N($R^{26}$)$_2$. In embodiments, $R^3$ is —$CH_2CH_2$N($R^{26}$)$_2$ and $R^{26}$ is independently unsubstituted methyl. In embodiments, $R^3$ is —$CH_2CH_2$N($R^{26}$)$_2$ and $R^{26}$ is independently unsubstituted ethyl. In embodiments, $R^3$ is —$CH_2CH_2$N($R^{26}$)$_2$ and $R^{26}$ is independently unsubstituted $C_1$-$C_3$ alkyl.

In embodiments, $R^3$ is independently hydrogen, substituted or unsubstituted $C_1$-$C_6$ alkyl, or substituted or unsubstituted 2 to 8 membered heteroalkyl. In embodiments, $R^3$ is independently hydrogen, $R^{26}$-substituted or unsubstituted alkyl, or $R^{26}$-substituted or unsubstituted heteroalkyl.

In embodiments, $R^3$ is independently hydrogen, $R^{26}$-substituted or unsubstituted alkyl, or $R^{26}$-substituted or unsubstituted heteroalkyl and $R^{26}$ is independently oxo, halogen, —$CX^{26}{}_3$, —$CHX^{26}{}_2$, —$CH_2X^{26}$, —$OCX^{26}{}_3$, —$OCH_2X^{26}$, —$OCHX^{26}{}_2$, —CN, —OH, —$NH_2$, —COOH, —$CONH_2$, —$NO_2$, —SH, unsubstituted $C_1$-$C_6$ alkyl, unsubstituted 2 to 6 membered heteroalkyl, unsubstituted $C_3$-$C_6$ cycloalkyl, unsubstituted 3 to 6 membered heterocycloalkyl, unsubstituted phenyl, or unsubstituted 5 to 6 membered heteroaryl.

In embodiments, $R^3$ is hydrogen. In embodiments, $R^3$ is —$(CH_2)_w$N($R^{26.1}$)($R^{26.2}$). w is an integer from 0 to 5 (e.g., 0, 1, 2, 3, 4, or 5). $R^{26.1}$ is any value of $R^{26}$ or H. $R^{26.2}$ is any value of $R^{26}$ or H. In embodiments, $R^3$ is substituted or unsubstituted alkyl (e.g., $C_1$-$C_8$, $C_1$-$C_6$, $C_1$-$C_4$, or $C_1$-$C_2$). In embodiments, $R^3$ is a substituted or unsubstituted alkenyl (e.g., $C_2$-$C_8$, $C_2$-$C_6$, or $C_2$-$C_4$). In embodiments, $R^3$ is

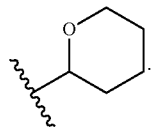 [SMILES: *C1CCCCO1]

In embodiments, $R^3$ is

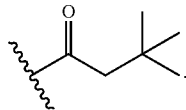 [SMILES: *C(=O)CC(C)(C)C]

In embodiments, $R^3$ is —$(CH_2)_2$N($CH_3$)$_2$. In embodiments, $R^3$ is

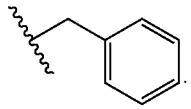 [SMILES: *Cc1ccccc1]

In embodiments, $R^3$ is

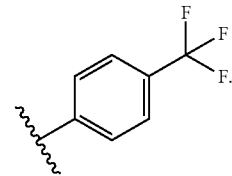 [SMILES: *c1ccc(C(F)(F)F)cc1]

In embodiments, $R^3$ is

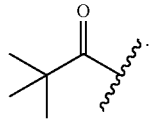 [SMILES: *C(=O)C(C)(C)C]

In embodiments, $R^3$ is

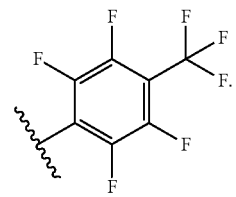 [SMILES: *c1c(F)c(F)c(C(F)(F)F)c(F)c1F]

In embodiments, $R^{26.1}$ is hydrogen, substituted or unsubstituted alkyl (e.g., $C_1$-$C_8$, $C_1$-$C_6$, $C_1$-$C_4$, or $C_1$-$C_2$), substituted or unsubstituted alkenyl (e.g., $C_2$-$C_8$, $C_2$-$C_6$, or $C_2$-$C_4$), substituted or unsubstituted alkynyl (e.g., $C_2$-$C_8$, $C_2$-$C_6$, or $C_2$-$C_4$), or substituted or unsubstituted phenyl. In embodiments, $R^{26.1}$ is unsubstituted methyl. In embodiments, $R^{26.1}$ is substituted with halogen, haloalkyl, alkylcarboxy, alkoxy, phenoxy, alkylamino, or alkylcarbonyl. In embodiments, $R^{26.1}$ is In embodiments, $R^{26.1}$ is

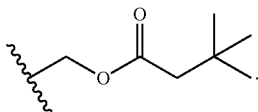 [SMILES: *COC(=O)CC(C)(C)C]

In embodiments, $R^{26.1}$ is independently unsubstituted methyl. In embodiments, $R^{26.1}$ is independently unsubstituted ethyl. In embodiments, $R^{26.1}$ is independently unsubstituted propyl. In embodiments, $R^{26.1}$ is independently unsubstituted isopropyl. In embodiments, $R^{26.1}$ is independently unsubstituted n-propyl. In embodiments, $R^{26.1}$ is independently unsubstituted butyl. In embodiments, $R^{26.1}$ is independently unsubstituted n-butyl. In embodiments, $R^{26.1}$ is independently unsubstituted t-butyl. In embodiments, $R^{26.1}$ is independently unsubstituted iso-butyl. In embodiments, $R^{26.1}$ is independently unsubstituted pentyl. In embodiments, $R^{26.1}$ is independently unsubstituted n-pentyl. In embodiments, $R^{26.1}$ is independently unsubstituted hexyl. In embodiments, $R^{26.1}$ is independently unsubstituted n-hexyl. In embodiments, $R^{26.1}$ is independently unsubstituted heptyl. In embodiments, $R^{26.1}$ is independently unsubstituted n-heptyl. In embodiments, $R^{26.1}$ is independently unsubstituted octyl. In embodiments, $R^{26.1}$ is independently unsubstituted n-octyl. In embodiments, $R^{26.1}$ is independently unsubstituted $C_1$-$C_8$ alkyl. In embodiments, $R^{26.2}$ is hydrogen, substituted or unsubstituted alkyl (e.g., $C_1$-$C_8$, $C_1$-$C_6$, $C_1$-$C_4$, or $C_1$-$C_2$), substituted or unsubstituted alkenyl (e.g., $C_2$-$C_8$, $C_2$-$C_6$, or $C_2$-$C_4$), substituted or unsubstituted alkynyl (e.g., $C_2$-$C_8$, $C_2$-$C_6$, or $C_2$-$C_4$), or substituted or unsubstituted phenyl. In embodiments, $R^{26.2}$ is unsubstituted methyl. In embodiments, $R^{26.2}$ is substituted with halogen, haloalkyl, alkylcarboxy, alkoxy, phenoxy, alkylamino, or alkylcarbonyl. In embodiments, $R^{26.2}$ is

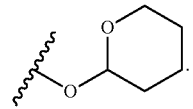 [SMILES: *OC1CCCCO1]

In embodiments, $R^{26.2}$ is

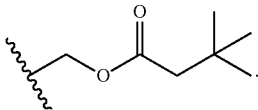 [SMILES: *COC(=O)CC(C)(C)C]

In embodiments, $R^{26.2}$ is independently unsubstituted methyl. In embodiments, $R^{26.2}$ is independently unsubstituted ethyl. In embodiments, $R^{26.2}$ is independently unsubstituted propyl. In embodiments, $R^{26.2}$ is independently unsubstituted isopropyl. In embodiments, $R^{26.2}$ is independently unsubstituted n-propyl. In embodiments, $R^{26.2}$ is independently unsubstituted butyl. In embodiments, $R^{26.2}$ is independently unsubstituted n-butyl. In embodiments, $R^{26.2}$ is independently unsubstituted t-butyl. In embodiments, $R^{26.2}$ is independently unsubstituted iso-butyl. In embodiments, $R^{26.2}$ is independently unsubstituted pentyl. In embodiments, $R^{26.2}$ is independently unsubstituted n-pentyl. In embodiments, $R^{26.2}$ is independently unsubstituted hexyl. In embodiments, $R^{26.2}$ is independently unsubstituted n-hexyl. In embodiments, $R^{26.2}$ is independently unsubstituted heptyl. In embodiments, $R^{26.2}$ is independently unsubstituted n-heptyl. In embodiments, $R^{26.2}$ is independently unsubstituted octyl. In embodiments, $R^{26.2}$ is independently unsubstituted n-octyl. In embodiments, $R^{26.2}$ is independently unsubstituted $C_1$-$C_8$ alkyl.

In embodiments, $R^4$ is independently $-CX^4_3$, $-CHX^4_2$, $-CH_2X^4$, $-OCX^4_3$, $-OCH_2X^4$, $-OCHX^4_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered).

In embodiments, $R^4$ is independently hydrogen. In embodiments, $R^4$ is independently $-CX^4_3$. In embodiments, $R^4$ is independently $-CHX^4_2$. In embodiments, $R^4$ is independently $-CH_2X^4$. In embodiments, $R^4$ is independently $-CN$. In embodiments, $R^4$ is independently $-COOH$. In embodiments, $R^4$ is independently $-CONH_2$. In embodiments, $R^4$ is independently $-CF_3$. In embodiments, $R^4$ is independently $-CHF_2$. In embodiments, $R^4$ is independently $-CH_2F$. In embodiments, $R^4$ is independently $-CH_3$. In embodiments, $R^4$ is independently $-CH_2CH_3$. In embodiments, $R^4$ is independently $-CH_2CH_2CH_3$. In embodiments, $R^4$ is independently $-CH(CH_3)_2$. In embodiments, $R^4$ is independently $-C(CH_3)_3$. In embodiments, $R^4$ is independently $-OCX^4_3$. In embodiments, $R^4$ is independently $-OCH_2X^4$. In embodiments, $R^4$ is independently $-OCHX^4_2$. In embodiments, $R^4$ is independently $-OH$. In embodiments, $R^4$ is independently $-NH_2$. In embodiments, $R^4$ is independently $-COOH$. In embodiments, $R^4$ is independently $-CONH_2$. In embodiments, $R^4$ is independently $-NO_2$. In embodiments, $R^4$ is independently $-SH$. In embodiments, $R^4$ is independently halogen. In embodiments, $R^4$ is independently $-F$. In embodiments, $R^4$ is independently $-Cl$. In embodiments, $R^4$ is independently $-Br$. In embodiments, $R^4$ is independently $-I$. In embodiments, $R^4$ is independently $-CF_3$. In embodiments, $R^4$ is independently $-CHF_2$. In embodiments, $R^4$ is independently $-CH_2F$. In embodiments, $R^4$ is independently $-OCF_3$. In embodiments, $R^4$ is independently $-OCH_2F$. In embodiments, $R^4$ is independently $-OCHF_2$. In embodiments, $R^4$ is independently $-OCH_3$. In embodiments, $R^4$ is independently $-OCH_2CH_3$. In embodiments, $R^4$ is independently $-OCH_2CH_2CH_3$. In embodiments, $R^4$ is independently $-OCH(CH_3)_2$. In embodiments, $R^4$ is independently $-OC(CH_3)_3$. In embodiments, $R^4$ is independently $-SCH_3$. In embodiments, $R^4$ is independently $-SCH_2CH_3$. In embodiments, $R^4$ is independently $-SCH_2CH_2CH_3$. In embodiments, $R^4$ is independently $-SCH(CH_3)_2$. In embodiments, $R^4$ is independently $-SC(CH_3)_3$. In embodiments, $R^4$ is independently $-CH_3$. In embodiments, $R^4$ is independently $-CH_2CH_3$. In embodiments, $R^4$ is independently $-CH_2CH_2CH_3$. In embodiments, $R^4$ is independently $-CH(CH_3)_2$. In embodiments, $R^4$ is independently $-C(CH_3)_3$. In embodiments, $R^4$ is independently $-SO_3H$. In embodiments, $R^4$ is independently $-SO_4H$. In embodiments, $R^4$ is independently —SO$_2$NH$_2$. In embodiments, R$^4$ is independently —NHNH$_2$. In embodiments, R$^4$ is independently —ONH$_2$. In embodiments, R$^4$ is independently —NHC=(O)NHNH$_2$. In embodiments, R$^4$ is independently —NHC=(O)NH$_2$. In embodiments, R$^4$ is independently —NHSO$_2$H. In embodiments, R$^4$ is independently —NHC=(O)H. In embodiments, R$^4$ is independently —NHC(O)—OH. In embodiments, R$^4$ is independently —NHOH.

In embodiments, R$^4$ is independently unsubstituted methyl. In embodiments, R$^4$ is independently unsubstituted ethyl. In embodiments, R$^4$ is independently unsubstituted propyl. In embodiments, R$^4$ is independently unsubstituted isopropyl. In embodiments, R$^4$ is independently unsubstituted n-propyl. In embodiments, R$^4$ is independently unsubstituted butyl. In embodiments, R$^4$ is independently unsubstituted n-butyl. In embodiments, R$^4$ is independently unsubstituted t-butyl. In embodiments, R$^4$ is independently unsubstituted pentyl. In embodiments, R$^4$ is independently unsubstituted n-pentyl. In embodiments, R$^4$ is independently unsubstituted hexyl. In embodiments, R$^4$ is independently unsubstituted n-hexyl. In embodiments, R$^4$ is independently unsubstituted heptyl. In embodiments, R$^4$ is independently unsubstituted n-heptyl. In embodiments, R$^4$ is independently unsubstituted octyl. In embodiments, R$^4$ is independently unsubstituted n-octyl. In embodiments, R$^4$ is independently unsubstituted benzyl. In embodiments, R$^4$ is independently unsubstituted C$_1$-C$_8$ alkyl. In embodiments, R$^4$ is independently halo-substituted methyl. In embodiments, R$^4$ is independently halo-substituted ethyl. In embodiments, R$^4$ is independently halo-substituted isopropyl. In embodiments, R$^4$ is independently halo-substituted n-propyl. In embodiments, R$^4$ is independently halo-substituted n-butyl. In embodiments, R$^4$ is independently halo-substituted t-butyl. In embodiments, R$^1$ is independently halo-substituted n-pentyl. In embodiments, R$^4$ is independently halo-substituted benzyl. In embodiments, R$^4$ is independently halo-substituted C$_1$-C$_8$ alkyl. In embodiments, R$^4$ is independently unsubstituted 2 to 6 membered heteroalkyl. In embodiments, R$^4$ is independently unsubstituted 2 to 7 membered heteroalkyl. In embodiments, R$^4$ is independently unsubstituted 2 to 8 membered heteroalkyl. In embodiments, R$^4$ is independently unsubstituted 2 to 9 membered heteroalkyl. In embodiments, R$^4$ is independently unsubstituted 2 to 10 membered heteroalkyl. In embodiments, R$^4$ is independently unsubstituted 3 to 10 membered heteroalkyl. In embodiments, R$^4$ is independently unsubstituted 4 to 10 membered heteroalkyl. In embodiments, R$^4$ is independently unsubstituted 5 to 10 membered heteroalkyl. In embodiments, R$^4$ is independently unsubstituted 6 to 10 membered heteroalkyl. In embodiments, R$^4$ is independently unsubstituted 7 to 10 membered heteroalkyl. In embodiments, R$^4$ is independently unsubstituted 8 to 10 membered heteroalkyl. In embodiments, R$^4$ is independently unsubstituted 6 to 10 membered heteroalkyl. In embodiments, R$^4$ is independently unsubstituted 7 to 9 membered heteroalkyl.

In embodiments, R$^4$ is independently substituted or unsubstituted alkyl (e.g., C$_1$-C$_8$, C$_1$-C$_6$, C$_1$-C$_4$, or C$_1$-C$_2$). In embodiments, R$^4$ is independently substituted alkyl (e.g., C$_1$-C$_8$, C$_1$-C$_6$, C$_1$-C$_4$, or C$_1$-C$_2$). In embodiments, R$^4$ is independently unsubstituted alkyl (e.g., C$_1$-C$_8$, C$_1$-C$_6$, C$_1$-C$_4$, or C$_1$-C$_2$). In embodiments, R$^4$ is independently unsubstituted methyl. In embodiments, R$^4$ is independently unsubstituted ethyl. In embodiments, R$^4$ is independently unsubstituted propyl. In embodiments, R$^4$ is independently unsubstituted isopropyl. In embodiments, R$^4$ is independently unsubstituted tert-butyl. In embodiments, R$^4$ is independently substituted or unsubstituted heteroalkyl (e.g., 2 to 8 membered, 2 to 6 membered, 4 to 6 membered, 2 to 3 membered, or 4 to 5 membered). In embodiments, R$^4$ is independently substituted heteroalkyl (e.g., 2 to 8 membered, 2 to 6 membered, 4 to 6 membered, 2 to 3 membered, or 4 to 5 membered). In embodiments, R$^4$ is independently unsubstituted heteroalkyl (e.g., 2 to 8 membered, 2 to 6 membered, 4 to 6 membered, 2 to 3 membered, or 4 to 5 membered). In embodiments, R$^4$ is independently substituted or unsubstituted cycloalkyl (e.g., C$_3$-C$_8$, C$_3$-C$_6$, C$_4$-C$_6$, or C$_5$-C$_6$). In embodiments, R$^4$ is independently substituted cycloalkyl (e.g., C$_3$-C$_8$, C$_3$-C$_6$, C$_4$-C$_6$, or C$_5$-C$_6$). In embodiments, R$^4$ is independently unsubstituted cycloalkyl (e.g., C$_3$-C$_8$, C$_3$-C$_6$, C$_4$-C$_6$, or C$_5$-C$_6$). In embodiments, R$^4$ is independently substituted or unsubstituted heterocycloalkyl (e.g., 3 to 8 membered, 3 to 6 membered, 4 to 6 membered, 4 to 5 membered, or 5 to 6 membered). In embodiments, R$^4$ is independently substituted heterocycloalkyl (e.g., 3 to 8 membered, 3 to 6 membered, 4 to 6 membered, 4 to 5 membered, or 5 to 6 membered). In embodiments, R$^4$ is independently unsubstituted heterocycloalkyl (e.g., 3 to 8 membered, 3 to 6 membered, 4 to 6 membered, 4 to 5 membered, or 5 to 6 membered). In embodiments, R$^4$ is independently substituted or unsubstituted aryl (e.g., C$_6$-C$_{10}$ or phenyl). In embodiments, R$^4$ is independently substituted aryl (e.g., C$_6$-C$_{10}$ or phenyl). In embodiments, R$^4$ is independently unsubstituted aryl (e.g., C$_6$-C$_{10}$ or phenyl). In embodiments, R$^4$ is independently substituted or unsubstituted heteroaryl (e.g., 5 to 10 membered, 5 to 9 membered, or 5 to 6 membered). In embodiments, R$^4$ is independently substituted heteroaryl (e.g., 5 to 10 membered, 5 to 9 membered, or 5 to 6 membered). In embodiments, R$^4$ is independently unsubstituted heteroaryl (e.g., 5 to 10 membered, 5 to 9 membered, or 5 to 6 membered).

In embodiments, R$^4$ is independently halogen, —CX$^4$$_3$, —CHX$^4$$_2$, —CH$_2$X$^4$, —OCX$^4$$_3$, —OCH$_2$X$^4$, —OCHX$^4$$_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, R$^{29}$-substituted or unsubstituted alkyl (e.g., C$_1$-C$_8$, C$_1$-C$_6$, C$_1$-C$_4$, or C$_1$-C$_2$), R$^{29}$-substituted or unsubstituted heteroalkyl (e.g., 2 to 8 membered, 2 to 6 membered, 4 to 6 membered, 2 to 3 membered, or 4 to 5 membered), R$^{29}$-substituted or unsubstituted cycloalkyl (e.g., C$_3$-C$_8$, C$_3$-C$_6$, C$_4$-C$_6$, or C$_5$-C$_6$), R$^{29}$-substituted or unsubstituted heterocycloalkyl (e.g., 3 to 8 membered, 3 to 6 membered, 4 to 6 membered, 4 to 5 membered, or 5 to 6 membered), R$^{29}$-substituted or unsubstituted aryl (e.g., C$_6$-C$_{10}$ or phenyl), or R$^{29}$-substituted or unsubstituted heteroaryl (e.g., 5 to 10 membered, 5 to 9 membered, or 5 to 6 membered). In embodiments, R$^4$ is independently halogen, —CX$^4$$_3$, —CHX$^4$$_2$, —CH$_2$X$^4$, —OCX$^4$$_3$, —OCH$_2$X$^4$, —OCHX$^4$$_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, unsubstituted alkyl (e.g., C$_1$-C$_8$, C$_1$-C$_6$, C$_1$-C$_4$, or C$_1$-C$_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., C$_3$-C$_8$, C$_3$-C$_6$, C$_4$-C$_6$, or C$_5$-C$_6$), unsubstituted heterocycloalkyl (e.g., 3 to 8 membered, 3 to 6 membered, 4 to 6 membered, 4 to 5 membered, or 5 to 6 membered), unsubstituted aryl (e.g., C$_6$-C$_{10}$ or phenyl), or unsubstituted heteroaryl (e.g., 5 to 10 membered, 5 to 9 membered, or 5 to 6 membered). X$^4$ is independently —F, —Cl, —Br, or —I. In embodiments, $R^4$ is independently unsubstituted methyl. In embodiments, $R^4$ is independently unsubstituted ethyl.

$R^{29}$ is independently oxo, halogen, $-CX^{29}_3$, $-CHX^{29}_2$, $-CH_2X^{29}$, $-OCX^{29}_3$, $-OCH_2X^{29}$, $-OCHX^{29}_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $R^{30}$-substituted or unsubstituted alkyl (e.g., $C_1$-$C_8$, $C_1$-$C_6$, $C_1$-$C_4$, or $C_1$-$C_2$), $R^{30}$-substituted or unsubstituted heteroalkyl (e.g., 2 to 8 membered, 2 to 6 membered, 4 to 6 membered, 2 to 3 membered, or 4 to 5 membered), $R^{30}$-substituted or unsubstituted cycloalkyl (e.g., $C_3$-$C_8$, $C_3$-$C_6$, $C_4$-$C_6$, or $C_5$-$C_6$), $R^{30}$-substituted or unsubstituted heterocycloalkyl (e.g., 3 to 8 membered, 3 to 6 membered, 4 to 6 membered, 4 to 5 membered, or 5 to 6 membered), $R^{30}$-substituted or unsubstituted aryl (e.g., $C_6$-$C_{10}$ or phenyl), or $R^{30}$-substituted or unsubstituted heteroaryl (e.g., 5 to 10 membered, 5 to 9 membered, or 5 to 6 membered). In embodiments, $R^{29}$ is independently oxo, halogen, $-CX^{29}_3$, $-CHX^{29}_2$, $-CH_2X^{29}$, $-OCX^{29}_3$, $-OCH_2X^{29}$, $-OCHX^{29}_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{29}$ is independently $-F$, $-Cl$, $-Br$, or $-I$. In embodiments, $R^{29}$ is independently unsubstituted methyl. In embodiments, $R^{29}$ is independently unsubstituted ethyl.

$R^{30}$ is independently oxo, halogen, $-CX^{30}_3$, $-CHX^{30}_2$, $-CH_2X^{30}$, $-OCX^{30}_3$, $-OCH_2X^{30}$, $-OCHX^{30}_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $R^{31}$-substituted or unsubstituted alkyl (e.g., $C_1$-$C_8$, $C_1$-$C_6$, $C_1$-$C_4$, or $C_1$-$C_2$), $R^{31}$-substituted or unsubstituted heteroalkyl (e.g., 2 to 8 membered, 2 to 6 membered, 4 to 6 membered, 2 to 3 membered, or 4 to 5 membered), $R^{31}$-substituted or unsubstituted cycloalkyl (e.g., $C_3$-$C_8$, $C_3$-$C_6$, $C_4$-$C_6$, or $C_5$-$C_6$), $R^{31}$-substituted or unsubstituted heterocycloalkyl (e.g., 3 to 8 membered, 3 to 6 membered, 4 to 6 membered, 4 to 5 membered, or 5 to 6 membered), $R^{31}$-substituted or unsubstituted aryl (e.g., $C_6$-$C_{10}$ or phenyl), or $R^{31}$-substituted or unsubstituted heteroaryl (e.g., 5 to 10 membered, 5 to 9 membered, or 5 to 6 membered). In embodiments, $R^{30}$ is independently oxo, halogen, $-CX^{30}_3$, $-CHX^{30}_2$, $-CH_2X^{30}$, $-OCX^{30}_3$, $-OCH_2X^{30}$, $-OCHX^{30}_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{30}$ is independently $-F$, $-Cl$, $-Br$, or $-I$. In embodiments, $R^{30}$ is independently unsubstituted methyl. In embodiments, $R^{30}$ is independently unsubstituted ethyl.

$R^{31}$ is independently oxo, halogen, $-CX^{31}_3$, $-CHX^{31}_2$, $-CH_2X^{31}$, $-OCX^{31}_3$, $-OCH_2X^{31}$, $-OCHX^{31}_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{31}$ is independently $-F$, $-Cl$, $-Br$, or $-I$. In embodiments, $R^{31}$ is independently unsubstituted methyl. In embodiments, $R^{31}$ is independently unsubstituted ethyl.

In embodiments, $R^4$ is independently halogen, $-CX^4_3$, $-CHX^4_2$, $-CH_2X^4$, $-OCX^4_3$, $-OCH_2X^4$, $-OCHX^4_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In embodiments, z4 is 0. In embodiments, z4 is 1. In embodiments, z4 is 2. In embodiments, z4 is 3. In embodiments, z4 is 4. In embodiments, z4 is 5.

In embodiments, $L^{1A}$ is a bond, substituted or unsubstituted alkylene, or substituted or unsubstituted heteroalkylene. In embodiments, $L^{1A}$ is a bond. In embodiments, $L^{1A}$ is $-CH_2-$. In embodiments, $L^{1A}$ is $-OCH_2-$. In embodiments, $L^{1A}$ is $-CH_2O-$. In embodiments, $L^{1A}$ is $-CH_2CH_2-$. In embodiments, $L^{1A}$ is $NHCH_2-$. In embodiments, $L^{1A}$ is $-CH_2NH-$. In embodiments, $L^{1A}$ is $-CH_2CH(CH_3)-$. In embodiments, $L^{1A}$ is $-CH_2C(CH_3)_2-$. In embodiments, $L^{1A}$ is $-CH_2CH_2CH_2-$. In embodiments, $L^{1A}$ is $-CH_2CH_2CH(CH_3)-$. In embodiments, $L^{1A}$ is $-CH_2CH_2C(CH_3)_2-$.

In embodiments, $L^{1A}$ is a bond, substituted or unsubstituted alkylene (e.g., $C_1$-$C_8$, $C_1$-$C_6$, $C_1$-$C_4$, or $C_1$-$C_2$) or substituted or unsubstituted heteroalkylene (e.g., 2 to 8 membered, 2 to 6 membered, 4 to 6 membered, 2 to 3 membered, or 4 to 5 membered).

In embodiments, $L^{1A}$ is independently substituted or unsubstituted alkylene (e.g., $C_1$-$C_8$, $C_1$-$C_6$, $C_1$-$C_4$, or $C_1$-$C_2$). In embodiments, $L^{1A}$ is independently substituted alkylene (e.g., $C_1$-$C_8$, $C_1$-$C_6$, $C_1$-$C_4$, or $C_1$-$C_2$). In embodiments, $L^{1A}$ is independently unsubstituted alkylene (e.g., $C_1$-$C_8$, $C_1$-$C_6$, $C_1$-$C_4$, or $C_1$-$C_2$). In embodiments, $L^{1A}$ is independently unsubstituted methylene. In embodiments, $L^{1A}$ is independently unsubstituted ethylene. In embodiments, $L^{1A}$ is independently unsubstituted propylene. In embodiments, $L^{1A}$ is independently unsubstituted isopropylene. In embodiments, $L^{1A}$ is independently unsubstituted tert-butylene. In embodiments, $L^{1A}$ is independently substituted or unsubstituted heteroalkylene (e.g., 2 to 8 membered, 2 to 6 membered, 4 to 6 membered, 2 to 3 membered, or 4 to 5 membered). In embodiments, $L^{1A}$ is independently substituted heteroalkylene (e.g., 2 to 8 membered, 2 to 6 membered, 4 to 6 membered, 2 to 3 membered, or 4 to 5 membered). In embodiments, $L^{1A}$ is independently unsubstituted heteroalkylene (e.g., 2 to 8 membered, 2 to 6 membered, 4 to 6 membered, 2 to 3 membered, or 4 to 5 membered).

In embodiments, $L^{1A}$ is independently bond, $R^{32A}$-substituted or unsubstituted alkylene (e.g., $C_1$-$C_8$, $C_1$-$C_6$, $C_1$-$C_4$, or $C_1$-$C_2$) or $R^{32A}$-substituted or unsubstituted heteroalkylene (e.g., 2 to 8 membered, 2 to 6 membered, 4 to 6 membered, 2 to 3 membered, or 4 to 5 membered). In embodiments, $L^{1A}$ is independently bond, unsubstituted alkylene (e.g., $C_1$-$C_8$, $C_1$-$C_6$, $C_1$-$C_4$, or $C_1$-$C_2$) or unsubstituted heteroalkylene (e.g., 2 to 8 membered, 2 to 6 membered, 4 to 6 membered, 2 to 3 membered, or 4 to 5 membered). In embodiments, $L^{1A}$ is independently unsubstituted methylene. In embodiments, $L^{1A}$ is independently unsubstituted ethylene. In embodiments, $L^{1A}$ is independently methyl-substituted methylene.

$R^{32A}$ is independently oxo, halogen, —$CX^{32A}_3$, —$CHX^{32A}_2$, —$CH_2X^{32A}$, —$OCX^{32A}_3$, —$OCH_2X^{32A}$, —$OCHX^{32A}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, $R^{33A}$-substituted or unsubstituted alkyl (e.g., $C_1$-$C_8$, $C_1$-$C_6$, $C_1$-$C_4$, or $C_1$-$C_2$), $R^{33A}$-substituted or unsubstituted heteroalkyl (e.g., 2 to 8 membered, 2 to 6 membered, 4 to 6 membered, 2 to 3 membered, or 4 to 5 membered), $R^{33A}$-substituted or unsubstituted cycloalkyl (e.g., $C_3$-$C_8$, $C_3$-$C_6$, $C_4$-$C_6$, or $C_5$-$C_6$), $R^{33A}$-substituted or unsubstituted heterocycloalkyl (e.g., 3 to 8 membered, 3 to 6 membered, 4 to 6 membered, 4 to 5 membered, or 5 to 6 membered), $R^{33A}$-substituted or unsubstituted aryl (e.g., $C_6$-$C_{10}$ or phenyl), or $R^{33A}$-substituted or unsubstituted heteroaryl (e.g., 5 to 10 membered, 5 to 9 membered, or 5 to 6 membered). In embodiments, $R^{32A}$ is independently oxo, halogen, —$CX^{32A}_3$, —$CHX^{32A}_2$, —$CH_2X^{32A}$, —$OCX^{32A}_3$, —$OCH_2X^{32A}$, —$OCHX^{32A}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{32A}$ is independently —F, —Cl, —Br, or —I. In embodiments, $R^{32A}$ is independently unsubstituted methyl. In embodiments, $R^{32A}$ is independently unsubstituted ethyl.

$R^{33A}$ is independently oxo, halogen, —$CX^{33A}_3$, —$CHX^{33A}_2$, —$CH_2X^{33A}$, —$OCX^{33A}_3$, —$OCH_2X^{33A}$, —$OCHX^{33A}_2$, —CN, —OH, —$NH_2$, —COOH, —$CONH_2$, —$NO_2$, —SH, —$SO_3H$, —$SO_4H$, —$SO_2NH_2$, —$NHNH_2$, —NHC=(O)$NHNH_2$, —NHC=(O)$NH_2$, —$NHSO_2H$, —NHC=(O)H, —NHC(O)—OH, —NHOH, $R^{34A}$-substituted or unsubstituted alkyl (e.g., $C_1$-$C_8$, $C_1$-$C_6$, $C_1$-$C_4$, or $C_1$-$C_2$), $R^{34A}$-substituted or unsubstituted heteroalkyl (e.g., 2 to 8 membered, 2 to 6 membered, 4 to 6 membered, 2 to 3 membered, or 4 to 5 membered), $R^{34A}$-substituted or unsubstituted cycloalkyl (e.g., $C_3$-$C_8$, $C_3$-$C_6$, $C_4$-$C_6$, or $C_5$-$C_6$), $R^{34A}$-substituted or unsubstituted heterocycloalkyl (e.g., 3 to 8 membered, 3 to 6 membered, 4 to 6 membered, 4 to 5 membered, or 5 to 6 membered), $R^{34A}$-substituted or unsubstituted aryl (e.g., $C_6$-$C_{10}$ or phenyl), or $R^{34A}$-substituted or unsubstituted heteroaryl (e.g., 5 to 10 membered, 5 to 9 membered, or 5 to 6 membered). In embodiments, $R^{33A}$ is independently oxo, halogen, —$CX^{33A}_3$, —$CHX^{33A}_2$, —$CH_2X^{33A}$, —$OCX^{33A}_3$, —$OCH_2X^{33A}$, —$OCHX^{33A}_2$, —CN, —OH, —$NH_2$, —COOH, —$CONH_2$, —$NO_2$, —SH, —$SO_3H$, —$SO_4H$, —$SO_2NH_2$, —$NHNH_2$, —NHC=(O)$NHNH_2$, —NHC=(O)$NH_2$, —$NHSO_2H$, —NHC=(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{33A}$ is independently —F, —Cl, —Br, or —I. In embodiments, $R^{33A}$ is independently unsubstituted methyl. In embodiments, $R^{33A}$ is independently unsubstituted ethyl.

$R^{34A}$ is independently oxo, halogen, —$CX^{34A}_3$, —$CHX^{34A}_2$, —$CH_2X^{34A}$, —$OCX^{34A}_3$, —$OCH_2X^{34A}$, —$OCHX^{34A}_2$, —CN, —OH, —$NH_2$, —COOH, —$CONH_2$, —$NO_2$, —SH, —$SO_3H$, —$SO_4H$, —$SO_2N_{112}$, —$NHNH_2$, —NHC=(O)$NHNH_2$, —NHC=(O)$NH_2$, —$NHSO_2H$, —NHC=(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{34A}$ is independently —F, —Cl, —Br, or —I. In embodiments, $R^{34A}$ is independently unsubstituted methyl. In embodiments, $R^{34A}$ is independently unsubstituted ethyl.

In embodiments, $L^{1A}$ is substituted or unsubstituted $C_1$-$C_6$ alkylene. In embodiments, $L^{1A}$ is unsubstituted $C_2$-$C_4$ alkylene. In embodiments, $L^{1A}$ is —$CH_2CH(CH_3)$—. In embodiments, $L^{1A}$ is —$CH_2CH_2$—.

In embodiments, $L^{1B}$ is a bond. In embodiments, $L^{1B}$ is —C(O)O—. In embodiments, $L^{1B}$ is —OC(O)—. In embodiments, $L^{1B}$ is —O—. In embodiments, $L^{1B}$ is —C(O)—. In embodiments, $L^{1B}$ is —NH—. In embodi ments, $L^{1B}$ is —NHC(O)—. In embodiments, $L^{1B}$ is —C(O)NH—.

In embodiments, $L^{1B}$ is —C(O)O—.

In embodiments, X is —F. In embodiments, X is —Cl. In embodiments, X is —Br. In embodiments, X is —I. In embodiments, $X^1$ is —F. In embodiments, $X^1$ is —Cl. In embodiments, $X^1$ is —Br. In embodiments, $X^1$ is —I. In embodiments, $X^2$ is —F. In embodiments, $X^2$ is —Cl. In embodiments, $X^2$ is —Br. In embodiments, $X^2$ is —I. In embodiments, $X^3$ is —F. In embodiments, $X^3$ is —Cl. In embodiments, $X^3$ is —Br. In embodiments, $X^3$ is —I. In embodiments, $X^4$ is —F. In embodiments, $X^4$ is —Cl. In embodiments, $X^4$ is —Br. In embodiments, $X^4$ is —I.

In embodiments, n1 is 0. In embodiments, n1 is 1. In embodiments, n1 is 2. In embodiments, n1 is 3. In embodiments, n1 is 4.

In embodiments, m1 is 1. In embodiments, m1 is 2.

In embodiments, v1 is 1. In embodiments, v1 is 2.

In embodiments, $L^{1A}$ is unsubstituted $C_2$-$C_4$ alkylene; $L^{1B}$ is —C(O)O—; and $R^1$ is hydrogen or unsubstituted $C_1$-$C_3$ alkyl.

In embodiments, $L^{1A}$ is unsubstituted $C_2$-$C_4$ alkylene; $L^{1B}$ is —C(O)O—; and $R^1$ is unsubstituted $C_1$-$C_3$ alkyl.

In embodiments, $L^{1A}$ is unsubstituted $C_2$-$C_4$ alkylene; $L^{1B}$ is —C(O)O—; and $R^1$ is —$CH_3$.

In embodiments, $L^{1A}$ is unsubstituted $C_2$-$C_4$ alkylene; $L^{1B}$ is —C(O)O—; and $R^1$ is hydrogen.

In embodiments, $L^{1-A}$ is —$CH_2CH(CH_3)$—; $L^{1B}$ is —C(O)O—; and $R^1$ is —$CH_3$.

In embodiments, $L^{1-A}$ is —$CH_2CH(CH_3)$—; $L^{1B}$ is —C(O)O—; and $R^1$ is hydrogen.

In embodiments, $L^{1A}$ is substituted or unsubstituted $C_1$-$C_6$ alkylene; $L^{1B}$ is —C(O)O—; $R^1$ is substituted or unsubstituted $C_1$-$C_6$ alkyl; $R^2$ is independently hydrogen, —$CX^2_3$, —$CHX^2_2$, —$CH_2X^2$, —C(O)$R^{2A}$, —C(O)O$R^{2A}$, —C(O)N$R^{2A}R^{2B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^3$ is independently hydrogen, —$CX^3_3$, —$CHX^3_2$, —$CH_2X^3$, —C(O)$R^{3A}$, —C(O)O$R^{3A}$, —C(O)N$R^{3A}R^{3B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^4$ is independently halogen, —$CX^4_3$, —$CHX^4_2$, —$CH_2X^4$, —$OCX^4_3$, —$OCH_2X^4$, —$OCHX^4_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; z4 is an integer from 0 to 5; each $R^{2A}$, $R^{2B}$, $R^{3A}$, and $R^{3B}$ is independently hydrogen, —$CX_3$, —CN, —COOH, —$CONH_2$, —$CHX_2$, —$CH_2X$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{2A}$ and $R^{2B}$ substituents bonded to the same nitrogen atom may optionally be joined to form a substituted or unsubstituted heterocycloalkyl or substituted or unsubstituted heteroaryl; $R^{3A}$ and $R^{3B}$ substituents bonded to the same nitrogen atom may optionally be joined to form a substituted or unsubstituted heterocycloalkyl or substituted or unsubstituted heteroaryl; and each X, $X^2$, $X^3$, and $X^4$ is independently —F, —Cl, —Br, or —I.

In embodiments, the compound has the formula:

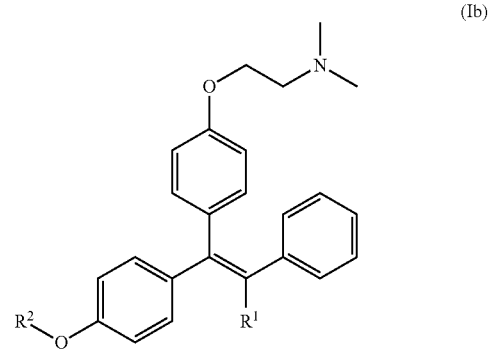

(Ib)

and $R^1$ and $R^2$ are as described herein.

In embodiments, the compound has the formula:

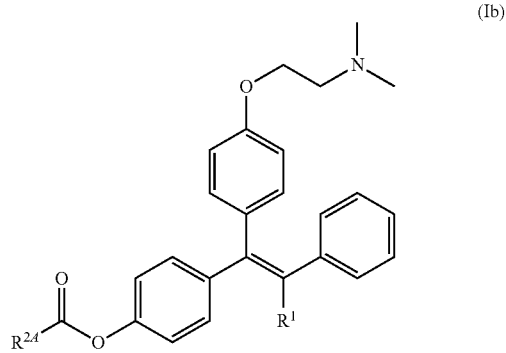

(Ib)

and $R^1$ and $R^{2A}$ are as described herein.

In embodiments, the compound has the formula:

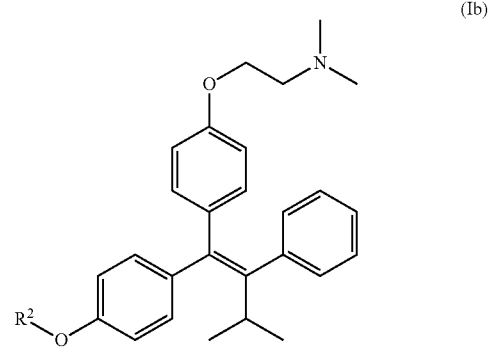

(Ib)

and $R^2$ is as described herein.

In embodiments, the compound has the formula:

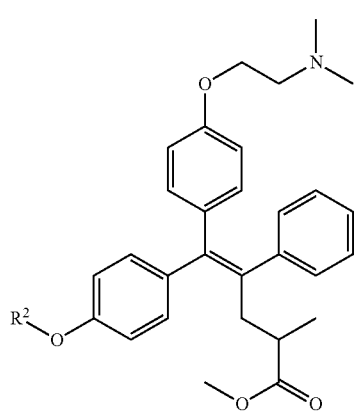

(Ib)

and R² is as described herein.

In embodiments, the compound has the formula:

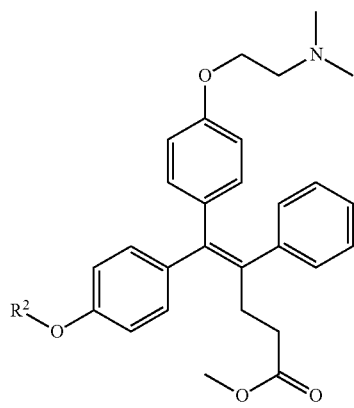

(Ib)

and R² is as described herein.

In embodiments, the compound has the formula:

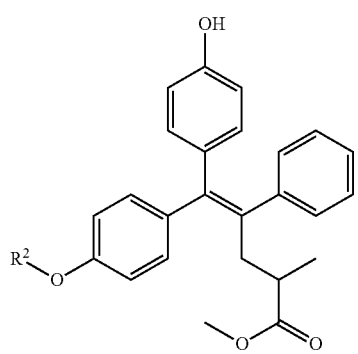

(Ib)

and R² is as described herein.

In embodiments, the compound has the formula:

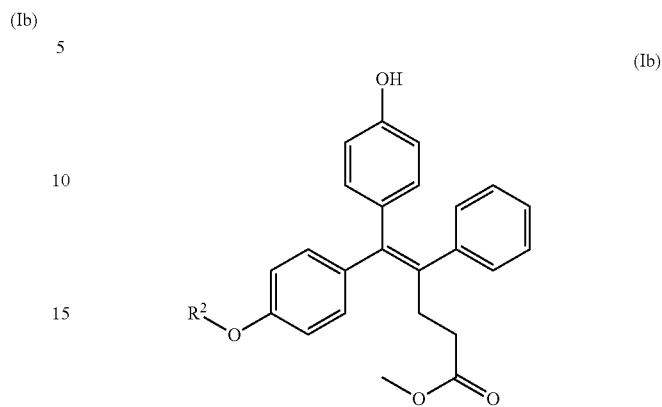

(Ib)

and R² is as described herein.

In embodiments, the compound has the formula:

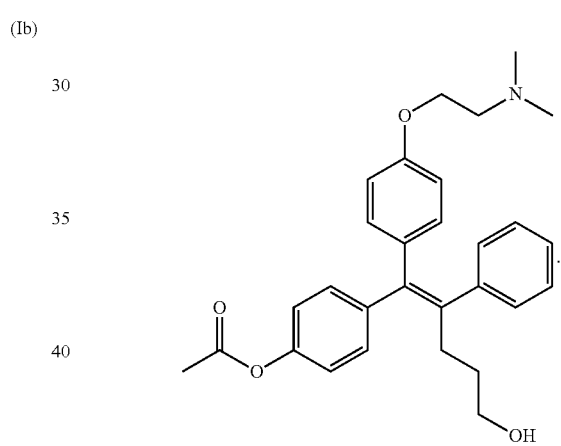

(Ib)

In embodiments, the compound has the formula:

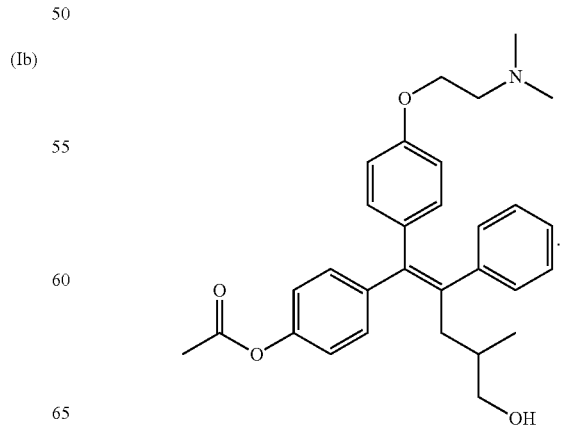

In embodiments, the compound has the formula:
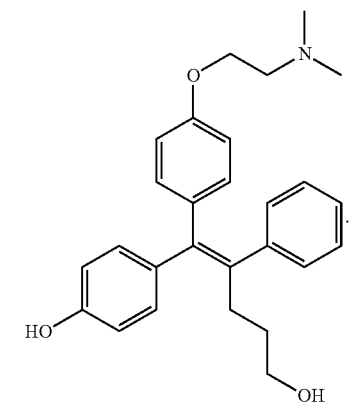
In embodiments, the compound has the formula:
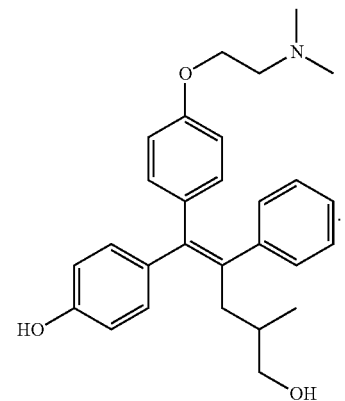
In embodiments, the compound has the formula:
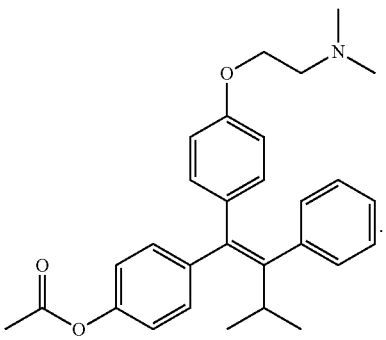 [SMILES: CC(=O)Oc1ccc(/C(=C(/c2ccccc2)C(C)C)c2ccc(OCCN(C)C)cc2)cc1]
In embodiments, the compound has the formula:
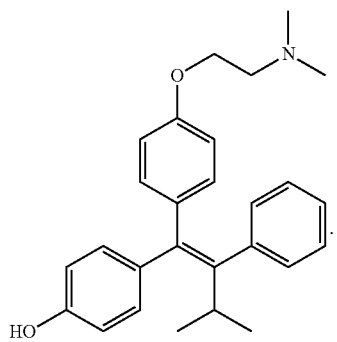
In embodiments, the compound has the formula:
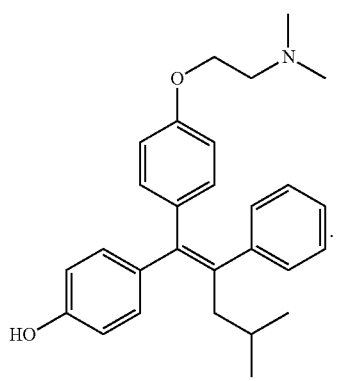 [SMILES: CC(C)C/C(=C(\c1ccc(O)cc1)c1ccc(OCCN(C)C)cc1)c1ccccc1]
In embodiments, the compound has the formula:
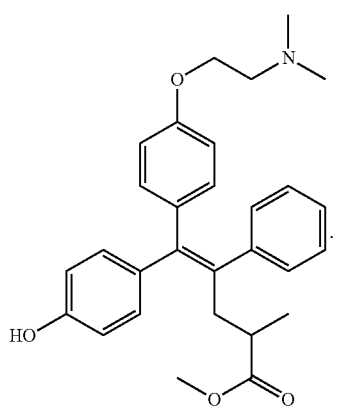

In embodiments, the compound has the formula:
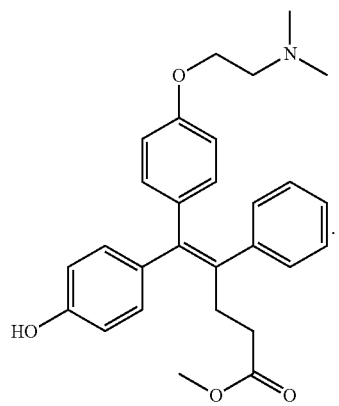 [SMILES: COC(=O)CC/C(=C(\c1ccc(O)cc1)c1ccc(OCCN(C)C)cc1)c1ccccc1]
In embodiments, the compound has the formula:
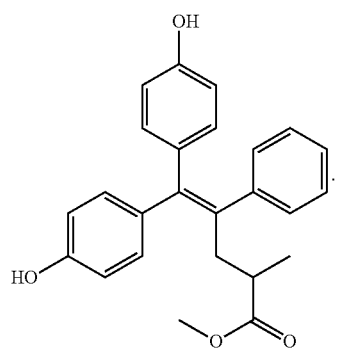 [SMILES: COC(=O)C(C)CC(=C(c1ccc(O)cc1)c1ccc(O)cc1)c1ccccc1]
In embodiments, the compound has the formula:
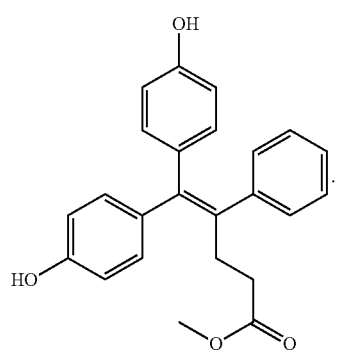
In embodiments, the compound is not
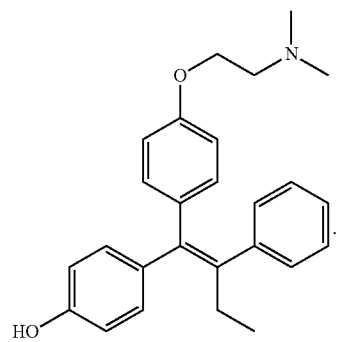
In embodiments, the compound is not
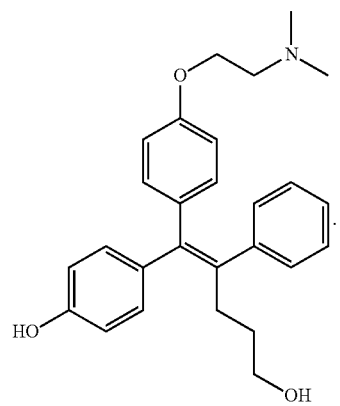 [SMILES: CN(C)CCOc1ccc(/C(=C(/CCCO)c2ccccc2)c2ccc(O)cc2)cc1]
In embodiments, the compound is not
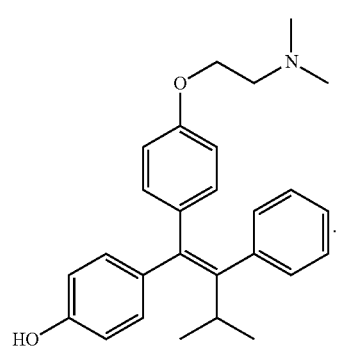 [SMILES: CC(C)/C(=C(\c1ccc(O)cc1)c1ccc(OCCN(C)C)cc1)c1ccccc1]

In embodiments, the compound is not

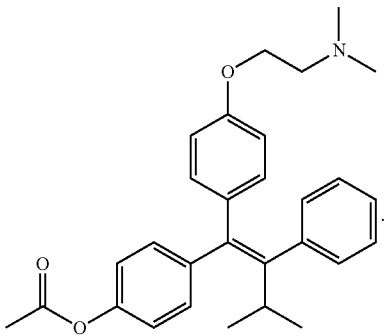 [SMILES: CC(=O)Oc1ccc(/C(=C(/c2ccccc2)C(C)C)c2ccc(OCCN(C)C)cc2)cc1]

In embodiments, the compound has the formula:

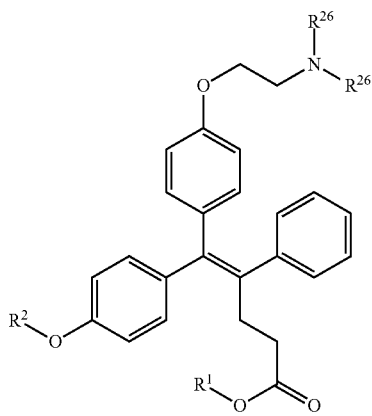

(Ib)

and $R^1$, $R^2$, and $R^{26}$ are as described herein.

In embodiments, the compound has the formula:

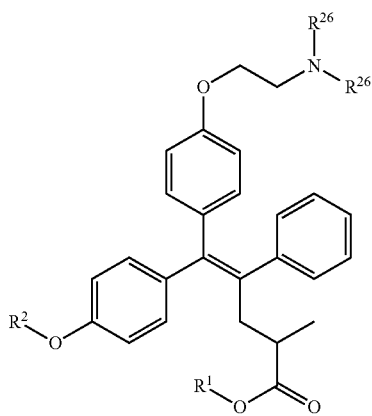

(Ib)

and $R^1$, $R^2$, and $R^{26}$ are as described herein.

Figure 2:
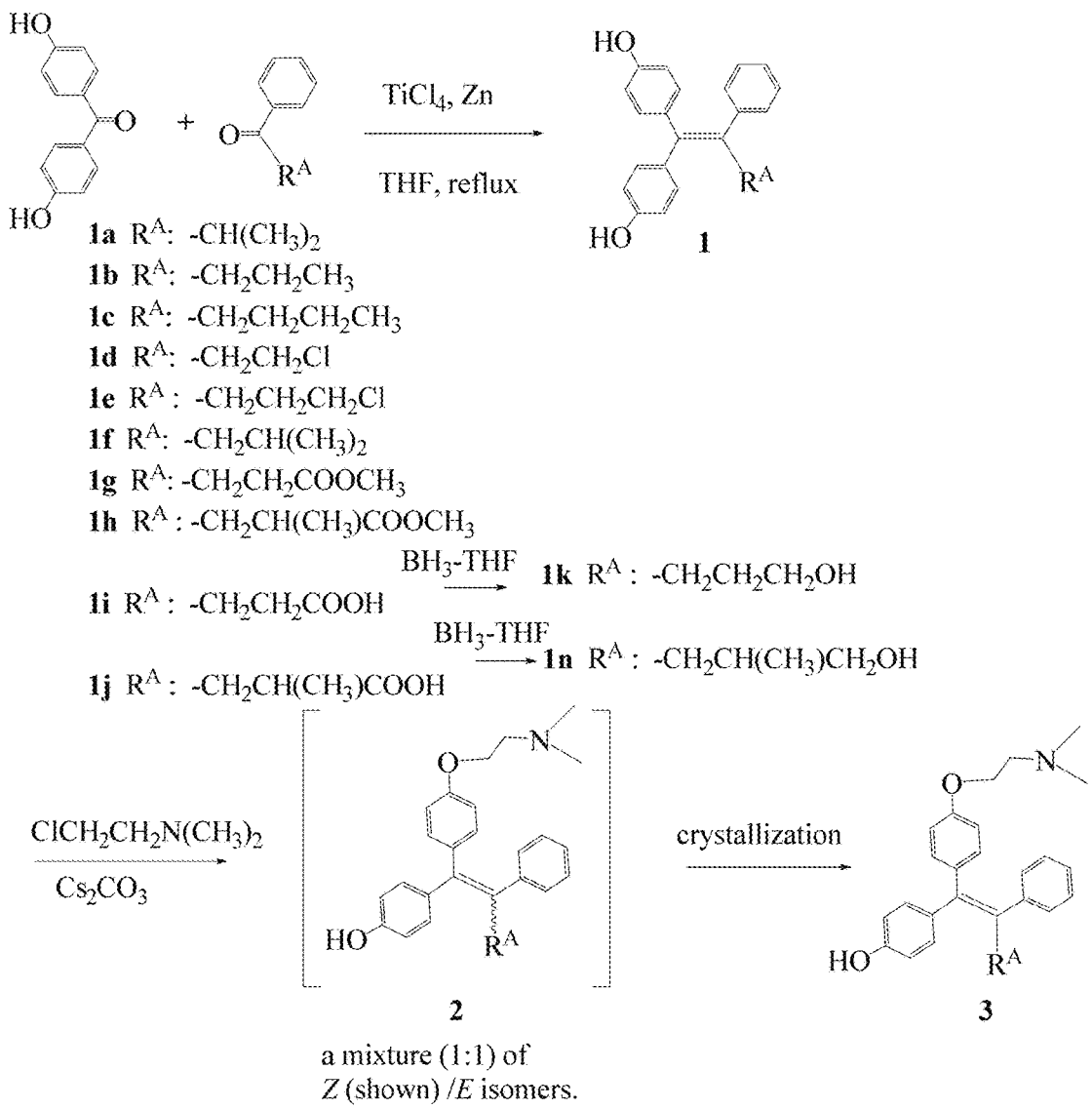
FIG. 2. Synthesis of 1,1-bis(4-hydroxyphenyl)-2-phenylethylene analogs chemset 1, installation of the basic side chain chemset 2, and stereo- and regiospecific production of the Z-isomer chemset 3.

In embodiments, the compound is compound 1a in FIG. 2. In embodiments, the compound is compound 1b in FIG. 2. In embodiments, the compound is compound 1c in FIG. 2. In embodiments, the compound is compound 1d in FIG. 2. In embodiments, the compound is compound 1e in FIG. 2. In embodiments, the compound is compound 1f in FIG. 2. In embodiments, the compound is compound 1g in FIG. 2. In embodiments, the compound is compound 1h in FIG. 2. In embodiments, the compound is compound 1i in FIG. 2. In embodiments, the compound is compound 1j in FIG. 2. In embodiments, the compound is compound 1k in FIG. 2. In embodiments, the compound is compound 1n in FIG. 2.

In embodiments, the compound is compound 2a in FIG. 2. In embodiments, the compound is compound 2b in FIG. 2. In embodiments, the compound is compound 2c in FIG. 2. In embodiments, the compound is compound 2d in FIG. 2. In embodiments, the compound is compound 2e in FIG. 2. In embodiments, the compound is compound 2f in FIG. 2. In embodiments, the compound is compound 2g in FIG. 2. In embodiments, the compound is compound 2h in FIG. 2. In embodiments, the compound is compound 2k in FIG. 2. In embodiments, the compound is compound 2n in FIG. 2.

In embodiments, the compound is compound 3a in FIG. 2. In embodiments, the compound is compound 3b in FIG. 2. In embodiments, the compound is compound 3c in FIG. 2. In embodiments, the compound is compound 3d in FIG. 2. In embodiments, the compound is compound 3e in FIG. 2. In embodiments, the compound is compound 3f in FIG. 2. In embodiments, the compound is compound 3g in FIG. 2. In embodiments, the compound is compound 3h in FIG. 2. In embodiments, the compound is compound 3k in FIG. 2. In embodiments, the compound is compound 3n in FIG. 2.

In embodiments, the compound is compound 4a(1), which is the compound 3a modified to have a 4-OC(O)CH$_3$ in place of the phenyl 4-OH of compound 3a, as shown in Table 1. In embodiments, the compound is compound 4b(1), which is the compound 3b modified to have a 4-OC(O)CH$_3$ in place of the phenyl 4-OH of compound 3b. In embodiments, the compound is compound 4c(1), which is the compound 3c modified to have a 4-OC(O)CH$_3$ in place of the phenyl 4-OH of compound 3c. In embodiments, the compound is compound 4d(1), which is the compound 3d modified to have a 4-OC(O)CH$_3$ in place of the phenyl 4-OH of compound 3d. In embodiments, the compound is compound 4e(1), which is the compound 3e modified to have a 4-OC(O)CH$_3$ in place of the phenyl 4-OH of compound 3e. In embodiments, the compound is compound 4f(1), which is the compound 3f modified to have a 4-OC(O)CH$_3$ in place of the phenyl 4-OH of compound 3f. In embodiments, the compound is compound 4g(1), which is the compound 3g modified to have a 4-OC(O)CH$_3$ in place of the phenyl 4-OH of compound 3g. In embodiments, the compound is compound 4h(1), which is the compound 3h modified to have a 4-OC(O)CH$_3$ in place of the phenyl 4-OH of compound 3h. In embodiments, the compound is compound 4k(1), which is the compound 3k modified to have a 4-OC(O)CH$_3$ in place of the phenyl 4-OH of compound 3k. In embodiments, the compound is compound 4n(1), which is the compound 3n modified to have a 4-OC(O)CH$_3$ in place of the phenyl 4-OH of compound 3n.

In embodiments, the compound is a compound of formula 4 of Table 1 (e.g. 4a(2), 4b(2), 4c(2), 4d(2), 4e(2), 4f(2), 4g(2), 4h(2), 4k(2), 4n(2), 4a(3), 4b(3), 4c(3), 4d(3), 4e(3), 4f(3), 4g(3), 4h(3), 4k(3), 4n(3), 4a(4), 4b(4), 4c(4), 4d(4), 4e(4), 4f(4), 4g(4), 4h(4), 4k(4), 4n(4), 4a(5), 4b(5), 4c(5), 4d(5), 4e(5), 4f(5), 4g(5), 4h(5), 4k(5), 4n(5), 4a(6), 4b(6), 4c(6), 4d(6), 4e(6), 4f(6), 4g(6), 4h(6), 4k(6), 4n(6), 4a(7), 4b(7), 4c(7), 4d(7), 4e(7), 4f(7), 4g(7), 4h(7), 4k(7), 4n(7), 4a(8), 4b(8), 4c(8), 4d(8), 4e(8), 4f(8), 4g(8), 4h(8), 4k(8), 4n(8), 4a(9), 4b(9), 4c(9), 4d(9), 4e(9), 4f(9), 4g(9), 4h(9), 4k(9), 4n(9), 4a(10), 4b(10), 4c(10), 4d(10), 4e(10), 4f(10), 4g(10), 4h(10), 4k(10), 4n(10), 4a(11), 4b(11), 4c(11), 4d(11), 4e(11), 4f(11), 4g(11), 4h(11), 4k(11), 4n(11), 4a(12), 4b(12), 4c(12), 4d(12), 4e(12), 4f(12), 4g(12), 4h(12), 4k(12), 4n(12), 4a(13), 4b(13), 4c(13), 4d(13), 4e(13), 4f(13), 4g(13), 4h(13), 4k(13), 4n(13), 4a(14), 4b(14), 4c(14), 4d(14), 4e(14), 4f(14), 4g(14), 4h(14), 4k(14), 4n(14), 4a(15), 4b(15), 4c(15), 4d(15), 4e(15), 4f(15), 4g(15), 4h(15), 4k(15), 4n(15), 4a(16), 4b(16), 4c(16), 4d(16), 4e(16), 4f(16), 4g(16), 4h(16), 4k(16), 4n(16), 4a(17), 4b(17), 4c(17), 4d(17), 4e(17), 4f(17), 4g(17), 4h(17), 4k(17), 4n(17), 4a(18), 4b(18), 4c(18), 4d(18), 4e(18), 4f(18), 4g(18), 4h(18), 4k(18), 4n(18), 4a(19), 4b(19), 4c(19), 4d(19), 4e(19), 4f(19), 4g(19), 4h(19), 4k(19), 4n(19), 4a(20), 4b(20), 4c(20), 4d(20), 4e(20), 4f(20), 4g(20), 4h(20), 4k(20), 4n(20), 4a(21), 4b(21), 4c(21), 4d(21), 4e(21), 4f(21), 4g(21), 4h(21), 4k(21), 4n(21), 4a(22), 4b(22), 4c(22), 4d(22), 4e(22), 4f(22), 4g(22), 4h(22), 4k(22), 4n(22), 4a(23), 4b(23), 4c(23), 4d(23), 4e(23), 4f(23), 4g(23), 4h(23), 4k(23), 4n(23), 4a(24), 4b(24), 4c(24), 4d(24), 4e(24), 4f(24), 4g(24), 4h(24), 4k(24), 4n(24), 4a(25), 4b(25), 4c(25), 4d(25), 4e(25), 4f(25), 4g(25), 4h(25), 4k(25), 4n(25), 4a(26), 4b(26), 4c(26), 4d(26), 4e(26), 4f(26), 4g(26), 4h(26), 4k(26), 4n(26), 4a(27), 4b(27), 4c(27), 4d(27), 4e(27), 4f(27), 4g(27), 4h(27), 4k(27), 4n(27), 4a(28), 4b(28), 4c(28), 4d(28), 4e(28), 4f(28), 4g(28), 4h(28), 4k(28), 4n(28), 4a(29), 4b(29), 4c(29), 4d(29), 4e(29), 4f(29), 4g(29), 4h(29), 4k(29), 4n(29), 4a(30), 4b(30), 4c(30), 4d(30), 4e(30), 4f(30), 4g(30), 4h(30), 4k(30), 4n(30), 4a(31), 4b(31), 4c(31), 4d(31), 4e(31), 4f(31), 4g(31), 4h(31), 4k(31), 4n(31), 4a(32), 4b(32), 4c(32), 4d(32), 4e(32), 4f(32), 4g(32), 4h(32), 4k(32), 4n(32), 4a(33), 4b(33), 4c(33), 4d(33), 4e(33), 4f(33), 4g(33), 4h(33), 4k(33), 4n(33), 4a(34), 4b(34), 4c(34), 4d(34), 4e(34), 4f(34), 4g(34), 4h(34), 4k(34), 4n(34), 4a(35), 4b(35), 4c(35), 4d(35), 4e(35), 4f(35), 4g(35), 4h(35), 4k(35), 4n(35), 4a(36), 4b(36), 4c(36), 4d(36), 4e(36), 4f(36), 4g(36), 4h(36), 4k(36), 4n(36), 4a(37), 4b(37), 4c(37), 4d(37), 4e(37), 4f(37), 4g(37), 4h(37), 4k(37), 4n(37), 4a(38), 4b(38), 4c(38), 4d(38), 4e(38), 4f(38), 4g(38), 4h(38), 4k(38), 4n(38), 4a(39), 4b(39), 4c(39), 4d(39), 4e(39), 4f(39), 4g(39), 4h(39), 4k(39), 4n(39), 4a(40), 4b(40), 4c(40), 4d(40), 4e(40), 4f(40), 4g(40), 4h(40), 4k(40), 4n(40), 4a(41), 4b(41), 4c(41), 4d(41), 4e(41), 4f(41), 4g(41), 4h(41), 4k(41), 4n(41), 4a(42), 4b(42), 4c(42), 4d(42), 4e(42), 4f(42), 4g(42), 4h(42), 4k(42), 4n(42), 4a(43), 4b(43), 4c(43), 4d(43), 4e(43), 4f(43), 4g(43), 4h(43), 4k(43), 4n(43), 4a(44), 4b(44), 4c(44), 4d(44), 4e(44), 4f(44), 4g(44), 4h(44), 4k(44), 4n(44), 4a(45), 4b(45), 4c(45), 4d(45), 4e(45), 4f(45), 4g(45), 4h(45), 4k(45), 4n(45), 4a(46), 4b(46), 4c(46), 4d(46), 4e(46), 4f(46), 4g(46), 4h(46), 4k(46), 4n(46), 4a(47), 4b(47), 4c(47), 4d(47), 4e(47), 4f(47), 4g(47), 4h(47), 4k(47), 4n(47), 4a(48), 4b(48), 4c(48), 4d(48), 4e(48), 4f(48), 4g(48), 4h(48), 4k(48), or 4n(48)).

In some embodiments, a compound as described herein may include multiple instances of $R^4$ and/or other variables. In such embodiments, each variable may optional be different and be appropriately labeled to distinguish each group for greater clarity. For example, where each $R^4$ is different, they may be referred to, for example, as $R^{4.1}$, $R^{1.2}$, $R^{1.3}$, $R^{4.4}$, $R^{4.5}$, respectively, wherein the definition of $R^4$ is assumed by $R^{4.1}$, $R^{4.2}$, $R^{4.3}$, $R^{4.4}$, $R^{4.5}$. The variables used within a definition of $R^1$ and/or other variables that appear at multiple instances and are different may similarly be appropriately labeled to distinguish each group for greater clarity. In some embodiments, the compound is a compound described herein (e.g., in an aspect, embodiment, example, claim, table, scheme, drawing, or figure).

In embodiments, unless otherwise indicated, a compound described herein is a racemic mixture of all stereoisomers. In embodiments, unless otherwise indicated, a compound described herein is a racemic mixture of all enantiomers. In embodiments, unless otherwise indicated, a compound described herein is a racemic mixture of two opposite stereoisomers. In embodiments, unless otherwise indicated, a compound described herein is a racemic mixture of two opposite enantiomers. In embodiments, unless otherwise indicated, a compound described herein is a single stereoisomer. In embodiments, unless otherwise indicated, a compound described herein is a single enantiomer. In embodiments, the compound is a compound described herein (e.g., in an aspect, embodiment, example, figure, table, scheme, or claim).

In embodiments, the compound contacts one or more amino acids corresponding to D248, E250, or Y321 of human estrogen-related receptor β. In embodiments, the compound contacts an amino acid corresponding to Y321 in human estrogen-related receptor β. In embodiments, the compound contacts an amino acids corresponding to D248 of human estrogen-related receptor β. In embodiments, the compound contacts an amino acids corresponding to E250 of human estrogen-related receptor β.

In embodiments, the compound contacts one or more amino acids corresponding to D273 or E275 of human estrogen-related receptor γ. In embodiments, the compound contacts an amino acid corresponding to D273 in human estrogen-related receptor γ. In embodiments, the compound contacts an amino acids corresponding to E275 of human estrogen-related receptor γ.

In embodiments, the compound (e.g., described herein) reduces mitochondrial β-oxidation rates (e.g., compared to absence of the compound). In embodiments, the compound (e.g., described herein) reduces levels of endogenous SHP (e.g., compared to absence of the compound). In embodiments, the compound (e.g., described herein) reduces long-chain fatty acid oxidation (e.g., compared to absence of the compound). In embodiments, the compound (e.g., described herein) reduces mitochondrial β-oxidation rates (e.g., in myocytes) (e.g., compared to absence of the compound). In embodiments, the compound (e.g., described herein) reduces lipid accumulation (e.g., in a subject) (e.g., compared to absence of the compound). In embodiments, the compound (e.g., described herein) increases insulin sensitivity (e.g., in a subject) (e.g., compared to absence of the compound). In embodiments, the compound (e.g., described herein) modulates glucose homeostasis (e.g., in a subject) (e.g., compared to absence of the compound). In embodiments, the compound (e.g., described herein) modulates triglyceride homeostasis (e.g., in a subject) (e.g., compared to absence of the compound). In embodiments, the compound (e.g., described herein) reduces the level of glucose (e.g., in a subject, in liver, in muscle) (e.g., compared to absence of the compound). In embodiments, the compound (e.g., described herein) reduces the level of triglycerides (e.g., in a subject, in liver, in muscle) (e.g., compared to absence of the compound). In embodiments, the compound (e.g., described herein) reduces the level of Lpin1 (e.g., in a subject) (e.g., compared to absence of the compound). In embodiments, the compound (e.g., described herein) reduces glucose blood level (e.g., in a subject) (e.g., compared to absence of the compound). In embodiments, the compound (e.g., described herein) reduces hyperglycemia (e.g., in a subject, in a diabetic subject) (e.g., compared to absence of the compound). In embodiments, the compound (e.g., described herein) reduces the level of diacylglycerol (DAG) (e.g., in a subject) (e.g., compared to absence of the compound). In embodiments, the compound (e.g., described herein) reduces the level of diacylglycerol (DAG) in liver (e.g., in a subject) (e.g., compared to absence of the compound). In embodiments, the compound (e.g., described herein) increases insulin signaling (e.g., in a subject) (e.g., compared to absence of the compound). In embodiments, the compound (e.g., described herein) improves insulin signaling (e.g., in a subject) (e.g., compared to absence of the compound). In embodiments, the compound (e.g., described herein) reduces contact between ERR (e.g., ERRγ or ERRβ) and peroxisome proliferator-activated receptor γ coactivator-1α (PGC-1α) (e.g., in a subject) (e.g., compared to absence of the compound).

In embodiments, the compound is not

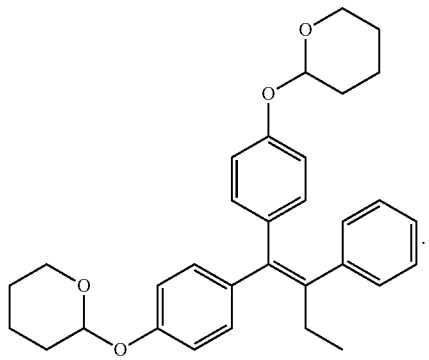 [SMILES: CCC(=C(c1ccc(OC2CCCCO2)cc1)c1ccc(OC2CCCCO2)cc1)c1ccccc1]

In embodiments, the compound is not

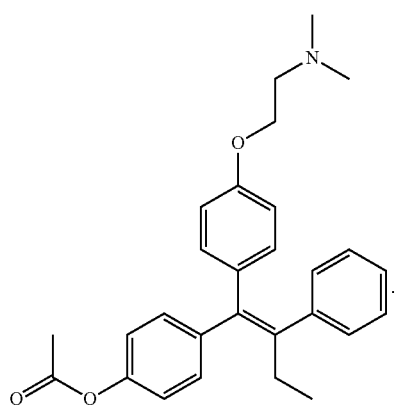 [SMILES: CC/C(=C(/c1ccc(OCCN(C)C)cc1)c1ccc(OC(C)=O)cc1)c1ccccc1]

In embodiments, the compound is not

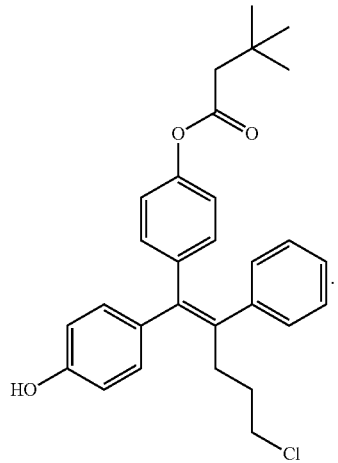 [SMILES: CC(C)(C)CC(=O)Oc1ccc(/C(=C(/CCCCl)c2ccccc2)c2ccc(O)cc2)cc1]

In embodiments, the compound is not

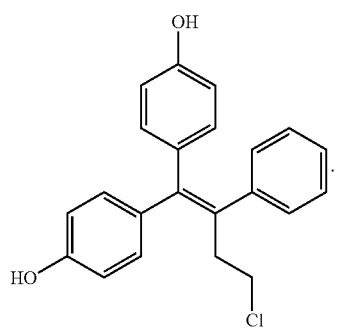 [SMILES: Oc1ccc(C(=C(CCCl)c2ccccc2)c2ccc(O)cc2)cc1]

In embodiments, the compound is not

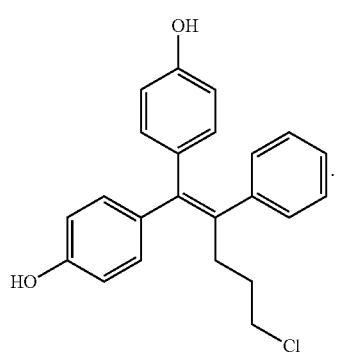 [SMILES: Oc1ccc(C(=C(CCCCl)c2ccccc2)c2ccc(O)cc2)cc1]

101
In embodiments, the compound is not
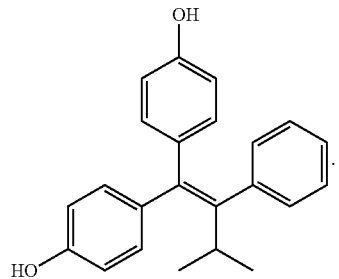 [SMILES: CC(C)C(=C(c1ccc(O)cc1)c1ccc(O)cc1)c1ccccc1]
In embodiments, the compound is not
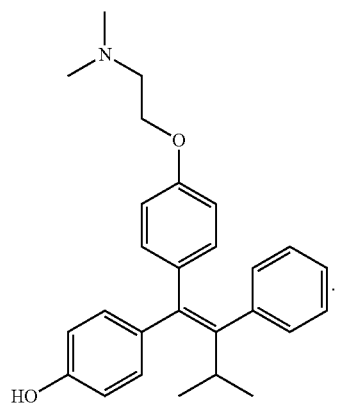 [SMILES: CC(C)/C(=C(\c1ccc(O)cc1)c1ccc(OCCN(C)C)cc1)c1ccccc1]
In embodiments, the compound is not
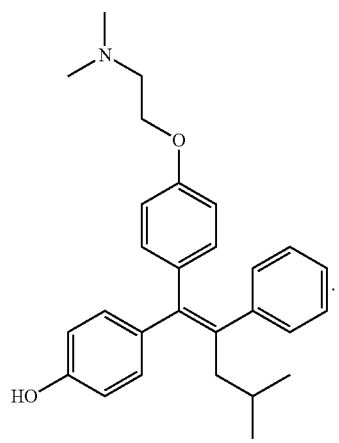 [SMILES: CC(C)C/C(=C(\c1ccc(O)cc1)c1ccc(OCCN(C)C)cc1)c1ccccc1]
102
In embodiments, the compound is not
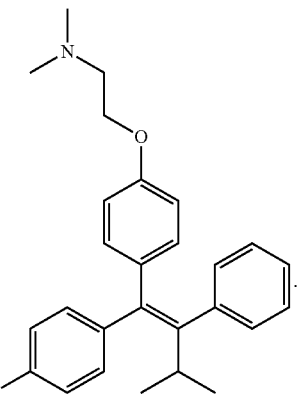
In embodiments, the compound is not
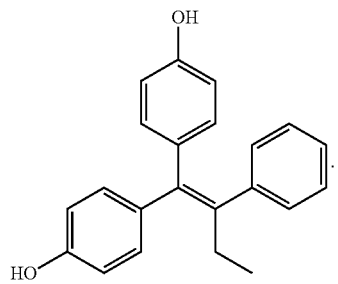 [SMILES: CCC(=C(c1ccc(O)cc1)c1ccc(O)cc1)c1ccccc1]
In embodiments, the compound is not
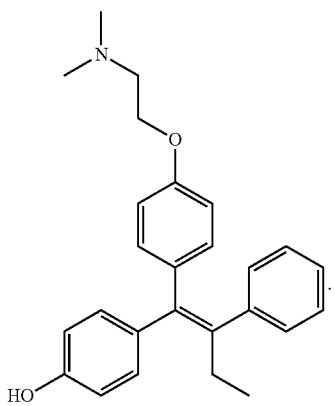 [SMILES: CC/C(=C(\c1ccc(O)cc1)c1ccc(OCCN(C)C)cc1)c1ccccc1]

103
In embodiments, the compound is not
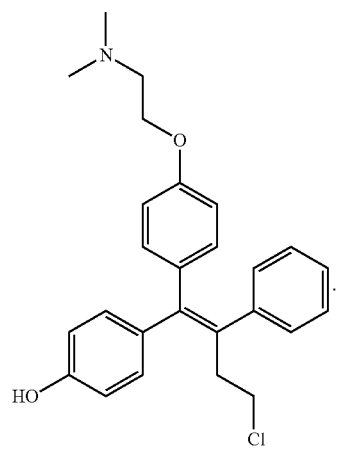 [SMILES: CN(C)CCOc1ccc(/C(=C(/CCCl)c2ccccc2)c2ccc(O)cc2)cc1]
In embodiments, the compound is not
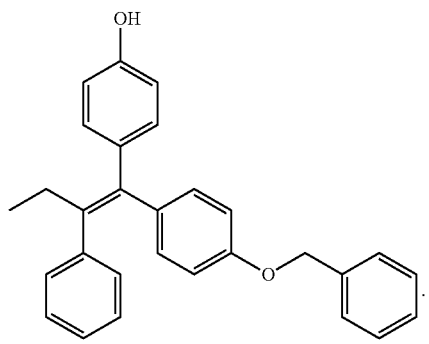 [SMILES: CC/C(=C(\c1ccc(O)cc1)c1ccc(OCc2ccccc2)cc1)c1ccccc1]
In embodiments, the compound is not
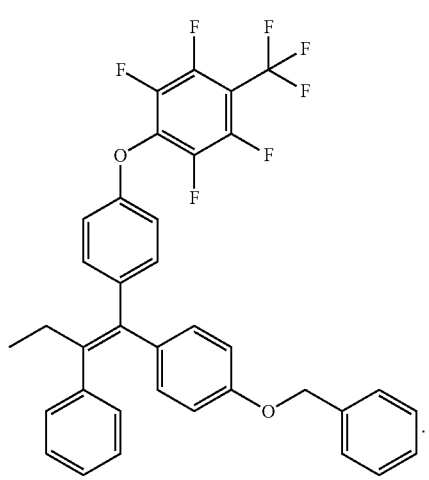 [SMILES: CC/C(=C(/c1ccc(OCc2ccccc2)cc1)c1ccc(Oc2c(F)c(F)c(C(F)(F)F)c(F)c2F)cc1)c1ccccc1]
104
In embodiments, the compound is not
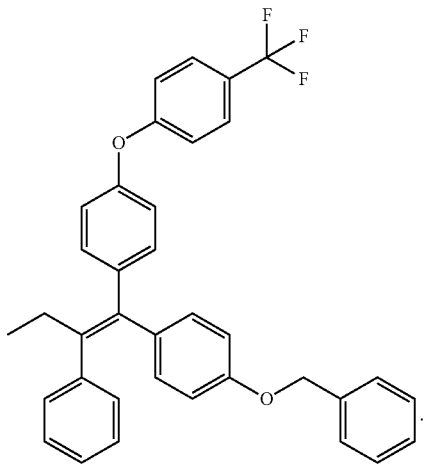 [SMILES: CC/C(=C(/c1ccc(OCc2ccccc2)cc1)c1ccc(Oc2ccc(C(F)(F)F)cc2)cc1)c1ccccc1]
In embodiments, the compound is not
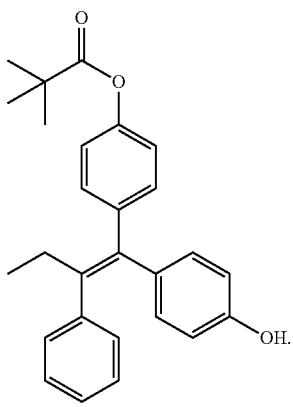 [SMILES: CC/C(=C(/c1ccc(O)cc1)c1ccc(OC(=O)C(C)(C)C)cc1)c1ccccc1]
In embodiments, the compound is not
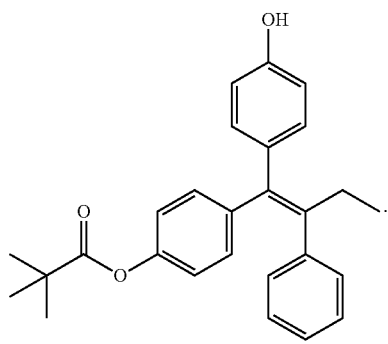 [SMILES: CC/C(=C(\c1ccc(O)cc1)c1ccc(OC(=O)C(C)(C)C)cc1)c1ccccc1]

105

In embodiments, the compound is not

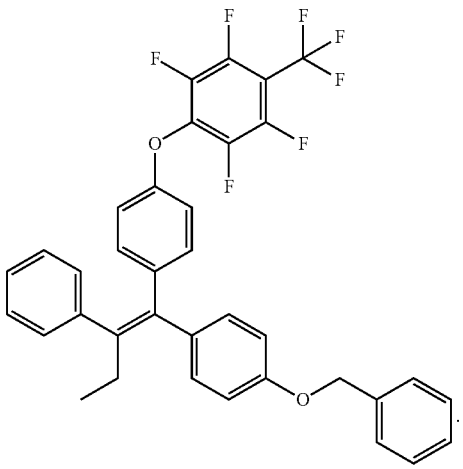 [SMILES: CC/C(=C(\c1ccc(OCc2ccccc2)cc1)c1ccc(Oc2c(F)c(F)c(C(F)(F)F)c(F)c2F)cc1)c1ccccc1]

In embodiments, the compound is not

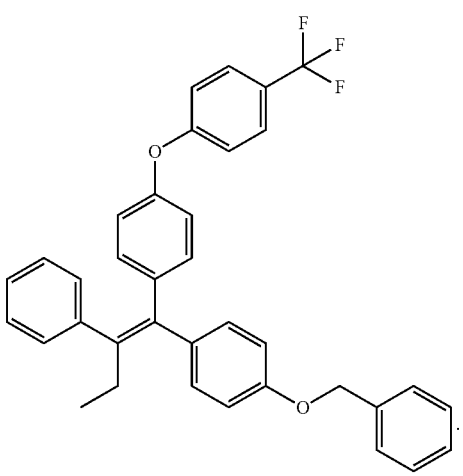 [SMILES: CC/C(=C(\c1ccc(OCc2ccccc2)cc1)c1ccc(Oc2ccc(C(F)(F)F)cc2)cc1)c1ccccc1]

In embodiments, the compound is not

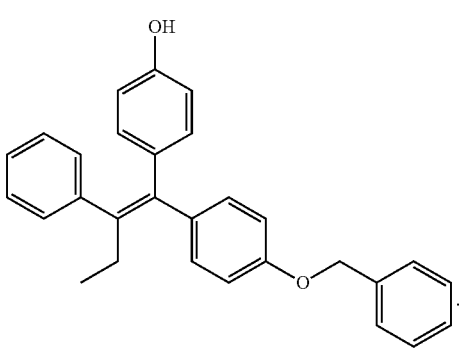 [SMILES: CC/C(=C(/c1ccc(O)cc1)c1ccc(OCc2ccccc2)cc1)c1ccccc1]

In embodiments, $R^1$ is not OH. In embodiments, $R^1$ is not $OCH_2(CH_2)_{10}CH_3$, In embodiments, $R^1$ is not $OCH_2CHCH_2$, In embodiments, $R^1$ is not substituted or unsubstituted alkyl (e.g., $C_1$-$C_8$, $C_1$-$C_6$, $C_1$-$C_4$, or $C_1$-$C_2$). In embodiments, $R^1$ is not a substituted or unsubstituted alkoxy (e.g., $C_1$-$C_8$, $C_1$-$C_6$, $C_1$-$C_4$, or $C_1$-$C_2$) (i.e., alkyl ether). In

106 embodiments, $R^1$ is not a substituted or unsubstituted alkyl ether (e.g., $C_1$-$C_8$, $C_1$-$C_6$, $C_1$-$C_4$, or $C_1$-$C_2$). In embodiments, $R^1$ is not a substituted or unsubstituted alkenoxy (e.g., $C_2$-$C_8$, $C_2$-$C_6$, or $C_2$-$C_4$) (i.e., alkenyl ether). In embodiments, $R^1$ is not a substituted or unsubstituted alkenyl ether (e.g., $C_2$-$C_8$, $C_2$-$C_6$, or $C_2$-$C_4$). In embodiments, $R^1$ is not

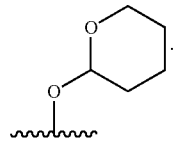 [SMILES: *OC1CCCCO1]

In embodiments, $R^1$ is not —$CH_2CH_3$. In embodiments, $R^1$ is not —$CH(CH_3)_2$. In embodiments, $R^1$ is not —$CH_2CH(CH_3)_2$. In embodiments, $R^1$ is not —$CH_2Cl$. In embodiments, $R^1$ is not —$CH_2CH_2Cl$. In embodiments, $R^1$ is not —$CH_2CH_2CH_2Cl$. In embodiments, $R^1$ is not substituted or unsubstituted alkyl (e.g., $C_1$-$C_8$, $C_1$-$C_6$, $C_1$-$C_4$, or $C_1$-$C_2$). In embodiments, $R^1$ is not substituted or unsubstituted alkenyl (e.g., $C_2$-$C_8$, $C_2$-$C_6$, or $C_2$-$C_4$). In embodiments, $R^1$ is not substituted or unsubstituted alkynyl (e.g., $C_2$-$C_8$, $C_2$-$C_6$, or $C_2$-$C_4$). In embodiments, $R^1$ is not halogen. In embodiments, $R^1$ is not substituted or unsubstituted alkylcarboxy (e.g., $C_1$-$C_8$, $C_1$-$C_6$, $C_1$-$C_4$, or $C_1$-$C_2$ alkyl). In embodiments, $R^1$ is not substituted or unsubstituted alkylamino (e.g., $C_1$-$C_8$, $C_1$-$C_4$, or $C_1$-$C_2$ alkyl). In embodiments, $R^1$ is not substituted or unsubstituted alkylcarbonyl (e.g., $C_1$-$C_8$, $C_1$-$C_6$, $C_1$-$C_4$, or $C_1$-$C_2$ alkyl). In embodiments, $L^{1A}$ is not a bond. In embodiments, $L^{1B}$ is not a bond.

In embodiments, -$L^{1A}$-$L^{1B}$-$R^1$ is not —OH. In embodiments, -$L^{1A}$-$L^{1B}$-$R^1$ is not —$OCH_2(CH_2)_{10}CH_3$, In embodiments -$L^{1A}$-$L^{1B}$-$R^1$ is not —$OCH_2CHCH_2$, In embodiments -$L^{1A}$-$L^{1B}$-$R^1$ is not substituted or unsubstituted alkyl (e.g., $C_1$-$C_8$, $C_1$-$C_6$, $C_1$-$C_4$, or $C_1$-$C_2$). In embodiments -$L^{1A}$-$L^{1B}$-$R^1$ is not a substituted or unsubstituted alkoxy (e.g., $C_1$-$C_8$, $C_1$-$C_6$, $C_1$-$C_4$, or $C_1$-$C_2$) (i.e., alkyl ether). In embodiments, -$L^{1A}$-$L^{1B}$-$R^1$ is not a substituted or unsubstituted alkyl ether (e.g., $C_1$-$C_8$, $C_1$-$C_6$, $C_1$-$C_4$, or $C_1$-$C_2$). In embodiments, -$L^{1A}$-$L^{1B}$-$R^1$ is not a substituted or unsubstituted alkenoxy (e.g., $C_2$-$C_8$, $C_2$-$C_6$, or $C_2$-$C_4$) (i.e., alkenyl ether). In embodiments, -$L^{1A}$-$L^{1B}$-$R^1$ is not a substituted or unsubstituted alkenyl ether (e.g., $C_2$-$C_8$, $C_2$-$C_6$, or $C_2$-$C_4$). In embodiments, -$L^{1A}$-$L^{1B}$-$R^1$ is not

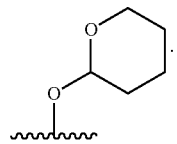

In embodiments, -$L^{1A}$-$L^{1B}$-$R^1$ is not —$CH_2CH_3$. In embodiments, -$L^{1A}$-$L^{1B}$-$R^1$ is not —$CH(CH_3)_2$. In embodiments, -$L^{1A}$-$L^{1B}$-$R^1$ is not —$CH_2CH(CH_3)_2$. In embodiments, -$L^{1A}$-$L^{1B}$-$R^1$ is not —$CH_2Cl$. In embodiments, -$L^{1A}$-$L^{1B}$-$R^1$ is not —$CH_2CH_2Cl$. In embodiments, -$L^{1A}$-$L^{1B}$-$R^1$ is not —$CH_2CH_2CH_2Cl$. In embodiments, -$L^{1A}$-$L^{1B}$-$R^1$ is not substituted or unsubstituted alkyl (e.g., $C_1$-$C_8$, $C_1$-$C_6$, $C_1$-$C_4$, or $C_1$-$C_2$). In embodiments, -$L^{1A}$-$L^{1B}$-$R^1$ is not substituted or unsubstituted alkenyl (e.g., $C_2$-$C_8$, $C_2$-$C_6$, or $C_2$-$C_4$). In embodiments, -$L^{1A}$-$L^{1B}$-$R^1$ is not substituted or unsubstituted alkynyl (e.g., $C_2$-$C_8$, $C_2$-$C_6$, or $C_2$-$C_4$). In embodiments, -L$^{1A}$-L$^{1B}$-R$^1$ is not halogen. In embodiments, -L$^{1A}$-L$^{1B}$-R$^1$ is not substituted or unsubstituted alkylcarboxy (e.g., $C_1$-$C_8$, $C_1$-$C_6$, $C_1$-$C_4$, or $C_1$-$C_2$ alkyl). In embodiments, -L$^{1A}$-L$^{1B}$-R$^1$ is not substituted or unsubstituted alkylamino (e.g., $C_1$-$C_8$, $C_1$-$C_6$, $C_1$-$C_4$, or $C_1$-$C_2$ alkyl). In embodiments, -L$^{1A}$-L$^{1B}$-R$^1$ is not substituted or unsubstituted alkylcarbonyl (e.g., $C_1$-$C_8$, $C_1$-$C_4$, or $C_1$-$C_2$ alkyl).

In embodiments, R$^2$ is not hydrogen. In embodiments, R$^2$ is not —CH$_2$(CH$_2$)$_{10}$CH$_3$. In embodiments, R$^2$ is not —CH$_2$CHCH$_2$. In embodiments, R$^2$ is not substituted or unsubstituted alkyl (e.g., $C_1$-$C_8$, $C_1$-$C_6$, $C_1$-$C_4$, or $C_1$-$C_2$). In embodiments, R$^2$ is not a substituted or unsubstituted alkenyl (e.g., $C_2$-$C_8$, $C_2$-$C_6$, or $C_2$-$C_4$). In embodiments, R$^2$ is not

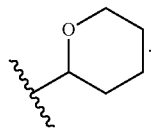 [SMILES: *C1CCCCO1]

In embodiments, R$^2$ is not

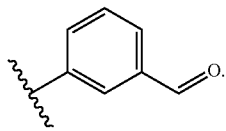 [SMILES: *c1cccc(C=O)c1]

In embodiments, R$^2$ is not

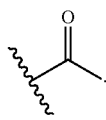

In embodiments, R$^2$ is not substituted or unsubstituted —C(O)alkyl (e.g., $C_1$-$C_8$, $C_1$-$C_6$, $C_1$-$C_4$, or $C_1$-$C_2$ alkyl). In embodiments, R$^2$ is not a substituted or unsubstituted —C(O)alkenyl (e.g., $C_2$-$C_8$, $C_2$-$C_6$, or $C_2$-$C_4$ alkenyl). In embodiments, R$^2$ is not

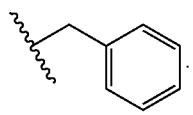 [SMILES: *Cc1ccccc1]

In embodiments, R$^2$ is not

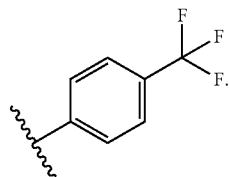 [SMILES: *c1ccc(C(F)(F)F)cc1]

In embodiments, R$^2$ is not

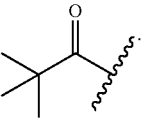 [SMILES: *C(=O)C(C)(C)C]

In embodiments, R$^2$ is not

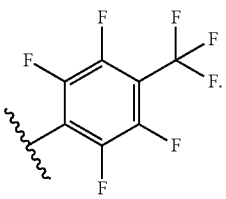 [SMILES: *c1c(F)c(F)c(C(F)(F)F)c(F)c1F]

In embodiments, R$^3$ is not hydrogen. In embodiments, R$^3$ is not —(CH$_2$)$_w$N(R$^{26.1}$)(R$^{26.2}$). w is an integer from 0 to 5 (e.g., 0, 1, 2, 3, 4, or 5). In embodiments, R$^3$ is not substituted or unsubstituted alkyl (e.g., $C_1$-$C_8$, $C_1$-$C_6$, $C_1$-$C_4$, or $C_1$-$C_2$). In embodiments, R$^3$ is not a substituted or unsubstituted alkenyl (e.g., $C_2$-$C_8$, $C_2$-$C_6$, or $C_2$-$C_4$). In embodiments, R$^3$ is not

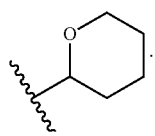

In embodiments, R$^3$ is not

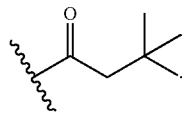

In embodiments, R$^3$ is not —(CH$_2$)$_2$N(CH$_3$)$_2$. In embodiments, R$^3$ is not

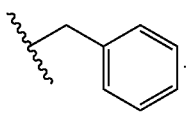

In embodiments, R$^3$ is not

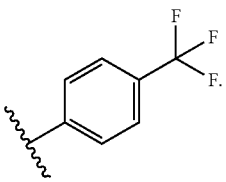 [SMILES: *c1ccc(C(F)(F)F)cc1]

In embodiments, $R^3$ is not

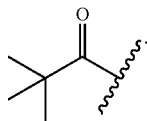 [SMILES: *C(=O)C(C)(C)C]

In embodiments, $R^3$ is not

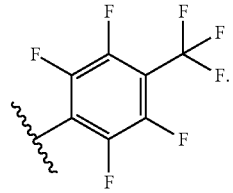 [SMILES: *c1c(F)c(F)c(C(F)(F)F)c(F)c1F]

In embodiments, $R^{26.1}$ is hydrogen, substituted or unsubstituted alkyl (e.g., $C_1$-$C_8$, $C_1$-$C_6$, $C_1$-$C_4$, or $C_1$-$C_2$), substituted or unsubstituted alkenyl (e.g., $C_2$-$C_8$, $C_2$-$C_6$, or $C_2$-$C_4$), substituted or unsubstituted alkynyl (e.g., $C_2$-$C_8$, $C_2$-$C_6$, or $C_2$-$C_4$), or substituted or unsubstituted phenyl. In embodiments, $R^{26.1}$ is unsubstituted methyl. In embodiments, $R^{26.1}$ is substituted with halogen, haloalkyl, alkylcarboxy, alkoxy, phenoxy, alkylamino, or alkylcarbonyl. In embodiments, $R^{26.1}$ is

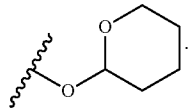

In embodiments, $R^{26.1}$ is

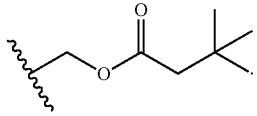

In embodiments, $R^{26.1}$ is independently unsubstituted methyl. In embodiments, $R^{26.1}$ is independently unsubstituted ethyl. In embodiments, $R^{26.1}$ is independently unsubstituted propyl. In embodiments, $R^{26.1}$ is independently unsubstituted isopropyl. In embodiments, $R^{26.1}$ is independently unsubstituted n-propyl. In embodiments, $R^{26.1}$ is independently unsubstituted butyl. In embodiments, $R^{26.1}$ is independently unsubstituted n-butyl. In embodiments, $R^{26.1}$ is independently unsubstituted t-butyl. In embodiments, $R^{26.1}$ is independently unsubstituted iso-butyl. In embodiments, $R^{26.1}$ is independently unsubstituted pentyl. In embodiments, $R^{26.1}$ is independently unsubstituted n-pentyl. In embodiments, $R^{26.1}$ is independently unsubstituted hexyl. In embodiments, $R^{26.1}$ is independently unsubstituted n-hexyl. In embodiments, $R^{26.1}$ is independently unsubstituted heptyl. In embodiments, $R^{26.1}$ is independently unsubstituted n-heptyl. In embodiments, $R^{26.1}$ is independently unsubstituted octyl. In embodiments, $R^{26.1}$ is independently unsubstituted n-octyl. In embodiments, $R^{26.1}$ is independently unsubstituted $C_1$-$C_8$ alkyl. In embodiments, $R^{26.2}$ is hydrogen, substituted or unsubstituted alkyl (e.g., $C_1$-$C_8$, $C_1$-$C_6$, $C_1$-$C_4$, or $C_1$-$C_2$), substituted or unsubstituted alkenyl (e.g., $C_2$-$C_8$, $C_2$-$C_6$, or $C_2$-$C_4$), substituted or unsubstituted alkynyl (e.g., $C_2$-$C_8$, $C_2$-$C_6$, or $C_2$-$C_4$), or substituted or unsubstituted phenyl. In embodiments, $R^{26.2}$ is unsubstituted methyl. In embodiments, $R^{26.2}$ is substituted with halogen, haloalkyl, alkylcarboxy, alkoxy, phenoxy, alkylamino, or alkylcarbonyl. In embodiments, $R^{26.2}$ is

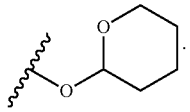 [SMILES: *OC1CCCCO1]

In embodiments, $R^{26.2}$ is

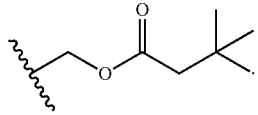

In embodiments, $R^{26.2}$ is independently unsubstituted methyl. In embodiments, $R^{26.2}$ is independently unsubstituted ethyl. In embodiments, $R^{26.2}$ is independently unsubstituted propyl. In embodiments, $R^{26.2}$ is independently unsubstituted isopropyl. In embodiments, $R^{26.2}$ is independently unsubstituted n-propyl. In embodiments, $R^{26.2}$ is independently unsubstituted butyl. In embodiments, $R^{26.2}$ is independently unsubstituted n-butyl. In embodiments, $R^{26.2}$ is independently unsubstituted t-butyl. In embodiments, $R^{26.2}$ is independently unsubstituted iso-butyl. In embodiments, $R^{26.2}$ is independently unsubstituted pentyl. In embodiments, $R^{26.2}$ is independently unsubstituted n-pentyl. In embodiments, $R^{26.2}$ is independently unsubstituted hexyl. In embodiments, $R^{26.2}$ is independently unsubstituted n-hexyl. In embodiments, $R^{26.2}$ is independently unsubstituted heptyl. In embodiments, $R^{26.2}$ is independently unsubstituted n-heptyl. In embodiments, $R^{26.2}$ is independently unsubstituted octyl. In embodiments, $R^{26.2}$ is independently unsubstituted n-octyl. In embodiments, $R^{26.2}$ is independently unsubstituted $C_1$-$C_8$ alkyl.

In embodiments, $R^4$ is not unsubstituted alkyl (e.g., $C_1$-$C_8$, $C_1$-$C_6$, $C_1$-$C_4$, or $C_1$-$C_2$). In embodiments, $R^4$ is not unsubstituted methyl. In embodiments, $R^4$ is not hydrogen. In embodiments, $R^4$ is not OH. In embodiments, $R^4$ is not halogen. In embodiments, $R^4$ is not —$CH_2CHCH_2$. In embodiments, $R^4$ is substituted or unsubstituted alkyl (e.g., $C_1$-$C_8$, $C_1$-$C_6$, $C_1$-$C_4$, or $C_1$-$C_2$), substituted or unsubstituted alkenyl (e.g., $C_2$-$C_8$, $C_2$-$C_6$, or $C_2$-$C_4$), or substituted or unsubstituted alkynyl (e.g., $C_2$-$C_8$, $C_2$-$C_6$, or $C_2$-$C_4$). In embodiments, $R^4$ is unsubstituted methyl. In embodiments, $R^4$ is substituted with halogen, haloalkyl, substituted or unsubstituted alkylcarboxy, substituted or unsubstituted alkoxy, substituted or unsubstituted phenoxy, substituted or unsubstituted alkylamino, or substituted or unsubstituted alkylcarbonyl.

III. Pharmaceutical Compositions

In an aspect is provided a pharmaceutical composition including a compound described herein, or pharmaceutically acceptable salt thereof, and a pharmaceutically acceptable excipient.

In embodiments of the pharmaceutical compositions, the compound, or pharmaceutically acceptable salt thereof, is included in a therapeutically effective amount.

In embodiments of the pharmaceutical compositions, the pharmaceutical composition includes a second agent (e.g. therapeutic agent). In embodiments of the pharmaceutical compositions, the pharmaceutical composition includes a second agent (e.g. therapeutic agent) in a therapeutically effective amount. In embodiments of the pharmaceutical compositions, the second agent is an agent for treating cancer. In embodiments, the second agent is an anti-cancer agent. In embodiments, the second agent is a chemotherapeutic. In embodiments, the second agent is an anti-inflammatory agent. In embodiments, the second agent is an agent for treating NASH. In embodiments, the second agent is an agent for treating NAFLD.

IV. Methods of Treatment

In an aspect is provided a method of treating non-alcoholic fatty liver disease (NAFLD), the method including administering to a subject in need thereof an effective amount of a compound described herein. In embodiments, the compound is included in a therapeutically effective amount.

In an aspect is provided a method of treating non-alcoholic steatohepatitis (NASH), the method including administering to a subject in need thereof an effective amount of a compound described herein. In embodiments, the compound is included in a therapeutically effective amount.

In an aspect is provided a method of treating cancer including administering to a subject in need thereof an effective amount of a compound described herein. In embodiments, the cancer is hepatocellular cancer. In embodiments, the cancer is breast cancer.

In an aspect is provided a method of treating a disease associated with Estrogen Related Receptor (e.g., ERRβ or ERRγ) activity including administering to a subject in need thereof an effective amount of a compound described herein. In embodiments, the disease is associated with ERRβ activity. In embodiments, the disease is associated with ERRγ activity.

In an aspect is provided a method of treating non-alcoholic fatty liver disease (NAFLD), the method including administering to a subject in need thereof an effective amount of a compound having the formula:

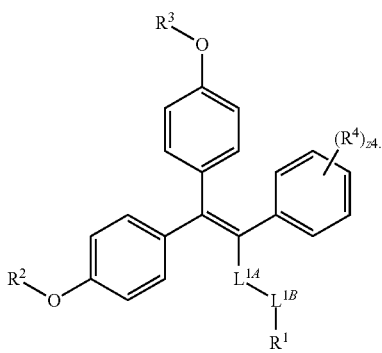

(I)

$L^{1A}$ is a bond, substituted or unsubstituted alkylene, or substituted or unsubstituted heteroalkylene. $L^{1B}$ is a bond, —C(O)O—, —OC(O)—, —O—, —C(O)—, —NH—, —NHC(O)—, or —C(O)NH—. $R^1$ is independently hydrogen, halogen, —CX$^1_3$, —CHX$^1_2$, —CH$_2$X$^1$, —OCX$^1_3$, —OCH$_2$X$^1$, —OCHX$^1_2$, —CN, —SO$_{n1}$R$^{1D}$, —SO$_{v1}$NR$^{1A}$R$^{1B}$, —NHC(O)NR$^{1A}$R$^{1B}$, —N(O)$_{m1}$, —NR$^{1A}$R$^{1B}$, —C(O)R$^{1C}$, —C(O)—OR$^{1C}$, —C(O)NR$^{1A}$R$^{1B}$, —OR$^{1D}$, —NR$^{1A}$SO$_2$R$^{1D}$, —NR$^{1A}$C(O)R$^{1C}$, —NR$^{1A}$C(O)OR$^{1C}$, —NR$^{1A}$OR$^{1C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^2$ is independently hydrogen, —CX$^2_3$, —CHX$^2_2$, —CH$_2$X$^2$, —C(O)R$^{2A}$, —C(O)OR$^{2A}$, —C(O)NR$^{2A}$R$^{2B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^3$ is independently hydrogen, —CX$^3_3$, —CHX$^3_2$, —CH$_2$X$^3$, —C(O)R$^{3A}$, —C(O)OR$^{3A}$, —C(O)NR$^{3A}$R$^{3B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^4$ is independently halogen, —CX$^4_3$, —CHX$^4_2$, —CH$_2$X$^4$, —OCX$^4_3$, —OCH$_2$X$^4$, —OCHX$^4_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. The symbol z4 is an integer from 0 to 5. Each $R^{1A}$, $R^{1B}$, $R^{1C}$, $R^{1D}$, $R^{2A}$, $R^{2B}$, $R^{3A}$, and $R^{3B}$ is independently hydrogen, —CX$_3$, —CN, —COOH, —CONH$_2$, —CHX$_2$, —CH$_2$X, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{1A}$ and $R^{1B}$ substituents bonded to the same nitrogen atom may optionally be joined to form a substituted or unsubstituted heterocycloalkyl or substituted or unsubstituted heteroaryl; $R^{2A}$ and $R^{2B}$ substituents bonded to the same nitrogen atom may optionally be joined to form a substituted or unsubstituted heterocycloalkyl or substituted or unsubstituted heteroaryl; $R^{3A}$ and $R^{3B}$ substituents bonded to the same nitrogen atom may optionally be joined to form a substituted or unsubstituted heterocycloalkyl or substituted or unsubstituted heteroaryl. Each X, $X^1$, $X^2$, $X^3$, and $X^4$ is independently —F, —Cl, —Br, or —I. The symbol n1 is independently an integer from 0 to 4. The symbols m1 and v1 are independently an integer from 1 to 2.

In an aspect is provided a method of treating non-alcoholic steatohepatitis (NASH), the method including administering to a subject in need thereof an effective amount of a compound having the formula:

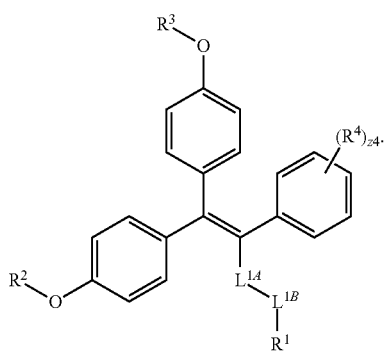

(I)

$L^{1A}$ is a bond, substituted or unsubstituted alkylene, or substituted or unsubstituted heteroalkylene. $L^{1B}$ is a bond, —C(O)O—, —OC(O)—, —O—, —C(O)—, —NH—, —NHC(O)—, or —C(O)NH—. $R^1$ is independently hydrogen, halogen, —CX$^1_3$, —CHX$^1_2$, —CH$_2$X$^1$, —OCX$^1_3$, —OCH$_2$X$^1$, —OCHX$^1_2$, —CN, —SO$_{n1}$R$^{1D}$, —SO$_{v1}$NR$^{1A}$R$^{1B}$, —NHC(O)NR$^{1A}$R$^{1B}$, —N(O)$_{m1}$, —NR$^{1A}$R$^{1B}$, —C(O)R$^{1C}$, —C(O)—OR$^{1C}$, —C(O)NR$^{1A}$R$^{1B}$, —OR$^{1D}$, —NR$^{1A}$SO$_2$R$^{1D}$, —NR$^{1A}$C(O)R$^{1C}$, —NR$^{1A}$C(O)OR$^{1C}$, —NR$^{1A}$OR$^{1C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^2$ is independently hydrogen, —CX$^2_3$, —CHX$^2_2$, —CH$_2$X$^2$, —C(O)R$^{2A}$, —C(O)OR$^{2A}$, —C(O)NR$^{2A}$R$^{2B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^3$ is independently hydrogen, —CX$^3_3$, —CHX$^3_2$, —CH$_2$X$^3$, —C(O)R$^{3A}$, —C(O)OR$^{3A}$, —C(O)NR$^{3A}$R$^{3B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^4$ is independently halogen, —CX$^4_3$, —CHX$^4_2$, —CH$_2$X$^4$, —OCX$^4_3$, —OCH$_2$X$^4$, —OCHX$^4_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC═(O)NHNH$_2$, —NHC═(O)NH$_2$, —NHSO$_2$H, —NHC═(O)H, —NHC(O)—OH, —NHOH, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. The symbol z4 is an integer from 0 to 5. Each $R^{1A}$, $R^{1B}$, $R^{1C}$, $R^{1D}$, $R^{2A}$, $R^{2B}$, $R^{3A}$, and $R^{3B}$ is independently hydrogen, —CX$_3$, —CN, —COOH, —CONH$_2$, —CHX$_2$, —CH$_2$X, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{1A}$ and $R^{1B}$ substituents bonded to the same nitrogen atom may optionally be joined to form a substituted or unsubstituted heterocycloalkyl or substituted or unsubstituted heteroaryl; $R^{2A}$ and $R^{2B}$ substituents bonded to the same nitrogen atom may optionally be joined to form a substituted or unsubstituted heterocycloalkyl or substituted or unsubstituted heteroaryl; $R^{3A}$ and $R^{3B}$ substituents bonded to the same nitrogen atom may optionally be joined to form a substituted or unsubstituted heterocycloalkyl or substituted or unsubstituted heteroaryl. Each X, $X^1$, $X^1$, $X^3$, and $X^4$ is independently —F, —Cl, —Br, or —I. The symbol n1 is independently an integer from 0 to 4. The symbols m1 and v1 are independently an integer from 1 to 2.

In embodiments, the method includes administering a second agent (e.g. therapeutic agent). In embodiments, the method includes administering a second agent (e.g. therapeutic agent) in a therapeutically effective amount. In embodiments, the second agent is an agent for treating cancer. In embodiments, the second agent is an anti-cancer agent. In embodiments, the second agent is a chemotherapeutic. In embodiments, the second agent is an agent for treating NASH. In embodiments, the second agent is an agent for treating NAFLD.

In embodiments, the method reduces mitochondrial β-oxidation rates (e.g., compared to absence of the compound). In embodiments, the method reduces levels of endogenous SHP (e.g., compared to absence of the compound). In embodiments, the method reduces long-chain fatty acid oxidation (e.g., compared to absence of the compound). In embodiments, the method reduces mitochondrial β-oxidation rates (e.g., in myocytes) (e.g., compared to absence of the compound). In embodiments, the method reduces lipid accumulation (e.g., in a subject) (e.g., compared to absence of the compound). In embodiments, the method increases insulin sensitivity (e.g., in a subject) (e.g., compared to absence of the compound). In embodiments, the method modulates glucose homeostasis (e.g., in a subject) (e.g., compared to absence of the compound). In embodiments, the method modulates triglyceride homeostasis (e.g., in a subject) (e.g., compared to absence of the compound). In embodiments, the method reduces the level of glucose (e.g., in a subject, in liver, in muscle) (e.g., compared to absence of the compound). In embodiments, the method reduces the level of triglycerides (e.g., in a subject, in liver, in muscle) (e.g., compared to absence of the compound). In embodiments, the method reduces the level of Lpin1 (e.g., in a subject) (e.g., compared to absence of the compound). In embodiments, the method reduces glucose blood level (e.g., in a subject) (e.g., compared to absence of the compound). In embodiments, the method reduces hyperglycemia (e.g., in a subject, in a diabetic subject) (e.g., compared to absence of the compound). In embodiments, the method reduces the level of diacylglyerol (DAG) (e.g., in a subject) (e.g., compared to absence of the compound). In embodiments, the method reduces the level of diacylglyerol (DAG) in liver (e.g., in a subject) (e.g., compared to absence of the compound). In embodiments, the method increases insulin signaling (e.g., in a subject) (e.g., compared to absence of the compound). In embodiments, the method improves insulin signaling (e.g., in a subject) (e.g., compared to absence of the compound). In embodiments, the method reduces contact between ERR (e.g., ERRγ or ERRβ) and peroxisome proliferator-activated receptor γ coactivator-1α (PGC-1α) (e.g., in a subject) (e.g., compared to absence of the compound).

In an aspect is provided a method of treating a proliferative disease, the method including administering to a subject in need thereof an effective amount of a compound described herein. In embodiments, the compound is included in a therapeutically effective amount.

In an aspect is provided a method of treating obesity, the method including administering to a subject in need thereof an effective amount of a compound described herein. In embodiments, the compound is included in a therapeutically effective amount.

In an aspect is provided a method of treating a hormone disorder, the method including administering to a subject in need thereof an effective amount of a compound described herein. In embodiments, the compound is included in a therapeutically effective amount.

In an aspect is provided a method of treating lipidemia, the method including administering to a subject in need thereof an effective amount of a compound described herein. In embodiments, the compound is included in a therapeutically effective amount.

In an aspect is provided a method of treating a lipid disorder, the method including administering to a subject in need thereof an effective amount of a compound described herein. In embodiments, the compound is included in a therapeutically effective amount.

In an aspect is provided a method of treating a metabolic disorder, the method including administering to a subject in need thereof an effective amount of a compound described herein. In embodiments, the compound is included in a therapeutically effective amount.

In an aspect is provided a method of treating syndrome X, the method including administering to a subject in need thereof an effective amount of a compound described herein. In embodiments, the compound is included in a therapeutically effective amount.

In an aspect is provided a method of treating diabetes, the method including administering to a subject in need thereof an effective amount of a compound described herein. In embodiments, the compound is included in a therapeutically effective amount.

In an aspect is provided a method of treating type 1 diabetes, the method including administering to a subject in need thereof an effective amount of a compound described herein. In embodiments, the compound is included in a therapeutically effective amount.

In an aspect is provided a method of treating type 2 diabetes, the method including administering to a subject in need thereof an effective amount of a compound described herein. In embodiments, the compound is included in a therapeutically effective amount.

In an aspect is provided a method of treating fibrosis (e.g., liver fibrosis), the method including administering to a subject in need thereof an effective amount of a compound described herein. In embodiments, the compound is included in a therapeutically effective amount.

V. Methods of Inhibition

In an aspect is provided a method of inhibiting estrogen-related receptor β activity, the method including contacting the estrogen-related receptor β with a compound described herein.

In embodiments, the compound inhibits estrogen-related receptor β at least 2-fold more potently than the compound inhibits estrogen-related receptor α. In embodiments, the compound inhibits estrogen-related receptor β at least 5-fold more potently than the compound inhibits estrogen-related receptor α. In embodiments, the compound inhibits estrogen-related receptor at least 10-fold more potently than the compound inhibits estrogen-related receptor α. In embodiments, the compound inhibits estrogen-related receptor β at least 100-fold more potently than the compound inhibits estrogen-related receptor α. In embodiments, the compound inhibits estrogen-related receptor β at least 2-fold more potently than the compound inhibits estrogen-related receptor γ. In embodiments, the compound inhibits estrogen-related receptor β at least 5-fold more potently than the compound inhibits estrogen-related receptor γ. In embodiments, the compound inhibits estrogen-related receptor β at least 10-fold more potently than the compound inhibits estrogen-related receptor γ. In embodiments, the compound inhibits estrogen-related receptor β at least 20-fold more potently than the compound inhibits estrogen-related receptor γ.

In embodiments, the estrogen-related receptor β is a human estrogen-related receptor β. In embodiments, the compound contacts one or more amino acids corresponding to D248, E250, or Y321 of human estrogen-related receptor β. In embodiments, the compound contacts an amino acid corresponding to Y321 in human estrogen-related receptor β. In embodiments, the compound contacts an amino acids corresponding to D248 of human estrogen-related receptor β In embodiments, the compound contacts an amino acids corresponding to E250 of human estrogen-related receptor β.

In embodiments, the method reduces mitochondrial β-oxidation rates (e.g., compared to absence of the compound). In embodiments, the method reduces levels of endogenous SHP (e.g., compared to absence of the compound). In embodiments, the method reduces long-chain fatty acid oxidation (e.g., compared to absence of the compound). In embodiments, the method reduces mitochondrial β-oxidation rates (e.g., in myocytes) (e.g., compared to absence of the compound). In embodiments, the method reduces lipid accumulation (e.g., in a subject) (e.g., compared to absence of the compound). In embodiments, the method increases insulin sensitivity (e.g., in a subject) (e.g., compared to absence of the compound). In embodiments, the method modulates glucose homeostasis (e.g., in a subject) (e.g., compared to absence of the compound). In embodiments, the method modulates triglyceride homeostasis (e.g., in a subject) (e.g., compared to absence of the compound). In embodiments, the method reduces the level of glucose (e.g., in a subject, in liver, in muscle) (e.g., compared to absence of the compound). In embodiments, the method reduces the level of triglycerides (e.g., in a subject, in liver, in muscle) (e.g., compared to absence of the compound). In embodiments, the method reduces the level of Lpin1 (e.g., in a subject) (e.g., compared to absence of the compound). In embodiments, the method reduces glucose blood level (e.g., in a subject) (e.g., compared to absence of the compound). In embodiments, the method reduces hyperglycemia (e.g., in a subject, in a diabetic subject) (e.g., compared to absence of the compound). In embodiments, the method reduces the level of diacylglyerol (DAG) (e.g., in a subject) (e.g., compared to absence of the compound). In embodiments, the method reduces the level of diacylglyerol (DAG) in liver (e.g., in a subject) (e.g., compared to absence of the compound). In embodiments, the method increases insulin signaling (e.g., in a subject) (e.g., compared to absence of the compound). In embodiments, the method improves insulin signaling (e.g., in a subject) (e.g., compared to absence of the compound). In embodiments, the method reduces contact between ERR (e.g., ERRγ or ERRβ) and peroxisome proliferator-activated receptor γ coactivator-1α (PGC-1α) (e.g., in a subject) (e.g., compared to absence of the compound).

VI. Embodiments

Embodiment P1

A method of treating non-alcoholic fatty liver disease, said method comprising administering to a subject in need thereof an effective amount of a compound having the formula:

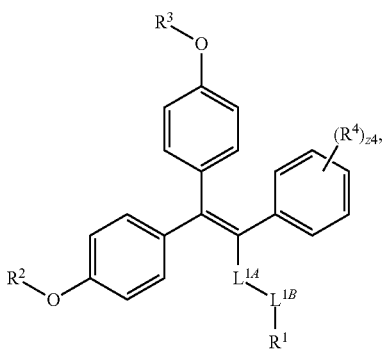

(I)

wherein,
$L^{1A}$ is a bond, substituted or unsubstituted alkylene, or substituted or unsubstituted heteroalkylene; $L^{1B}$ is a bond, —C(O)O—, —OC(O)—, —O—, —C(O)—, —NH—, —NHC(O)—, or —C(O)NH—; $R^1$ is independently hydrogen, halogen, —CX$^1_3$, —CHX$^1_2$, —CH$_2$X$^1$, —OCX$^1_3$, —OCH$_2$X$^1$, —OCHX$^1_2$, —CN, —SO$_{v1}$NR$^{1A}$R$^{1B}$, —NHC(O)NR$^{1A}$R$^{1B}$, —N(O)$_{m1}$, —NR$^{1A}$R$^{1B}$, —C(O)R$^{1C}$, —C(O)—OR$^{1C}$, —C(O)NR$^{1A}$R$^{1B}$, —OR$^{1D}$, —NR$^{1A}$SO$_2$R$^{1D}$, —NR$^{1A}$C(O)R$^{1C}$, —NR$^{1A}$C(O)OR$^{1C}$, —NR$^{1A}$OR$^{1C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^2$ is independently hydrogen, —CX$^2_3$, —CHX$^2_2$, —CH$_2$X$^2$, —C(O)R$^{2A}$, —C(O)OR$^{2A}$, —C(O)NR$^{2A}$R$^{2B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^3$ is independently hydrogen, —CX$^3_3$, —CHX$^3_2$, —CH$_2$X$^3$, —C(O)R$^{3A}$, —C(O)OR$^{3A}$, —C(O)NR$^{3A}$R$^{3B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^4$ is independently halogen, —CX$^4_3$, —CHX$^4_2$, —CH$_2$X$^4$, —OCX$^4_3$, —OCH$_2$X$^4$, —OCHX$^4_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; z4 is an integer from 0 to 5; each $R^{1A}$, $R^{1B}$, $R^{1C}$, $R^{1D}$, $R^{2A}$, $R^{2B}$, $R^{3A}$, and $R^{3B}$ is independently hydrogen, —CX$_3$, —CN, —COOH, —CONH$_2$, —CHX$_2$, —CH$_2$X, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{1A}$ and $R^{1B}$ substituents bonded to the same nitrogen atom may optionally be joined to form a substituted or unsubstituted heterocycloalkyl or substituted or unsubstituted heteroaryl; $R^{2A}$ and $R^{2B}$ substituents bonded to the same nitrogen atom may optionally be joined to form a substituted or unsubstituted heterocycloalkyl or substituted or unsubstituted heteroaryl; $R^{3A}$ and $R^{3B}$ substituents bonded to the same nitrogen atom may optionally be joined to form a substituted or unsubstituted heterocycloalkyl or substituted or unsubstituted heteroaryl; each X, $X^1$, $X^2$, $X^3$, and $X^4$ is independently —F, —Cl, —Br, or —I; n1 is an integer from 0 to 4; and m1 and v1 are independently an integer from 1 to 2.

Embodiment P2

A method of treating non-alcoholic steatohepatitis, said method comprising administering to a subject in need thereof an effective amount of a compound having the formula:

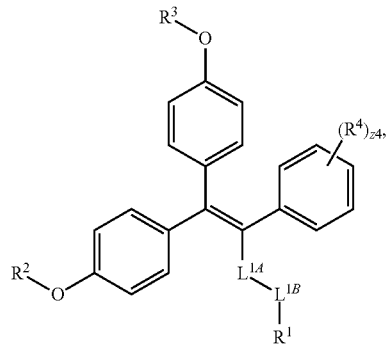

(I)

wherein,
$L^{1A}$ is a bond, substituted or unsubstituted alkylene, or substituted or unsubstituted heteroalkylene; $L^{1B}$ is a bond, —C(O)O—, —OC(O)—, —O—, —C(O)—, —NH—, —NHC(O)—, or —C(O)NH—; $R^1$ is independently hydrogen, halogen, —CX$^1_3$, —CHX$^1_2$, —CH$_2$X$^1$, —OCX$^1_3$, —OCH$_2$X$^1$, —OCHX$^1_2$, —CN, —SO$_{n1}$R$^{1D}$, —SO$_{v1}$NR$^{1A}$R$^{1B}$, —NHC(O)NR$^{1A}$R$^{1B}$, —N(O)$_{m1}$, —NR$^{1A}$R$^{1B}$, —C(O)R$^{1C}$, —C(O)—OR$^{1C}$, —C(O)NR$^{1A}$R$^{1B}$, —OR$^{1D}$, —NR$^{1A}$SO$_2$R$^{1D}$, —NR$^{1A}$C(O)R$^{1C}$, —NR$^{1A}$C(O)OR$^{1C}$, —NR$^{1A}$OR$^{1C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^2$ is independently hydrogen, —CX$^2_3$, —CHX$^2_2$, —CH$_2$X$^2$, —C(O)R$^{2A}$, —C(O)OR$^{2A}$, —C(O)NR$^{2A}$R$^{2B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^3$ is independently hydrogen, —CX$^3_3$, —CHX$^3_2$, —CH$_2$X$^3$, —C(O)R$^{3A}$, —C(O)OR$^{3A}$, —C(O)NR$^{3A}$R$^{3B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^4$ is independently halogen, —CX$^4_3$, —CHX$^4_2$, —CH$_2$X$^4$, —OCX$^4_3$, —OCH$_2$X$^4$, —OCHX$^4_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

z4 is an integer from 0 to 5; each $R^{1A}$, $R^{1B}$, $R^{1C}$, $R^{1D}$, $R^{2A}$, $R^{2B}$, $R^{3A}$, and $R^{3B}$ is independently hydrogen, $-CX_3$, $-CN$, $-COOH$, $-CONH_2$, $-CHX_2$, $-CH_2X$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{1A}$ and $R^{1B}$ substituents bonded to the same nitrogen atom may optionally be joined to form a substituted or unsubstituted heterocycloalkyl or substituted or unsubstituted heteroaryl; $R^{2A}$ and $R^{2B}$ substituents bonded to the same nitrogen atom may optionally be joined to form a substituted or unsubstituted heterocycloalkyl or substituted or unsubstituted heteroaryl; $R^{3A}$ and $R^{3B}$ substituents bonded to the same nitrogen atom may optionally be joined to form a substituted or unsubstituted heterocycloalkyl or substituted or unsubstituted heteroaryl; each X, $X^1$, $X^2$, $X^3$, and $X^4$ is independently $-F$, $-Cl$, $-Br$, or $-I$; n1 is an integer from 0 to 4; and m1 and v1 are independently an integer from 1 to 2.

Embodiment P3

The method of one of embodiments P1 to P2 wherein the compound has the formula:

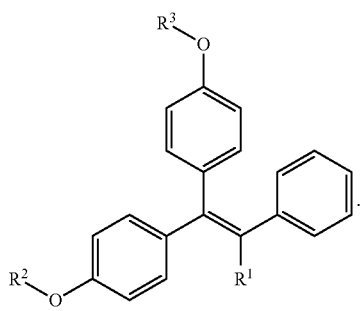

(Ib)

Embodiment P4

The method of one of embodiments P1 to P3, wherein $R^1$ is substituted or unsubstituted alkyl or substituted or unsubstituted heteroalkyl.

Embodiment P5

The method of one of embodiments P1 to P3, wherein $R^1$ is substituted or unsubstituted $C_1$-$C_6$ alkyl or substituted or unsubstituted 2 to 6 heteroalkyl.

Embodiment P6

The method of one of embodiments P1 to P3, wherein $R^1$ is $R^{20}$-substituted or unsubstituted $C_1$-$C_6$ alkyl or $R^{20}$-substituted or unsubstituted 2 to 6 heteroalkyl; $R^{20}$ is independently oxo, halogen, $-CX^{20}_3$, $-CHX^{20}_2$, $-CH_2X^{20}$, $-OCX^{20}_3$, $-OCH_2X^{20}$, $-OCHX^{20}_2$, $-CN$, $-OH$, $-COOH$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $R^{21}$-substituted or unsubstituted alkyl, $R^{21}$-substituted or unsubstituted heteroalkyl, $R^{21}$-substituted or unsubstituted cycloalkyl, $R^{21}$-substituted or unsubstituted heterocycloalkyl, $R^{21}$-substituted or unsubstituted aryl, or $R^{21}$-substituted or unsubstituted heteroaryl; $R^{21}$ is independently oxo, halogen, $-CX^{21}_3$, $-CHX^{21}_2$, $-CH_2X^{21}$, $-OCX^{21}_3$, $-OCH_2X^{21}$, $-OCHX^{21}_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $R^{22}$-substituted or unsubstituted alkyl, $R^{22}$-substituted or unsubstituted heteroalkyl, $R^{22}$-substituted or unsubstituted cycloalkyl, $R^{22}$-substituted or unsubstituted heterocycloalkyl, $R^{22}$-substituted or unsubstituted aryl, or $R^{22}$-substituted or unsubstituted heteroaryl; $R^{22}$ is independently oxo, halogen, $-CX^{22}_3$, $-CHX^{22}_2$, $-CH_2X^{22}$, $-OCX^{22}_3$, $-OCH_2X^{22}$, $-OCHX^{22}_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, unsubstituted alkyl, unsubstituted heteroalkyl, unsubstituted cycloalkyl, unsubstituted heterocycloalkyl, unsubstituted aryl, or unsubstituted heteroaryl; and $X^{20}$, $X^{21}$, and $X^{22}$ are independently $-F$, $-Cl$, $-Br$, or $-I$.

Embodiment P7

The method of one of embodiments P1 to P3, wherein $R^1$ is -(unsubstituted $C_2$-$C_4$ alkylene)-C(O)O-(unsubstituted $C_1$-$C_3$ alkyl).

Embodiment P8

The method of one of embodiments P1 to P3, wherein $R^1$ is -(unsubstituted $C_2$-$C_4$ alkylene)-C(O)OCH$_3$.

Embodiment P9

The method of one of embodiments P1 to P3, wherein $R^1$ is $-CH_2CH(CH_3)C(O)OCH_3$.

Embodiment P10

The method of one of embodiments P1 to P3, wherein $R^1$ is unsubstituted $C_1$-$C_6$ alkyl.

Embodiment P11

The method of one of embodiments P1 to P3, wherein $R^1$ is unsubstituted $C_2$-$C_4$ alkyl.

Embodiment P12

The method of one of embodiments P1 to P3, wherein $R^1$ is unsubstituted isopropyl.

Embodiment P13

The method of one of embodiments P1 to P27, wherein $R^2$ is independently hydrogen, $-C(O)R^{2A}$, $-C(O)-OR^{2A}$, $-C(O)NR^{2A}R^{2B}$, $R^{23}$-substituted or unsubstituted alkyl, $R^{23}$-substituted or unsubstituted heteroalkyl, $R^{23}$-substituted or unsubstituted cycloalkyl, $R^{23}$-substituted or unsubstituted heterocycloalkyl, $R^{23}$-substituted or unsubstituted aryl, or $R^{23}$-substituted or unsubstituted heteroaryl; $R^{23}$ is independently oxo, halogen, $-CX^{23}_3$, $-CHX^{23}_2$, $-CH_2X^{23}$, $-OCX^{23}_3$, $-OCH_2X^{23}$, $-OCHX^{23}_2$, $-CN$, $-OH$, $-NH_2$, $-COOH$, $-CONH_2$, $-NO_2$, $-SH$, $-SO_3H$, $-SO_4H$, $-SO_2NH_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —COOR$^{24}$, —C(O)R$^{24}$, —CONHR$^{24}$, R$^{24}$-substituted or unsubstituted alkyl, R$^{24}$-substituted or unsubstituted heteroalkyl, R$^{24}$-substituted or unsubstituted cycloalkyl, R$^{24}$-substituted or unsubstituted heterocycloalkyl, R$^{24}$-substituted or unsubstituted aryl, or R$^{24}$-substituted or unsubstituted heteroaryl; R$^{24}$ is independently oxo,
halogen, —CX$^{24}_3$, —CHX$^{24}_2$, —CH$_2$X$^{24}$, —OCX$^{24}_3$, —OCH$_2$X$^{24}$, —OCHX$^{24}_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, R$^{25}$-substituted or unsubstituted alkyl, R$^{25}$-substituted or unsubstituted heteroalkyl, R$^{25}$-substituted or unsubstituted cycloalkyl, R$^{25}$-substituted or unsubstituted heterocycloalkyl, R$^{25}$-substituted or unsubstituted aryl, or R$^{25}$-substituted or unsubstituted heteroaryl; R$^{25}$ is independently oxo,
halogen, —CX$^{25}_3$, —CHX$^{25}_2$, —CH$_2$X$^{25}$, —OCX$^{25}_3$, —OCH$_2$X$^{25}$, —OCHX$^{25}_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, unsubstituted alkyl, unsubstituted heteroalkyl, unsubstituted cycloalkyl, unsubstituted heterocycloalkyl, unsubstituted aryl, or unsubstituted heteroaryl; R$^{2A}$ is independently
hydrogen, —CX$^{2A}_3$, —CHX$^{2A}_2$, —CH$_2$X$^{2A}$, —CN, —COOH, —CONH$_2$, R$^{23A}$-substituted or unsubstituted alkyl, R$^{23A}$-substituted or unsubstituted heteroalkyl, R$^{23A}$-substituted or unsubstituted cycloalkyl, R$^{23A}$-substituted or unsubstituted heterocycloalkyl, R$^{23A}$-substituted or unsubstituted aryl, or R$^{23A}$-substituted or unsubstituted heteroaryl; R$^{23A}$ is independently oxo,
halogen, —CX$^{23A}_3$, —CHX$^{23A}_2$, —CH$_2$X$^{23A}$, —OCX$^{23A}_3$, —OCH$_2$X$^{23A}$, —OCHX$^{23A}_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, R$^{24A}$-substituted or unsubstituted alkyl, R$^{24A}$-substituted or unsubstituted heteroalkyl, R$^{24A}$-substituted or unsubstituted cycloalkyl, R$^{24A}$-substituted or unsubstituted heterocycloalkyl, R$^{24A}$-substituted or unsubstituted aryl, or R$^{24A}$-substituted or unsubstituted heteroaryl; R$^{24A}$ is independently oxo, halogen, —CX$^{24A}_3$, —CHX$^{24A}_2$, —CH$_2$X$^{24A}$, —OCX$^{24A}_3$, —OCH$_2$X$^{24A}$, —OCHX$^{24A}_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, R$^{25A}$-substituted or unsubstituted alkyl, R$^{25A}$-substituted or unsubstituted heteroalkyl, R$^{25A}$-substituted or unsubstituted cycloalkyl, R$^{25A}$-substituted or unsubstituted heterocycloalkyl, R$^{25A}$-substituted or unsubstituted aryl, or R$^{25A}$-substituted or unsubstituted heteroaryl; R$^{25A}$ is independently oxo, halogen, —CX$^{25A}_3$, —CHX$^{25A}_2$, —CH$_2$X$^{25A}$, —OCX$^{25A}_3$, —OCH$_2$X$^{25A}$, —OCHX$^{25A}_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, unsubstituted alkyl, unsubstituted heteroalkyl, unsubstituted cycloalkyl, unsubstituted heterocycloalkyl, unsubstituted aryl, or unsubstituted heteroaryl; R$^{2B}$ is independently
hydrogen, —CX$^{2B}_3$, —CHX$^{2B}_2$, —CH$_2$X$^{2B}$, —CN, —COOH, —CONH$_2$, unsubstituted alkyl, unsubstituted heteroalkyl, unsubstituted cycloalkyl, unsubstituted heterocycloalkyl, unsubstituted aryl, or unsubstituted heteroaryl; and X$^{2A}$, X$^{2B}$, X$^{23}$, X$^{24}$, X$^{25}$, X$^{23A}$, X$^{24A}$, and X$^{25A}$ are independently —F, —Cl, —Br, or —I.

Embodiment P14

The method of one of embodiments P1 to P27, wherein R$^2$ is independently hydrogen, —C(O)R$^{2A}$, —C(O)OR$^{2A}$, —C(O) NR$^{2A}$R$^{2B}$, -(unsubstituted C$_1$-C$_4$ alkylene)-COOR$^{24}$, -(unsubstituted C$_1$-C$_4$ alkylene)-C(O)R$^{24}$, -(unsubstituted C$_1$-C$_4$ alkylene)-CONHR$^{24}$, R$^{23}$-substituted or unsubstituted C$_1$-C$_6$ alkyl, R$^{23}$-substituted or unsubstituted 2 to 6 membered heteroalkyl, R$^{23}$-substituted or unsubstituted C$_3$-C$_6$ cycloalkyl, R$^{23}$-substituted or unsubstituted 3 to 6 membered heterocycloalkyl, R$^{23}$-substituted or unsubstituted phenyl, or R$^{23}$-substituted or unsubstituted 5 to 6 membered heteroaryl; R$^{23}$ is independently oxo, halogen, —CX$^{23}_3$, —CHX$^{23}_2$, —CH$_2$X$^{23}$, —OCX$^{23}_3$, —OCH$_2$X$^{23}$, —OCHX$^{23}_2$, —CN, —OH, —NH$_2$, —COOH, —CONH$_2$, —NO$_2$, —SH, R$^{24}$-substituted or unsubstituted C$_1$-C$_6$ alkyl, R$^{24}$-substituted or unsubstituted 2 to 6 membered heteroalkyl, R$^{24}$-substituted or unsubstituted C$_3$-C$_6$ cycloalkyl, R$^{24}$-substituted or unsubstituted 3 to 6 membered heterocycloalkyl, R$^{24}$-substituted or unsubstituted phenyl, or R$^{24}$-substituted or unsubstituted 5 to 6 membered heteroaryl; R$^{24}$ is independently oxo,
halogen, —CX$^{24}_3$, —CHX$^{24}_2$, —CH$_2$X$^{24}$, —OCX$^{24}_3$, —OCH$_2$X$^{24}$, —OCHX$^{24}_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, R$^{25}$-substituted or unsubstituted C$_1$-C$_6$ alkyl, R$^{25}$-substituted or unsubstituted 2 to 6 membered heteroalkyl, R$^{25}$-substituted or unsubstituted C$_3$-C$_6$ cycloalkyl, R$^{25}$-substituted or unsubstituted 3 to 6 membered heterocycloalkyl, R$^{25}$-substituted or unsubstituted phenyl, or R$^{25}$-substituted or unsubstituted 5 to 6 membered heteroaryl; R$^{25}$ is independently oxo,
halogen, —CX$^{25}_3$, —CHX$^{25}_2$, —CH$_2$X$^{25}$, —OCX$^{25}_3$, —OCH$_2$X$^{25}$, —OCHX$^{25}_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, unsubstituted C$_1$-C$_6$ alkyl, unsubstituted 2 to 6 membered heteroalkyl, unsubstituted C$_3$-C$_6$ cycloalkyl, unsubstituted 3 to 6 membered heterocycloalkyl, unsubstituted phenyl, or unsubstituted 5 to 6 membered heteroaryl; R$^{2A}$ is independently hydrogen, —CX$^{2A}_3$, —CHX$^{2A}_2$, —CH$_2$X$^{2A}$, —CN, —COOH, —CONH$_2$, R$^{23A}$-substituted or unsubstituted C$_1$-C$_6$ alkyl, R$^{23A}$-substituted or unsubstituted 2 to 6 membered heteroalkyl, R$^{23A}$-substituted or unsubstituted C$_3$-C$_6$ cycloalkyl, R$^{23A}$-substituted or unsubstituted 3 to 6 membered heterocycloalkyl, R$^{23A}$-substituted or unsubstituted phenyl, or R$^{23A}$-substituted or unsubstituted 5 to 6 membered heteroaryl; R$^{23A}$ is independently oxo,
halogen, —CX$^{23A}_3$, —CHX$^{23A}_2$, —CH$_2$X$^{23A}$, —OCX$^{23A}_3$, —OCH$_2$X$^{23A}$, —OCHX$^{23A}_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, R$^{24A}$-substituted or unsubstituted C$_1$-C$_6$ alkyl, R$^{24A}$-substituted or unsubstituted 2 to 6 membered heteroalkyl, R$^{24A}$-substituted or unsubstituted C$_3$-C$_6$ cycloalkyl, R$^{24A}$-substituted or unsubstituted 3 to 6 membered heterocycloalkyl, $R^{24A}$-substituted or unsubstituted phenyl, or $R^{24A}$-substituted or unsubstituted 5 to 6 membered heteroaryl; $R^{24A}$ is independently oxo, halogen, $-CX^{24A}{}_3$, $-CHX^{24A}{}_2$, $-CH_2X^{24A}$, $-OCX^{24A}{}_3$, $-OCH_2X^{24A}$, $-OCHX^{24A}{}_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $R^{25A}$-substituted or unsubstituted $C_1$-$C_6$ alkyl, $R^{25A}$-substituted or unsubstituted 2 to 6 membered heteroalkyl, $R^{25A}$-substituted or unsubstituted $C_3$-$C_6$ cycloalkyl, $R^{25A}$-substituted or unsubstituted 3 to 6 membered heterocycloalkyl, $R^{25A}$-substituted or unsubstituted phenyl, or $R^{25A}$-substituted or unsubstituted 5 to 6 membered heteroaryl; $R^{25A}$ is independently oxo, halogen, $-CX^{25A}{}_3$, $-CHX^{25A}{}_2$, $-CH_2X^{25A}$, $-OCX^{25A}{}_3$, $-OCH_2X^{25A}$, $-OCHX^{25A}{}_2$, $-CN$, $-OH$, $-NH_2$, $-COOH$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, unsubstituted $C_1$-$C_6$ alkyl, unsubstituted 2 to 6 membered heteroalkyl, unsubstituted $C_3$-$C_6$ cycloalkyl, unsubstituted 3 to 6 membered heterocycloalkyl, unsubstituted phenyl, or unsubstituted 5 to 6 membered heteroaryl; $R^{2B}$ is independently hydrogen, $-CX^{2B}{}_3$, $-CHX^{2B}{}_2$, $-CH_2X^{2B}$, $-CN$, $-COOH$, $-CONH_2$, unsubstituted $C_1$-$C_6$ alkyl, unsubstituted 2 to 6 membered heteroalkyl, unsubstituted $C_3$-$C_6$ cycloalkyl, unsubstituted 3 to 6 membered heterocycloalkyl, unsubstituted phenyl, or unsubstituted 5 to 6 membered heteroaryl; and $X^{24}$, $X^{2B}$, $X^{23}$, $X^{24}$, $X^{25}$, $X^{23A}$, $X^{24A}$, and $X^{25A}$ are independently $-F$, $-Cl$, $-Br$, or $-I$.

Embodiment P15

The method of one of embodiments P1 to P27, wherein $R^2$ is independently hydrogen, $-C(O)$-(unsubstituted $C_1$-$C_3$ alkyl), or unsubstituted $C_1$-$C_3$ alkyl.

Embodiment P16

The method of one of embodiments P1 to P27, wherein $R^2$ is independently hydrogen.

Embodiment P17

The method of one of embodiments P1 to P27, wherein $R^2$ is independently $-C(O)CH_3$.

Embodiment P18

The method of one of embodiments P1 to P31, wherein $R^3$ is independently hydrogen, $-CX^3{}_3$, $-CHX^3{}_2$, $-CH_2X^3$, substituted or unsubstituted $C_1$-$C_6$ alkyl, or substituted or unsubstituted 2 to 8 membered heteroalkyl.

Embodiment P19

The method of one of embodiments P1 to P31, wherein $R^3$ is independently hydrogen, $R^{26}$-substituted or unsubstituted alkyl, or $R^{26}$-substituted or unsubstituted heteroalkyl; $R^{26}$ is independently oxo, halogen, $-CX^{26}{}_3$, $-CHX^{26}{}_2$, $-CH_2X^{26}$, $-OCX^{26}{}_3$, $-OCH_2X^{26}$, $-OCHX^{26}{}_2$, $-CN$, $-OH$, $-NH_2$, $-COOH$, $-CONH_2$, $-NO_2$, $-SH$, $R^{27}$-substituted or unsubstituted $C_1$-$C_6$ alkyl, $R^{27}$-substituted or unsubstituted 2 to 6 membered heteroalkyl, $R^{27}$-substituted or unsubstituted $C_3$-$C_6$ cycloalkyl, $R^{27}$-substituted or unsubstituted 3 to 6 membered heterocycloalkyl, $R^{27}$-substituted or unsubstituted phenyl, or $R^{27}$-substituted or unsubstituted 5 to 6 membered heteroaryl; $R^{27}$ is independently oxo, halogen, $-CX^{27}{}_3$, $-CHX^{27}{}_2$, $-CH_2X^{27}$, $-OCX^{27}{}_3$, $-OCH_2X^{27}$, $-OCHX^{27}{}_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC=(O)$ $NH_2$, $-NHSO_2H$, $-NHC=(O)H$, $-NHC(O)-OH$, $-NHOH$, $R^{28}$-substituted or unsubstituted $C_1$-$C_6$ alkyl, $R^{28}$-substituted or unsubstituted 2 to 6 membered heteroalkyl, $R^{28}$-substituted or unsubstituted $C_3$-$C_6$ cycloalkyl, $R^{28}$-substituted or unsubstituted 3 to 6 membered heterocycloalkyl, $R^{28}$-substituted or unsubstituted phenyl, or $R^{28}$-substituted or unsubstituted 5 to 6 membered heteroaryl; $R^{28}$ is independently oxo, halogen, $-CX^{28}{}_3$, $-CHX^{28}{}_2$, $-CH_2X^{28}$, $-OCX^{28}{}_3$, $-OCH_2X^{28}$, $-OCHX^{28}{}_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-NHC(O)NHNH_2$, $-NHC=(O)NH_2$, $-NHSO_2H$, $-NHC=(O)H$, $-NHC(O)-OH$, $-NHOH$, unsubstituted $C_1$-$C_6$ alkyl, unsubstituted 2 to 6 membered heteroalkyl, unsubstituted $C_3$-$C_6$ cycloalkyl, unsubstituted 3 to 6 membered heterocycloalkyl, unsubstituted phenyl, or unsubstituted 5 to 6 membered heteroaryl; and $X^{26}$, $X^{27}$, and $X^{28}$ are independently $-F$, $-Cl$, $-Br$, or $-I$.

Embodiment P20

The method of one of embodiments P1 to P31, wherein $R^3$ is independently hydrogen or $-CH_2CH_2N$(unsubstituted $C_1$-$C_3$ alkyl)$_2$.

Embodiment P21

The method of one of embodiments P1 to P31, wherein $R^3$ is hydrogen.

Embodiment P22

The method of one of embodiments P1 to P31, wherein $R^3$ is $-CH_2CH_2N(CH_3)_2$.

Embodiment P23

A compound having the formula:

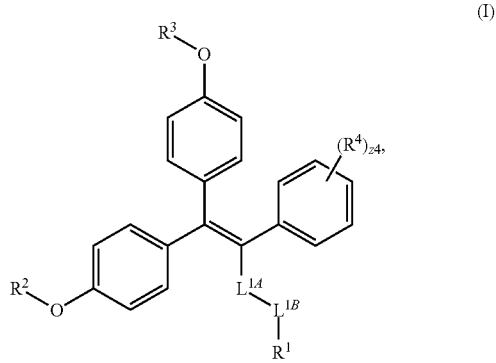

(I)

wherein,
$L^{1A}$ is substituted or unsubstituted $C_1$-$C_6$ alkylene; $L^{1B}$ is $-C(O)O-$; $R^1$ is substituted or unsubstituted $C_1$-$C_6$ alkyl; $R^2$ is independently hydrogen, $-CX^2{}_3$, $-CHX^2{}_2$, —$CH_2X^2$, —$C(O)R^{2A}$, —$C(O)OR^{2A}$, —$C(O)NR^{2A}R^{2B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^3$ is independently hydrogen, —$CX^3_3$, —$CHX^3_2$, —$CH_2X^3$, —$C(O)R^{3A}$, —$C(O)OR^{3A}$, —$C(O)NR^{3A}R^{3B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^4$ is independently halogen, —$CX^4_3$, —$CHX^4_2$, —$CH_2X^4$, —$OCX^4_3$, —$OCH_2X^4$, —$OCHX^4_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC$=(O)$NHNH_2$, —$NHC$=(O)$NH_2$, —$NHSO_2H$, —$NHC$=(O)H, —NHC(O)—OH, —NHOH, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; z4 is an integer from 0 to 5; each $R^{2A}$, $R^{2B}$, $R^{3A}$, $R^{3B}$ is independently hydrogen, —$CX_3$, —CN, —COOH, —$CONH_2$, —$CHX_2$, —$CH_2X$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{2A}$ and $R^{2B}$ substituents bonded to the same nitrogen atom may optionally be joined to form a substituted or unsubstituted heterocycloalkyl or substituted or unsubstituted heteroaryl; $R^{3A}$ and $R^{3B}$ substituents bonded to the same nitrogen atom may optionally be joined to form a substituted or unsubstituted heterocycloalkyl or substituted or unsubstituted heteroaryl; and each X, $X^2$, $X^3$, and $X^4$ is independently —F, —Cl, —Br, or —I.

Embodiment P24

The compound of embodiment P23 having the formula:

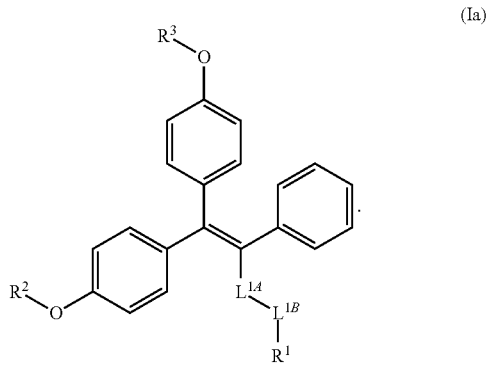

(Ia)

Embodiment P25

The compound of one of embodiments P23 to P24, wherein $L^{1A}$ is unsubstituted $C_2$-$C_4$ alkylene; $L^{1B}$ is —C(O)O—; and $R^1$ is unsubstituted $C_1$-$C_3$ alkyl.

Embodiment P26

The compound of one of embodiments P23 to P24, wherein $L^{1A}$ is unsubstituted $C_2$-$C_4$ alkylene; $L^{1B}$ is —C(O)O—; and $R^1$ is —$CH_3$.

Embodiment P27

The compound of one of embodiments P23 to P24, wherein $L^{1A}$ is —$CH_2CH(CH_3)$—; $L^{1B}$ is —C(O)O—; and $R^1$ is —$CH_3$.

Embodiment P28

The compound of one of embodiments P23 to P27, wherein $R^2$ is independently hydrogen, —C(O)-(unsubstituted $C_1$-$C_3$ alkyl), or $R^{23}$-substituted or unsubstituted $C_1$-$C_6$ alkyl; $R^{23}$ is independently oxo, halogen, —$CX^{23}_3$, —$CHX^{23}_2$, —$CH_2X^{23}$, —$OCX^{23}_3$, —$OCH_2X^{23}$, —$OCHX^{23}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC$=(O)$NHNH_2$, —$NHC$=(O)$NH_2$, —$NHSO_2H$, —$NHC$=(O)H, —NHC(O)—OH, —NHOH, unsubstituted $C_1$-$C_6$ alkyl, unsubstituted 2 to 6 membered heteroalkyl, unsubstituted $C_3$-$C_6$ cycloalkyl, unsubstituted 3 to 6 membered heterocycloalkyl, unsubstituted phenyl, or unsubstituted 5 to 6 membered heteroaryl; and $X^{23}$ is independently —F, —Cl, —Br, or —I.

Embodiment P29

The compound of one of embodiments P23 to P27, wherein $R^2$ is independently hydrogen, —C(O)-(unsubstituted $C_1$-$C_3$ alkyl), or unsubstituted $C_1$-$C_3$ alkyl.

Embodiment P30

The compound of one of embodiments P23 to P27, wherein $R^2$ is independently hydrogen.

Embodiment P31

The compound of one of embodiments P23 to P27, wherein $R^2$ is independently —$C(O)CH_3$.

Embodiment P32

The compound of one of embodiments P23 to P31, $R^3$ is independently hydrogen, substituted or unsubstituted $C_1$-$C_6$ alkyl, or substituted or unsubstituted 2 to 8 membered heteroalkyl.

Embodiment P33

The compound of one of embodiments P23 to P31, $R^3$ is independently hydrogen, $R^{26}$-substituted or unsubstituted alkyl, or $R^{26}$-substituted or unsubstituted heteroalkyl; $R^{26}$ is independently oxo, halogen, —$CX^{26}_3$, —$CHX^{26}_2$, —$CH_2X^{26}$, —$OCX^{26}_3$, —$OCH_2X^{26}$, —$OCHX^{26}_2$, —CN, —OH, —$NH_2$, —COOH, —$CONH_2$, —$NO_2$, —SH, unsubstituted $C_1$-$C_6$ alkyl, unsubstituted 2 to 6 membered heteroalkyl, unsubstituted $C_3$-$C_6$ cycloalkyl, unsubstituted 3 to 6 membered heterocycloalkyl, unsubstituted phenyl, or unsubstituted 5 to 6 membered heteroaryl; and $X^{26}$ is independently —F, —Cl, —Br, or —I.

Embodiment P34

The compound of one of embodiments P23 to P31, $R^3$ is independently hydrogen or —$CH_2CH_2N$(unsubstituted $C_1$-$C_3$ alkyl)$_2$.

Embodiment P35

The compound of one of embodiments P23 to P31, $R^3$ is hydrogen.

Embodiment P36

The compound of one of embodiments P23 to P31, $R^3$ is —CH$_2$CH$_2$N(CH$_3$)$_2$.

Embodiment P37

A pharmaceutical composition comprising the compound of any one of embodiments P23 to P36 and a pharmaceutically acceptable excipient.

Embodiment P38

A method of inhibiting estrogen-related receptor β activity, said method comprising contacting the estrogen-related receptor β with the compound of one of embodiments P23 to P36.

Embodiment P39

The method of embodiment P38, wherein the compound inhibits estrogen-related receptor β at least 2-fold more potently than the compound inhibits estrogen-related receptor α.

Embodiment P40

The method of embodiment P38, wherein the compound inhibits estrogen-related receptor β at least 5-fold more potently than the compound inhibits estrogen-related receptor α.

Embodiment P41

The method of embodiment P38, wherein the compound inhibits estrogen-related receptor β at least 10-fold more potently than the compound inhibits estrogen-related receptor α.

Embodiment P42

The method of embodiment P38, wherein the compound inhibits estrogen-related receptor β at least 100-fold more potently than the compound inhibits estrogen-related receptor α.

Embodiment P43

The method of one of embodiments P38 to P42, wherein the compound inhibits estrogen-related receptor β at least 2-fold more potently than the compound inhibits estrogen-related receptor γ.

Embodiment P44

The method of one of embodiments P38 to P42, wherein the compound inhibits estrogen-related receptor β at least 5-fold more potently than the compound inhibits estrogen-related receptor γ.

Embodiment P45

The method of one of embodiments P38 to P42, wherein the compound inhibits estrogen-related receptor β at least 10-fold more potently than the compound inhibits estrogen-related receptor γ.

Embodiment P46

The method of one of embodiments P38 to P42, wherein the compound inhibits estrogen-related receptor β at least 20-fold more potently than the compound inhibits estrogen-related receptor γ.

VII. Additional Embodiments

Embodiment 1

A method of treating non-alcoholic fatty liver disease, said method comprising administering to a subject in need thereof an effective amount of a compound having the formula:

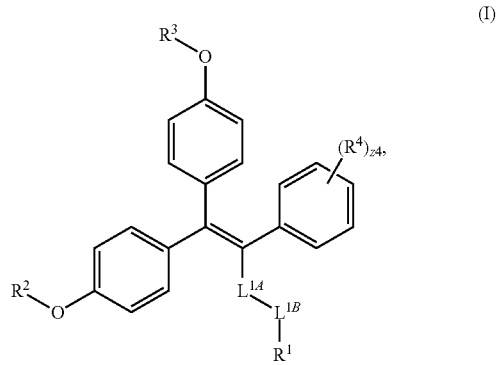

wherein, $L^{1A}$ is a bond, substituted or unsubstituted alkylene, or substituted or unsubstituted heteroalkylene; $L^{1B}$ is a bond, —C(O)O—, —OC(O)—, —O—, —C(O)—, —NH—, —NHC(O)—, or —C(O)NH—; $R^1$ is independently hydrogen, halogen, —CX$^1_3$, —CHX$^1_2$, —CH$_2$X$^1$, —OCX$^1_3$, —OCH$_2$X$^1$, —OCHX$^1_2$, —CN, —SO$_{n1}$R$^{1D}$, —SO$_{v1}$NR$^{1A}$R$^{1B}$, —NHC(O)NR$^{1A}$R$^{1B}$, —N(O)$_{m1}$, —NR$^{1A}$R$^{1B}$, —C(O)R$^{1C}$, —C(O)—OR$^{1C}$, —C(O)NR$^{1A}$R$^{1B}$, —OR$^{1D}$, —NR$^{1A}$SO$_2$R$^{1D}$, —NR$^{1A}$C(O)R$^{1C}$(O)OR$^{1C}$, —NR$^{1A}$ OR$^{1C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^2$ is independently hydrogen, —CX$^2_3$, —CHX$^2_2$, —CH$_2$X$^2$, —C(O)R$^{2A}$, —C(O)OR$^{2A}$, —C(O)NR$^{2A}$R$^{2B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^3$ is independently hydrogen, —CX$^3_3$, —CHX$^3_2$, —CH$_2$X$^3$, —C(O)R$^{3A}$, —C(O)OR$^{3A}$, —C(O)NR$^{3A}$R$^{3B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^4$ is independently halogen, —CX$^4_3$, —CHX$^4_2$, —CH$_2$X$^4$, —OCX$^4_3$, —OCH$_2$X$^4$, —OCHX$^4_2$, —CN, —OH, —NH$_2$, —COOH, —CONH$_2$, —NO₂, —SH, —SO₃H, —SO₄H, —SO₂NH₂, —NHNH₂, —ONH₂, —NHC=(O)NHNH₂, —NHC=(O)NH₂, —NHSO₂H, —NHC=(O)H, —NHC(O)—OH, —NHOH, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; z4 is an integer from 0 to 5; each $R^{1A}$, $R^{1B}$, $R^{1C}$, $R^{1D}$, $R^{2A}$, $R^{2B}$, $R^{3A}$, and $R^{3B}$ is independently hydrogen, —CX₃, —CN, —COOH, —CONH₂, —CHX₂, —CH₂X, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{1A}$ and $R^{1B}$ substituents bonded to the same nitrogen atom may optionally be joined to form a substituted or unsubstituted heterocycloalkyl or substituted or unsubstituted heteroaryl; $R^{2A}$ and $R^{2B}$ substituents bonded to the same nitrogen atom may optionally be joined to form a substituted or unsubstituted heterocycloalkyl or substituted or unsubstituted heteroaryl; $R^{3A}$ and $R^{3B}$ substituents bonded to the same nitrogen atom may optionally be joined to form a substituted or unsubstituted heterocycloalkyl or substituted or unsubstituted heteroaryl; each X, $X^1$, $X^2$, $X^3$, and $X^4$ is independently —F, —Cl, —Br, or —I; n1 is an integer from 0 to 4; and m1 and v1 are independently an integer from 1 to 2.

Embodiment 2

A method of treating non-alcoholic steatohepatitis, said method comprising administering to a subject in need thereof an effective amount of a compound having the formula:

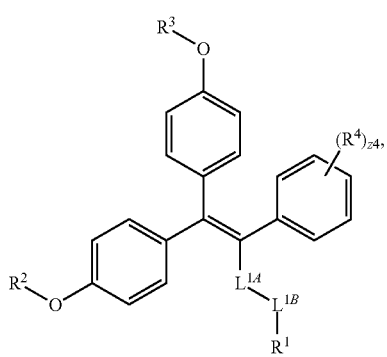

(I)

wherein, $L^{1A}$ is a bond, substituted or unsubstituted alkylene, or substituted or unsubstituted heteroalkylene; $L^{1B}$ is a bond, —C(O)O—, —OC(O)—, —O—, —C(O)—, —NH—, —NHC(O)—, or —C(O)NH—; $R^1$ is independently hydrogen, halogen, —CX¹₃, —CHX¹₂, —CH₂X¹, —OCX¹₃, —OCH₂X¹, —OCHX¹₂, —CN, —SO$_{n1}$R$^{1D}$, —SO$_{v1}$NR$^{1A}$R$^{1B}$, —NHC(O)NR$^{1A}$R$^{1B}$, —N(O)$_{m1}$, —C(O)R$^{1C}$, —C(O)—OR$^{1C}$, —C(O)NR$^{1A}$R$^{1B}$, —OR$^{1D}$, —NR$^{1A}$SO₂R$^{1D}$, —NR$^{1A}$C(O)R$^{1C}$, —NR$^{1A}$C(O)OR$^{1C}$, —NR$^{1A}$OR$^{1C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^2$ is independently hydrogen, —CX²₃, —CHX²₂, —CH₂X², —C(O)R$^{2A}$, —C(O)OR$^{2A}$, —C(O)NR$^{2A}$R$^{2B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^3$ is independently hydrogen, —CX³₃, —CHX³₂, —CH₂X³, —C(O)R$^{3A}$, —C(O)OR$^{3A}$, —C(O)NR$^{3A}$R$^{3B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^4$ is independently halogen, —CX⁴₃, —CHX⁴₂, —CH₂X⁴, —OCX⁴₃, —OCH₂X⁴, —OCHX⁴₂, —CN, —OH, —NH₂, —COOH, —CONH₂, —NO₂, —SH, —SO₃H, —SO₄H, —SO₂NH₂, —NHNH₂, —ONH₂, —NHC=(O)NHNH₂, —NHC=(O)NH₂, —NHSO₂H, —NHC=(O)H, —NHC(O)—OH, —NHOH, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; z4 is an integer from 0 to 5; each $R^{1A}$, $R^{1B}$, $R^{1C}$, $R^{1D}$, $R^{2A}$, $R^{2B}$, $R^{3A}$, and $R^{3B}$ is independently hydrogen, —CX₃, —CN, —COOH, —CONH₂, —CHX₂, —CH₂X, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{1A}$ and $R^{1B}$ substituents bonded to the same nitrogen atom may optionally be joined to form a substituted or unsubstituted heterocycloalkyl or substituted or unsubstituted heteroaryl; $R^{2A}$ and $R^{2B}$ substituents bonded to the same nitrogen atom may optionally be joined to form a substituted or unsubstituted heterocycloalkyl or substituted or unsubstituted heteroaryl; $R^{3A}$ and $R^{3B}$ substituents bonded to the same nitrogen atom may optionally be joined to form a substituted or unsubstituted heterocycloalkyl or substituted or unsubstituted heteroaryl; each X, $X^1$, $X^2$, $X^3$, and $X^4$ is independently —F, —Cl, —Br, or —I; n1 is an integer from 0 to 4; and m1 and v1 are independently an integer from 1 to 2.

Embodiment 3

The method of one of embodiments 1 to 2, wherein the compound has the formula:

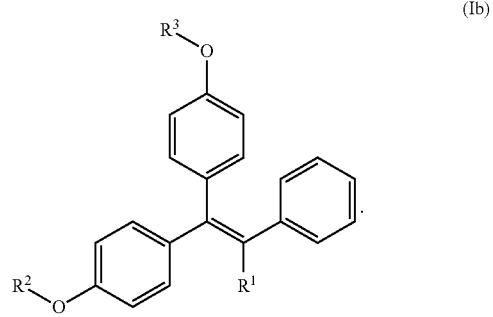

(Ib)

Embodiment 4

The method of one of embodiments 1 to 3, wherein $R^1$ is substituted or unsubstituted alkyl or substituted or unsubstituted heteroalkyl.

Embodiment 5

The method of one of embodiments 1 to 3, wherein $R^1$ is substituted or unsubstituted $C_1$-$C_6$ alkyl or substituted or unsubstituted 2 to 6 heteroalkyl.

Embodiment 6

The method of one of embodiments 1 to 3, wherein $R^1$ is $R^{20}$-substituted or unsubstituted $C_1$-$C_6$ alkyl or $R^{20}$-substituted or unsubstituted 2 to 6 heteroalkyl; $R^{20}$ is independently oxo, halogen, —$CX^{20}_3$, —$CHX^{20}_2$, —$CH_2X^{20}$, —$OCX^{20}_3$, —$OCH_2X^{20}$, —$OCHX^{20}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)NHNH_2$, —NHC=(O)NH_2$, —$NHSO_2H$, —NHC=(O)H, —NHC(O)—OH, —NHOH, $R^{21}$-substituted or unsubstituted alkyl, $R^{21}$-substituted or unsubstituted heteroalkyl, $R^{21}$-substituted or unsubstituted cycloalkyl, $R^{21}$-substituted or unsubstituted heterocycloalkyl, $R^{21}$-substituted or unsubstituted aryl, or $R^{21}$-substituted or unsubstituted heteroaryl; $R^{21}$ is independently oxo,
halogen, —$CX^{21}_3$, —$CHX^{21}_2$, —$CH_2X^{21}$, —$OCX^{21}_3$, —$OCH_2X^{21}$, —$OCHX^{21}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)NHNH_2$, —NHC=(O)NH_2$, —$NHSO_2H$, —NHC=(O)H, —NHC(O)—OH, —NHOH, $R^{22}$-substituted or unsubstituted alkyl, $R^{22}$-substituted or unsubstituted heteroalkyl, $R^{22}$-substituted or unsubstituted cycloalkyl, $R^{22}$-substituted or unsubstituted heterocycloalkyl, $R^{22}$-substituted or unsubstituted aryl, or $R^{22}$-substituted or unsubstituted heteroaryl; $R^{22}$ is independently oxo,
halogen, —$CX^{22}_3$, —$CHX^{22}_2$, —$CH_2X^{22}$, —$OCX^{22}_3$, —$OCH_2X^{22}$, —$OCHX^{22}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)NHNH_2$, —NHC=(O)NH_2$, —$NHSO_2H$, —NHC=(O)H, —NHC(O)—OH, —NHOH, unsubstituted alkyl, unsubstituted heteroalkyl, unsubstituted cycloalkyl, unsubstituted heterocycloalkyl, unsubstituted aryl, or unsubstituted heteroaryl; and $X^{20}$, $X^{21}$, and $X^{22}$ are independently —F, —Cl, —Br, or —I.

Embodiment 7

The method of one of embodiments 1 to 3, wherein $R^1$ is -(unsubstituted $C_2$-$C_4$ alkylene)-C(O)O-(unsubstituted $C_1$-$C_3$ alkyl).

Embodiment 8

The method of one of embodiments 1 to 3, wherein $R^1$ is -(unsubstituted $C_2$-$C_4$ alkylene)-C(O)OCH_3$.

Embodiment 9

The method of one of embodiments 1 to 3, wherein $R^1$ is —$CH_2CH(CH_3)C(O)OCH_3$.

Embodiment 10

The method of one of embodiments 1 to 3, wherein $R^1$ is unsubstituted $C_1$-$C_6$ alkyl.

Embodiment 11

The method of one of embodiments 1 to 3, wherein $R^1$ is unsubstituted $C_2$-$C_4$ alkyl.

Embodiment 12

The method of one of embodiments 1 to 3, wherein $R^1$ is unsubstituted isopropyl.

Embodiment 13

The method of one of embodiments 1 to 12, wherein $R^2$ is independently hydrogen, —C(O)$R^{2A}$, —C(O)—O$R^{2A}$, —C(O)NR$^{2A}R^{2B}$, $R^{23}$-substituted or unsubstituted alkyl, $R^{23}$-substituted or unsubstituted heteroalkyl, $R^{23}$-substituted or unsubstituted cycloalkyl, $R^{23}$-substituted or unsubstituted heterocycloalkyl, $R^{23}$-substituted or unsubstituted aryl, or $R^{23}$-substituted or unsubstituted heteroaryl; $R^{23}$ is independently oxo,
halogen, —$CX^{23}_3$, —$CHX^{23}_2$, —$CH_2X^{23}$, —$OCX^{23}_3$, —$OCH_2X^{23}$, —$OCHX^{23}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)NHNH_2$, —NHC=(O)NH_2$, —$NHSO_2H$, —NHC=(O)H, —NHC(O)—OH, —NHOH, —COOR$^{24}$, —C(O)R$^{24}$, —CONHR$^{24}$, $R^{24}$-substituted or unsubstituted alkyl, $R^{24}$-substituted or unsubstituted heteroalkyl, $R^{24}$-substituted or unsubstituted cycloalkyl, $R^{24}$-substituted or unsubstituted heterocycloalkyl, $R^{24}$-substituted or unsubstituted aryl, or $R^{24}$-substituted or unsubstituted heteroaryl; $R^{24}$ is independently oxo,
halogen, —$CX^{24}_3$, —$CHX^{24}_2$, —$CH_2X^{24}$, —$OCX^{24}_3$, —$OCH_2X^{24}$, —$OCHX^{24}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)NHNH_2$, —NHC=(O)NH_2$, —$NHSO_2H$, —NHC=(O)H, —NHC(O)—OH, —NHOH, $R^{25}$-substituted or unsubstituted alkyl, $R^{25}$-substituted or unsubstituted heteroalkyl, $R^{25}$-substituted or unsubstituted cycloalkyl, $R^{25}$-substituted or unsubstituted heterocycloalkyl, $R^{25}$-substituted or unsubstituted aryl, or $R^{25}$-substituted or unsubstituted heteroaryl; $R^{25}$ is independently oxo,
halogen, —$CX^{25}_3$, —$CHX^{25}_2$, —$CH_2X^{25}$, —$OCX^{25}_3$, —$OCH_2X^{25}$, —$OCHX^{25}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)NHNH_2$, —NHC=(O)NH_2$, —$NHSO_2H$, —NHC=(O)H, —NHC(O)—OH, —NHOH, unsubstituted alkyl, unsubstituted heteroalkyl, unsubstituted cycloalkyl, unsubstituted heterocycloalkyl, unsubstituted aryl, or unsubstituted heteroaryl; $R^{2A}$ is independently
hydrogen, —$CX^{2A}_3$, —$CHX^{2A}_2$, —$CH_2X^{2A}$, —CN, —COOH, —$CONH_2$, $R^{23A}$-substituted or unsubstituted alkyl, $R^{23A}$-substituted or unsubstituted heteroalkyl, $R^{23A}$-substituted or unsubstituted cycloalkyl, $R^{23A}$-substituted or unsubstituted heterocycloalkyl, $R^{23A}$-substituted or unsubstituted aryl, or $R^{23A}$-substituted or unsubstituted heteroaryl; $R^{23A}$ is independently oxo,
halogen, —$CX^{23A}_3$, —$CHX^{23A}_2$, —$CH_2X^{23A}$, —$OCX^{23A}_3$, —$OCH_2X^{23A}$, —$OCHX^{23A}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)NHNH_2$, —NHC=(O)NH_2$, —$NHSO_2H$, —NHC=(O)H, —NHC(O)—OH, —NHOH, $R^{24A}$-substituted or unsubstituted alkyl, $R^{24A}$-substituted or unsubstituted heteroalkyl, $R^{24A}$-substituted or unsubstituted cycloalkyl, $R^{24A}$-substituted or unsubstituted heterocycloalkyl, $R^{24A}$-substituted or unsubstituted aryl, or $R^{24A}$-substituted or unsubstituted heteroaryl; $R^{24A}$ is independently oxo, halogen, $-CX^{24A}_3$, $-CHX^{24A}_2$, $-CH_2X^{24A}$, $-OCX^{24A}_3$, $-OCH_2X^{24A}$, $-OCHX^{24A}_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $R^{25A}$-substituted or unsubstituted alkyl, $R^{25A}$-substituted or unsubstituted heteroalkyl, $R^{25A}$-substituted or unsubstituted cycloalkyl, $R^{25A}$-substituted or unsubstituted heterocycloalkyl, $R^{25A}$-substituted or unsubstituted aryl, or $R^{25A}$-substituted or unsubstituted heteroaryl; $R^{25A}$ is independently oxo, halogen, $-CX^{25A}_3$, $-CHX^{25A}_2$, $-CH_2X^{25A}$, $-OCX^{25A}_3$, $-OCH_2X^{25A}$, $-OCHX^{25A}_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, unsubstituted alkyl, unsubstituted heteroalkyl, unsubstituted cycloalkyl, unsubstituted heterocycloalkyl, unsubstituted aryl, or unsubstituted heteroaryl; $R^{2B}$ is independently hydrogen, $-CX^{2B}_3$, $-CHX^{2B}_2$, $-CH_2X^{2B}$, $-CN$, $-COOH$, $-CONH_2$, unsubstituted alkyl, unsubstituted heteroalkyl, unsubstituted cycloalkyl, unsubstituted heterocycloalkyl, unsubstituted aryl, or unsubstituted heteroaryl; and $X^{2A}$, $X^{2B}$, $X^{23}$, $X^{24}$, $X^{25}$, $X^{23A}$, $X^{24A}$, and $X^{25A}$ are independently $-F$, $-Cl$, $-Br$, or $-I$.

Embodiment 14

The method of one of embodiments 1 to 12, wherein $R^2$ is independently hydrogen, $-C(O)R^{2A}$, $-C(O)OR^{2A}$, $-C(O)NR^{2A}R^{2B}$, -(unsubstituted $C_1$-$C_4$ alkylene)-$COOR^{24}$, -(unsubstituted $C_1$-$C_4$ alkylene)-$C(O)R^{24}$, -(unsubstituted $C_1$-$C_4$ alkylene)-$CONHR^{24}$, $R^{23}$-substituted or unsubstituted $C_1$-$C_6$ alkyl, $R^{23}$-substituted or unsubstituted 2 to 6 membered heteroalkyl, $R^{23}$-substituted or unsubstituted $C_3$-$C_6$ cycloalkyl, $R^{23}$-substituted or unsubstituted 3 to 6 membered heterocycloalkyl, $R^{23}$-substituted or unsubstituted phenyl, or $R^{23}$-substituted or unsubstituted 5 to 6 membered heteroaryl; $R^{23}$ is independently oxo, halogen, $-CX^{23}_3$, $-CHX^{23}_2$, $-CH_2X^{23}$, $-OCX^{23}_3$, $-OCH_2X^{23}$, $-OCHX^{23}_2$, $-CN$, $-OH$, $-NH_2$, $-COOH$, $-CONH_2$, $-NO_2$, $-SH$, $R^{24}$-substituted or unsubstituted $C_1$-$C_6$ alkyl, $R^{24}$-substituted or unsubstituted 2 to 6 membered heteroalkyl, $R^{24}$-substituted or unsubstituted $C_3$-$C_6$ cycloalkyl, $R^{24}$-substituted or unsubstituted 3 to 6 membered heterocycloalkyl, $R^{24}$-substituted or unsubstituted phenyl, or $R^{24}$-substituted or unsubstituted 5 to 6 membered heteroaryl; $R^{24}$ is independently oxo, halogen, $-CX^{24}_3$, $-CHX^{24}_2$, $-CH_2X^{24}$, $-OCX^{24}_3$, $-OCH_2X^{24}$, $-OCHX^{24}_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $R^{25}$-substituted or unsubstituted $C_1$-$C_6$ alkyl, $R^{25}$-substituted or unsubstituted 2 to 6 membered heteroalkyl, $R^{25}$-substituted or unsubstituted $C_3$-$C_6$ cycloalkyl, $R^{25}$-substituted or unsubstituted 3 to 6 membered heterocycloalkyl, $R^{25}$-substituted or unsubstituted phenyl, or $R^{25}$-substituted or unsubstituted 5 to 6 membered heteroaryl; $R^{25}$ is independently oxo, halogen, $-CX^{25}_3$, $-CHX^{25}_2$, $-CH_2X^{25}$, $-OCX^{25}_3$, $-OCH_2X^{25}$, $-OCHX^{25}_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, unsubstituted $C_1$-$C_6$ alkyl, unsubstituted 2 to 6 membered heteroalkyl, unsubstituted $C_3$-$C_6$ cycloalkyl, unsubstituted 3 to 6 membered heterocycloalkyl, unsubstituted phenyl, or unsubstituted 5 to 6 membered heteroaryl; $R^{2A}$ is independently hydrogen, $-CX^{2A}_3$, $-CHX^{2A}_2$, $-CH_2X^{2A}$, $-CN$, $-COOH$, $-CONH_2$, $R^{23A}$-substituted or unsubstituted $C_1$-$C_6$ alkyl, $R^{23A}$-substituted or unsubstituted 2 to 6 membered heteroalkyl, $R^{23A}$-substituted or unsubstituted $-C_3$-$C_6$ cycloalkyl, $R^{23A}$-substituted or unsubstituted 3 to 6 membered heterocycloalkyl, $R^{23A}$-substituted or unsubstituted phenyl, or $R^{23A}$-substituted or unsubstituted 5 to 6 membered heteroaryl; $R^{23A}$ is independently oxo, halogen, $-CX^{23A}_3$, $-CHX^{23A}_2$, $-CH_2X^{23A}$, $-OCX^{23A}_3$, $-OCH_2X^{23A}$, $-OCHX^{23A}_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $R^{24A}$-substituted or unsubstituted $C_1$-$C_6$ alkyl, $R^{24A}$-substituted or unsubstituted 2 to 6 membered heteroalkyl, $R^{24A}$-substituted or unsubstituted $C_3$-$C_6$ cycloalkyl, $R^{24A}$-substituted or unsubstituted 3 to 6 membered heterocycloalkyl, $R^{24A}$-substituted or unsubstituted phenyl, or $R^{24A}$-substituted or unsubstituted 5 to 6 membered heteroaryl; $R^{24A}$ is independently oxo, halogen, $-CX^{24A}_3$, $-CHX^{24A}_2$, $-CH_2X^{24A}$, $-OCX^{24A}_3$, $-OCH_2X^{24A}$, $-OCHX^{24A}_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $R^{25A}$-substituted or unsubstituted $C_1$-$C_6$ alkyl, $R^{25A}$-substituted or unsubstituted 2 to 6 membered heteroalkyl, $R^{25A}$-substituted or unsubstituted $C_3$-$C_6$ cycloalkyl, $R^{25A}$-substituted or unsubstituted 3 to 6 membered heterocycloalkyl, $R^{25A}$-substituted or unsubstituted phenyl, or $R^{25A}$-substituted or unsubstituted 5 to 6 membered heteroaryl; $R^{25A}$ is independently oxo, halogen, $-CX^{25A}_3$, $-CHX^{25A}_2$, $-CH_2X^{25A}$, $-OCX^{25A}_3$, $-OCH_2X^{25A}$, $-OCHX^{25A}_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, unsubstituted $C_1$-$C_6$ alkyl, unsubstituted 2 to 6 membered heteroalkyl, unsubstituted $C_3$-$C_6$ cycloalkyl, unsubstituted 3 to 6 membered heterocycloalkyl, unsubstituted phenyl, or unsubstituted 5 to 6 membered heteroaryl; $R^{2B}$ is independently hydrogen, $-CX^{2B}_3$, $-CHX^{2B}_2$, $-CH_2X^{2B}$, $-CN$, $-COOH$, $-CONH_2$, unsubstituted $C_1$-$C_6$ alkyl, unsubstituted 2 to 6 membered heteroalkyl, unsubstituted $C_3$-$C_6$ cycloalkyl, unsubstituted 3 to 6 membered heterocycloalkyl, unsubstituted phenyl, or unsubstituted 5 to 6 membered heteroaryl; and $X^{2A}$, $X^{2B}$, $X^{23}$, $X^{24}$, $X^{25}$, $X^{23A}$, $X^{24A}$, and $X^{25A}$ are independently $-F$, $-Cl$, $-Br$, or $-I$.

Embodiment 15

The method of one of embodiments 1 to 12, wherein $R^2$ is independently hydrogen, $-C(O)$-(unsubstituted $C_1$-$C_3$ alkyl), or unsubstituted $C_1$-$C_3$ alkyl.

Embodiment 16

The method of one of embodiments 1 to 12, wherein $R^2$ is independently hydrogen.

Embodiment 17

The method of one of embodiments 1 to 12, wherein $R^2$ is independently —C(O)CH$_3$.

Embodiment 18

The method of one of embodiments 1 to 17, wherein $R^3$ is independently hydrogen, —CX$^3_3$, —CHX$^3_2$, —CH$_2$X$^3$, substituted or unsubstituted C$_1$-C$_6$ alkyl, or substituted or unsubstituted 2 to 8 membered heteroalkyl.

Embodiment 19

The method of one of embodiments 1 to 17, wherein $R^3$ is independently hydrogen, $R^{26}$-substituted or unsubstituted alkyl, or $R^{26}$-substituted or unsubstituted heteroalkyl; $R^{26}$ is independently oxo, halogen, —CX$^{26}_3$, —CHX$^{26}_2$, —CH$_2$X$^{26}$, —OCX$^{26}_3$, —OCH$_2$X$^{26}$, —OCHX$^{26}_2$, —CN, —OH, —NH$_2$, —COOH, —CONH$_2$, —NO$_2$, —SH, $R^{27}$-substituted or unsubstituted C$_1$-C$_6$ alkyl, $R^{27}$-substituted or unsubstituted 2 to 6 membered heteroalkyl, $R^{27}$-substituted or unsubstituted C$_3$-C$_6$ cycloalkyl, $R^{27}$-substituted or unsubstituted 3 to 6 membered heterocycloalkyl, $R^{27}$-substituted or unsubstituted phenyl, or $R^{27}$-substituted or unsubstituted 5 to 6 membered heteroaryl; $R^{27}$ is independently oxo, halogen, —CX$^{27}_3$, —CHX$^{27}_2$, —CH$_2$X$^{27}$, —OCX$^{27}_3$, —OCH$_2$X$^{27}$, —OCHX$^{27}_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, $R^{28}$-substituted or unsubstituted C$_1$-C$_6$ alkyl, $R^{28}$-substituted or unsubstituted 2 to 6 membered heteroalkyl, $R^{28}$-substituted or unsubstituted C$_3$-C$_6$ cycloalkyl, $R^{28}$-substituted or unsubstituted 3 to 6 membered heterocycloalkyl, $R^{28}$-substituted or unsubstituted phenyl, or $R^{28}$-substituted or unsubstituted 5 to 6 membered heteroaryl; $R^{28}$ is independently oxo, halogen, —CX$^{28}_3$, —CHX$^{28}_2$, —CH$_2$X$^{28}$, —OCX$^{28}_3$, —OCH$_2$X$^{28}$, —OCHX$^{28}_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, unsubstituted C$_1$-C$_6$ alkyl, unsubstituted 2 to 6 membered heteroalkyl, unsubstituted C$_3$-C$_6$ cycloalkyl, unsubstituted 3 to 6 membered heterocycloalkyl, unsubstituted phenyl, or unsubstituted 5 to 6 membered heteroaryl; and X$^{26}$, X$^{27}$, and X$^{28}$ are independently —F, —Cl, —Br, or —I.

Embodiment 20

The method of one of embodiments 1 to 17, wherein $R^3$ is independently hydrogen or —CH$_2$CH$_2$N(unsubstituted C$_1$-C$_3$ alkyl)$_2$.

Embodiment 21

The method of one of embodiments 1 to 17, wherein $R^3$ is hydrogen.

Embodiment 22

The method of one of embodiments 1 to 17, wherein $R^3$ is —CH$_2$CH$_2$N(CH$_3$)$_2$.

Embodiment 23

A compound having the formula:

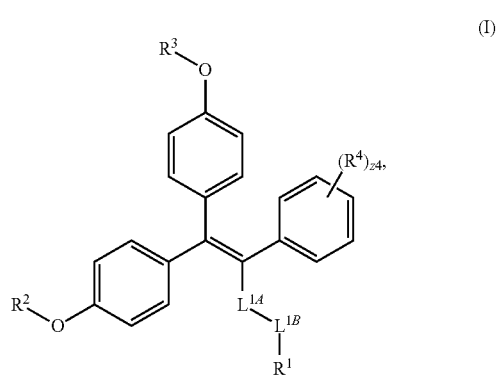

(I)

wherein, $L^{1A}$ is substituted or unsubstituted C$_1$-C$_6$ alkylene; $L^{1B}$ is —C(O)O—; $R^1$ is hydrogen or substituted or unsubstituted C$_1$-C$_6$ alkyl; $R^2$ is independently hydrogen, —CX$^2_3$, —CHX$^2_2$, —CH$_2$X$^2$, —C(O)R$^{2A}$, —C(O)OR$^{2A}$, —C(O)NR$^{2A}$R$^{2B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^3$ is independently hydrogen, —CX$^3_3$, —CHX$^3_2$, —CH$_2$X$^3$, —C(O)R$^{3A}$, —C(O)OR$^{3A}$, —C(O)NR$^{3A}$R$^{3B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^4$ is independently halogen, —CX$^4_3$, —CHX$^4_2$, —CH$_2$X$^4$, —OCX$^4_3$, —OCH$_2$X$^4$, —OCHX$^4_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; z4 is an integer from 0 to 5; each $R^{2A}$, $R^{2B}$, $R^{3A}$, and $R^{3B}$ is independently hydrogen, —CX$_3$, —CN, —COOH, —CONH$_2$, —CHX$_2$, —CH$_2$X, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{2A}$ and $R^{2B}$ substituents bonded to the same nitrogen atom may optionally be joined to form a substituted or unsubstituted heterocycloalkyl or substituted or unsubstituted heteroaryl; $R^{3A}$ and $R^{3B}$ substituents bonded to the same nitrogen atom may optionally be joined to form a substituted or unsubstituted heterocycloalkyl or substituted or unsubstituted heteroaryl; and each X, X$^2$, X$^3$, and X$^4$ is independently —F, —Cl, —Br, or —I.

Embodiment 24

The compound of embodiment 23 having the formula:

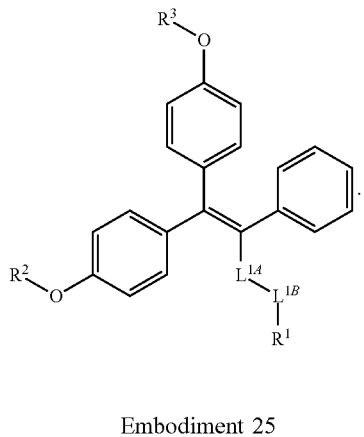

(Ia)

Embodiment 25

The compound of one of embodiments 23 to 24, wherein $L^{1A}$ is unsubstituted $C_2$-$C_4$ alkylene; $L^{1B}$ is —C(O)O—; and $R^1$ is unsubstituted $C_1$-$C_3$ alkyl.

Embodiment 26

The compound of one of embodiments 23 to 24, wherein $L^{1A}$ is unsubstituted $C_2$-$C_4$ alkylene; $L^{1B}$ is —C(O)O—; and $R^1$ is —$CH_3$.

Embodiment 27

The compound of one of embodiments 23 to 24, wherein $L^{1A}$ is —$CH_2CH(CH_3)$—; $L^{1B}$ is —C(O)O—; and $R^1$ is —$CH_3$.

Embodiment 28

The compound of one of embodiments 23 to 27, wherein $R^2$ is independently hydrogen, —C(O)-(unsubstituted $C_1$-$C_3$ alkyl), or $R^{23}$-substituted or unsubstituted $C_1$-$C_6$ alkyl; $R^{23}$ is independently oxo,
halogen, —$CX^{23}_3$, —$CHX^{23}_2$, —$CH_2X^{23}$, —$OCX^{23}_3$, —$OCH_2X^{23}$, —$OCHX^{23}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)NHNH$_2$, —NHC=(O)NH$_2$, —NHSO$_2$H, —NHC=(O)H, —NHC(O)—OH, —NHOH, unsubstituted $C_1$-$C_6$ alkyl, unsubstituted 2 to 6 membered heteroalkyl, unsubstituted $C_3$-$C_6$ cycloalkyl, unsubstituted 3 to 6 membered heterocycloalkyl, unsubstituted phenyl, or unsubstituted 5 to 6 membered heteroaryl; and $X^{23}$ is independently —F, —Cl, —Br, or —I.

Embodiment 29

The compound of one of embodiments 23 to 27, wherein $R^2$ is independently hydrogen, —C(O)-(unsubstituted $C_1$-$C_3$ alkyl), or unsubstituted $C_1$-$C_3$ alkyl.

Embodiment 30

The compound of one of embodiments 23 to 27, wherein $R^2$ is independently hydrogen.

Embodiment 31

The compound of one of embodiments 23 to 27, wherein $R^2$ is independently —C(O)CH$_3$.

Embodiment 32

The compound of one of embodiments 23 to 31, wherein $R^3$ is independently hydrogen, substituted or unsubstituted $C_1$-$C_6$ alkyl, or substituted or unsubstituted 2 to 8 membered heteroalkyl.

Embodiment 33

The compound of one of embodiments 23 to 31, wherein $R^3$ is independently hydrogen, $R^{26}$-substituted or unsubstituted alkyl, or $R^{26}$-substituted or unsubstituted heteroalkyl; $R^{26}$ is independently oxo,
halogen, —$CX^{26}_3$, —$CHX^{26}_2$, —$CH_2X^{26}$, —$OCX^{26}_3$, —$OCH_2X^{26}$, —$OCHX^{26}_2$, —CN, —OH, —$NH_2$, —COOH, —$CONH_2$, —$NO_2$, —SH, unsubstituted $C_1$-$C_6$ alkyl, unsubstituted 2 to 6 membered heteroalkyl, unsubstituted $C_3$-$C_6$ cycloalkyl, unsubstituted 3 to 6 membered heterocycloalkyl, unsubstituted phenyl, or unsubstituted 5 to 6 membered heteroaryl; and $X^{26}$ is independently —F, —Cl, —Br, or —I.

Embodiment 34

The compound of one of embodiments 23 to 31, wherein $R^3$ is independently hydrogen or —CH$_2$CH$_2$N(unsubstituted $C_1$-$C_3$ alkyl)$_2$.

Embodiment 35

The compound of one of embodiments 23 to 31, wherein $R^3$ is hydrogen.

Embodiment 36

The compound of one of embodiments 23 to 31, wherein $R^3$ is —CH$_2$CH$_2$N(CH$_3$)$_2$.

Embodiment 37

A pharmaceutical composition comprising the compound of any one of embodiments 23 to 36 and a pharmaceutically acceptable excipient.

Embodiment 38

A method of inhibiting estrogen-related receptor β activity, said method comprising contacting the estrogen-related receptor β with the compound of one of embodiments 23 to 36.

Embodiment 39

The method of embodiment 38, wherein the compound inhibits estrogen-related receptor β at least 2-fold more potently than the compound inhibits estrogen-related receptor α.

Embodiment 40

The method of embodiment 38, wherein the compound inhibits estrogen-related receptor β at least 5-fold more potently than the compound inhibits estrogen-related receptor α.

Embodiment 41

The method of embodiment 38, wherein the compound inhibits estrogen-related receptor β at least 10-fold more potently than the compound inhibits estrogen-related receptor α.

Embodiment 42

The method of embodiment 38, wherein the compound inhibits estrogen-related receptor β at least 100-fold more potently than the compound inhibits estrogen-related receptor α.

Embodiment 43

The method of one of embodiments 38 to 42, wherein the compound inhibits estrogen-related receptor β at least 2-fold more potently than the compound inhibits estrogen-related receptor γ.

Embodiment 44

The method of one of embodiments 38 to 42, wherein the compound inhibits estrogen-related receptor β at least 5-fold more potently than the compound inhibits estrogen-related receptor γ.

Embodiment 45

The method of one of embodiments 38 to 42, wherein the compound inhibits estrogen-related receptor β at least 10-fold more potently than the compound inhibits estrogen-related receptor γ.

Embodiment 46

The method of one of embodiments 38 to 42, wherein the compound inhibits estrogen-related receptor β at least 20-fold more potently than the compound inhibits estrogen-related receptor γ.

EXAMPLES

Example 1. Identification of Novel Inverse Agonists of Estrogen-Related Receptors ERRγ and ERRβ

Nuclear receptors are ligand-dependent transcription factors that regulate gene expression in response to small molecule ligands. Orphan members of the nuclear receptor superfamily, which have no identified endogenous ligand, are involved in regulation of many aspects of cellular metabolism including mitochondrial energetics as well as cholesterol, bile acid and glucose metabolism.[1] Therefore, they represent an important class of molecular targets for the treatment or prevention of a wide array of diseases.

The estrogen-related receptor (ERR) orphan receptor subfamily comprises three subtypes, ERRα, ERRβ, and ERRγ. The ERRs are first orphan nuclear receptors identified based on their structural similarity with the estrogen receptor (ER).[1] Although it was originally believed that the developmental and physiological roles of ERRs were quite distinct from those of the classic ERs, recent studies have shown that in some contexts ERRs share target genes, coregulatory proteins, ligands, and sites of action with the ERs.[2] Such evidence has been extensively reviewed.[3] ERRs play an important role in the transcriptional control of metabolic genes involved in the generation and utilization of cellular energy.[4] Thus, ERRs might present a therapeutic target for the prevention of obesity and type 2 diabetes.[5] Although the ERRα, ERRβ, and ERRγ isoforms all share considerable amino acid sequence identity with ERs in both the DNA binding domain (DBD) and ligand binding domain (LBD), they do not respond to natural estrogens, such as $E_2$ (17β-estradiol, FIG. 1).[6-8]

ERRs are primarily expressed in the heart, skeletal muscle, brain, kidney, pancreas, placenta, and liver and are predicted to have significant differences in their ligand-binding preferences.[9-10] However, the mechanisms governing target gene selectivity of the individual ERR isoforms are not well understood. ERRα regulates genes involved in mitochondrial biogenesis (Gabpa/NRF2a, Tfam), fission/fusion (Mfn1 and 2, Opa1) as well as metabolic enzymes of β-oxidation (Acadm) and ETC/oxphos (Sdha, Cytc) pathways in conjunction with PGC-1α (peroxisome proliferator-activated receptor gamma coactivator 1α), a master regulator of lipid and glucose homeostasis.[11] In cancer cells ERRα also regulates cellular metabolism as well as genes relevant to proliferation and metastasis and is associated with poor prognosis in human breast cancer.[12-13] ERRα expression correlates HER2 status and has been shown to mediate the effects of growth factor signaling on metabolic reprogramming that is required for the development of chemoresistance.[14-15] Thus, ERRα is considered a potential drug target with potential to treat metabolic disorders and cancer.[16-18]

ERRβ is present early in the developing placenta in a subset of cells in extra-embryonic ectoderm destined to make up the chorion.[19-20] ERRβ is likely essential for reproduction.[21] ERRβ expression is essential for the maintenance of pluripotency and self-renewal potential in mouse embryonic stem cells and is among the core transcription factors that can reprogram fibroblasts into pluripotent stem cells.[22-23] Biochemical evidence also suggests that ERRβ may be a potential therapeutic target involved in cancers and metabolic disorders.[24] However, studies have been hampered by the embryonic lethality of ERRβ−/− mouse model and the lack of small molecule modulators to study ERRβ function. Selective ERRβ ligands would provide an invaluable research tool to examine the biological function of ERRβ.

ERRγ regulates gluconeogenesis in liver and is a potential candidate drug target to reverse hyperglycemia and hepatic fat accumulation in the context of insulin resistance.[25-26] ERRγ/PGC-1β promotes oxidative metabolism in cancer cells,[27] and unlike ERRα, ERRγ expression is a favorable biomarkers in human breast cancer. Thus, targeting the ERRγ pathway may be a powerful therapeutic strategy to treat metabolic disorders and cancer.[28]

The ability to recruit a wide array of functionally distinct coregulators provides each receptor with the potential to regulate a single gene in different ways depending on the relative concentration and posttranslational status of each coregulator in the cell. This has led to the concept of nuclear receptor ligands with tissue- or gene-selective activities, i.e. selective nuclear receptor modulators. Crystal structures of ERRγ bound to distinct ligands such as 4-hydroxy-tamoxifen exhibit distinct conformational changes in the ERRγ ligand binding domain. A consequence of these ligand-specific conformations is that different ligands can promote differential affinities for the numerous coregulators that are present in any given cell. The net result of these distinct molecular signatures is that different ligands can have distinct transcriptional activities on different genes or in different tissues. In effect, different coregulator peptides can be used as "conformation probes" to sort ligands into those with distinct classes of downstream target genes. This has important therapeutic implications as it offers the possibility of identifying synthetic nuclear receptor ligands that display therapeutic activity without known side-effects. A critical step to advance the understanding of ERR biology is to design or identify selective modulators (agonists and inverse agonists) that can be used to target isoform specific processes in cells and in vivo. Notably, no endogenous ligand for any of the ERRs has been identified to date. The synthetic selective ligands developed to target ERRα are described as inverse agonists (antagonists of constitutive ERR activity) and agonists,[29-30] and have been utilized in cell culture and in vivo studies to investigate the physiologic activity of ERRα. However, little is known about the molecular mechanisms or biological activities downstream of ERRβ and ERRγ receptor activation because of the lack of selective ERRβ/γ ligands.

Recently, a small molecule agonist of the ERRγ and ERRβ was identified that mimics the protein ligand PGC-1α in activating human ERRβ and ERRγ,[31-32] and compounds including Z-4-OHT and DES (FIG. 1), have been shown to act as nonselective ERRγ inverse agonists.[33-35] Structure-based approach was used to design the ERRγ selective inverse agonist GSK5182 and its analog (FIG. 1).[36-37] Likewise, 4-methylenesterols isolated from the marine sponge steroids, have been reported to act as ERRβ antagonists.[38] However, these new antagonists exhibit lower potency than DES in transactivation experiments. ERRγ regulates the expression of genes involved in bile acid metabolism, ERRγ inverse agonist can protect the liver from the development of fibrosis and cirrhosis of NASH through this and other mechanisms. ERRγ regulates a wide variety of target genes critically involved in the control of bile acids, lipid, and glucose homeostasis, and in the regulation of immune responses. CYP7A, (cholesterol 7α-hydroxylase), the rate-limiting enzyme in bile acid synthesis, overexpression results in a marked activation of the classic pathway of bile acid biosynthesis leading to the accumulation of high concentrations of bile acids and, ultimately, hepatocyte injury and impaired liver function. Activation of cannabinoid receptor type 1 (CB1 receptor) signaling induced ERRγ mediated transcription of the CYP7A1 gene. Overexpression of ERRγ increased CYP7A1 expression in vitro and in vivo, whereas knockdown of ERRγ attenuated CYP7A1 expression. Deletion analysis of the CYP7A1 gene promoter and a ChIP assay revealed an ERRγ binding site on the CYP7A1 gene promoter. SHP (Small heterodimer partner) inhibited the transcriptional activity of ERRγ and thus regulated CYP7A1 expression. Overexpression of ERRγ led to increased bile acid levels, whereas an inverse agonist of ERRγ, GSK5182, reduced CYP7A1 expression and bile acid synthesis. Finally, GSK5182 significantly reduced hepatic CB1 receptor mediated induction of CYP7A1 expression and bile acid synthesis in alcohol-treated mice. These results provide the molecular mechanism linking ERRγ and bile acid metabolism (Zhang, et al., Biochem. J. (2015) 470, 181-1, incorporated by reference in its entirety for all purposes). It underlies the therapeutic rationale for ERRγ inverse agonists in the linkage of cholestatic liver diseases where ERRγ repression can protect the liver from the development of fibrosis and cirrhosis of NASH through these and other mechanisms.

Despite these advances, the development of ERRβ and ERRγ inverse agonists with better potency and selectivity remains a formidable challenge. As a part of our ongoing program to explore novel classes of ERR modulators with the goal of increasing the potency and selectivity for ERRβ and ERRγ subtypes which might prove to be of therapeutic value in treating a variety of ERRβ and ERRγ-linked pathologies, we applied a strategy of altering the structure of triarylethylene core which is a template of Z-4-OHT. The compound Z-4-OHT has a very poor inverse agonist profile for ERRγ and ERRβ but binds to the LBD of these receptors; therefore it was used as a scaffold to generate higher potency antagonists. The design was based on SAR of Z-4-OHT analogs combined with analysis of the X-ray crystal structures of Z-4-OHT bound to the ligand binding domains of ERRγ and ERα. Analogs bearing extension or branched alkyl groups at the C2 position of the triarylethylene core with the basic side chain exhibited improved binding affinity and selectivity profiles for ERRγ compared to Z-4-OHT.[39] The existing X-ray crystal structure of Z-4-OHT bound to ERRγ and ERα LBD provided a model for the molecular basis of activity and selectivity.[36] Described herein are the chemical synthesis and SAR (structure-activity relationship) for several triarylethylene derivatives as well as molecular modeling of receptor binding and in vitro activity profiles of the compounds.

Based on the recent structural studies we proposed the synthesis of targeted arrays of small, triarylethylenes as ERRγ and ERRβ ligands. The resultant core scaffold of triarylethylenes could be derivatized at three distinct sites: at the aliphatic side chain on the C2 of triarylethylene position, the OH group on the 4-position of phenyl A-ring, and alkylaminoethoxy-basic side chain on the 4-position of phenyl B-ring (see FIG. 1). We first examined the biological activities of several different types of alkylaminoethoxy-basic side chain into the phenyl B-ring but did not find significant changes to the potency and selectivity toward ERRγ and ERRβ with sidechains tested. Therefore, an aliphatic side chain on the C2 of triarylethylene and 4-OH group on the phenyl A-ring were targeted to improve the potency and selectivity toward to ERRγ and ERRβ.

Combining molecular basis, structure consideration, and chemical feasibility, the initial strategy consisted of traditional medicinal chemistry and paralleled an approach involving various substitutions on the triarylethylene core in an attempt to increase the ERRβ and ERRγ specificity while performing the inverse agonistic selectivity on ERRγ and ERRβ. The Z isomer of 4-OHT has the required antiestrogenic activity, while the (E)-4-OHT has only about 5% of its affinity for the ER.[40] To determine if Z-4-OHT would have selectivity on ERRs, we tested the Z-4-OHT and E-4-OHT isomers in ERRβ and ERRγ activity. The Z isomer of 4-OHT has the required activity on the ERRγ and ERRβ, but the E-4-OHT was much less active for the ERR targets. Thus, analogues of triarylethylenes with a basic side chain having a Z-form are desired.

In order to establish a chemical library with various functionalities and structural diversity, we first focused on the extended ethyl side chains of triarylethylene core. Retrosynthetically, we found that 1,1-bis(4-hydroxyphenyl)-2-phenylethylene could serve as a key template for the conversion to a series of analogs structurally related to the Z-4-OHT. We have previously described the synthesis of Z-4-OHT in a regio- and stereo-selective controlled manner.[41] Our intention was to extend this method to versatile production of 1,1-bis(4-hydroxyphenyl)-2-phenylalkenes via McMurry chemistry which is a well-known established methodology for the cross-coupling reaction (FIG. 2).[42]

The 1,1-bis(4-hydroxyphenyl)-2-phenylethylenes were synthesized by coupling 4,4'-dihydroxybenzophenone with various propiophenone derivatives to introduce $R_1$ groups and make chemset 1 (FIG. 2). To expand the number of accessible analogs, a McMurry reductive coupling between 4,4'-dihydroxybenzophenone reacting with the readily-available reagents such as isobutyrophenone, isovalerophenone, 4-oxo-4-phenyl-butyric acid methyl ester, 2-methyl-4-oxo-4-phenyl-butyric acid methyl ester, 3-benzoylpropionic acid, and 2-methyl-4-oxo-4-phenylbutyric acid in the presence of zinc and titanium tetrachloride in dry THF under reflux conditions was performed. The desired 1,1-bis(4-hydroxyphenyl)-2-phenylalkenes (1a-n) were obtained in good yields. The carboxylic acid groups in 1i and 1j were reduced using $BH_3$-THF to give the corresponding alcohols 1k and 1n in 75 and 74% yields, respectively. In chemset 1, 1c and 1d are known compounds and we have re-synthesized them in excellent yields by McMurry chemistry compared to the existing synthesis of Gust, Gauthier and coworkers.[43-44]

Figure 3:
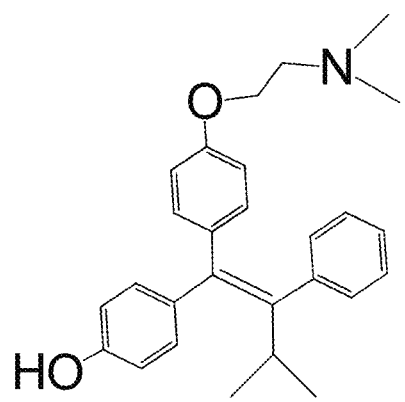
FIG. 3. X-ray crystallographic structure of 3a indicated that the active geometric isomer 3a is Z-form generated in a region controlled manner.
Figure 3:
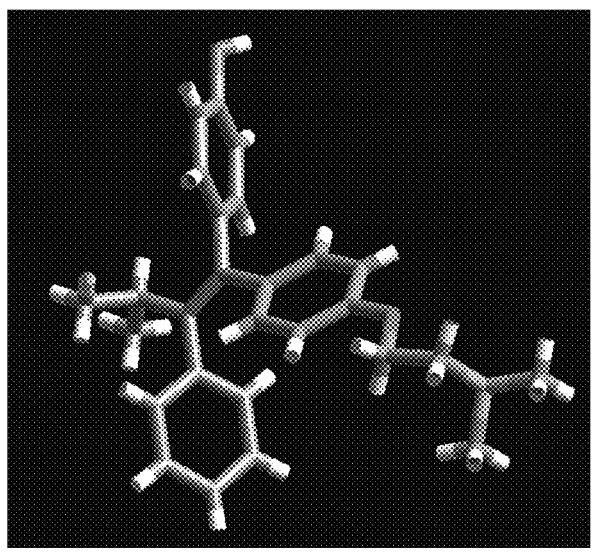

Next, we coupled compounds 1a-h, 1k, and 1n directly with 2-(dimethylamino)ethyl chloride hydrochloride using a known method,[45] and obtained an equimolar mixture of the geometric isomers of (E,Z)-4-[1-(4-dimethylaminoethoxy-phenyl)-2-phenyl-but-1-enyl]-phenols 2, as depicted in FIG. 2. The initial coupling reaction favored the formation of geometric Z-isomer, but it was then converted to a monoalkylated geometric mixture after a while. In this procedure, monoalkylated geometric isomers are the majority, while the dialkylated products were detected in trace quantities. Note that Z-4-OHT is more potent than E-4-OHT for the ERRβ/γ in the cell-based cotransfection assay. Thus, the fixed ring analogs of substituted 1,1-bis(4-hydroxyphenyl)-2-phenyl-alkenes in 3 series with Z-isomer are of high interest for this project. Treatment of the crude mixture 2 of two E/Z stereoisomers in 1:1 ratio were easily separated by selective crystallization, and in some cases, by flash chromatography. A series of geometric mixture E/Z in 2 series as pure regio-selective Z-isomer 3 was ultimately effectively separated. Examples include crystallization of the white solid 2a with a 1:1 Z/E ratio from warm methanol which led to white crystals 3a. The absolute configuration assignment of 3a was determined as Z-isomer by X-ray structure analysis ((FIG. 3). Other configurations of the stereo Z-isomer in chemset 3 were determined by NOE measurements and $^1$H NMR. Alternatively, the geometric isomers of pure Z-form in chemset 3 are very easily identified by general $^1$H NMR because Z-form analogs have upfield NMR signals of the 2-dimethylaminoethoxy chain protons compared to the corresponding E-isomer by using $CD_3OD$ as a solvent. By the improved synthetic methodology we were able to minimize the number of synthetic steps and develop a purification methodology for the production of a series of new Z-isomer analogs derived from Z-4-OHT, compared to the Gauthier and GSK method which requires protective groups and pivaloate deprotection.[36] The general synthetic route used to prepare substituted hydroxylated 1,1,2-tribenzyl-but-1-enes of the Z-isomer are outlined in FIG. 2.

Previously the hydroxyl group on the phenyl A-ring of Z-4-OHT was believed to be important for the binding affinity toward to the ERα.[46] Z-4-OHT has higher affinity for ERα than ERRγ because of the similarity between ERRγ and ERα in the first shell of the ligand binding pocket. Note that the hydroxyl group on the phenyl A-ring interacts with ERRγ in Glu-275 and Arg-316 (ERα Glu-353 and Arg-394), and the LBDs of ERRγ and ERRβ are almost identical. This implies that the optimization in the 4-OH in the phenyl A-ring would be challenging for the increase of the potency on the ERRγ. Furthermore, SAR from X-ray crystal structures of Z-4-OHT bound to the LBD of ERRγ suggested that the binding pocket may tolerate small substituents other than hydroxyl group.[47] In order to assess if the simple substituent variations of 4-OH group on the phenyl A-ring interaction would lead to the improved potent and selectivity for ERRγ and ERRβ, next, we designed and synthesized a small focused chemical library of phenyl A-ring with diversity at position of 4-OH to generate structure-activity relationship (SAR). To speed the synthesis, we applied solution-phase parallel synthetic techniques to exploit variant functionalities as $R^B$ to maximize the efficient interactions in molecular levels at the binding pockets of ERRγ and ERRβ.

Compounds 3a and 3h have been selected as building blocks based on their improved inverse agonist functional profile for the ERRγ and ERRβ. Thus, the hydroxyl function of active precursors 3a and 3h was converted into the chemset 4 by esterification and alkylation reactions to introduce a series of ester or ether pharmacophores as diversity to the 4-position of phenyl A-ring. The 48 commercially available chemical reagents were selected on the basis of diversity, the criteria being lipophilicities and chemistry compatibility to achieve more flexible substitution patterns. This combinatorial synthesis offers the advantage of compatibility with a series of functionalities. Table 1 shows the chemical structures of the final $R^B$ at the phenyl A-ring moiety by varying the hydrophobicity and size of the system. The identity of each of the final compounds was confirmed by $^1$H and $^{13}$C NMR.

TABLE 1.

Combinatorial synthesis of a library of precursors 3a, 3h with diversity at position 4-OH of the pendant phenyl A-ring was synthesized using parallel solution-phase synthetic techniques to induce $R^B$ functions.

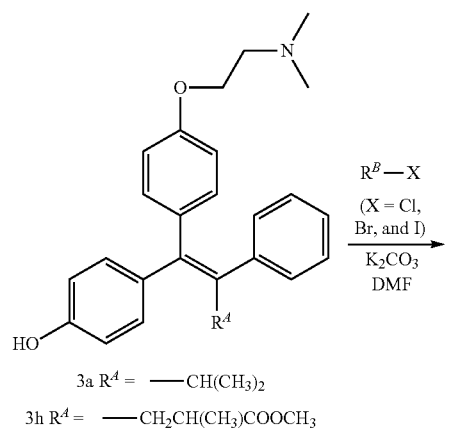

3a $R^4$ = —CH(CH$_3$)$_2$

3h $R^4$ = —CH$_2$CH(CH$_3$)COOCH$_3$

TABLE 1.-continued
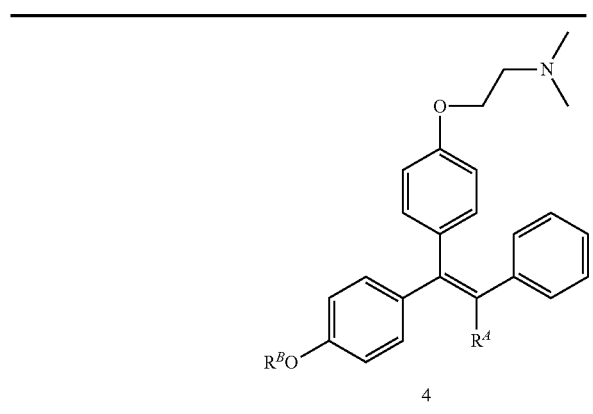
4
| | |
|---|---|
| $R^B(1)$ | 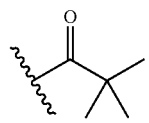 [SMILES: *C(=O)C(C)(C)C] |
| $R^B(2)$ | 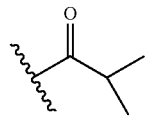 [SMILES: *C(=O)C(C)C] |
| $R^B(3)$ | 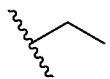 |
| $R^B(4)$ | 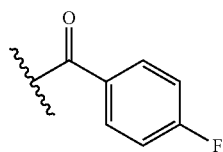 [SMILES: *C(=O)c1ccc(F)cc1] |
| $R^B(5)$ | 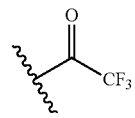 [SMILES: *C(=O)C(F)(F)F] |
| $R^B(6)$ | 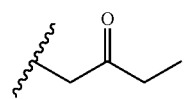 [SMILES: *CC(=O)CC] |
| $R^B(7)$ | 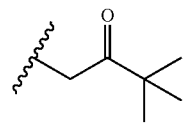 [SMILES: *CC(=O)C(C)(C)C] |
| $R^B(8)$ | 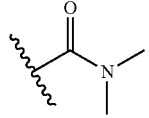 [SMILES: *C(=O)N(C)C] |
| $R^B(9)$ | 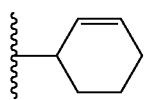 |
| $R^B(10)$ | 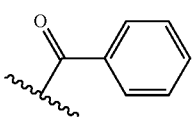 [SMILES: *C(=O)c1ccccc1] |
| $R^B(11)$ | 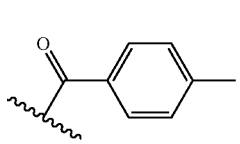 |
| $R^B(12)$ | 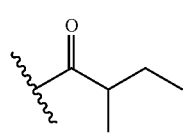 [SMILES: *C(=O)C(C)CC] |
| $R^B(13)$ | |
| $R^B(14)$ | |
| $R^B(15)$ | |
| $R^B(16)$ | |
| $R^B(17)$ | |
| $R^B(18)$ | |
| $R^B(19)$ | |
| $R^B(20)$ | |
| $R^B(21)$ | |

TABLE 1.-continued

| | |
|---|---|
| R^B(22) | isobutyl ketone group |
| R^B(23) | butyl ketone group |
| R^B(24) | vinyl ketone group |
| R^B(25) | ethyl ketone group |
| R^B(26) | isopentyl ketone group |
| R^B(27) | pentyl ketone group |
| R^B(28) | hexyl ketone group |
| R^B(29) | 2-thienylmethyl ketone group |
| R^B(30) | benzyl group |
| R^B(31) | 3-methylphenyl ketone group |
| R^B(32) | N,N-diethyl amide group |
| R^B(33) | -CH$_2$CF$_3$ |
| R^B(34) | methyl ketone group (acetonyl) |
| R^B(35) | phenyl ketone group |
| R^B(36) | 4-fluorobenzyl group |
| R^B(37) | 2-fluorobenzyl group |
| R^B(38) | -CH$_2$COOCH$_3$ |
| R^B(39) | tert-butyl 2,2-dimethylpropanoate group |
| R^B(40) | methyl 2,2-dimethylpropanoate group |
| R^B(41) | 2,2-dimethyl phenyl ketone group |
| R^B(42) | 2-thienyl ketone group (via CH$_2$) |
| R^B(43) | 3-fluorophenyl ketone group |
| R^B(44) | 2-furyl ketone group (via CH$_2$) |
| R^B(45) | -CH$_3$ |

TABLE 1.-continued

| | |
|---|---|
| R<sup>B</sup>(46) | 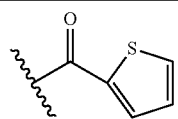 |
| R<sup>B</sup>(47) | 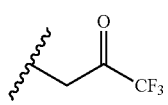 |
| R<sup>B</sup>(48) | 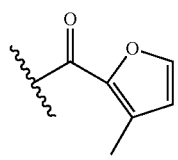 [SMILES: *C(=O)c1occc1C] |

To achieve different types of esters and an alternative access to substituted ethers in chemset 4, a total of 48 commercially available acyl chlorides and alkyl halides were reacted in hot DMF containing potassium or cesium carbonates as the base. The optimal temperature for the reaction was 50° C. The construction of a focused small library by parallel solution-phase synthesis was carried out in a Mettler-Toledo Bohdan RAM organic synthesizer with an automated liquid handling robot. A workstation of Mettler-Toledo system was used to tare each reactant vial in an array of vials. After the added reagent was weighed, it was diluted to the desired concentration with organic solvents and vortexed. Various combinations of reactants were then transferred to each of reaction tubes for the screw synthesizer. The solution-phase in the library synthesis always posed a challenge in purification procedures. To get quick and efficient purification in higher purity in sufficient quantity for cell-based biological testing, the Biotage Quad 3 automated medium pressure flash chromatography was used for parallel purification. The crude mixtures were then directly purified by automated unit system which performed 12 simultaneous flash chromatographs using prepacked silica gel columns. Twenty fractions could be easily obtained from each run in under 20 minutes. The average yields of the targeted compounds were >85% and purity >82%. The resulting fractions were analyzed by flow injection NMR to confirm the chemical structures by $^1$H and $^{13}$C NMR. By this protocol, a total of 96 corresponding esters and ethers of chemset 4 were obtained in fair yields.

To assess the functional transcriptional activity of these compounds, cell-based assays using chimeric receptor Gal4 DNA-binding domain (DBD)-NR ligand binding domain cotransfection assay (LBDs of ERRα, ERRγ, and ERRβ) were performed. As an initial screen to determine the ERRγ and ERRβ inhibitory activity and selectivity, all compounds were evaluated for in vitro potency and selectivity by transfection testing, using CV-1 cells transfected with human and mouse ERRs. MH100×4 is a luciferase reporter with four copies of a GAL4 UASG response element, where GAL-I refers to the ligand-binding domain of the indicated receptor fused to the C-terminus of the GAL4 DNA-binding domain. Assays were performed using a Biomek automated workstation in which the genes for the nuclear receptor, as well as a plasmid containing a response element upstream of a luciferase cDNA, are transfected into CV-1 cells. Compounds were evaluated for their ability to inhibit human ERRs at 0.03, 0.1, 0.5, 1, 2.5, 3, and 10 µM test concentrations. Those compounds that showed good ERRβ and ERRγ potency and selectivity were evaluated at additional concentrations. Z-4-OHT used as a known ERRγ and ERRβ inverse agonist to compare the constitutive activity of unliganded ERRγ and ERRβ. A series of synthetic compounds of this focused library has been identified and showed similar activities at the 1 µM concentration as compared with Z-4-OHT.

In 2002, Gust and coworkers[43] reported a series of C2-alkyl substituted of triarylethylene derivatives without basic side chains. They came to the conclusion that those compounds they synthesized without a basic side chain in the B-ring possessed the same antagonistic potency for ERs as compared with Z-4-OHT which contains a basic side chain that was believed exhibiting antagonistic activity of 4-OHT on the ERs.[46] However, the tested compounds by Gust and co-workers did not cover extensive studies of the structure-function relationship for the activity on the ERRs. Thus, we explored if compounds in chemset 1, which is in the absence of basic side chain functionality, would also exert some biological effects by modulating the activities of ERRs. The compounds in chemset 1 have been evaluated by cell-based screening for inverse agonistic activity against ERRs. As compared to the Z-4-OHT, most of the new analogs in chemset 1 did not possess ERRs activity, but possess ERs activity. We came to the conclusion that in the class of 1,1-bis(4-hydroxyphenyl)-2-phenylalkenes, having a basic side chain is not a prerequisite for exhibiting antagonistic effect on the ER receptor. The antiestrogenic properties comprising estrogen receptor binding depend only on the length of the $C_2$-alkyl chain. These results are consistent with previous findings that removal of the dimethylaminoethoxy side chain of Z-4-OHT did not decrease the antagonistic effects on the MCF-7-2a cell line.[45]

Figure 4A:
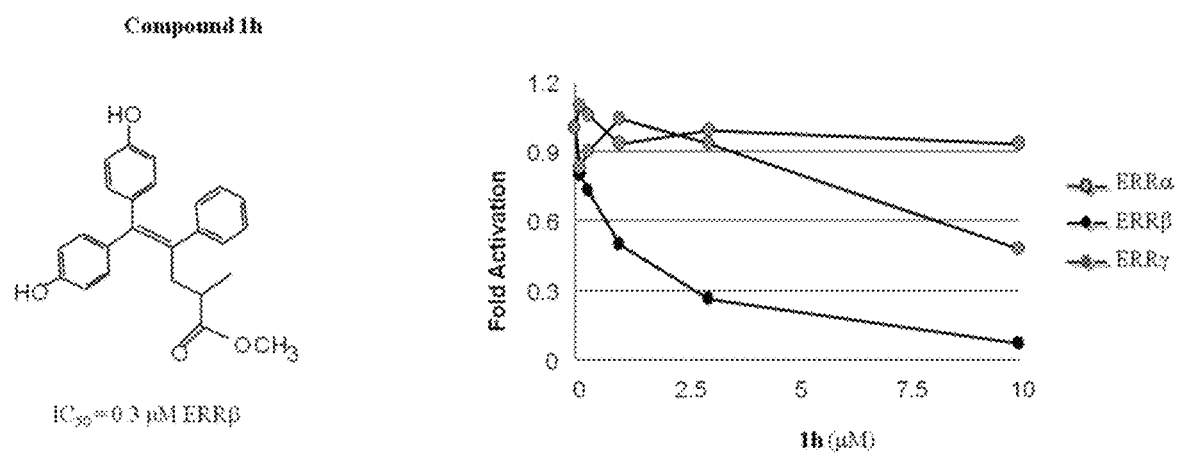
FIGS. 4A-4B. Compound 1g and 1h in chemset 1 have been identified as selective inverse agonists for the ERRβ.
Figure 4B:
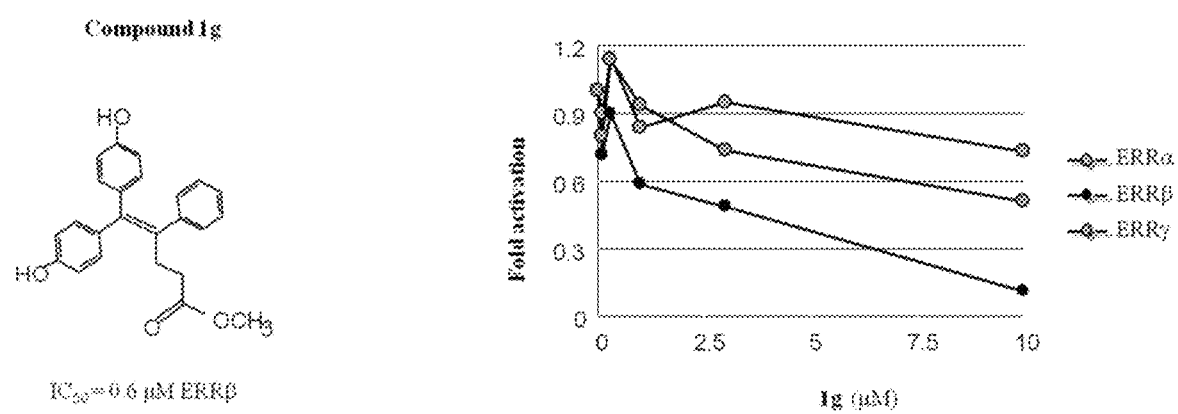
Figure 5A:
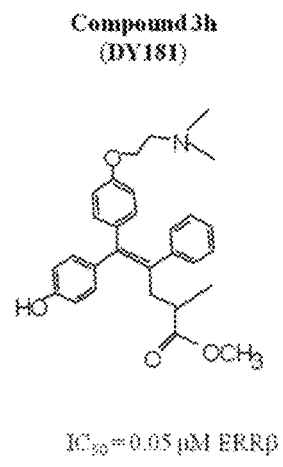
FIGS. 5A-5B. Compounds 3h (DY181) and 3g have been identified as selective inverse agonists for the ERRβ.
Figure 5A:
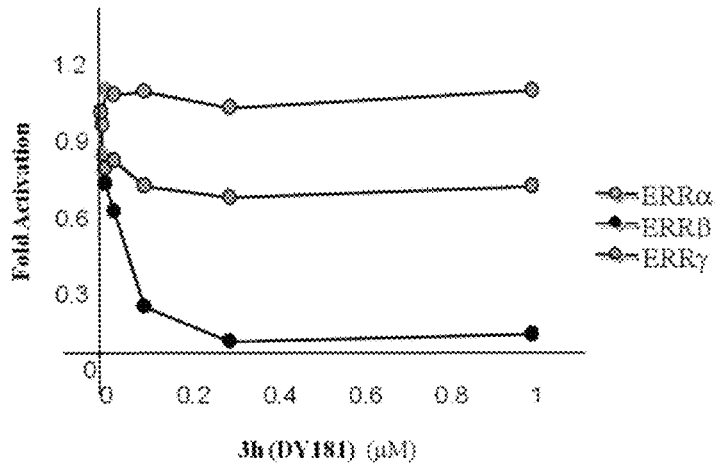
Figure 5B:
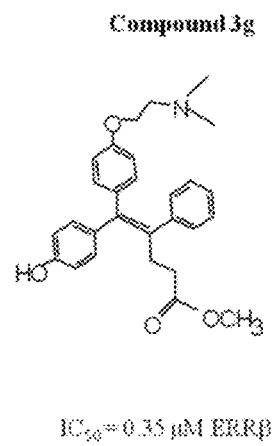
Figure 5B:
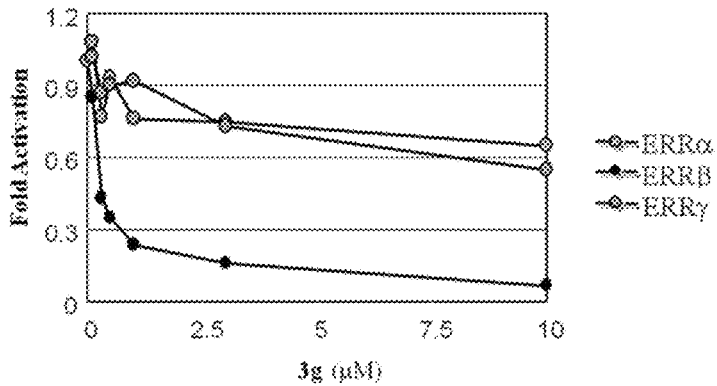
Figure 6A:
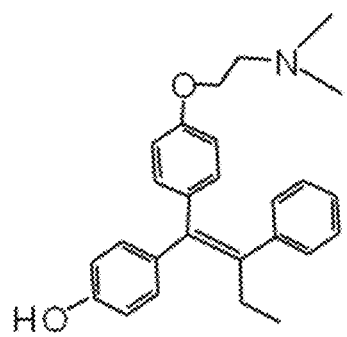
FIGS. 6A-6B. Compound 4a (DY40) was evaluated in potency and selectivity by cell-based transactivation assays using CV-1 cells transfected with human and mouse ERRs. CV-1 cells were transfected with reporter constructs and expression vectors and the fold activation of the reporter construct was determined at several concentrations.
Figure 6A:
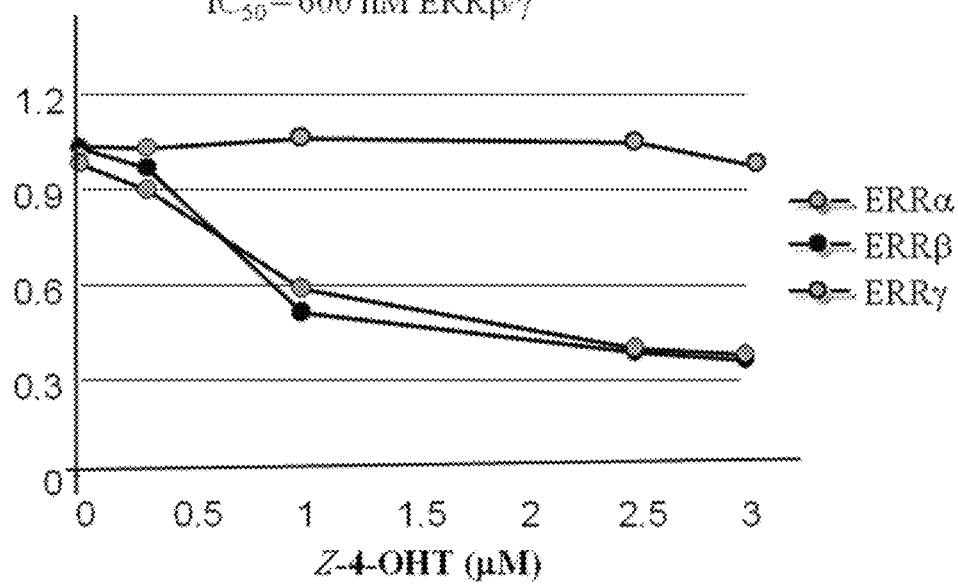
Figure 6B:
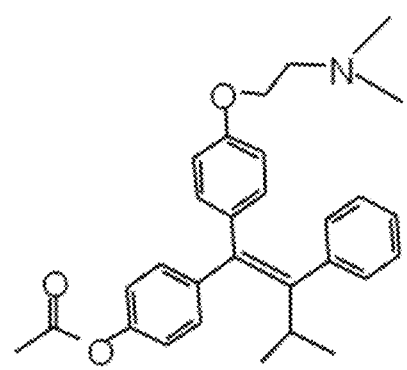
Figure 6B:
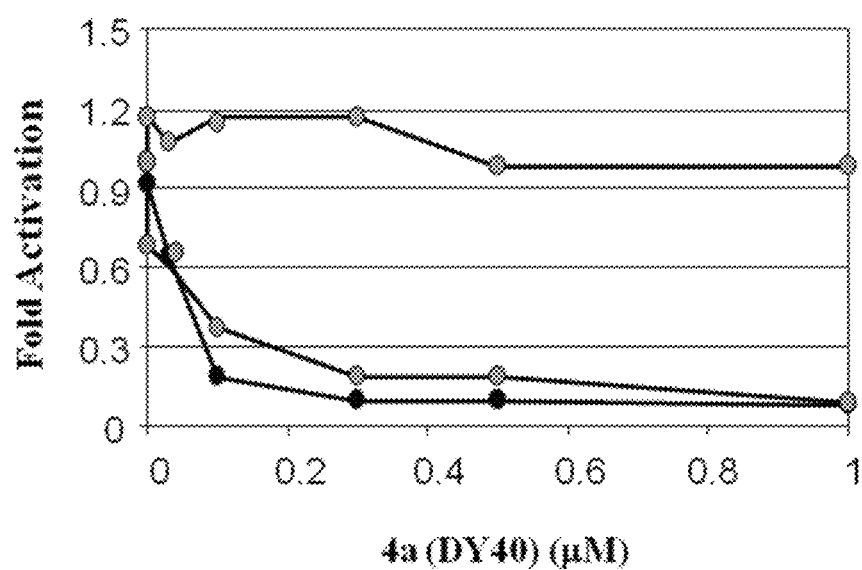

However, as shown in FIG. 4, compounds 1g and 1h were found to be active and have selectivity for ERRβ with $IC_{50}$ values of 0.6 and 0.3 µM, respectively. This is a surprising finding because compounds 1g and 1h exhibited excellent selectivity and inverse agonist efficacy on the ERRβ and they were not active for the ERRα, also were not active for the ERRγ receptor at the higher dose. In contrast, the analogs 1g and 1h, which possessed the corresponding extended ethyl side chains bearing methyl esters in the C2-alkyl substituted system and did not bear any basic side chain on the phenyl B-ring, displayed improved selectivity profiles toward the ERRβ (FIG. 4). This demonstrated that the presence of the extended methyl ester side chain on the C2-alkyl position is important for the ERRβ to gain an antagonistic activity.

Having a basic side chain is not a prerequisite for exhibiting high binding affinity and antagonistic effects on the ER. However, as predictable, having a basic side chain of 1,1-bis(4-hydroxyphenyl)-2-phenylalkenes contributes to high binding affinity and inverse agonistic effects on the ERRγ. Wherein the triarylethylene system, it can be seen that a dimethylaminoethoxy basic side chain on one of the phenolic groups (phenyl B-ring) increase ERRγ inverse agonistic activity and selectivity.[36] In our experiments variation of a side chain on the C2 of triarylethylene core with basic side chain appeared to be beneficial for ERRγ, and for the ERRβ inhibitory activity. All of the resulting compounds in 3 series were found to possess the inverse agonistic potency on the ERRγ and ERRβ. The data are shown in Table 2 with a subset of the active compounds as examples. This study confirmed that the introduction of basic side chain on the para-position of the phenyl B-ring contributes to providing generally improved potencies on the ERRγ and ERRβ.

Interestingly, as can be seen in Table 2, replacing an ethyl group of Z-4-OHT with an isopropyl group substituent (3a) led to an increase in inhibitory activity. The potency of 3a was increased on the ERRγ and ERRβ ($IC_{50}$=0.29/0.21 µM) by 3-fold as compared to the Z-4-OHT. However, when an isopropyl was replaced by an isobutyl group, the resulted compound (3f) has slightly less potency on ERRγ and ERRβ ($IC_{50}$=1.0/0.75 µM) compared to Z-4-OHT, as well as 3-fold ERRβ/γ potency less than 3a, as shown in the Table 2. Particularly less inhibitory activities or a loss of inverse agonistic activity on the ERRγ were observed with those compounds additionally bearing longer and bulkier groups at the C-2 position. This result demonstrated that the ethyl group at the C2-extension position could be replaced with small alkyls without substantial loss of activity. The isopropyl group at the C2-position (3a) seems beneficial in terms of increasing potency on the ERRγ and ERRβ.

However, in contrast, when the isopropyl group at the C2-position (3a) was changed to the methyl esters located at the extended ethyl side chain, the corresponding compounds 3g and 3h (DY181) exhibited significant ERRβ binding affinity and selectivity which has no effect on ERα, ERβ, ERRα, and ERRγ transcriptional activity up to 3 µM. As shown in FIG. 5, the most potent ERRβ inverse agonist 3h with an extended methyl ester group at the C2-position has been identified with excellent selectivity over ERRα/γ. Compound 3h (DY181) displayed the highest ERRβ affinity ($IC_{50}$=50 nM). These results are consistent with previous findings from chemset 1 (1h and 1g) wherein the extension of C-2 ethyl side chain system having corresponding methyl esters appeared to be beneficial for ERRβ activity. Apparently, a combination of extension of C-2 ethyl side chain system having corresponding methyl ester and a basic side chain contributes high potency and inverse agonistic effect on the ERRβ receptor.

Combinatorial construction of a focused library by carrying out solution phase-assisted synthesis led to 96 analogs by removal of the hydroxyl group (4-OH) or replacing it with small acetyl and alkyl substituents. Analogs which loaded onto the 4-position of hydroxyl on the A-phenyl ring in chemset 4 as $R^B$ were generated by incorporating esters or ethers to potentially increase lipophilic character which would be beneficial for ligands to interact with the hydrophobic LBD of ERRs. Ligands with small acetoxy improved potency and selectivity on the ERRγ, whereas some other ligands with bulkier substituents as $R^B$ showed less potency and were sterically not well tolerated by ERRβ and ERRγ. Several interesting compounds derived from 3a having acetoxy have been identified in 4 series in repressing ERRβ and ERRγ. The acetate analog, exemplified by DY40 (4a {$R^B$(1)}) derived from 3a showed the greatest functional potency with the $IC_{50}$ of 10 nM as shown in FIG. 6. The improved potency and inverse agonist activity of the acetoxy-substituted analog 4a {$R^B$(1)} demonstrated that an acetoxy group on the A-ring instead of hydroxyl seems to efficiently diversify the potency of ERRβ and ERRγ.

In fact, in chemset 4, small substituents $R^B$ led to a slight increase inhibitory activity, and some bulky $R^B$ substituents further attenuated activity of ERRβ and ERRγ. We proposed that the bulkier $R^B$ substituents are not suitable for ERRγ and ERRβ activity, and probably the LBD of the receptors may not be regulated and tolerated by bigger molecules. Thus, the size and shape of the ligand are key factors for the protein modulation. However, analogs which loaded onto the 4-position of hydroxyl on the A-phenyl ring in chemset 4 as $R^B$ from the precursor 3h did not improve the potency as compared with DY40 (4a). To gain further insight into the selectivity on the ERRs, the same reaction expanded to a 0.5 g scale of compounds 4a{$R^B$(1)} resulted in an 88% yields. Additional experiments included the compounds 3k and 3n which were also converted into the corresponding analogs 4k{$R^B$(1)}, and 4n{$R^B$(1)} in a 0.5 g scale production resulted in 82%, and 79 yields, respectively.

In vitro Functional Data for Selected Compounds at ERRs Receptors. A high-throughput binding assay using cell-based assay at different concentrations was carried out with the LBD of ERRs. From initial screening against ERRs, over thirty active compounds have been identified as having ERRγ and ERRβ affinity, and data are highly reproducible. Data were re-evaluated for 12 members of library (2 members in chemset 1, 6 in chemset 3, and 3 members in chemset 4). A summary of the $IC_{50}$ values that were derived from in vitro transactivation assays against the human ERRα, ERRβ and mouse ERRγ subtypes for compounds (1g, 1h, 3a, 3f, 3h, 3g, 3k, 3n, 4a, 4k, and 4n) with Z-4-OHT is outlined in Table 2. As shown in Table 2, compound 4a (DY40) as an inverse agonist of ERRβ and ERRγ displayed the greatest functional potency (($IC_{50}$=10 nM) at about 60-fold greater than Z-4-OHT. The acetylating of compounds 4k and 4n efficiently increased the affinity for ERRβ and ERRγ almost 3 to 7-fold as compared with 3k and 3n. These data indicated that the acetoxy group on phenyl A-ring is beneficial for the ERRβ and ERRγ in terms of potency and selectivity. The selective members of three chemsets exhibited a wide range of inverse agonistic activity on ERRβ and ERRγ and clearly indicated that these new compounds all were inactive on ERRα.

Interestingly, among them, 1g, 1h, 3g, and 3h were identified as ERRβ inverse agonists. 3a, 3f, 3g, 3n, 4a, 4k, and 4n were identified as ERRβ and ERRγ inverse agonists. These most promising inverse agonists indicated that the ERRβ and ERRγ inhibitory potency and selectivity could be extremely sensitive to changes in chemical structure within a modified series. However, based on the selectivity evaluation, except for compounds 1g, 1h, 3g, and 3h, the number of compounds we synthesized in this project cannot fully separate ERRγ activity from ER activity. For example, 4a (DY40) remains an antagonist potency of ERα.

TABLE 2

A select set of Z-4-OHT analogs on ERRα, β, and γ binding affinities.

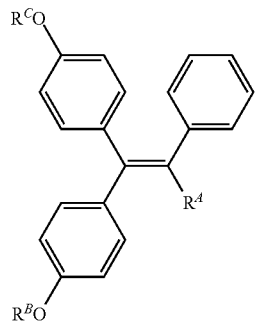

| Compound | $R^A$ | $R^B$ | $R^C$ | ERRα $IC_{50}$ (μM) | ERRβ $IC_{50}$ (μM) | ERRγ $IC_{50}$ (μM) |
|---|---|---|---|---|---|---|
| Z-4-OHT | $CH_2CH_3$ | H | $(CH_2)_2N(CH_3)_2$ | NA | 0.65 | 0.6 |
| 1h | $CH_2CH(CH_3)COOCH_3$ | H | H | NA | 0.3 | 5.5 |
| 1g | $CH_2CH_2COOCH_3$ | H | H | NA | 0.6 | 6.5 |
| 3a | $CH(CH_3)_2$ | H | $(CH_2)_2N(CH_3)_2$ | NA | 0.21 | 0.29 |
| 3f | $CH_2CH(CH_3)_2$ | H | $(CH_2)_2N(CH_3)_2$ | NA | 0.75 | 1 |
| 3h (DY181) | $CH_2CH(CH_3)COOCH_3$ | H | $(CH_2)_2N(CH_3)_2$ | NA | 0.05 | 2.78 |
| 3g | $CH_2CH_2COOCH_3$ | H | $(CH_2)_2N(CH_3)_2$ | NA | 0.35 | 3.5 |
| 3k (Z-GSK5182) | $CH_2CH_2CH_2OH$ | H | $(CH_2)_2N(CH_3)_2$ | NA | 3.5 | 2.7 |
| 3n | $CH_2CH(CH_3)CH_2OH$ | H | $(CH_2)_2N(CH_3)_2$ | NA | 2.25 | 2.5 |
| 4a (DY40) | $CH(CH_3)_2$ | $CH_3CO$ | $(CH_2)_2N(CH_3)_2$ | NA | 0.01 | 0.01 |
| 4k | $CH_2CH_2CH_2OH$ | $CH_3CO$ | $(CH_2)_2N(CH_3)_2$ | NA | 1.1 | 0.3 |
| 4n | $CH_2CH(CH_3)CH_2OH$ | $CH_3CO$ | $(CH_2)_2N(CH_3)_2$ | NA | 0.55 | 0.35 |

NA = not active at 10 μM. $IC_{50}$ is the concentration of test compound that gave 50% maximum efficacy. CV-1 cells were co-transfected with appropriate reporter constructs and expression vectors. The fold activation of the reporter construct by ligand was determined at several concentrations of selected compounds. No induction of ERRα dependent transcription was observed for any of the compounds in tested.[49]

Figure 7A:
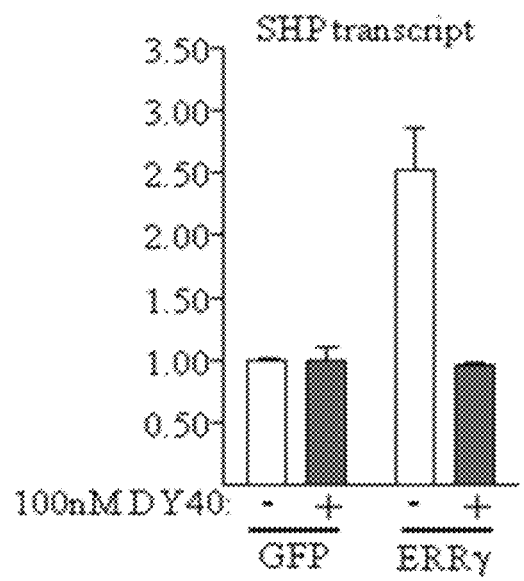
FIGS. 7A-7C. Compound 4a (DY40) inhibits expression of a specific ERRγ target gene and reduces mitochondrial β-oxidation rates.
Figure 7B:
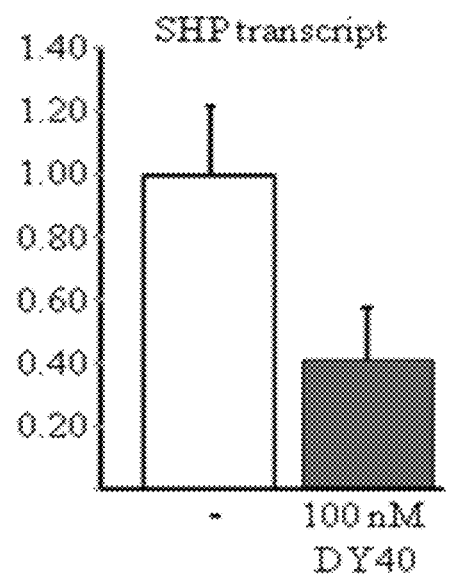

Validation of DY40 effects on endogenous ERRγ target gene expression and metabolism in cell based models. We next examined whether the newly synthesized DY40 could repress endogenous expression of an ERRγ target gene. Previous studies showed that ERRγ is a constitutive activator of the small heterodimer partner (SHP) gene, which is selectively regulated by ERRγ via a direct binding of the receptor to a site located in the proximal promoter region.[50-51] Consistent with these findings, ERRγ over-expression in 293HEK upregulated the SHP transcript by 2.5-fold and treatment with 100 nM DY40 completely blocked ERRγ mediated induction (FIG. 7A). We also evaluated the effects of the compound in C2C12 myotubes that have significant endogenous ERRγ expression. Consistent with the observed effects in 293HEK cells, DY40 repressed endogenous SHP transcript levels by ~60% in C2C12 myotubes (FIG. 7B).

Figure 7C:
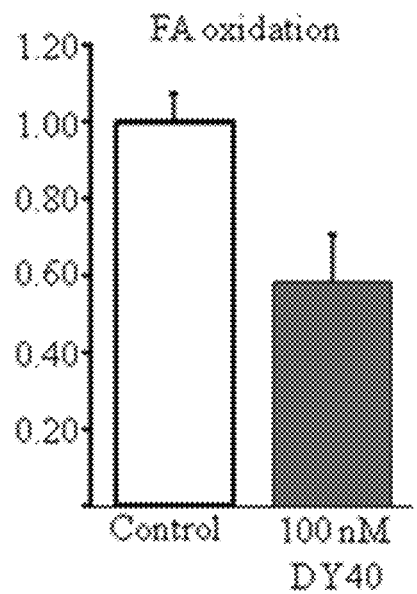

Previous studies have shown that ERRγ deficient myocytes have reduced capacity oxidize long-chain fatty acids.[52] Therefore, we investigated the effects of treatment with DY40 on β-oxidation rates in C2C12 myotubes. Treatment of C2C12 myotubes with DY40 for 48 hours resulted in a significant reduction in palmitate oxidation rates (~42%) in myocytes compared to vehicle-treated controls (FIG. 7C). Notably, knockdown of ERRγ expression in C2C12 decreased oxidation by the same magnitude. Collectively, these data demonstrate robust and selective effects of DY40 on ERRγ dependent gene regulation and metabolism in cells.

Computational modeling of ERR and binding of compound 3h (DY181) to ERRβ. To further understand the specific inhibition of compound 3h (DY181) to ERRβ protein over ERRγ, we implemented computational tools to predict the binding modes of DY181 to ERR proteins. The homology model of ERRβ protein in ligand binding domain (193-433a.a.) was built by using SWISS-MODEL[53] based on the X-ray crystal structure of ERRγ (PDB code 2EWP),[36] which has sequence identity of 77%. The model was further optimized to assign the hydroxyl, Asn, Gln and His residue states, and followed by structural minimization using Schrödinger Maestro software. The best docking poses of compound DY181 on ERR proteins were predicted by using our in-house developed All-Around Docking (AAD)[54] algorithm, which are displayed in FIG. 8. AAD methodology searches the best binding site and binding pose around the whole protein surface without any knowledge of the possible locations of docking pocket.

Figure 8A:
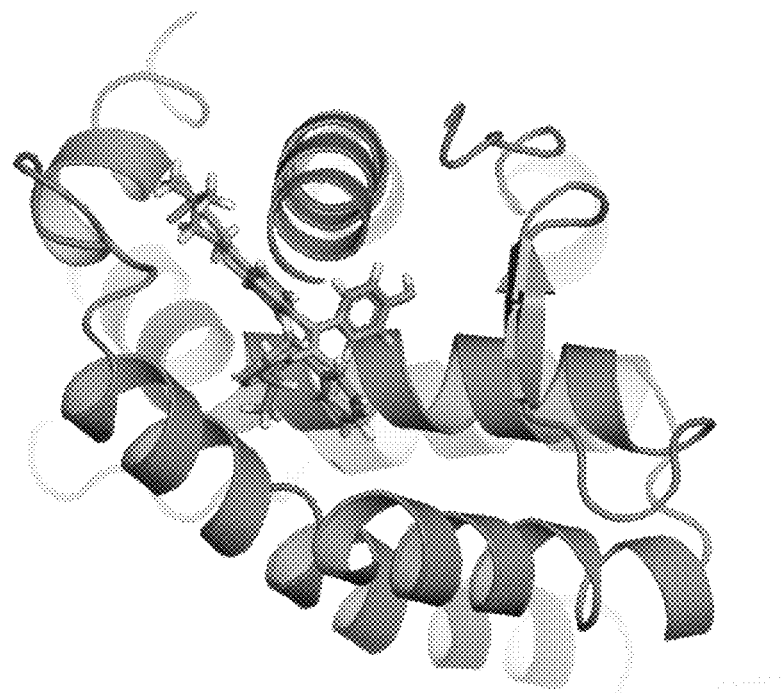
FIGS. 8A-8C. Binding models of compound 3h (DY181) in ligand binding domain of ERR proteins.
Figure 8B:
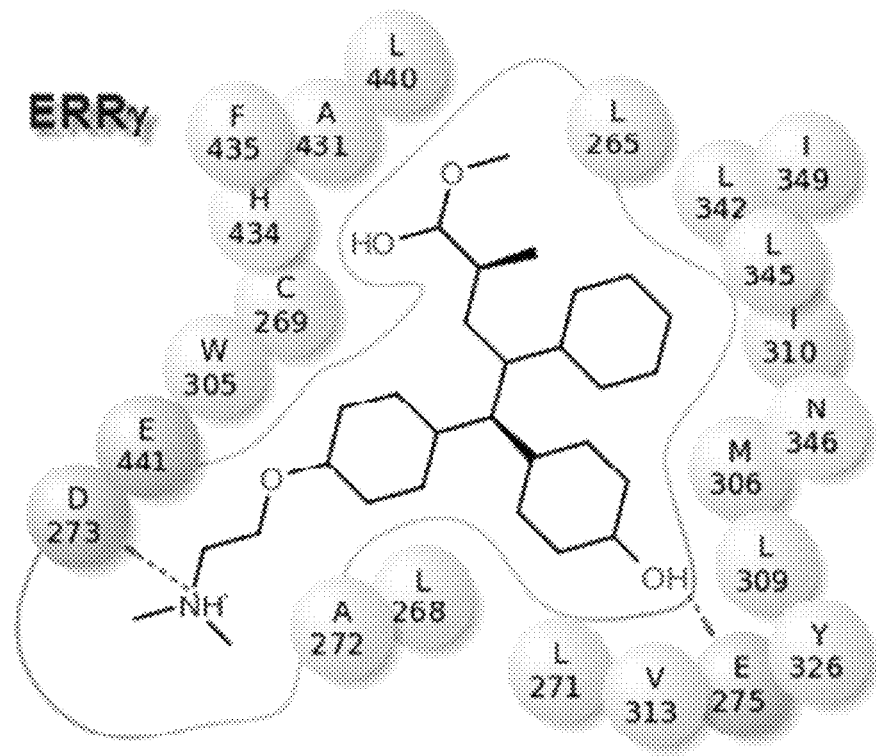
Figure 8C:
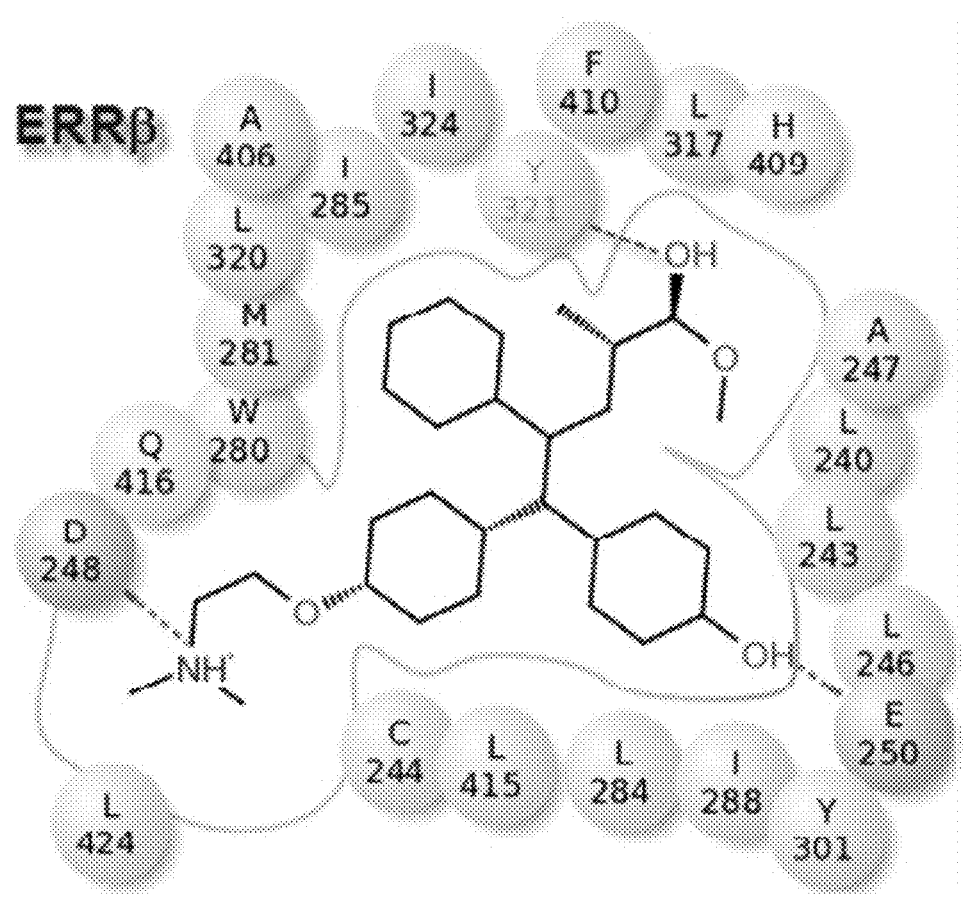

As depicted in FIG. 8A by using our AAD method, compound DY181 binds ERRβ at the same pocket on ERRγ protein as that of compound GSK5182 in crystal structure. Two hydrogen bonds are formed with D273 and E275 residues, which are displayed in FIG. 8B. As shown in FIG. 8C, DY181 binds ERRβ protein at the same ligand-binding pocket as well. However, besides the two hydrogen bonds formed with corresponding D248 and E250 residues, an extra hydrogen bond with Y321 residue is also produced. The additional hydrogen bond between DY181 and Y321 in ERRβ should result in higher binding affinity. Consequently, DY181 shows selectivity on ERRβ over ERRγ.

In conclusion, we have developed rational strategies that allowed us to successfully identify a series of novel analogs structurally related to Z-4-OHT to modulate the activity of estrogen-related receptors (ERRγ and ERRβ), which are constitutively active. All of the resulting compounds were primarily evaluated by using a well-established cell-based luciferase reporter gene assay to determine their effects in a cellular system. It is preferred that the mechanism is inverse agonism and occurs by the novel compound binding directly to the ligand binding domain of the receptors. Among the identified inverse agonists of ERRγ and ERRβ, compound 4a (DY40) is the most potent compound described to date which potently suppressed the transcriptional functions of ERRγ with $IC_{50}$=0.01 µM in a cell-based reporter gene assay and antagonizes ERRγ with a potency approximately 60 times greater than Z-4-OHT. Compound 3h (DY181) has also been identified as a selective inverse agonist for the ERRβ with excellent selectivity and potency. Our computational modes show that DY181 (3h) can form a strong hydrophobic interaction with ERRβ which is predicted to bind more strongly than ERRγ. These studies provided valuable information and opportunity to expand the series in search of more potent, selective, and druglike molecules. Compounds DY40 (4a) and DY181 (3h) may represent unique chemical tools in the elucidation of ERRγ and ERRβ functions and could be new agents for the treatment of metabolic disorders and related cancer. Studies aimed at further profiling these compounds in vitro and expanding the SAR of these analogs with the goal of developing ERRβ and ERRγ modulators that can be delivered orally and are active in vivo are under way.

Example 2. Compounds

General Procedures:

Organic reagents were purchased from commercial suppliers unless otherwise noted and were used without further purification. All solvents were analytical or reagent grade. All reactions were carried out in flame-dried glassware under argon or nitrogen. Melting points were determined and reported automatically by an optoelectronic sensor in open capillary tubes and were uncorrected. $^1$H NMR and $^{13}$C NMR spectra were measured at 600 MHz and 125 MHz respectively, and using $CDCl_3$ or $CD_3OD$ as the solvents and tetramethylsilane ($Me_4Si$) as the internal standard. Flash column chromatography was performed using Sigma-Aldrich silica gel 60A (200-400 mesh), carried out under moderate pressure by using columns of an appropriate size packed and eluted with appropriate eluents. Silica gel chromatography was performed on a Biotage flash column gradient pump system using 15 cm long columns. All reactions were monitored by TLC on precoated plates (silica gel HLF). TLC spots were visualized either by exposure to iodine vapors or by irradiation with UV light. Organic solvents were removed in vacuum by rotary evaporator. Elemental analyses were performed by Columbia Analytical Services, Inc. Tucson, Ariz.

Method A. McMurry Reductive Coupling Reaction.

To a stirred suspension of zinc powder (31 mmol) in dry THF (30 mL) was added $TiCl_4$ (14 mmol), under Ar, at −10° C. When the addition was complete, the mixture was warmed to room temperature and then refluxed. After titanium reagent was refluxed for 2.5 h, the mixture was cooled to 0 degree C. and then a solution of 4,4'-hydroxybenzophenone (2.3 mmol) and substituted-phenone (6.7 mmol) in dry THF (40 mL) at 0° C. was added to the mixture. Upon completion of addition of solution, the mixture was refluxed in the dark for 2.5 h, cooled to room temperature (25° C.); and quenched with 10% aqueous potassium carbonate (50 mL) and extracted with EtOAc. The organic layer was washed with brine, dried over $MgSO_4$, and concentrated in vacuo.

1,1-Bis (4-hydroxyphenyl)-2-phenylbut-3-methyl-1-ene (1a)

To a stirred suspension of zinc powder (2.0 g, 31 mmol) in dry THF (30 mL) was added $TiCl_4$ (1.5 mL, 14 mmol), under Ar, at −10° C. When the addition was complete, the mixture was warmed to room temperature and then refluxed. After titanium reagent was refluxed for 2.5 h, the mixture was cooled to 0 degree C. and then a solution of 4,4'-hydroxybenzophenone (0.5 g, 2.3 mmol) and isobutyrophenone (1.0 g, 6.7 mmol) in dry THF (40 mL) at 0° C. was added to the mixture. Upon completion of addition of solution, the mixture was refluxed in the dark for 2.5 h, cooled to room temperature; and quenched with 10% aqueous potassium carbonate (50 mL) and extracted with EtOAc. The organic layer was washed with brine, dried over $MgSO_4$, and concentrated in vacuo. Flash column chromatography (8:2 hexanes/EtOAc) afforded 1a (0.68 g, 89%) as a white solid: mp 137.7° C.; $^1$H NMR (600 MHz, $CDCl_3$) δ 7.27-7.18 (m, 5H), 7.12 (d, 2H), 7.07 (d, 2H), 6.81 (d, 2H), 6.45 (d, 2H), 4.70 (s, 1H), 4.41 (s, 1H), 3.05 (m, 1H), 0.96 (d, 6H); $^{13}$C NMR (125 MHz, $CDCl_3$) δ 157.0, 155.9, 146.0, 141.5, 140.2, 136.1, 136.0, 132.3, 132.1, 131.4, 128.1, 127.0, 115.9, 114.8, 32.8, 22.2. Anal. Calcd for $C_{23}H_{22}O_2$: C, 83.60; H, 6.71. Found: C, 83.78; H, 6.66.

1,1-Bis (4-hydroxyphenyl)-2-phenylpent-1-ene (1b)

Compound 1b was synthesized using Method A with 4,4'-hydroxybenzophenone and propiophenone. The crude product was purified by flash column chromatography (8:2 hexanes/EtOAc) afforded 1b (1.35 g, 70%) as a white solid: mp 192.7° C. Crystallization from warm EtOAc gave white crystals (1b): mp 195.0° C. (lit. mp 142-145° C.).[43] $^1$H NMR (600 MHz, $CD_3OD$) δ 7.06-7.03 (m, 5H), 6.99 (d, 2H), 6.75 (d, 2H), 6.49 (d, 2H), 6.37 (d, 2H), 2.39 (q, 2H), 1.33 (m, 2H), 0.80 (t, 3H); $^{13}$C NMR (125 MHz, $CD_3OD$) δ 157.1, 157.2, 144.5, 140.3, 136.5, 136.2, 136.1, 131.6, 130.8, 130.5, 128.8, 126.8, 115.6, 115.5, 39.0, 23.1, 14.5. Anal. Calcd for $C_{23}H_{22}O_2$: C, 83.60; H, 6.71. Found: C, 83.95; H, 6.94.

1,1-Bis (4-hydroxyphenyl)-2-phenylhex-1-ene (1c)

This compound was prepared using method A. The crude product was purified by flash column chromatography (1:1 $Et_2O$/hexanes) afforded 1c (5.02 g, 79%) as a white solid: mp 170.6° C. Crystallization from warm EtOAc gave white crystals (1c): mp 171.4° C. (lit. mp 158° C.).[43] $^1$H NMR (600 MHz, $CD_3OD$) δ 7.13-7.06 (m, 5H), 7.01 (d, 2H), 6.75 (d, 2H), 6.64 (d, 2H), 6.39 (d, 2H), 2.42 (t, 2H), 1.22 (m, 4H), 0.76 (t, 3H); $^{13}$C NMR (125 MHz, $CD_3OD$) δ 157.9, 156.2, 144.6, 140.4, 140.2, 136.5, 136.2, 133.0, 132.2, 131.6, 131.3, 128.8, 126.8, 115.7, 115.5, 114.5, 36.6, 32.3, 23.8, 14.4. Anal. Calcd for $C_{24}H_{24}O_2$: C, 83.69; H, 7.02. Found: C, 83.42; H, 7.15.

1,1-Bis (4-hydroxyphenyl)-2-phenyl-4-chlorobut-1-ene (1d)

This compound was prepared using method A. The crude product was purified by flash column chromatography (8:2 hexanes/EtOAc) afforded 1d (1.35 g, 70%) as a white solid:

mp 184.5° C. Crystallization from warm EtOAc gave white crystals (1d): mp 187.8° C.; $^1$H NMR (600 MHz, CDCl$_3$) δ 7.18-7.11 (m, 7H), 6.85 (d, 2H), 6.75 (d, 2H), 6.50 (d, 2H), 4.77 (s, 1H), 4.54 (s, 1H), 3.42 (t, 2H), 2.97 (t, 2H); $^{13}$C NMR (125 MHz, CD$_3$OD) δ 157.5, 156.6, 143.3, 143.0, 135.6, 135.5, 132.9, 131.6, 130.8, 129.1, 127.3, 115.9, 115.1, 114.6, 43.6, 39.8. Anal. Calcd for C$_{22}$H$_{19}$ClO$_2$: C, 75.32; H, 5.46, Cl, 10.11. Found: C, 75.77; H, 5.65, Cl, 10.28.

1,1-Bis (4-hydroxyphenyl)-2-phenyl-5-chloropent-1-ene (1e)

This compound was prepared using method A. The crude product was purified by flash column chromatography (8:2 hexanes/EtOAc) afforded 1e (2.66 g, 72%) as a white solid: mp 165.2° C. Crystallization from warm EtOAc gave white crystals (1e): mp 169.3° C. $^1$H NMR (600 MHz, CD$_3$OD) δ 7.17-7.08 (m, 5H), 7.02 (d, 2H), 6.77 (d, 2H), 6.66 (d, 2H), 6.40 (d, 2H), 3.40 (t, 2H), 2.60 (m, 2H), 1.77 (m, 2H); $^{13}$C NMR (125 MHz, CD$_3$OD) δ 153.3, 152.1, 139.7, 137.1, 134.3, 131.8, 131.5, 128.6, 127.2, 126.4, 124.6, 122.7, 111.5, 110.7, 41.3, 30.1, 28.9. Anal. Calcd for C$_{23}$H$_{21}$ClO$_2$: C, 75.71; H, 5.58; Cl, 9.72. Found: C, 75.37; H, 5.77; Cl, 9.61.

1,1-Bis (4-hydroxyphenyl)-2-phenyl-4-methylpent-1-ene (1f)

This compound was prepared using method A. The crude product was purified by flash column chromatography (8:2 hexanes/EtOAc) afforded 1f (0.45 g, 85%) as a white solid. Crystallization from warm EtOAc gave white crystals: mp 172.8° C.; $^1$H NMR (600 MHz, CD$_3$OD) δ 7.13-7.01 (m, 7H), 6.75 (d, 2H), 6.66 (d, 2H), 6.38 (d, 2H), 2.34 (d, 2H), 1.47 (m, 1H), 0.78 (d, 6H); $^{13}$C NMR (125 MHz, CD$_3$OD) δ 156.9, 156.2, 144.3, 141.2, 139.8, 136.5, 136.2, 132.7, 131.7, 130.8, 128.7, 126.7, 115.7, 115.1, 44.9, 27.7, 23.0. Anal. Calcd for C$_{24}$H$_{24}$O$_2$: C, 83.69; H, 7.02. Found: C, 83.78; H, 6.66.

5,5-Bis (4-hydroxyphenyl)-2-methyl-4-phenyl-pent-4-enoic acid methyl ester (1h)

This compound was prepared using method A. The crude product was purified by flash column chromatography (1:1 hexanes/EtOAc) afforded 1h (1.45 g, 78%) as a white solid: mp 197.2° C. $^1$H NMR (600 MHz, CD$_3$OD) δ 7.15 (t, 2H), 7.09 (d, 3H), 7.02 (d, 2H), 6.77 (d, 2H), 6.66 (d, 2H), 6.39 (d, 2H), 2.43 (s, 3H), 2.83 (m, 1H), 2.58 (m, 1H), 2.38 (m, 1H), 1.02 (d, 3H). $^{13}$C NMR (125 MHz, CD$_3$OD) δ 178.6, 157.3, 156.5, 143.2, 142.6, 137.5, 136.0, 135.8, 133.6, 132.8, 131.6, 128.7, 127.2, 116.1, 115.1, 52.0, 40.1, 39.8, 17.4. Anal. Calcd for C$_{25}$H$_{24}$O$_4$.¼H$_2$O: C, 76.49; H, 6.16. Found: C, 76.41; H, 6.30.

5,5-Bis (4-hydroxyphenyl)-4-phenyl-pent-4-enoic acid methyl ester (1g)

This compound was prepared using method A. The crude product was purified by flash column chromatography (1:1 hexanes/EtOAc) afforded 1g (3.35 g, 89%) as a white solid: mp 191.0° C. $^1$H NMR (600 MHz, CD$_3$OD) δ 7.17 (t, 2H), 7.11 (d, 3H), 7.03 (d, 2H), 6.79 (d, 2H), 6.67 (d, 2H), 6.41 (d, 2H), 3.53 (s, 3H), 2.78 (t, 2H), 2.29 (t, 2H); $^{13}$C NMR (125 MHz, CD$_3$OD) δ 175.4, 157.5, 156.6, 143.4, 141.9, 137.9, 136.0, 135.7, 133.0, 131.5, 130.9, 129.0, 127.3, 116.0, 115.1, 52.0, 34.3, 32.3. Anal. Calcd for C$_{24}$H$_{22}$O$_4$: C, 76.99; H, 5.92. Found: C, 76.80; H, 6.06.

5,5-Bis-(4-hydroxyphenyl)-pent-4-enoic-acid (1i)

This compound was prepared using method A. The crude product was purified by flash column chromatography (9:1 CH$_2$Cl$_2$/MeOH) afforded 1j (1.82 g, 76%) as a white solid: mp 215.2° C. $^1$H NMR (600 MHz, CD$_3$OD) δ 7.17 (t, 3H), 7.13 (d, 2H), 7.05 (d, 2H), 6.79 (d, 2H), 6.68 (d, 2H), 6.42 (d, 2H), 2.77 (t, 2H), 2.25 (t, 2H); $^{13}$C NMR (125 MHz, CD$_3$OD) δ 175.6, 156.0, 155.1, 142.1, 140.2, 136.6, 134.7, 134.4, 131.6, 130.1, 129.5, 127.6, 125.8, 114.6, 113.7, 32.9, 31.0. Anal. Calcd for C$_{23}$H$_{20}$O$_4$.2H$_2$O: C, 69.70; H, 5.10. Found: C, 70.00; H, 5.20.

5,5-Bis-(4-hydroxyphenyl)-pent-4-ene-1-ol (1k)

A solution of BH$_3$-THF (3.0 mL, 1.0 M solution in THF, 5 mmol) was added dropwise to a solution of 5,5-Bis-(4-hydroxyphenyl)-pent-4-enoic-acid (1i) (0.4 g, 1 mmol) in dry THF (10 mL) at 0° C. When the addition was complete, the mixture was warmed to room temperature and then stirred for 3.5 h. The mixture was cooling to 0° C. and quenched with 1 N NaOH (2 mL). The mixture was then diluted with saturated NH$_4$Cl (10 mL) and EtOAc (20 ml). Aqueous layer was extracted with EtOAc (2×20 mL). The combined organic extracts were washed with water, brine, and dried over Na$_2$SO$_4$, and concentrated in vacuo. Solidification by EtOAc afforded 1k (0.26 g, 75%) as a white solid: mp 215.8° C.; $^1$H NMR (600 MHz, CD$_3$OD) δ 7.13-7.09 (m, 5H), 7.02 (d, 2H), 6.76 (d, 2H), 6.65 (d, 2H), 6.40 (d, 2H), 3.39 (t, 2H), 2.49 (m, 2H), 1.54 (t, 2H); $^{13}$C NMR (125 MHz, CD$_3$OD) δ 155.8, 154.9, 142.9, 139.2, 138.3, 135.0, 134.7, 131.6, 130.2, 129.4, 127.5, 125.5, 114.4, 113.6, 61.7, 31.9, 31.7. Anal. Calcd for C$_{23}$H$_{22}$O$_3$.½H$_2$O: C, 77.71; H, 6.24. Found: C, 77.21; H, 6.26.

5,5-Bis (4-hydroxy-phenyl)-2-methyl-4-phenyl-pent-4-enoic acid (1j)

This compound was prepared using method A. The crude product was purified by flash column chromatography (1:1H/EtOAc) afforded 1j (1.22 g, 63%) as a white solid: mp 245.9° C. $^1$H NMR (600 MHz, CD$_3$OD) δ 7.15 (t, 5H), 6.79 (d, 2H), 6.66 (d, 2H), 6.51 (d, 2H), 6.40 (d, 2H), 2.87 (m, 1H), 2.58 (m, 1H), 2.30 (t, 1H), 1.04 (d, 3H); $^{13}$C NMR (125 MHz, CD$_3$OD) δ 178.9, 155.7, 155.0, 141.8, 141.1, 136.2, 134.6, 131.3, 130.3, 129.6, 127.5, 125.8, 114.5, 113.7, 38.4, 37.6, 15.8. Anal. Calcd for C$_{24}$H$_{22}$O$_4$.¾H$_2$O: C, 74.29; H, 5.72. Found: C, 74.09; H, 5.68.

5,5-Bis-(4-hydroxyphenyl)-2-methyl-pent-4-ene-1-ol (1n)

A solution of BH$_3$-THF (3.0 mL, 1.0 M solution in THF, 3 mmol) was added dropwise to a solution of 5,5-Bis (4-hydroxy-phenyl)-2-methyl-4-phenyl-pent-4-enoic acid (1j) (0.25 g, 0.67 mmol) in dry THF (5 mL) at 0° C. When the addition was complete, the mixture was warmed to room temperature and then stirred for 3.5 h. The mixture was cooling to 0° C. and quenched with 1 N NaOH (1 mL). The mixture was then diluted with saturated NH$_4$Cl (10 mL) and EtOAc (20 ml). Aqueous layer was extracted with EtOAc (2×20 mL). The combined organic extracts were washed with water, brine, and dried over Na$_2$SO$_4$, and concentrated in vacuo. The crude product was purified by flash column chromatography (1:1H/EtOAc) afforded 1n (0.16 g, 67%) as a white solid: mp 201.0° C.; $^1$H NMR (600 MHz, CD$_3$OD) δ 7.17-7.09 (m, 5H), 7.04 (d, 2H), 6.78 (d, 2H), 6.68 (d, 2H), 6.40 (d, 2H), 3.37 (t, 1H), 3.15 (t, 1H), 2.54 (m, 1H), 2.31 (t, 1H), 1.56 (m, 1H); $^{13}$C NMR (125 MHz, CD$_3$OD) δ 155.6, 154.8, 142.7, 140.2, 137.6, 135.0, 134.8, 131.3, 130.3, 129.5, 127.4, 125.5, 114.4, 113.6, 66.9, 38.3, 33.8, 15.4. Anal. Calcd for C$_{24}$H$_{24}$O$_3$.H$_2$O: C, 76.17; H, 6.39. Found: C, 76.04; H, 6.41.

Method B.

Monoalkylated with 2-(dimethylamino) ethyl chloride hydrochloride. A solution of (1a-1n) (1.4 mmol) in DMF (5 mL) was treated with Cs$_2$CO$_3$ (3.3 mmol) and heated in an oil bath at 70-80° C. The resulting suspension was treated with 2-(dimethylamino)ethyl chloride hydrochloride (5 mmol) in a small portion over a 15 min. period and stirred for 2.5 h. After cooling at rt., the reaction mixture was poured into saturated ammonium chloride (10 mL) and extracted with ethyl acetate (3×15 mL). The combined organic phase was washed with brine (3×15 mL), dried, and concentrated.

(Z)-4-[1-(4-Dimethylaminoethoxy-phenyl)-3-methyl-2-phenyl-but-1-enyl]-phenol (3a)

This compound was prepared using method B. A solution of 1,1-Bis (4-hydroxyphenyl)-2-phenylbut-3-methyl-1-ene (1a) (0.45 g, 1.4 mmol) in DMF (5 mL) was treated with Cs$_2$CO$_3$ (1.06 g, 3.3 mmol) and heated in an oil bath at 70-80° C. The resulting suspension was treated with 2-(dimethylamino)ethyl chloride hydrochloride (0.75 g, 5 mmol) in a small portion over a 15 min. period and stirred for 2.5 h. After cooling at rt., the reaction mixture was poured into saturated ammonium chloride (10 mL) and extracted with ethyl acetate (3×15 mL). The combined organic phase was washed with brine (3×15 mL), dried, and concentrated. Flash chromatography (9:1 CH$_2$Cl$_2$/MeOH) afforded desired product (2a) (0.35 g, 64%) as a 1:1 mixture of E/Z isomers (beige solid). Crystallization of the solid with a 1:1 E/Z ratio (15 mg) from methanol gave white crystals (3a) (6.1 mg): mp 168.8° C. $^1$H NMR (600 MHz, CD$_3$OD) δ 7.17-7.05 (m, 7H), 6.80 (d, 2H), 6.74 (d, 2H), 6.38 (d, 2H), 3.88 (t, 2H), 2.68 (t, 2H), 3.02 (m, 1H), 2.31 (s, 6H), 0.94 (d, 6H). $^{13}$C NMR (125 MHz, CD$_3$OD) δ 157.8, 157.1, 141.3, 140.0, 137.5, 135.8, 132.3, 132.1, 131.4, 128.2, 126.8, 116.0, 114.2, 66.3, 59.1, 45.8, 32.8, 22.2. Anal. Calcd for C$_{27}$H$_{31}$NO$_2$: C, 80.76; H, 7.78; N, 3.49. Found: C, 80.91; H, 7.81; N, 3.42.

(Z)-4-{1-[4-(2-Dimethylamino-ethoxy)-phenyl]-4-methyl-2-phenyl-pent-1-enyl}-phenol (3b)

This compound was prepared using method B. The crude product was purified by flash column chromatography (9:1 CH$_2$Cl$_2$/MeOH) afforded 0.2 g (2b) (51%) as a 1:1 mixture of E/Z isomers as white solid. Crystallization of the solid with a 1:1 E/Z ratio from methanol gave white crystals (3b): mp 158.2° C. $^1$H NMR (600 MHz, CD$_3$OD) δ 7.16 (m, 5H), 7.04 (m, 2H), 6.79 (d, 2H), 6.53 (d, 2H), 6.31 (d, 2H), 3.90 (t, 2H), 2.72 (t, 2H), 2.36 (m, 2H), 2.34 (s, 6H), 1.50 (m, 1H), 0.80 (d, 6H); $^{13}$C NMR (125 MHz, CD$_3$OD) δ 158.5, 157.7, 144.3, 140.6, 137.5, 136.0, 135.8, 133.6, 132.8, 131.6, 128.7, 127.6, 116.1, 109.6, 65.8, 46.8, 45.3, 45.2, 27.9, 23.9. Anal. Calcd for C$_{28}$H$_{33}$NO$_2$: C, 80.93; H, 8.00; N, 3.37. Found: C, 80.92; H, 7.93, N, 3.29.

(Z)-5-[4-(2-Dimethylamino-ethoxy)-phenyl]-5-(4-hydroxyphenyl)-2-methyl-4-phenyl-pent-4-enoic acid methyl ester (3h, DY181)

This compound was prepared using method B. The crude product was purified by flash column chromatography (9:1 CH$_2$Cl$_2$/MeOH) afforded 0.2 g (51%) as a 1:1 mixture of E/Z isomers as semisolid (2h). Crystallization of the semisolid with a 1:1 E/Z ratio from methanol gave white crystals (3h): mp 132.3° C. $^1$H NMR (600 MHz, CD$_3$OD) δ 7.16 (m, 5H), 7.04 (d, 2H), 6.78 (dd, 4H), 6.67 (d, 2H), 3.95 (t, 2H), 3.45 (s, 3H), 2.84 (m, 1H), 2.68 (t, 2H), 2.56 (m, 1H), 2.38 (m, 1H), 2.29 (s, 6H), 1.04 (d, 3H); $^{13}$C NMR (125 MHz, CD$_3$OD) δ 178.6, 157.3, 156.5, 143.2, 142.6, 137.5, 136.0, 135.8, 133.6, 132.8, 131.6, 128.7, 127.2, 116.1, 1151, 52.0, 40.1, 39.8, 17.4. Anal. Calcd for C$_{29}$H$_{33}$NO$_4$.¼H$_2$O: C, 75.05; H, 7.17; N, 3.01. Found: C, 74.99; H, 7.39; N, 3.01.

(Z)-5-[4-(2-Dimethylamino-ethoxy)-phenyl]-5-(4-hydroxyphenyl)-4-phenyl-pent-4-enoic acid methyl ester (3g)

This compound was prepared using method B. The crude product was purified by flash column chromatography (9:1 CH$_2$Cl$_2$/MeOH) afforded 0.25 g (2g) (43%) as a 1:1 mixture of E/Z isomers as a yellow solid. Crystallization of the solid with a 1:1 Z/E ratio from methanol gave a white solid as a geometric pure isomer (3g): mp 163.1° C. $^1$H NMR (600 MHz, CD$_3$OD) δ 7.16 (d, 2H), 7.11 (t, 3H), 7.04 (d, 2H), 6.78 (dd, 4H), 6.58 (d, 2H), 3.96 (t, 2H), 3.53 (s, 3H), 2.79 (t, 2H), 2.68 (t, 2H), 2.30 (t, 2H), 2.27 (s, 6H). $^{13}$C NMR (125 MHz, CD$_3$OD) δ 175.3, 158.3, 157.6, 143.3, 141.6, 138.4, 137.1, 135.8, 132.9, 131.5, 130.9, 129.1, 127.4, 116.1, 114.4, 66.4, 59.1, 52.0, 45.8, 34.3, 32.3. Anal. Calcd for C$_{28}$H$_{31}$NO$_4$.2H$_2$O: C, 70.22; H, 6.48; N, 2.89. Found: C, 70.53; H, 6.41; N, 2.89.

(Z)-5-[4-(2-Dimethylamino-ethoxy)-phenyl]-5-(4-hydroxyphenyl)-4-phenyl-pent-4-ene-1-ol (3k) (GSK5182)

This compound was prepared using method B. A solution of 5,5-Bis-(4-hydroxyphenyl)-pent-4-ene-1-ol (1k) (0.5 g, 1.4 mmol) in DMF (5 mL) was treated with Cs$_2$CO$_3$ (1.37 g, 4.2 mmol) and heated in an oil bath at 70-80° C. The resulting suspension was treated with 2-(dimethylamino) ethyl chloride hydrochloride (0.43 g, 3 mmol) in a small portion over a 15 min. period and stirred for 3.5 h. After cooling at rt., the reaction mixture was poured into saturated ammonium chloride (10 mL), and extracted with ethyl acetate (3×15 mL). The combined organic phase was washed with brine (3×15 mL), dried, and concentrated. Flash chromatography (9:1 CH$_2$Cl$_2$/MeOH) afforded desired product (2k) (0.29 g, 50%) as a 1:1 mixture of E/Z isomers (yellow oil). Crystallization of the oil from methanol gave white crystals (3k), mp 168.8° C. $^1$H NMR (600 MHz, CD$_3$OD) δ 7.14-7.07 (m, 5H), 7.03 (d, 2H), 6.78 (dd, 4H), 6.58 (d, 2H), 3.96 (t, 2H), 3.42 (t, 2H), 2.73 (t, 2H), 2.52 (t, 2H), 2.33 (s, 6H), 1.54 (t, 2H). $^{13}$C NMR (125 MHz, CD$_3$OD) δ 158.1, 157.3, 144.2, 140.4, 137.6, 136.2, 133.0, 131.7, 130.9, 129.0, 127.1, 115.9, 114.4, 66.1, 63.1, 59.0, 45.7, 33.4, 33.1. Anal. Calcd for C$_{27}$H$_{31}$NO$_3$: C, 77.67; H, 7.48; N, 3.35. Found: C, 77.57; H, 7.50; N, 3.49.

(Z)-4-{1-[4-(2-Dimethylamino-ethoxy)-phenyl]-5-hydroxy-4-methyl-2-phenyl-pent-1-enyl}-phenol (3n)

This compound was prepared using method B. The crude product was purified by flash column chromatography (8:2

CH$_2$Cl$_2$/MeOH) afforded 0.57 g (41%) as a 1:1 mixture of E/Z isomers as yellow oil (2n). Flash chromatography (9:1 CH$_2$Cl$_2$/MeOH) afforded desired product as a Z-isomers (yellow solid). Crystallization of the solid from methanol gave white crystals (3n): mp 153.5° C. $^1$H NMR (600 MHz, CD$_3$OD) δ 7.11 (m, 5H), 7.06 (d, 2H), 6.79 (dd, 4H), 6.57 (d, 2H), 3.95 (t, 2H), 3.37 (m, 2H), 3.17 (m, 1H), 2.72 (t, 2H), 2.53 (m, 1H), 2.35 (s, 6H), 1.56 (m, 1H), 0.85 (d, 3H); $^{13}$C NMR (125 MHz, CD$_3$OD) δ 156.6, 155.7, 142.5, 140.0, 138.1, 136.2, 134.7, 131.3, 130.3, 129.5, 127.4, 125.6, 114.5, 112.9, 67.1, 64.9, 57.6, 44.3, 38.3, 34.1, 15.8. Anal. Calcd for C$_{28}$H$_{33}$NO$_3$.½H$_2$O: C, 76.32; H, 7.55; N, 3.18. Found: C, 76.56; H, 7.84; N, 3.23.

Method C. Acetalization.

A solution of 3a-3n (1.2 mmol) and acetyl chloride (5 mmol) of in pyridine (5 mL) were refluxed for 1 hr. Then, ice water was added, the aqueous layer was extracted with ether, and the organic extracts were washed with saturated NaHCO$_3$ solution. The combined organic phase was washed with brine (3×20 mL), dried, and concentrated.

(E)-4-{1-[4-(2-dimethylamino-ethoxy)-phenyl]-3-methyl-2-phenyl-but-1-enyl}-phenyl acetate (4a, DY40)

This compound was prepared using method C. (0.5 g 1.2 mmol) of (Z)-4-[1-(4-Dimethylaminomethoxy-phenyl)-3-methyl-2-phenyl-but-1-enyl]-phenol (3a) and 0.39 g (5 mmol) of acetyl chloride in pyridine (5 mL) were refluxed for 1 hr. Then, ice water was added, the aqueous layer was extracted with ether, and the organic extracts were washed with saturated NaHCO$_3$ solution. The combined organic phase was washed with brine (3×20 mL), dried, and concentrated. Flash chromatography (dichloromethane-methanol 9:1) afforded colorless oil as an oil (0.47 g, 88% yield). $^1$H NMR (600 MHz, CDCl$_3$) δ 7.23 (d, 2H), 7.22 (d, 2H), 7.10-6.99 (m, 5H), 6.77 (d, 2H), 6.50 (d, 2H), 3.88 (t, 2H), 2.96 (m, 1H), 2.67 (t, 2H), 2.31 (s, 6H), 2.23 (s, 3H), 0.89 (d, 6H).). $^{13}$C NMR (125 MHz, CDCl$_3$) δ 170.8, 157.9, 150.6, 147.4, 142.1, 138.9, 136.5, 132.2, 131.9, 131.8, 128.6, 128.1, 127.3, 126.8, 122.6, 115.6, 114.6, 114.5, 67.2, 59.6, 47.2, 32.3, 22.1. Anal. Calcd for C$_{30}$H$_{37}$NO$_3$: C, 78.40; H, 8.11; N, 3.05. Found: C, 78.50; H, 7.58; N, 3.09.

(E)-Acetic acid 5-[4-(2-dimethylamino-ethoxy)-phenyl]-5-(4-hydroxy-phenyl)-4-phenyl-pent-4-ene-1-ol (4k)

This compound was prepared using method C. 0.05 g (0.1 mmol) of (Z)-5-[4-(2-Dimethylamino-ethoxy)-phenyl]-5-(4-hydroxyphenyl)-4-phenyl-pent-4-ene-1-ol (3k) was dissolved in dry acetone (5 mL) and potassium carbonate (0.08 g, 0.6 mmol) was added. Acetyl chloride (0.05 g, 0.6 mmol) was added at 0° C. and the reaction mixture was stirred at 0° C. for 2 hours. Then, ice water was added, the aqueous layer was extracted with EtOAc (3×15 ml). The combined organic phase was washed with water, brine, dried over Na$_2$SO$_4$ and concentrated. Flash chromatography (dichloromethane-methanol 9:1) afforded colorless oil as a desired compound (0.037 g, 82% yield). $^1$H NMR (600 MHz, CD$_3$OD) δ 7.27 (d, 2H), 7.16 (t, 5H), 7.11 (d, 2H), 6.81 (d, 2H), 6.60 (d, 2H), 3.94 (t, 2H), 3.42 (t, 2H), 2.69 (t, 2H), 2.54 (t, 2H), 2.30 (s, 6H), 2.27 (s, 3H), 1.58 (t, 2H). $^{13}$C NMR (125 MHz, CD$_3$OD) δ169.8, 156.9, 149.6, 142.3, 141.1, 139.9, 138.2, 135.4, 131.6, 130.2, 129.4, 127.7, 125.9, 121.1, 113.2, 65.0, 61.5, 57.6, 44.4, 32.0, 31.6, 19.6. Anal. Calcd for C$_{29}$H$_{33}$NO$_4$.½H$_2$O: C, 74.17; H, 7.09; N, 2.98. Found: C, 74.19; H, 7.13; N, 2.91.

(E)-Acetic acid 5-[4-(2-dimethylamino-ethoxy)-phenyl]-5-(4-hydroxy-phenyl)-2-methyl-4-phenyl-pent-4-ene-1-ol (4n)

This compound was prepared using method C. 0.05 g (0.1 mmol) of (Z)-4-{1-[4-(2-Dimethylamino-ethoxy)-phenyl]-5-hydroxy-4-methyl-2-phenyl-pent-1-enyl}-phenol (3n) was dissolved in dry acetone (5 mL) and potassium carbonate (0.08 g, 0.6 mmol) was added. Acetyl chloride (0.05 g, 0.6 mmol) was added at 0° C. and the reaction mixture was stirred at 0° C. for 2 hours. Then, ice water was added and the aqueous layer was extracted with EtOAc (3×15 ml). The combined organic phase was washed with water, brine, dried over Na$_2$SO$_4$ and concentrated. Flash chromatography (dichloromethane-methanol 9:1) afforded colorless semi-solid as a desired compound (0.037 g, 79% yield). $^1$H NMR (600 MHz, CD$_3$OD) δ 7.22 (d, 2H), 7.12 (m, 5H), 7.06 (d, 2H), 6.77 (d, 2H), 6.55 (d, 2H), 3.91 (t, 2H), 3.30 (t, 1H), 3.15 (m, 1H), 2.65 (t, 2H), 2.52 (m, 1H), 2.27 (s, 6H), 2.24 (m, 1H), 2.21 (s, 3H), 1.51 (t, 1H), 0.82 (d, 3H). $^{13}$C NMR (125 MHz, CD$_3$OD) δ168.3, 155.2, 147.8, 140.3, 139.5, 137.5, 137.4, 133.8, 129.7, 128.6, 127.8, 125.9, 124.3, 119.5, 111.5, 65.4, 63.2, 55.9, 51.8, 45.7, 36.6, 32.3, 17.9, 14.1. Anal. Calcd for C$_{30}$H$_{35}$NO$_4$: C, 76.08; H, 7.45; N, 2.96. Found: C, 76.23; H, 7.61; N, 2.91.

Method D.

General procedure for the combinatorial solution-phase parallel preparation of small chemical library in Chemset 4. (Z)-4-[1-(4-Dimethylaminoethoxy-phenyl)-3-methyl-2-phenyl-but-1-enyl]-phenol (3a) (4.02 g, 10 mmol) was dissolved in dry DMF (100 mL) to make a 10 mM stock solution. The stock solution was transferred automatically in the Neptune work station of Bohdan from source reactant vials to the tubes of the 48-tube reaction block (1.0 ml/tube, 0.1 mmol/tube). Powder K$_2$CO$_3$ (6 equiv) was added to each tube. The reaction block was shaken for 30 min. A workstation of Mettler-Toledo system has been used to tare each reactant vial in an array of vials. Forty-eight different acyl chlorides and alkyl halides reagents (6 equiv, 0.6 mmol) were transferred automatically from reagents vials to each reactor block tube. The reaction mixture was vigorously shaken at warm condition (50° C.) for 12 h in a RAM organic synthesizer. The work-up procedure was carried out in a workstation of Mettler-Toledo system. 1 mL of H$_2$O was transferred automatically to each reactor block tube. The resultant mixture was extracted which was performed by transferring 1 mL of EtOAc to each reactor block tube. The mixture was stirred at ambient temperature for 1 h. The extraction was performed three times (3×1 mL). The combined organic layers (extracts) were transferred to 48 vials which were dried and concentrated in Savant concentrator to get crude yellow oils in total 48 substituted derivatives. Each of crude library member was dissolved in 0.2 mL of CH$_2$Cl$_2$ following purification by using the Biotage Quad 3 automated medium pressure flash chromatography (dichloromethane-methanol 9:1). The average yields of the targeted compounds in >85% and purity in >82%. The resulting fractions were analyzed by flow injection NMR to confirm the chemical structures by $^1$H and $^{13}$C NMR.

(E)-4-{1-[4-(2-dimethylamino-ethoxy)-phenyl]-2-phenyl-but-1-enyl}-phenyl acetate (4a {R$^B$(1)}, DY40)

This compound was prepared using method D. $^1$H NMR (600 MHz, CDCl$_3$) δ 7.23 (d, 2H), 7.22 (d, 2H), 7.10-6.99

(m, 5H), 6.77 (d, 2H), 6.50 (d, 2H), 3.88 (t, 2H), 2.96 (m, 1H), 2.67 (t, 2H), 2.31 (s, 6H), 2.23 (s, 3H), 0.89 (d, 6H).). $^{13}$C NMR (125 MHz, CDCl$_3$) δ 170.8, 157.9, 150.6, 147.4, 142.1, 138.9, 136.5, 132.2, 131.9, 131.8, 128.6, 128.1, 127.3, 126.8, 122.6, 115.6, 114.6, 114.5, 67.2, 59.6, 47.2, 32.3, 22.1.

(E)-4-{1-[4-(2-dimethylamino-ethoxy)-phenyl]-3-methyl-2-phenyl-but-1-enyl}-phenyl acetate (4b, {R$^B$ (2)})

This compound was prepared using method D. $^1$H NMR (600 MHz, CDCl$_3$) δ 7.23 (d, 2H), 7.22 (d, 2H), 7.10-6.99 (m, 5H), 6.77 (d, 2H), 6.50 (d, 2H), 3.88 (t, 2H), 2.96 (m, 1H), 2.67 (t, 2H), 2.60 (q, 2H), 2.33 (s, 6H), 1.27 (t, 3H), 0.89 (d, 6H).). $^{13}$C NMR (125 MHz, CDCl$_3$) δ 170.8, 157.9, 150.6, 147.4, 142.1, 138.9, 136.5, 132.2, 131.9, 131.8, 128.6, 128.1, 127.3, 126.8, 122.6, 115.6, 114.6, 114.5, 67.2, 59.6, 47.2, 32.3, 22.1. Anal. Calcd for C$_{29}$H$_{33}$NO$_3$: C, 78.52; H, 7.50; N, 3.16. Anal. Calcd for C$_{29}$H$_{33}$NO$_3$: C, 78.52; H, 7.50; N, 3.16. Found: C, 78.50; H, 7.58; N, 3.09.

(E)-4-{1-[4-(2-Dimethylamino-ethoxy)-phenyl]-2-phenyl-pent-1-enyl}-pentyl)-phenyl acetate (4c{R$^B$ (1)})

The compound 4c was prepared from 3c by using method C in 80% yield. It was obtained as colorless oil. $^1$H NMR (600 MHz, CDCl$_3$) δ 7.21-7.05 (m, 7H), 6.89 (d, 2H), 6.75 (d, 2H), 6.55 (d, 1H), 6.46 (d, 1H), 4.09 (t, 1H), 3.93 (t, 1H), 2.74 (t, 1H), 2.64 (t, 1H), 2.44 (t, 2H), 2.35 (s, 3H), 2.28 (s, 3H), 2.19 (s, 3H), 1.24 (m, 4H), 0.81 (t, 3H).

Cell culture. CV-1 cells were grown in Dulbecco's modified Eagle's medium supplemented with 10% resin charcoalstripped fetal bovine serum, 50 U/ml penicillin G, and 50 μg/ml streptomycin sulfate (DMEM-FBS) at 37° C. in 5% CO$_2$. One day prior to transfection, cells were plated to 50%-80% confluence using phenol red free DMEM-FBS. The adenoviral construct, Ad-GFP and Ad-ERRα have been described.[55] Propagation of recombinant adenovirus was performed in 293 cells as described.[11]

Cell-Based Reporter Gene Assays.

Cell based transactivation assays were performed in CV-1 cells as described.[49] ERR activity was assayed with a GAL4 reporter construct and fusion proteins containing the ligand binding domains of human ERRα, human ERRβ and mouse ERRγ linked to the DNA binding domain of yeast GAL4. Human ERα and ERβ were examined as full-length proteins using an estrogen receptor responsive reporter construct. Reporter constructs (300 ng/10$^5$ cells) and cytomegalovirus-driven expression vectors (20-50 ng/10$^5$ cells) were added as indicated along with CMX-β-gal (500 ng/10$^5$ cells) as an internal control. Cells were transiently transfected by Lipofectamine as described.[56] Cells were incubated with DNA complexed liposomes for 2 hours and subsequently treated for approximately 45 hr with phenol red free DMEM FBS containing the indicated compounds. After exposure to ligand, the cells were harvested and assayed for luciferase and β-galactosidase activity. All points were assayed in triplicate and varied by less than 15%. Each experiment was repeated three or more times with similar results. Fold activation is reported.

Quantitative Real-Time PCR.

RNA was isolated from myocytes using Trizol (Invitrogen, Carlsbad, Calif., USA). RNA (1 μg) was reverse transcribed using the iScript cDNA Synthesis Kit (Bio-Rad, Hercules, Calif., USA). PCR was performed in 15 μL reactions containing 1×SYBR Green reagent and 0.1 μM gene-specific primers using the iQ5 Real-Time PCR system (Bio-Rad).

Experimental transcript levels were normalized to 36B4 ribosomal RNA analyzed in separate reactions. The SHP primers used are as follows: mouse Shp FWD 5'-CTGCA-GGTCGTCCGACTATTC-3' (SEQ ID NO:1), RV 5'-AGT-GAGCCTCCTGTTGCAGG-3' (SEQ ID NO:2); human SHP FWD 5'-TCAAGTCCATTCCGACCAGC-3' (SEQ ID NO:3); RV 5'-AAGAAGGCCAGCGATGTCAA-3' (SEQ ID NO:4). Primers sequences for 36B4 have been previously published.[52, 57]

Fatty Acid Oxidation Assay.

The analysis of fatty acid oxidation rates in cells was performed as previously described.[57] Fatty acid $^3$H-[9,10]-palimitic acid was complexed to fatty acid-free BSA and this complex was added to 30 uM unlabeled palmitate. The radiolabeled palmitate substrate was diluted in PBS and incubated with cells for 2 hours. The substrate was removed and radiolabeled aqueous metabolites ($^3$H2O) released to the media were measured by scintillation counting. The calculated rates were normalized to total cellular protein.

Statistical Analysis.

All quantitative data are presented as mean±S.E.M or mean±S.D. Significant differences between mean values were determined by unpaired Student's t test. A p-value of ≤0.05 was considered significant and is denoted by asterisks (*).

Example 3. Targeting ERRγ to Treat NASH

Type 2 diabetes in particular has recently become more common, along with the obesity epidemic. Notably, obesity and type-2 diabetes are key risk factors associated with abnormal regulation of hepatic glucose production leading to Nonalcoholic steatohepatitis (NASH), an extreme form of nonalcoholic fatty liver disease (NAFLD) having the presence of hepatic steatosis with inflammation and hepatocyte injury. The growing incidence of metabolic disease has led to an intense interest in identifying new molecular targets and pharmacologic agents to treat and/or prevent these metabolic disorders. Much attention has been paid recently to the functions of ERRs, the orphan nuclear receptors for their potential roles as new therapeutic targets implicated in the etiology of metabolic disorders. Thus, there is clearly a need to understand the molecular events linking metabolism, metabolic disease and NASH, and to translate these findings into novel therapeutic strategies.

The nuclear orphan receptor ERRγ is a molecular target for treating NASH. Our data demonstrate that ERRγ is a key metabolic integrator that regulates lipid accumulation, insulin sensitivity, triglyceride and glucose homeostasis in the liver and muscle, indicating the essential bifurcations of ERRγ in numerous metabolic pathways. Since dysregulation of glucose homeostasis and insulin sensitivity is often associated with obesity, diabetes and diabetic NASH, suggesting that ERRγ is a novel transcriptional regulator contributing to the development of diabetic NASH.

Example 4. ERRγ is a Therapeutic Target for Human NASH

ERRγ is a transcriptional regulator of hepatic LIPIN1 and ERRγ is a link between NASH and LIPIN pathway in DAG (diacylglycerol)/TG synthesis based on induction of LIPIN pathway in DAG/TG synthesis and evidence of the ERRγ regulation of hepatic gluconeogenesis in the liver. This dramatic linkage between ERRγ and LIPIN pathway in DAG/TG synthesis may indicate the expression of the gene encoding Lpin1 is under the control of the ERRγ and its coactivator the peroxisome proliferator-activated receptor γ coactivator-1α (PGC-1α). ERRγ regulation of lipin shown in heart and liver, points to relevance of ERRγ target gene regulation in liver to NASH. Finally, expression of ERRγ appears to be higher in human HCC specimens (Kim, et al.). Taken together, these results suggest a novel role of ERRγ as a molecular target for both NASH and HCC. ERRγ modulators provide a targeted metabolic therapy against NASH.

Example 5. Targeting ERRγ & LIPIN Pathway in DAG/TG Synthesis to Treat NASH

Lipin1 is an intracellular protein that was first identified by using a positional cloning approach to localize the causative mutation in the fatty liver dystrophic (fld) mouse. Fld mice exhibit neonatal hepatic steatosis, life-long deficiencies in adipose tissue development, insulin resistance, and increased susceptibility to developing atherosclerotic lesions. LIPIN1 was later shown to be involved in lipid and glucose metabolism in a variety of tissues, including adipose tissue, liver, and skeletal muscle. Lipin1 interacts with the peroxisome proliferator-activated receptor α (PPARα) and its coactivator protein PPARγ coactivator-1α (PGC-1α) and increases expression of genes involved in fatty acid oxidation (FAO) in liver.

LIPIN1 has been reported to perform important roles in the regulation of intracellular lipid levels. Their mutations induce lipodystrophy, myoglobinuria, and inflammatory disorders. Recently, the phosphatidic acid phosphatase function of LIPINs has been associated with the perturbation of hepatic insulin receptor signaling via the diacylglycerol-mediated stimulation of PKCε activity. Interestingly, it has been demonstrated that Lipin family proteins are bifunctional intracellular proteins that regulate metabolism by acting as coregulators of DNA-bound transcription factors and also dephosphorylate phosphatidate to form DAG in the triglyceride synthesis pathway.[1]

The research [1] also demonstrated that the expression of the gene encoding Lpin1 is under the control of the ERRs and their coactivator the peroxisome proliferator-activated receptor γ coactivator-1α (PGC-1α). PGC-1α, ERRα, or ERRγ overexpression increased Lpin1 transcription in cultured ventricular myocytes and the ERRs were associated with response elements in the first intron of the Lpin1 gene. Concomitant RNAi-mediated knockdown of ERRα and ERRγ abrogated the induction of lipin 1 expression by PGC-1α overexpression. Consistent with these data, 3-fold overexpression of PGC-1α in intact myocardium of transgenic mice increased cardiac lipin 1 and ERRα/γ expression. Similarly, injection of the 02-adrenergic agonist clenbuterol induced PGC-1α and lipin1 expression, and the induction in lipin1 after clenbuterol occurred in a PGC-1α-dependent manner. In contrast, expression of PGC-1a, ERRα, ERRγ, and lipin 1 was down-regulated in failing heart. Cardiac phosphatidic acid phosphohydrolase activity was also diminished, while cardiac phosphatidate content was increased, in failing heart. Collectively, these data suggest that lipin1 is the principal lipin protein in the myocardium and is regulated in response to physiologic and pathologic stimuli that impact cardiac metabolism.

Interestingly, independent studies have established a very similar relationship between ERRγ and liver disease. Overexpression of ERRγ significantly increased LIPIN1 expression in primary hepatocytes, whereas the abolition of ERRγ gene expression attenuated the expression of LIPIN1. Also, knockdown of ERRγ improves hyperglycemia in diabetic mice. Strong labeling of apoptotic hepatocytes were observed and genes involved in inflammation and in cell cycle control were up-regulated in ERRγ-overexpression mice. Deletion and mutation analyses of the LIPIN1 promoter showed that ERRγ exerts its effect on the transcriptional regulation of LIPIN1 via ERRE1 of the LIPIN1 promoter, as confirmed by ChIP assay. The studies also determined that the gene transcription of LIPIN1 by ERRγ is controlled by the competition between PGC-1α and SHP (small heterodimer partner). Additionally, ERRγ leads to the induction of hepatic LIPIN1 expression and DAG production in vivo. As expected, ERRγ inverse agonist restores the impaired insulin signaling induced by LIPIN1-mediated PKCε activation. Indicate that ERRγ is a novel transcriptional regulator of LIPIN1 and ERRγ-mediated induction of LIPIN1 results in the perturbation of hepatic insulin signaling through DAG-mediated activation of PKCε.[2]

Example 6

To examine if ERRγ is a potential target for the treatment of diabetes and its complications, we are investigating the therapeutic potential of ERRγ modulator in insulin resistance, fat accumulation and diabetic-related diseases. ERRγ inverse agonist restores the impaired insulin signaling induced by LIPIN1-mediated PKCε activation were elucidated from studies of 293T and HepG2 cells, as well as in animal models of insulin-resistant (db/db mice) and diet-induced obesity (DIO) mice. To investigate the molecular mechanism by which ERRγ regulates LIPIN1 gene expression, the effects of ERRγ in the induction of hepatic LIPIN1 expression and DAG production in vivo were determined. Consistent with the in vitro results, the hepatic overexpression of ERRγ via the tail vein injection of Ad-ERRγ resulted in a marked induction of LIPIN1 compared with controls. Additionally, hepatic DAG levels were also significantly increased by overexpression, thereby suggesting that ERRγ does indeed regulate hepatic LIPIN1 expression, resulting in DAG production both in vitro and in vivo. Since ERRγ stimulates LIPIN1 expression, the effects of ERRγ inverse agonist on the regulation of LIPIN1 by ERRγ in HepG2 cells were evaluated. ERRγ inverse agonist resulted in a marked reduction of ERRγ-induced LIPIN1 promoter activity in a dose-dependent manner. Additionally, the ERRγ-mediated induction of LIPIN1 mRNA was significantly reduced by ERRγ inverse agonist treatment in rat primary hepatocytes but not that of ERRγ Y326A, which cannot interact with ERRγ inverse agonist; this suggests that the inverse agonist selectively inhibits the transcriptional activity of ERRγ.

Since LIPIN1 has a PAP function to catalyze the conversion of PA to DAG, which is a precursor of triglyceride, indicating that DAG functions as a link between lipid accumulation and insulin signaling. Additionally, the inhibition of inverse agonist of ERRγ in LIPIN1-mediated DAG production was determined, suggesting that the inhibition of transcriptional activity of ERRγ by its inverse agonist could be an attractive pathway for the suppression of LIPIN1-mediated DAG production in NASH treatment.

Example 7. Adipose Tissue and Regulation of Obesity/Energy Balance (ERRβ)

We reason that selective targeting of ERRγ/β has more robust effects in diabetes. In fact, ERRγ inverse agonist GSK5182 is effectively at lowering body weight, adipose mass, and hepatic lipid accumulation in db/db and DIO Mice. However, we tested GSK5182 using a reporter gene assay in transiently transfected CV-1 cells, and found that it has beneficial effects on ERRγ, but mixed ERRγ/β activity.

The physiologic role of ERRβ has been elusive and difficult to study since homozygous deletion of the Esrrb gene results in impaired placental formation and death at 9.5-10.5 d.p.c.[3] Recently two viable conditional ERRβ-/- mouse models were generated, one driving deletion in embryo and the other in the CNS. While these knockouts do not target the adipose tissue, they reveal a function for ERRβ in hypothalamic regulation of feeding behavior, satiety, whole body energy balance.[4] In the studies by Byerly and colleagues, the Sox2-Cre:ERRβlox/lox mice in which ERRβ was knocked out in the developing embryo are lean with increased activity and basal metabolic rate. Despite this change in body composition, the mice consumed more food consistent with increased hypothalamic expression of neuropeptide Y (NPY) and agouti-related peptide (Agrp), neuropeptides that regulate feeding and energy expenditure. These results suggest that the phenotype originates in the CNS.

To test this notion the Nestin-Cre:ERRβlox/lox mice the Esrrb gene was selectively disrupted in the developing nervous system. ERRβ expression is eliminated in neurons within the hindbrain, the CNS region with the highest ERRβ expression. Loss of ERRβ results in an increased lean: adipose mass ratio and increased energy expenditure despite increased feeding frequency. The feeding behavior is dissociated from NPY expression, which is reduced in Nestin-Cre:ERRβlox/lox mice. Both of the ERRβ deficient mouse strains show a preference for carbohydrate metabolism as demonstrated by a higher respiratory exchange ratio and have enhanced insulin sensitivity. Interestingly, ERRγ expression was increased in both ERRβ/models, suggesting that some of the metabolic changes may be driven by ERRγ activation. Indeed, pharmacologic activation of ERRγ in the presence or absence of ERRβ reduced NPY expression, decreased satiety and increased feeding frequency.[4] The association between feeding behavior and NPY expression is complex, so the changes in NPY expression in these models may be secondary to altered glucose metabolism with enhanced insulin sensitivity or to changes in stress hormone (i.e. corticosterone) levels.[4] The counter-regulatory pattern of ERRβ and ERRγ has significant implications for the mechanism by which ERRs regulate CNS effects on whole body energy balance. The ERRβ and ERRγ homodimers may simply regulate expression of overlapping target genes, and ERRγ upregulation drives the observed gene expression changes in ERRβ null mice. Alternately, ERRβ: ERRγ heterodimers may be involved in differential regulation of target genes when their relative expression levels change. Thus, the expression ratio between ERRβ and ERRγ may be an important graded mechanism to modulate feeding behavior by altering the expression of genes that control satiety and whole-body energy balance.[1]

REFERENCES

Huss, et al., Biochimica et Biophysica Acta 2015, 1852, 1912-1927.
Kim, D. K. et al. J. Biol. Chem. 2011, 286, 38035-42.
Luo, J. et al., Nature, 1997, 388, 778-782.
Byerly, et al., European Journal of Neuroscience, 2013, 37, 1033-1047.
1. Giguère, V.; Yang, N.; Segui, P.; Evans, R. M. Nature 1988, 331, 91.
2. Giguere, V. Trends Endocrinol. Metab. Rev. 2002, 5, 13.
3. Vanacker, J. M.; Delmarre, C.; Guo, X.; Laudet, V. Cell Growth Differ. 1998, 9, 1007.
4. Audet-Walshi, É.; Giguère, V. Acta Pharmacologica Sinica 2015, 36, 51.
5. Yang, X.; Downes, M.; Yu, R. T.; Bookout, A. L.; He, W.; Straume, M.; Mangelsdorf, D. J.; Evans, R. M. Cell 2006, 126, 801.
6. Horard, B.; Vanacker, J. M. J. Mol. Endocrinol. 2003, 31, 349.
7. Wang, L.; Zuercher, W. J.; Consler, T. G.; Lambert, M. H.; Miller, A. B.; Orband-Miller, L. A.; McKee, D. D.; Willson, T. M.; Nolte, R. T. J. Biol. Chem. 2006, 281, 37773.
8. Gaillard, S.; Dwyer, M. A.; McDonnell, D. P. Mol. Endocrinol. 2007, 21, 62.
9. Giguère V. Endocr. Rev. 2008, 29, 677.
10. Villena, J. A.; Kralli, A. Trends Endocrinol. Metab. 2008, 19, 269.
11 Huss, J. M.; Torra, I. P.; Staels, B.; Giguere, V.; Kelly, D. P. Mol. Cell Biol. 2004, 24, 9079.
12 Ariazi, E. A.; Clark, G. M.; Mertz, J. E. Cancer Res. 2002, 62, 6510.
13 Suzuki, T.; Miki, Y.; Moriya, T.; Shimada, N.; Ishida, T.; Hirakawa, H.; Ohuchi, N.; Sasano, H. Cancer Res. 2004, 64, 4670.
14 Chang, C. Y.; Kazmin, D.; Jasper, J. S.; Kunder, R.; Zuercher, W. J.; McDonnell, D. P. Cancer Cell 2011, 20, 500.
15 Deblois, G.; Smith, H. W.; Tam, I. S.; Gravel, S-P.; Savage, P.; Labbe, D. P.; Tremblay, M. L.; Park, M.; St-Pierre, J.; Muller, W. J.; et al. Nature communications 2016, 7, 12156.
16 Handschin, C.; Mootha, V. K. Drug Discovery Today: Ther. Strategies 2005, 2, 151.
17 Ariazi, E. A.; Jordan, V. C. Curr. Top. Med. Chem. 2006, 6, 181.
18 Kraus, R. J.; Ariazi, E. A.; Farrell, M. L.; Mertz, J. J. Biol. Chem. 2002, 277, 24826.
19 Mitsunaga, K.; Araki, K.; Mizusaki, H.; Morohashi, K.; Haruna, K.; Nakagata, N.; Giguere, V.; Yamamura, K.; Abe, K. Mech. Dev. 2004, 121, 237.
20 Ichida, M.; Nemoto, S.; Finkel, T. J. Biol. Chem. 2002, 277, 50991.
21 Chen, J.; Nathans, J. Dev Cell 2007, 13, 325.
22 Feng, B.; Ng, J. H.; Heng, J. C.; Ng, H. H. Cell Stem Cell. 2009, 4, 301.
23 Ivanova, N.; Dobrin, R.; Lu, R.; Kotenko, I.; Levorse, J.; DeCoste, C.; Schafer, X.; Lun, Y.; Lemischka, I. R. Nature 2006, 442, 533.
24 Yu, S.; Wong, Y. C.; Wang, X. H.; Ling, M. T.; Ng, C. F.; Chen, S. et al. Oncogene 2008, 27, 3313.
25 Heard, D. J.; Norby, P. L.; Holloway, J.; Vissing, H. Mol. Endocrinol. 2000, 14, 382.
26 Kim, D-K.; Kim, J. R.; Koh, M. et al. J. Biol. Chem. 2011, 286, 38035.
27 Eichner, L. J.; Perry, M-C, Dufour, C. R.; Bertos, N.; Park, M.; St-Pierre, J.; Gigue`re, V. Cell Metab. 2010, 12, 352.
28 Ijichi, N.; Shigekawa, T.; Ikeda, K.; Horie-Inoue, K.; Fujimura, T.; Tsudad, H.; Osaki, A.; Saeki, T.; Inoue, S. Journal of Steroid Biochemistry & Molecular Biology, 2011, 123, 1.
29 Busch, B. B.; Stevens, W. C., Jr.; Martin, R.; Ordentlich, P.; Zhou, S.; Sapp, D. W.; Horlick, R. A.; Mohan, R. J. Med. Chem. 2004, 47, 5593.

30 Peng, L.; Gao, X.; Duan, L.; Ren, X.; Wu, D.; Ding, K. *J. Med. Chem.* 2011, 54, 7729.
31 Zuercher, W. J.; Gaillard, S.; Orband-Miller, L. A.; Chao, E. Y. H.; Shearer, B. G.; Jones, D. G.; Miller, A. B.; Collins, J. L.; McDonnell, D. P.; Willson, T. M. *J. Med. Chem.* 2005, 48, 3107.
32 Yu, D. D.; Forman, B. M. Identification of an agonist ligand for estrogen-related receptors ERRβ/γ. *Bioorg. Med. Chem. Lett.* 2005, 15, 1311.
33 Coward, P.; Lee, D.; Hull, M. V.; Lehmann, J. M. *PNAS*, 2001, 98, 8880.
34 Tremblay G. B.; Bergeron D.; Giguere V. *Endocrinology*, 2001, 142, 4572.
35 Tremblay, G. B.; Kunath, T.; Bergeron, D.; Lapointe, L.; Champigny, C.; Bader, J. A. et al. *Genes. Dev.* 2001, 15, 833.
36 Chao, E. Y. H.; Collins, J. L.; Gaillard, S.; Miller, A. B.; Wang, L.; Orband-Miller, L. A.; Nolte, R. T.; McDonnell, D. P.; Willson, T. M.; Zuercher, W. *J. Bioorg. Med. Chem. Lett.* 2006, 16, 821.
37 Kim, J.; Chin, J.; Im, C. Y.; Yoo, E. K.; Woo, S.; Hwang, H. J.; Cho, J-h.; Seo, K-a.; Song, J.; Hwang, H.; Kim, K-H.; Kim, N. D.; Yoon, S. K.; Jeon, J-H.; Yoon, S-Y.; Jeon, Y. H. Choi, H-S.; Lee, I-K.; Kim, S. H.; Cho, S. *J. European Journal of Medicinal Chemistry*, 2016, 120, 338.
38 Di Micco, S; Renga, B; Carino, A; D'Auria, M. V.; Zampella, A.; Riccio, R.; Fiorucci, S.; Bifulco, G. *Steroids* 2014, 80, 51.
39 Greschik, H.; Wurtz, Jean-Marie; Sanglier, S.; Bourguet, W.; van Dorsselaer, A.; Moras, D.; Renaud, Jean-paul. *Molecular Cell*, 2002, 9, 303.
40 Robertson, D. W.; Katzenellenbogen, J. A.; Long, D. J.; Rorke, E. A.; Katzenellenbogen, B. S. *J. Steroid Biochem.* 1982, 16, 1.
41 Yu, D. D.; Forman, M. B. *J. Org. Chem.,* 2003, 24, 9489.
42 McMurry, J. E.; Fleming, M. P. *J. Org. Chem.* 1976, 41, 896.
43 Lubczyk, V.; Bachmann, H.; Gust, R. *J. Med. Chem.* 2002, 45, 5358.
44 Gauthier, S.; Mailhot, J.; Labrie, F. *J. Org. Chem.,* 1996, 61, 3890.
45 Schnrider, M. R.; von Angerer, E.; Schonenberger, H.; Michel, R. T.; Fortmeyer, H. P. *J. Med. Chem.* 1982, 25, 1070.
46 Jordan, V. C.; Koch, R.; Langan, S.; McCague, R. *Endocrinology* 1988, 122, 1449.
47 Kim, Y.; Koh, M.; Kim, D.; Choi, H.; Park, S. B. *J. Comb. Chem.* 2009, 11, 928.
48 Lubczyk, V.; Bachmann, H.; Gust, R. *J. Med. Chem.* 2003, 46, 1484.
49 Wang, H.; Chen, J.; Hollister, K.; Sower, L. C.; Forman, B. M. *Mol. Cell* 1999, 3, 543.
50 Sanyal, S.; Kim, J-Y.; Kim, H-J.; Takeda, J.; Lee, Y-K.; Moore, D. D.; Choi, H-S. *J. Biol. Chem.* 2002, 277, 1739.
51 Sanyal, S.; Matthews, Jason.; Bouton, D.; Kim, H-J.; Choi, H-S.; Treuter, E.; Gustafsson, J-A. *Mol. Endocrinol* 2004, 18, 312.
52 Murray, J.; Auwerx, J.; Huss, J. M. *FASEB Journal* 2013, 27, 135.
53 Biasini, M.; Bienert, S.; Waterhouse, A.; Arnold, K.; Studer, G.; Schmidt, T.; Kiefer, F.; Cassanno, T. G.; Bertoni, M.; Bordoli, L.; Schwede, T. *Nucleic Acids Research* 2014, 42, W252.
54 Nam, S.; Wen, W.; Schroeder, A.; Herrmann, A.; Yu, H.; Cheng, X.; Merz, K. H.; Eisenbrand, G.; Li, H.; Yuan, Y. C.; Jove, R. *Mol. Oncol.* 2013, 7, 369.
55 Dufour, C. R.; Wilson, B. J.; Huss, J. M.; Kelly, D. P.; Alaynick, W. A.; Downes, M.; Evans, R. M.; Blanchette, M.; Giguere, V. *Cell Metab.* 2007, 5, 345.
56 Forman, B. M.; Goode, E.; Chen, J.; Oro, A. E.; Bradley, D. J.; Perlmann, T.; Noonan, D. J.; Burka, L. T.; McMorris, T.; Lamph, W. W. Evans, R. M. Weinberger, C. *Cell,* 1995, 81, 687.
57 Murray, J.; Huss, J. M. *Journal of Physiology* 2011, 301, C630.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method of treating non-alcoholic fatty liver disease or non-alcoholic steatohepatitis, said method comprising administering to a subject having non-alcoholic fatty liver disease or non-alcoholic steatohepatitis an effective amount of a compound having the formula:

(Ia)

wherein, $L^{1A}$ is a bond, substituted or unsubstituted alkylene, or substituted or unsubstituted heteroalkylene;

$L^{1B}$ is a bond, —C(O)O—, —OC(O)—, —O—, —C(O)—, —NH—, —NHC(O)—, or —C(O)NH—;

$R^1$ is independently hydrogen, halogen, —$CX^1_3$, —$CHX^1_2$, —$CH_2X^1$, —$OCX^1_3$, —$OCH_2X^1$, —$OCHX^1_2$, —CN, —$SO_{n1}R^{1D}$, —$SO_{v1}NR^{1A}R^{1B}$, —NHC(O)$NR^{1A}R^{1B}$, —N(O)$_{m1}$, —$NR^{1A}R^{1B}$ C(O) $R^{1C}$, —C(O)—$OR^{1C}$, —C(O)$NR^{1A}R^{1B}$, —$OR^{1D}$, —$NR^{1A}SO_2R^{1D}$, —$NR^{1A}C(O)R^{1C}$, —$NR^{1A}C(O)$ $OR^{1C}$, —$NR^{1A}OR^{1C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^2$ is independently hydrogen, —$CX^2_3$, —$CHX^2_2$, —$CH_2X^2$, —$C(O)R^{2A}$, —$C(O)OR^{2A}$, —C(O) $NR^{2A}R^{2B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^3$ is independently hydrogen, —$CX^3_3$, —$CHX^3_2$, —$CH_2X^3$, —$C(O)R^{3A}$, —$C(O)OR^{3A}$, —C(O) $NR^{3A}R^{3B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

each $R^{1A}$, $R^{1B}$, $R^{1C}$, $R^{1D}$, $R^{2A}$, $R^{2B}$, $R^{3A}$, and $R^{3B}$ is independently hydrogen, —$CX_3$, —CN, —COOH, —$CONH_2$, —$CHX_2$, —$CH_2X$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{1A}$ and $R^{1B}$ substituents bonded to the same nitrogen atom may optionally be joined to form a substituted or unsubstituted heterocycloalkyl or substituted or unsubstituted heteroaryl; $R^{2A}$ and $R^{2B}$ substituents bonded to the same nitrogen atom may optionally be joined to form a substituted or unsubstituted heterocycloalkyl or substituted or unsubstituted heteroaryl; $R^{3A}$ and $R^{3B}$ substituents bonded to the same nitrogen atom may optionally be joined to form a substituted or unsubstituted heterocycloalkyl or substituted or unsubstituted heteroaryl;

each X, $X^1$, $X^2$, and $X^3$ is independently —F, —Cl, —Br, or —I;

n1 is an integer from 0 to 4; and m1 and v1 are independently an integer from 1 to 2.

2. The method of claim 1, wherein, $L^{1A}$ is —$CH_2CH(CH_3)$—, —$CH_2C(CH_3)_2$—, —$CH_2CH_2CH(CH_3)$—, or —$CH_2CH_2C(CH_3)_2$;

$L^{1B}$ is a bond or —C(O)O—;

$R^1$ is hydrogen or substituted or unsubstituted $C_1$-$C_6$ alkyl;

$R^2$ is independently hydrogen, —$CX^2_3$, —$CHX^2_2$, —$CH_2X^2$, —$C(O)R^{2A}$, —$C(O)OR^{2A}$, —C(O) $NR^{2A}R^{2B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R³ is independently hydrogen, —CX³³, —CHX³², —CH₂X³, —C(O)R³ᴬ, —C(O)OR³ᴬ, —C(O)NR³ᴬR³ᴮ, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

each R²ᴬ, R²ᴮ, R³ᴬ, and R³ᴮ is independently hydrogen, —CX₃, —CN, —COOH, —CONH₂, —CHX₂, —CH₂X, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; R²ᴬ and R²ᴮ substituents bonded to the same nitrogen atom may optionally be joined to form a substituted or unsubstituted heterocycloalkyl or substituted or unsubstituted heteroaryl; R³ᴬ and R³ᴮ substituents bonded to the same nitrogen atom may optionally be joined to form a substituted or unsubstituted heterocycloalkyl or substituted or unsubstituted heteroaryl; and each X, X², and X³ is independently —F, —Cl, —Br, or —I.

3. The method of claim 2, wherein
L¹ᴬ is —CH₂CH(CH₃)—, —CH₂C(CH₃)₂—, —CH₂CH₂CH(CH₃)—, or —CH₂CH₂C(CH₃)₂;
L¹ᴮ is —C(O)O—; and
R¹ is unsubstituted C₁-C₃ alkyl.

4. The method of claim 2, wherein
L¹ᴬ is —CH₂CH(CH₃)—, —CH₂C(CH₃)₂—, —CH₂CH₂CH(CH₃)—, or —CH₂CH₂C(CH₃)₂—;
L¹ᴮ is —C(O)O—; and
R¹ is —CH₃.

5. The method of claim 2, wherein
L¹ᴬ is —CH₂CH(CH₃)—;
L¹ᴮ is —C(O)O—; and
R¹ is —CH₃.

6. The method of claim 2, wherein R² is independently hydrogen, —C(O)-(unsubstituted C₁-C₃ alkyl), or R²³-substituted or unsubstituted C₁-C₆ alkyl;

R²³ is independently oxo, halogen, —CX²³₃, —CHX²³₂, —CH₂X²³, —OCX²³₃, —OCH₂X²³, —OCHX²³₂, —CN, —OH, —NH₂, —COOH, —CONH₂, —NO₂, —SH, —SO₃H, —SO₄H, —SO₂NH₂, —NHNH₂, —ONH₂, —NHC=(O)NHNH₂, —NHC=(O)NH₂, —NHSO₂H, —NHC=(O)H, —NHC(O)—OH, —NHOH, unsubstituted C₁-C₆ alkyl, unsubstituted 2 to 6 membered heteroalkyl, unsubstituted C₃-C₆ cycloalkyl, unsubstituted 3 to 6 membered heterocycloalkyl, unsubstituted phenyl, or unsubstituted 5 to 6 membered heteroaryl; and X²³ is independently —F, —Cl, —Br, or —I.

7. The method of claim 2, wherein R² is independently hydrogen, —C(O)-(unsubstituted C₁-C₃ alkyl), or unsubstituted C₁-C₃ alkyl.

8. The method of claim 2, wherein R² is independently hydrogen.

9. The method of claim 2, wherein R² is independently —C(O)CH₃.

10. The method of claim 2, wherein R³ is independently hydrogen, substituted or unsubstituted C₁-C₆ alkyl, or substituted or unsubstituted 2 to 8 membered heteroalkyl.

11. The method of claim 2, wherein R³ is independently hydrogen, R²⁶-substituted or unsubstituted alkyl, or R²⁶-substituted or unsubstituted heteroalkyl;

R²⁶ is independently oxo, halogen, —CX²⁶₃, —CHX²⁶₂, —CH₂X²⁶, —OCX²⁶₃, —OCH₂X²⁶, —OCHX²⁶₂, —CN, —OH, —NH₂, —COOH, —CONH₂, —NO₂, —SH, unsubstituted C₁-C₆ alkyl, unsubstituted 2 to 6 membered heteroalkyl, unsubstituted C₃-C₆ cycloalkyl, unsubstituted 3 to 6 membered heterocycloalkyl, unsubstituted phenyl, or unsubstituted 5 to 6 membered heteroaryl; and X²⁶ is independently —F, —Cl, —Br, or —I.

12. The method of claim 2, wherein R³ is independently hydrogen or —CH₂CH₂N(unsubstituted C₁-C₃ alkyl)₂.

13. The method of claim 2, wherein R³ is hydrogen.

14. The method of claim 2, wherein R³ is —CH₂CH₂N(CH₃)₂.

15. The method of claim 2, wherein the compound is

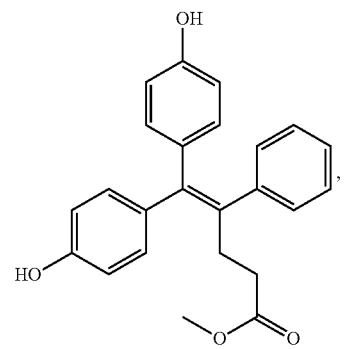

,

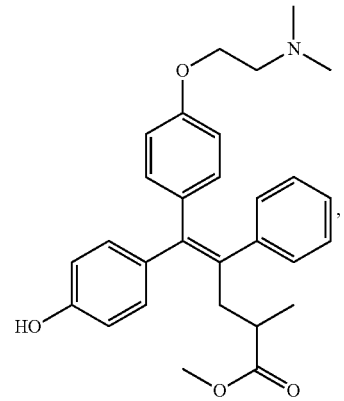

,

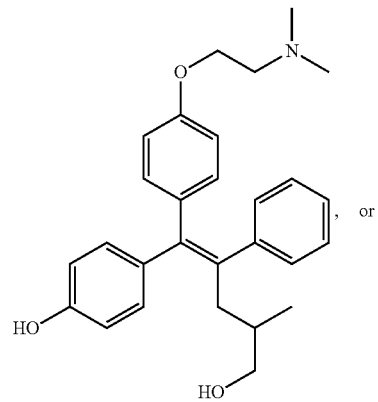

, or

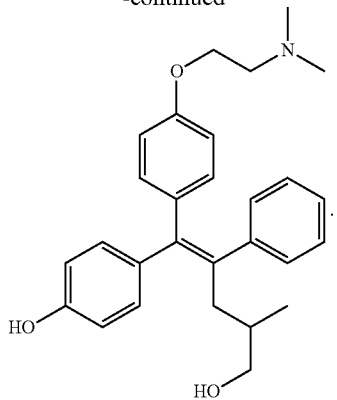

16. The method of claim 1, wherein the compound is administered in a pharmaceutical composition further comprising a pharmaceutically acceptable excipient.

17. The method of claim 2, wherein
$L^{1A}$ is —CH$_2$CH(CH$_3$)—, —CH$_2$C(CH$_3$)$_2$—, —CH$_2$CH$_2$CH(CH$_3$)—, or —CH$_2$CH$_2$C(CH$_3$)$_2$—;
$L^{1B}$ is a bond; and
$R^1$ is hydroxy-substituted methyl, hydroxy-substituted ethyl, hydroxy-substituted isopropyl, hydroxy-substituted n-propyl, hydroxy-substituted n-butyl, or hydroxy-substituted t-butyl.

18. The method of claim 1, wherein,
$L^{1A}$ is unsubstituted C$_2$-C$_4$ alkylene;
$L^{1B}$ is —C(O)O—;
$R^1$ is hydrogen or substituted or unsubstituted C$_1$-C$_6$ alkyl;
$R^2$ is independently hydrogen, —CX$^2_3$, —CHX$^2_2$, —CH$_2$X$^2$, —C(O)R$^{2A}$, —C(O)OR$^{2A}$, —C(O)NR$^{2A}$R$^{2B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
$R^3$ is independently —CX$^3_3$, —CHX$^3_2$, —CH$_2$X$^3$, —C(O)R$^{3A}$, —C(O)OR$^{3A}$, —C(O)NR$^{3A}$R$^{3B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
each $R^{2A}$, $R^{2B}$, $R^{3A}$, and $R^{3B}$ is independently hydrogen, —CX$_3$, —CN, —COOH, —CONH$_2$, —CHX$_2$, —CH$_2$X, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{2A}$ and $R^{2B}$ substituents bonded to the same nitrogen atom may optionally be joined to form a substituted or unsubstituted heterocycloalkyl or substituted or unsubstituted heteroaryl; $R^{3A}$ and $R^{3B}$ substituents bonded to the same nitrogen atom may optionally be joined to form a substituted or unsubstituted heterocycloalkyl or substituted or unsubstituted heteroaryl; and
each X, X$^2$, and X$^3$ is independently —F, —Cl, —Br, or —I.

19. The method of claim 18, wherein
$L^{1A}$ is unsubstituted C$_2$-C$_4$ alkylene;
$L^{1B}$ is —C(O)O—; and
$R^1$ is —H or unsubstituted C$_1$-C$_3$ alkyl.

20. The method of claim 18, wherein $R^3$ is independently substituted or unsubstituted C$_1$-C$_6$ alkyl, or substituted or unsubstituted 2 to 8 membered heteroalkyl.

21. The method of claim 18, wherein $R^3$ is independently $R^{26}$-substituted or unsubstituted alkyl, or $R^{26}$-substituted or unsubstituted heteroalkyl;
$R^{26}$ is independently oxo, halogen, —CX$^{26}_3$, —CHX$^{26}_2$, —CH$_2$X$^{26}$, —OCX$^{26}_3$, —OCH$_2$X$^{26}$, —OCHX$^{26}_2$, —CN, —OH, —NH$_2$, —COOH, —CONH$_2$, —NO$_2$, —SH, unsubstituted C$_1$-C$_6$ alkyl, unsubstituted 2 to 6 membered heteroalkyl, unsubstituted C$_3$-C$_6$ cycloalkyl, unsubstituted 3 to 6 membered heterocycloalkyl, unsubstituted phenyl, or unsubstituted 5 to 6 membered heteroaryl; and
$X^{26}$ is independently —F, —Cl, —Br, or —I.

22. The method of claim 18, wherein $R^3$ is —CH$_2$CH$_2$N (unsubstituted C$_1$-C$_3$ alkyl)$_2$.

23. The method of claim 18, wherein $R^3$ is —CH$_2$CH$_2$N (CH$_3$)$_2$.

24. The method of claim 18, wherein the compound is

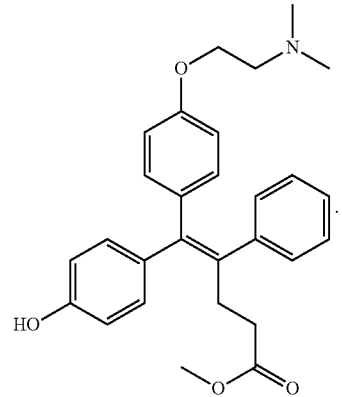 [SMILES: COC(=O)CC/C(=C(\c1ccc(O)cc1)c1ccc(OCCN(C)C)cc1)c1ccccc1]

25. The method of claim 1, wherein the compound is

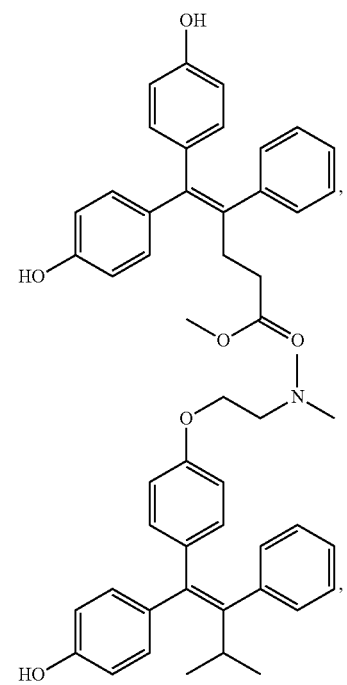

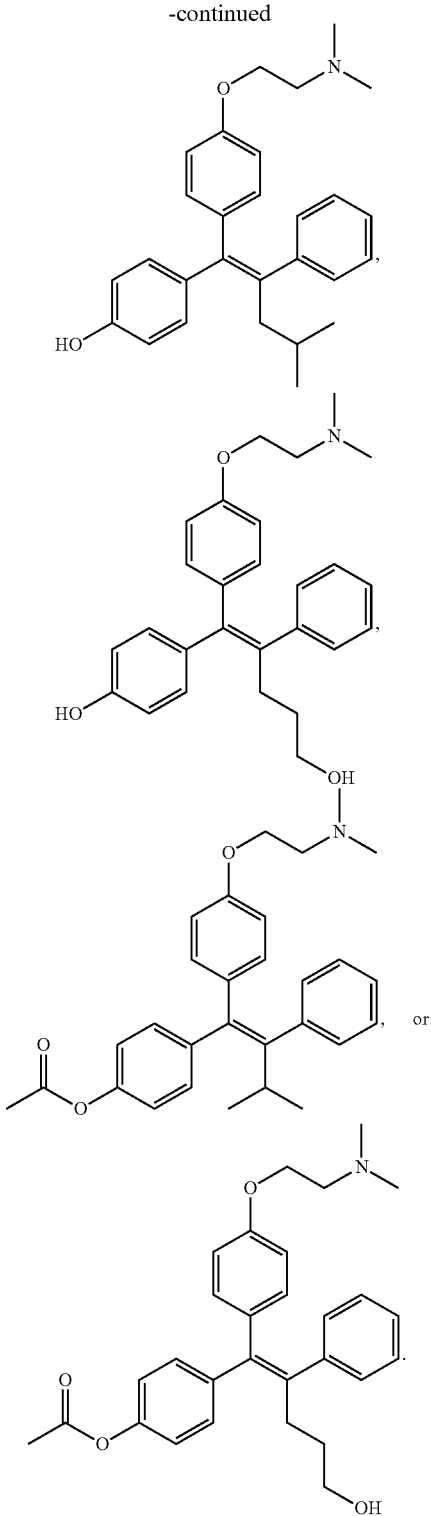

26. The method of claim 1, wherein $L^{1A}$ is a bond or substituted or unsubstituted $C_1$-$C_6$ alkylene.

27. The method of claim 1, wherein $L^{1B}$ is a bond, —C(O)O—, —OC(O)—, or —C(O)—.

28. The method of claim 1, wherein $R^1$ is independently hydrogen, halogen, —$CX^1_3$, —$CHX^1_2$, —$CH_2X^1$, —$OCX^1_3$, —$OCH_2X^1$, —$OCHX^1_2$, —C(O)$R^{1C}$, —C(O)O$R^{1C}$, substituted or unsubstituted alkyl, substituted or unsubstituted heteroalkyl, substituted or unsubstituted cycloalkyl, substituted or unsubstituted heterocycloalkyl; each $R^{1C}$ is independently hydrogen, —$CX_3$, —$CHX_2$, —$CH_2X$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; and each X and $X^1$ is independently —F, —Cl, —Br, or —I.

29. The method of claim 1, wherein, $L^{1A}$ is unsubstituted $C_2$-$C_4$ alkylene;

$L^{1B}$ is —C(O)O—;

$R^1$ is hydrogen or substituted or unsubstituted $C_1$-$C_6$ alkyl;

$R^2$ is independently hydrogen, —$CX^2_3$, —$CHX^2_2$, —$CH_2X^2$, —C(O)$R^{2A}$, —C(O)O$R^{2A}$, —C(O)$NR^{2A}R^{2B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^3$ is independently hydrogen, —$CX^3_3$, —$CHX^3_2$, —$CH_2X^3$, —C(O)$R^{3A}$, —C(O)O$R^{3A}$, —C(O)$NR^{3A}R^{3B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

each $R^{2A}$, $R^{2B}$, $R^{3A}$, and $R^{3B}$ is independently hydrogen, —$CX_3$, —CN, —COOH, —$CONH_2$, —$CHX_2$, —$CH_2X$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{2A}$ and $R^{2B}$ substituents bonded to the same nitrogen atom may optionally be joined to form a substituted or unsubstituted heterocycloalkyl or substituted or unsubstituted heteroaryl; $R^{3A}$ and $R^{3B}$ substituents bonded to the same nitrogen atom may optionally be joined to form a substituted or unsubstituted heterocycloalkyl or substituted or unsubstituted heteroaryl; and each X, $X^2$, and $X^3$ is independently —F, —Cl, —Br, or —I.

* * * * *